(12) United States Patent
Dub et al.

(10) Patent No.: US 10,550,139 B2
(45) Date of Patent: Feb. 4, 2020

(54) POLYDENTATE LIGANDS AND THEIR COMPLEXES FOR MOLECULAR CATALYSIS

(71) Applicant: Triad National Security, LLC, Los Alamos, NM (US)

(72) Inventors: Pavel A. Dub, Los Alamos, NM (US); John Cameron Gordon, Los Alamos, NM (US)

(73) Assignee: Triad National Security, LLC, Los Alamos, NM (US)

(*) Notice: Subject to any disclaimer, the term of this patent is extended or adjusted under 35 U.S.C. 154(b) by 0 days.

(21) Appl. No.: 15/375,055

(22) Filed: Dec. 9, 2016

(65) Prior Publication Data
US 2017/0088571 A1    Mar. 30, 2017

Related U.S. Application Data

(63) Continuation-in-part of application No. PCT/US2015/034793, filed on Jun. 9, 2015.

(60) Provisional application No. 62/268,080, filed on Dec. 16, 2015, provisional application No. 62/136,085, filed on Mar. 20, 2015, provisional application No. 62/130,977, filed on Mar. 10, 2015, provisional application No. 62/118,386, filed on Feb. 19, 2015, provisional application No. 62/009,483, filed on Jun. 9, 2014.

(51) Int. Cl.
C07D 295/00    (2006.01)
C07F 9/53    (2006.01)

(52) U.S. Cl.
CPC .................. C07F 9/5304 (2013.01)

(58) Field of Classification Search
CPC .................................................. C07D 295/00
See application file for complete search history.

(56) References Cited

U.S. PATENT DOCUMENTS

| | | | |
|---|---|---|---|
| 4,895,840 A * | 1/1990 | Shanklin, Jr. ......... | C07C 317/28 514/217.03 |
| 9,000,212 B2 | 4/2015 | Touge et al. | |
| 9,328,079 B2 | 5/2016 | Ohkuma et al. | |
| 10,196,414 B2 | 2/2019 | Geisser et al. | |
| 2007/0149575 A1 | 6/2007 | Schnatterer et al. | |
| 2013/0171067 A1 | 7/2013 | Guminski et al. | |
| 2014/0163257 A1 | 6/2014 | Hori et al. | |
| 2016/0326199 A1 | 11/2016 | Geisser et al. | |

FOREIGN PATENT DOCUMENTS

| | | |
|---|---|---|
| WO | WO 01/83436 A2 | 11/2001 |
| WO | WO 2011/048727 | 4/2011 |
| WO | WO 2012/026201 | 3/2012 |
| WO | WO 2012/048646 A1 | 4/2012 |
| WO | WO 2012/137460 | 10/2012 |
| WO | WO 2012/144650 | 10/2012 |
| WO | WO 2013/065867 | 5/2013 |
| WO | WO 2015/110515 | * 7/2015 |
| WO | WO 2015/163440 | 10/2015 |
| WO | WO 2015/191505 | 12/2015 |

OTHER PUBLICATIONS

Registry No. 1002277-95-3, File Registry on STN, Feb. 8, 2008.*
Registry No. 1342746-15-9, File Registry on STN, Nov. 8, 2011.*
Peruzzo et al., Inorganica Chimica Acta 387 (2012) 163-172.*
International Search Report issued in International Application No. PCT/US2015/034793, dated Sep. 2, 2015, 4 pages.
Written Opinion of the International Searching Authority issued in International Application No. PCT/US2015/034793, dated Sep. 2, 2015, 7 pages.
Combariza et al., "The utility of ion-molecule reactions in a quadrupole ion trap mass spectrometer for analyzing metal complex coordination structure", Analytica Chimica Acta, 496:233-248 (2003).
Huang et al., "Studies on tetranuclear copper (II) complexes of a macrocyclic ligand bearing 2-thiophenoethylamine pendant arms", Journal of Molecular Structure, 983:186-193 (2010).
Zhang et al., "Asymmetric transfer hydrogenation of aromatic ketones with chiral diamino-thiophene/iridium catalyst systems", Journal of Molecular Catalysis A: Chemical, 307:149-153 (2009).
Rey et al., "Synthesis and Characterization of Mixed-Ligand Oxorhenium Complexes with SNN Type of Ligand. Isolation of a Novel ReO[SN][S][S] Complex", Inorg. Chem., 39:4211-4218 (2000).
Kuriyama et al., "Catalytic hydrogenation of esters. Development of an efficient catalyst and processes for synthesizing (R)-1,2-propanediol and 2-(1-methoxy)ethanol," Org. Process Res. Dev., 16(1): 166-171, Nov. 29, 2011.
Matsumura et al., "Chiral Ruthenbicyclic Complexes: Precatalysts for Rapid Enantioselective and Wide-Scope Hydrogenation of Ketones," J. Am. Chem. Soc., 133(28): 10696-10699, Jun. 16, 2011.
Non-Final Office Action issued for U.S. Appl. No. 15/944,503 dated Dec. 14, 2018.

(Continued)

Primary Examiner — Rebecca L Anderson
(74) Attorney, Agent, or Firm — Klarquist Sparkman, LLP

(57) ABSTRACT

Embodiments of the present disclosure relate generally to novel achiral and chiral sulfur-, nitrogen- and phosphorus-containing ligands, designated as NNS-type, P(O)NS-type, PNS-type, SNNS-type, SNNP(O)-type, or SNNP-type polydentate ligands and transition metal complexes of these ligands, including iridium complexes having PNS-type and NNS-type ligands. The catalysts derived from these ligands and transition metal complexes may be used in a wide range of catalytic reactions, including hydrogenation and transfer hydrogenation of unsaturated organic compounds, dehydrogenation of alcohols and boranes, various dehydrogenative couplings, chemoselective hydrogenation of α,β-unsaturated alcohols, and other catalytic transformations.

20 Claims, 9 Drawing Sheets

(56) References Cited

OTHER PUBLICATIONS

Touge et al., "Efficient Access to Chiral Benzhydrols via Asymmetric Transfer Hydrogenation of Unsymmetrical Benzophenones with Bifunctional Oxo-Tethered Ruthenium Catalysts," *J. Am. Chem. Soc.*, 138(32): 10084-10087, Jul. 27, 2016.

Touge et al., Oxo-Tethered Ruthenium (II) Complex as a Bifunctional Catalyst for Asymmetric Transfer Hydrogenation and $H_2$ Hydrogenation, *J. Am. Chem. Soc.*, 133(38): 14960-14963, Aug. 26, 2011.

U.S. Appl. No. 15/944,503, filed Apr. 3, 2018.

\* cited by examiner

POLYDENTATE LIGANDS AND THEIR COMPLEXES FOR MOLECULAR CATALYSIS

CROSS REFERENCE TO RELATED APPLICATIONS

This application claims priority to and the benefit of U.S. Provisional Application No. 62/268,080, filed Dec. 16, 2015, titled "CHEMOSELECTIVE HYDROGENATION OF α,β-UNSATURATED ALCOHOLS WITH HOMOGENOUS Ir-CATALYSTS SUPPORTED BY N,S-HETEROATOMS," the entire content of which is incorporated herein by reference. This application is also a continuation-in-part and national stage entry of International Application No. PCT/US2015/034793, filed Jun. 9, 2015 and titled "POLYDENTATE LIGANDS AND THEIR COMPLEXES FOR MOLECULAR CATALYSIS," which claims priority to and the benefit of U.S. Provisional Application Ser. No. 62/136,085, filed Mar. 20, 2015; 62/130,977, filed Mar. 10, 2015; 62/118,386, filed Feb. 19, 2015; and 62/009,483, filed Jun. 9, 2014. The entire content of each of the applications listed in this paragraph is incorporated herein by reference.

STATEMENT REGARDING FEDERAL RIGHTS

This invention was made with government support under Contract No. DE-AC52-06NA25396 awarded by the U.S. Department of Energy. The government has certain rights in the invention.

TECHNICAL FIELD

Embodiments of the present disclosure relate generally to polydentate ligands and transition metal complexes of these ligands, some of which are relevant to the area of so-called bifunctional metal-ligand M/NH cooperative molecular catalysis. The catalysts can be used in a wide range of catalytic reactions, including hydrogenation and transfer hydrogenation of unsaturated organic compounds, dehydrogenation of alcohols and boranes, various dehydrogenative couplings, catalytic C—N and C—C bond-forming reactions, hydration of nitriles, and aerobic oxidation of alcohols into ketones, esters, and other functional groups. For example, iridium catalysts supported by ligands including heteroatoms such as nitrogen and sulfur can be used as homogenous catalysts for the chemoselective hydrogenation of α,β-unsaturated alcohols.

BACKGROUND

Progress in the field of homogeneous catalysis, including homogeneous catalysis of hydrogenation reactions, often involves the development of new ligands and transition metal complexes including these ligands as active precatalysts and/or catalysts. The vast majority of ligands used to support transition metal complexes used in homogeneous catalysis are based on P and/or N donor atoms, and an enormous number of such ligands have been designed and synthesized over the past four decades.

It is generally accepted that polydentate chelating ligands bearing NH functionalities (e.g., functional groups) play a crucial role in so-called bifunctional metal-ligand (M/NH) cooperative molecular catalysis, in which a non-innocent ligand is proposed to directly participate in substrate activation via interaction with an N—H group and/or in bond cleavage/formation via N—H proton transfer to or from the substrate. As used herein, the term "non-innocent ligand" is used interchangeably with the term "bifunctional ligand" to refer to a situation in which a ligand interacts with the substrate, including but not limited to hydrogen bonding between the ligand and substrate and direct transfer of atoms and/or electrons between the ligand and substrate or ligand and metal during the chemical reaction. Bifunctional molecular catalysis based on metal-ligand M/NH cooperation was originally developed for asymmetric hydrogenation and transfer hydrogenation of ketones and imines, and is now applicable to a variety of chemical transformations with a wide scope and high practicability. They include practical hydrogenation of carboxylic and carbonic acid derivatives, hydrogenation and electroreduction of $CO_2$, various acceptorless dehydrogenations, asymmetric Michael reaction (addition) of 1,3-dicarbonyl compounds with cyclic enones and nitroalkenes, stereoselective catalytic C—N_ENREF_42 and C—C bond-forming reactions, aerobic oxidative kinetic resolution of racemic secondary alcohols, asymmetric hydration of nitriles, and others.

Given the utility of these catalysts, there is interest in further ligand and catalyst design for the production of commercially important chemicals and intermediates.

α,β-unsaturated alcohols are of great commercial importance, as they are widely used in fragrances, pharmaceutical industries, intermediates in fine chemicals syntheses, etc. Such alcohols may be synthesized using α,β-unsaturated ketones as substrates or starting materials. Non-limiting examples of α,β-unsaturated ketone substrates may have the general form:

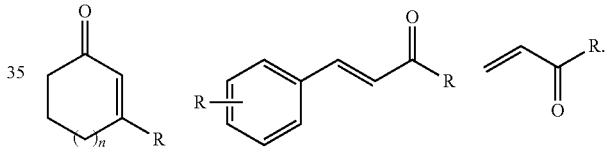

The production of α,β-unsaturated alcohols via chemoselective hydrogenation of α,β-unsaturated ketones using molecular hydrogen is quite challenging because of the higher reactivity of the C═C bond compared with that of the C═O group, and hence a tendency to form either the saturated ketone or the fully hydrogenated alcohol. Moreover, the α,β-unsaturated alcohol formed in the hydrogenation reaction may isomerize to the corresponding saturated ketones under commonly used reaction conditions, resulting in lower selectivity for the unsaturated alcohol. Therefore, achieving high C═O/C═C chemoselectivity is a challenge.

C═O/C═C chemoselectivity may be attained via an appropriate catalyst. Examples of such catalysts in the related art are both homogenous and heterogeneous, including a homogenous catalyst having a substrate-to-catalyst ratio (S/C)=5000 (Dowpharma), and a catalyst having an S/C=20,000 (Chirotech Technology Limited). However, these and other prior examples are limited by various drawbacks, including the relatively small S/C ratios. One example of Noyori's catalyst (e.g., a BINAP-Ru complex) showed a higher S/C ratio of 100,000, but required a prolonged reaction time at elevated pressures. (43 hours and 80 atm $H_2$). These conditions limit the use of such catalysts.

SUMMARY

One or more embodiments of the present disclosure are directed to several new classes of ligands, transition metal complexes comprising these ligands, and methods of hydrogenating substrates using these complexes as precatalysts. Some of these ligands show an insensitivity to air and the ability to easily vary structures based on cheap, readily available starting materials (i.e., fine-tuning of ligand conformational, steric and electronic properties), and use simple synthetic procedures and protocols consistent with the concepts of green chemistry.

One or more embodiments of the present disclosure provide ligands having a structure represented by Formula (I), Formula (II), Formula (III), or Formula (IV):

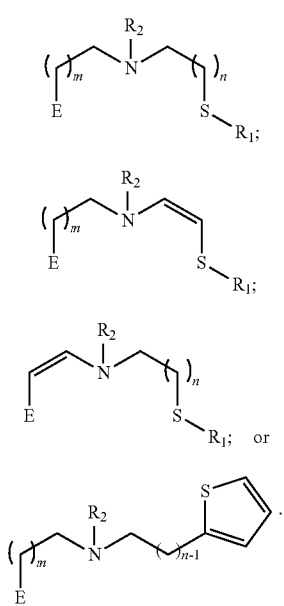

In Formulae I through IV, E may be:

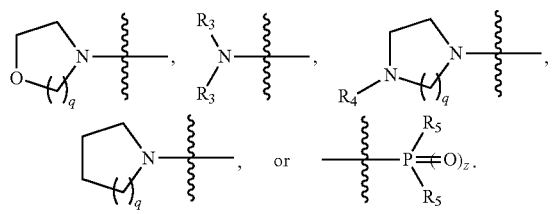

Additionally, $R_1$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group.

$R_2$, $R_3$, and $R_4$ may independently at each occurrence be a hydrogen atom (H), a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group.

$R_5$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, a substituted or unsubstituted arylalkyl group, a substituted or unsubstituted alkoxy group, or a substituted or unsubstituted aryloxy group.

Also, in Formulae I through IV, m may be 1, 2, 3, 4, or 5; n may be 1, 2, 3, 4, or 5; q may be 1, 2, 3, or 4; and z may be 0 or 1.

In some embodiments, the ligand represented by Formula (I) is not:

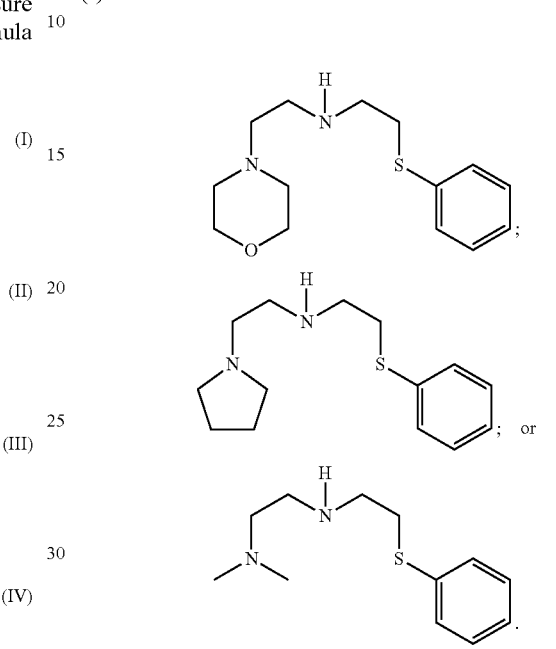

One or more embodiments of the present disclosure provide ligands having a structure represented by Formula (V), Formula (VI), Formula (VII), Formula (VIII), Formula (IX), or Formula (X):

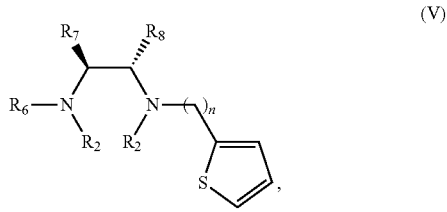

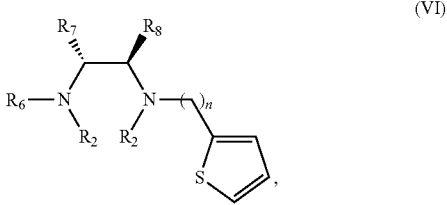

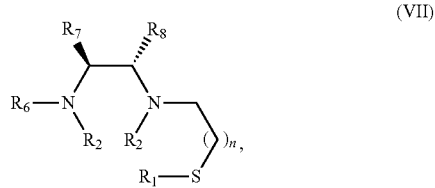

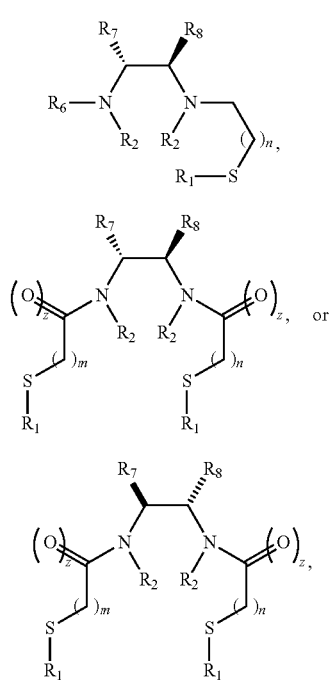

or an achiral isomer, enantiomer, diastereomer, isomeric mixture, and/or salt thereof.

In Formulae V through X, $R_1$, $R_2$, q, and z may each be the same as defined above in connection with the ligands represented by Formulae (I) to (IV). Additionally, m may be 1, 2, 3, 4, or 5; n may be 1, 2, 3, 4, or 5; and z may be 0 or 1.

Also, in Formulae V through X, $R_6$ may be H, —$(CH_2)_n$—S—$R_1$, —$(CH_2)_n$-(2-thiophenyl), or —$(CH_2)_n$—$P(O)_z(R_5)_2$.

$R_7$ and $R_8$ may each independently be H, a substituted or unsubstituted $C_{1-6}$ alkyl group, a substituted or unsubstituted aryl or heteroaryl group, or a substituted or unsubstituted arylalkyl group. In some embodiments, $R_7$ and $R_8$ are connected via a bridging group to form a 5-7 membered cyclic or heterocyclic ring including the carbons to which they are bound. In some embodiments, only one of $R_7$ and $R_8$ is H. Note that in the structures represented by Formulae (IX) and (X), when z is 0, the carbonyl group is a methylene group.

In some embodiments, when the $R_1$ or $R_2$ groups are substituted or unsubstituted alkyl or aryl groups, and are held in a conformation that places at least one C—H bond near the metal center when the ligand is bound in the metal, the ligand may undergo C—H activation at that C—H bond. As used herein, the term "C—H activation" is used in its art-recognized sense to refer to an organometallic reaction in which the C—H bond is broken in the presence of the metal, and a metal-H and a metal-C bond are formed in its place. In some embodiments, when the $R_1$ or $R_2$ group is an aryl group, the C—H activation may occur at a position ortho- to the heteroatom substituted by the $R_1$ or $R_2$ group, and may be referred to as ortho-metallation. The metal may be any transition metal or post-transition metal capable of this type of reaction, including a second and third row transition metal, for example, ruthenium (Ru), tungsten (W), iridium (Ir), rhodium (Rh), zirconium (Zr), rhenium (Re), osmium (Os), and platinum (Pt).

In some embodiments, an iridium-based catalyst chelated with one of the above ligands may be used for the chemoselective hydrogenation of α,β-unsaturated alcohols. In some embodiments, the structure of this catalyst may be:

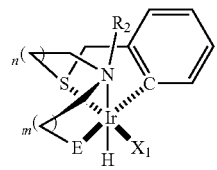

in which E may be:

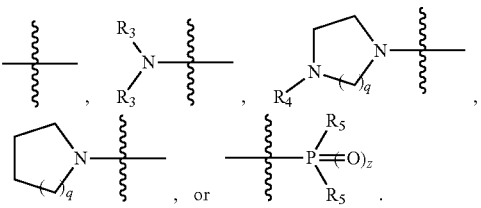

$R_2$ may be H, Me, Et, BN, or an alkyl group.

$R_3$ and $R_4$ may independently at each occurrence be H, a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group.

$R_5$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, a substituted or unsubstituted arylalkyl group, a substituted or unsubstituted alkoxy group, or a substituted or unsubstituted aryloxy group.

Additionally, m may be 1, 2, 3, 4, or 5; n may be 1, 2, 3, 4, or 5; q may be 1, 2, 3, or 4; and z may be 0 or 1.

$X_1$ and $X_2$ may each independently be H, OTf, $BH_4$, or a halide, for example, Cl.

Subset genera and specific examples are included as non-limiting examples. In some of these subsets, the substituted or unsubstituted $C_{1-6}$ alkyl of $R_2$ may comprise pendant phosphine or phosphine oxide moieties, as described further herein. As used herein, the term "pendant" is used in its art-recognized sense to refer to a moiety at or near the opposite terminus of the group that may have the ability to physically and electronically interact with the metal center, active site, substrate, reaction intermediates and/or product, for example, by forming a ligand-metal or ligand-substrate bond.

In some embodiments, metal coordination complexes may include any of the ligands described herein coordinated to at least one transition metal. These coordination complexes, also described herein as pre-catalysts, may include mononuclear and dinuclear metal complexes. As used herein, the terms "mononuclear" and "dinuclear" are used in their art-recognized senses to refer to the presence of one and two metal atoms, respectively, in a single catalyst molecule. Subset genera and specific examples are included as non-limiting examples.

Some embodiments of the present disclosure include the use of the inventive catalysts in the catalytic hydrogenation of unsaturated organic precursors, including methods of affecting or controlling these transformations. Subset genera may include uses and methods in which the source of hydrogen is dihydrogen, isopropanol, formic acid, a formic acid-triethylamine azeotropic mixture (e.g., azeotrope), or a combination thereof, and where the reducible organic substrate includes at least one unsaturated bond, such as an >C=C< (alkenyl) bond, —C≡C— (alkynyl) bond, >C=O (carbonyl) group, >C=N— bond, —C≡N (nitrile) group, —N=O (nitroso) group, or —N=N— (azo) bond. Some embodiments include the use of the inventive catalysts, for example, bifunctional catalysts used in dehydrogenation reactions of alcohols and boranes, various dehydrogenative coupling reactions, stereoselective and achiral C—N and C—C bond-forming reactions, hydrations of nitriles, and aerobic oxidative transformations of alcohols into ketones and esters, as well as methods of affecting or controlling these reactions. Some embodiments of the present disclosure include the use of the inventive catalysts, for example, Ir-based or N,S heterotom-containing catalysts, in chemoselective hydrogenation reactions to produce α,β-unsaturated alcohols.

In some methods, according to embodiments of the present disclosure, the compound or combination of compounds that actively catalyzes a reaction (e.g., "the active catalyst") may be the coordination complex as described herein, or may be derived in situ from the coordination complex before or during use in the reaction. For example, the active catalyst may be produced from the coordination complex via a reaction such as ligand association/dissociation, oxidation, and/or reduction. However, embodiments of the present disclosure are not limited thereto. While the methods and uses do not depend on the correctness or incorrectness of any suggested catalytic model, it will be understood that the complex affecting the transformation or catalysis may involve a combination of as-described and in situ-derived complexes, and that embodiments of the present disclosure encompass both. In specific subgenera or embodiments of the present disclosure, the reaction conditions may include the use of a strong base, e.g., an alkoxide, hydroxide, or a mixture thereof, as a co-catalyst.

The general description and the following detailed description are exemplary and explanatory only and do not restrict the scope of embodiments of the present disclosure, as defined in the appended claims. Other aspects of embodiments of the present disclosure will be apparent to those skilled in the art in view of the detailed descriptions and examples provided herein.

BRIEF DESCRIPTION OF THE DRAWINGS

The summary, as well as the following detailed description, will be further understood when read in conjunction with the appended drawings. For the purpose of furthering understanding of this disclosure, example embodiments are shown in the drawings; however, embodiments of the disclosure are not limited to the specific methods, compositions, and devices thus disclosed. In addition, the drawings are not necessarily drawn to scale. In the drawings.

DETAILED DESCRIPTION

Figure 1:
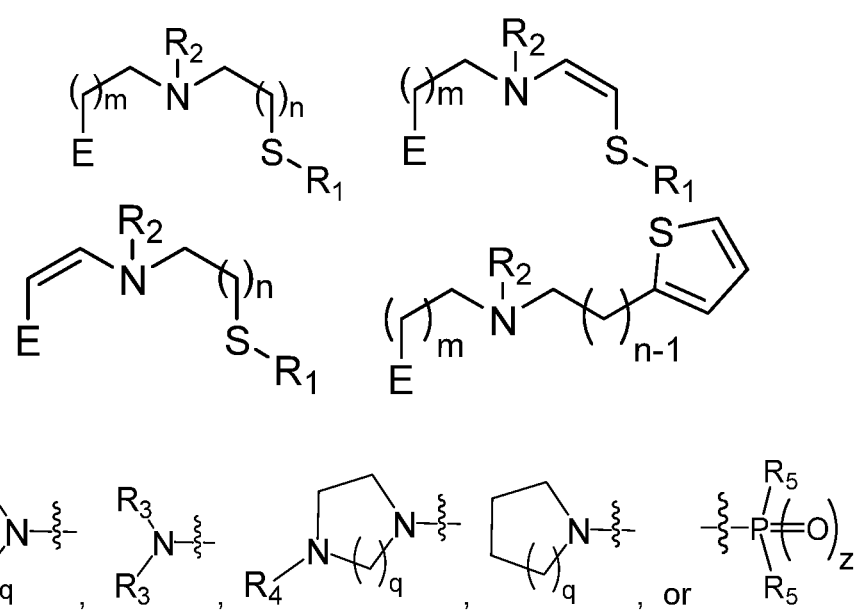
FIG. 1 and FIG. 2 show structures of several of the inventive ligands.

One or more embodiments of the present disclosure are directed to several new classes of ligands, catalysts including these ligands, and methods of catalyzing a wide range of reactions using these catalysts.

Embodiments of the present disclosure may be understood more readily by reference to the following description taken in connection with the accompanying drawings and examples, all of which form a part of this disclosure. It is to be understood that this disclosure is not limited to the specific products, methods, processes, conditions, or parameters described or shown herein, and that the terminology used herein is for the purpose of describing particular embodiments by way of example only and is not intended to be limiting. Similarly, unless specifically otherwise stated, any description as to a possible mechanism or mode of action or reason for improvement is meant to be illustrative only, and the embodiments described herein are not to be constrained by the correctness or incorrectness of any such suggested mechanism or mode of action or reason for improvement. Throughout the specification, claims, and drawings, it will be recognized that the descriptions refer to compositions (e.g., ligands, catalysts, and reaction mixtures) and processes of making and using said compositions. That is, where the disclosure describes or claims a feature or embodiment associated with a composition or a method of making or using a composition, it will be appreciated that such a description or claim is intended to extend the described or claimed features or embodiments to other embodiments in each of these contexts (i.e., compositions, methods of making, and methods of using; e.g., features of ligands may be incorporated into the corresponding catalysts, and vice versa).

Terms

In the present disclosure, references using the singular forms "a", "an", and "the" additionally include the plural reference, and references to a particular numerical value include at least that particular value but are not limited to that value, unless the context clearly indicates otherwise. Thus, for example, a reference to "a material" is a reference to at least one of such materials and equivalents thereof known to those skilled in the art, and so forth.

When a value is expressed as an approximation (e.g., approximate value) by use of the descriptor "about" or like terms, it will be understood that the particular (e.g., specific or exact) value is included as an embodiment. In general, use of the term "about" indicates an approximation that can vary depending on the desired properties sought to be obtained by the disclosed subject matter, and is to be interpreted in the specific context in which it is measured and/or used, based on its function. A person having ordinary skill in the art at the time will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated as a range include every value within that range.

It is to be appreciated that features of embodiments of the present disclosure which are, for clarity, described herein in connection with some embodiments, may also be provided in combination in other embodiments. That is, unless obviously incompatible or specifically excluded, each individual feature of the described embodiments is deemed to be combinable with any other feature of any described embodiments, and such a combination is considered to be within the scope of embodiments of the present disclosure. Conversely, various features of embodiments of the present disclosure that are, for brevity, described in the context of some embodiments, may also be provided separately or in any sub-combination. Finally, while embodiments may be described as part of a series of steps or part of a more general structure, each said step or part may also be considered an embodiment, and may be combinable with other features of other embodiments.

The transitional terms "comprising", "consisting essentially of", and "consisting of" are intended to connote their generally accepted meanings in the patent vernacular; that is, (i) "comprising", which is synonymous with "including", "containing", or "characterized by", is inclusive or open-ended and does not exclude additional, unrecited elements or method or process steps; (ii) "consisting of" excludes any element, step, or ingredient not specified in the claim with limited exceptions (e.g., incidental or expected impurities); and (iii) "consisting essentially of" limits the scope of a claim to the specified materials or steps "and those that do not materially affect the basic and novel characteristic(s)" of the claimed embodiments of the present disclosure. Embodiments described in terms of the phrase "comprising" (or its equivalents), also include embodiments that may be independently described in terms of "consisting of" and "consisting essentially of." For those embodiments described in terms of "consisting essentially of", the basic and novel characteristic of a process according to embodiments of the present disclosure is the ability to efficiently catalyze any of the catalytic reactions discussed herein, including reduction of organic substrates and carbon dioxide, oxidation (e.g., acceptorless dehydrogenation of secondary alcohols and aerobic oxidation with oxygen), borylative cyclization, stereoselective catalytic C—N_ENREF_42 and C—C bond-forming reactions, and catalytic hydration.

When a list is presented, unless stated otherwise, it is to be understood that the list encompasses each individual element of that list, and every combination of elements in that list. For example, a list of components presented as "A, B, or C" is to be interpreted as including the components, "A," "B," "C," "A or B," "A or C," "B or C," or "A, B, or C." Similarly, for example, where m and n are described in terms of 1, 2, 3, 4, or 5, it should be appreciated that these also include those embodiments where m and/or n are 1; 2; 3; 4; 5; 1 or 2; 1 or 3; 1 or 4; 1 or 5; 2 or 3; 2 or 4; 2; or 5; 3 or 4; 3 or 5; 4 or 5; 1, 2, or 3; 1, 2, or 4; 1, 2, or 5; 1, 3, or 4; 1, 3, or 5; 1, 4, or 5; 2, 3, or 4; 2, 3, or 5; 2, 4, or 5; 3, 4, or 5; 1, 2, 3, or 4; or 1, 2, 3, or 5.

Unless defined otherwise, all technical and scientific terms used herein have the same meaning as commonly understood by one of ordinary skill in the art. Although any methods and materials similar or equivalent to those described herein can also be used in the practice or testing of embodiments of the present disclosure, representative illustrative methods and materials are described herein without limiting the scope of this disclosure.

Throughout this specification, unless otherwise specified (e.g., through specific and contradictory or altering definition), words and terms are to be afforded their normal meaning, as would be understood by those skilled in the relevant art.

The term "alkyl" as used herein refers to a linear, branched, or cyclic saturated hydrocarbon group typically (although not necessarily) containing 1 to about 24 carbon atoms, and in some embodiments 1 to about 12 carbon atoms. Non-limiting examples of alkyl groups include methyl, ethyl, n-propyl, isopropyl, n-butyl, isobutyl, tert-butyl, octyl, decyl, and the like, as well as cycloalkyl groups such as cyclopentyl, cyclohexyl and the like. The term "lower alkyl" as used herein refers to an alkyl group of 1 to 6 carbon atoms, and the term "cycloalkyl" as used herein refers to a cyclic alkyl group, typically having 3 to 8, and in some embodiments 5 to 7 carbon atoms. The term "substituted alkyl" refers to alkyl groups substituted with one or more substituent groups. If not otherwise indicated, the terms "alkyl" and "lower alkyl" include linear, branched, cyclic, unsubstituted, and/or substituted alkyl and lower alkyl groups, respectively.

The term "alkoxy" as used herein refers to an substituted or unsubstituted alkyl group bound through a single, terminal ether linkage. An "alkoxy" group may be represented as —O-alkyl, where the alkyl may be the same as defined above. The term "lower alkoxy" group as used herein refers to an alkoxy group containing 1 to 6 carbon atoms.

As used herein, the term "aromatic" refers to ring moieties having $\pi$ electron counts that satisfy the Hückel 4n+2 rule for aromaticity, and includes both aryl (i.e., carbocyclic) and heteroaryl (also called heteroaromatic) structures, including aryl (e.g., phenyl), aralkyl (e.g., benzyl), alkaryl (e.g., tolyl), heteroaryl (e.g., pyridinyl), heteroaralkyl (e.g., pyridinylmethylene), and alk-heteroaryl (e.g., methylpyridinyl) moieties, and oligomeric and polymeric analogs thereof.

The term "aryl" as used herein, and unless otherwise specified, refers to substituted or unsubstituted aromatic substituents or structures containing at least one aromatic ring, where multiple aromatic rings may be fused together, directly linked (e.g., by a bond), or indirectly linked (such that the different aromatic rings are bound to a common group such as a methylene or ethylene moiety). Unless otherwise modified, the term "aryl" as used herein refers to carbocyclic structures. In some embodiments, an aryl group may include 5 to 24 carbon atoms, and in some embodiments, an aryl group may include 6 to 14 carbon atoms. Non-limiting examples of aryl groups containing one aromatic ring or two fused or linked aromatic rings may include, for example, phenyl, tolyl, naphthyl, biphenyl, diphenylether, diphenylamine, benzophenone, and the like. As used herein, the term "substituted aryl" refers to an aryl moiety substituted with one or more substituent groups, and the terms "heteroatom-containing aryl" and "heteroaryl" may be interchangeably used to refer to aryl substituents in which at least one carbon atom is replaced with a heteroatom, as will be described in further detail infra.

As used herein, the term "aryloxy" refers to a substituted or unsubstituted aryl group bound through a single, terminal ether linkage, where "aryl" is as defined above. An "aryloxy" group may be represented as —O-aryl, where aryl is the same as defined above.

As used herein, the terms "aralkyl" or "arylalkyl" refer to an alkyl group substituted with a substituted or unsubstituted aryl group, where "aryl" and "alkyl" are the same as defined above. In some embodiments, an aralkyl group may include 6 to 24 carbon atoms, and in some embodiments, an aralkyl group may include 6 to 16 carbon atoms. Non-limiting examples of aralkyl groups may include benzyl, 2-phenylethyl, and the like.

As used herein, the term "acyl" refers to groups having the formula —(CO)-alkyl, —(CO)-aryl, or —(CO)-aralkyl, and the term "acyloxy" refers to groups having the formula —O(CO)-alkyl, —O(CO)-aryl, or —O(CO)-aralkyl, where "alkyl", "aryl", and "aralkyl" are the same as defined above.

As used herein, the term "catalyst" is intended to connote a compound capable of catalyzing a synthetic reaction, as would be readily understood by a person having ordinary skill in the art. The term is used in the present context of coordination complexes for clarity and convenience only, and is not intended to limit the scope of such complexes to this purpose. In this regard, the terms "coordination complex" and "catalyst" may be interchangeably used, and a person having ordinary skill in the art would be able to understand these terms in the context of the description. As is understood by those skilled in the art, the term "bifunctional M/NH catalyst" refers to a transition metal complex bearing at least one NH functionality. It is not intended to limit, in any way, the number or types of catalytic reactions to which the catalyst may be effectively applied.

As used herein, the terms "cyclic" and "ring" may be used interchangeably, and both refer to alicyclic or aromatic groups that may be substituted or unsubstituted, may be a hydrocarbon or include heteroatoms, and/or may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo", "halide", and "halogen" are used in the conventional sense to refer to a chloro, bromo, fluoro, or iodo substituent, atom, ligand, or group.

As used herein, the terms "substrate" and "organic substrate" are intended to connote discrete small molecules (sometimes described as "organic compounds"), oligomers, and polymers containing the named functional group or unsaturated bond.

As used herein, the term "ligand" is intended to connote a compound or atom capable of coordinating to (e.g., forming an ionic or covalent bond with) a metal atom or ion, including a transition metal atom or ion, as well as a compound or atom that is actually coordinated to such a metal, including a transition metal atom or ion. The term is used in the present context for clarity and convenience only, and is not intended to limit the scope of such compounds to this purpose. In this regard, references to compounds and ligands may be used interchangeably, and a person having ordinary skill in the art would be able to understand the terms in the context of the description. In addition, where a structure or formula is presented for a ligand or compound, it should also be appreciated that this structure or formula includes any structural, functional or chemical equivalents (e.g., the scope of embodiments includes any isomers, tautomers, or charge-bearing structural equivalents and their counter ions). In the case of amines (e.g., amine ligands), this includes amines quaternized, for example, by alkyl or benzyl halides or protic acids.

As used herein, the term "substituent" or "substituent group" refers to an atom or group of atoms which replaces a hydrogen atom on the parent group. As used herein, the term "substituted", as in "substituted alkyl," "substituted aryl," and the like, as alluded to in some of the aforementioned definitions, is intended to connote that in the alkyl, aryl, heteroaryl, or other moiety, at least one hydrogen atom bound to a carbon (or other) atom is replaced with one or more non-hydrogen substituents. Non-limiting examples of such substituents may include functional groups such as halogens (e.g., F, Cl, Br, I), hydroxyl groups, $C_1$-$C_{24}$ alkyl groups (including $C_{3-8}$ cycloalkyl), $C_1$-$C_{24}$ alkoxy groups, $C_5$-$C_{24}$ aryl groups, $C_5$-$C_{24}$ aryloxy groups, acyl groups (including $C_1$-$C_{24}$ alkylcarbonyl (—CO-alkyl) and $C_6$-$C_{24}$ arylcarbonyl (—CO-aryl)), $C_2$-$C_{24}$ alkoxycarbonyl groups ((CO)—O-alkyl), $C_6$-$C_{24}$ aryloxycarbonyl groups (—(CO)—O-aryl), carboxy groups (—COOH), carboxylato groups (—COO—), carbamoyl groups (—(CO)—$NH_2$), cyano groups (—C≡N), formyl groups (—(CO)—H), nitro groups, amino groups (—$NH_2$), mono-($C_1$-$C_{24}$ alkyl)-substituted amino groups, di-($C_1$-$C_{24}$ alkyl)-substituted amino groups, phosphines, and phosphine oxides. Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, references to alcohols, aldehydes, amines, carboxylic acids, ketones, or other similarly reactive functional groups may also include their protected analogs.

As used herein, the term "pendant" is used in its art-recognized sense to refer to a moiety at or near the opposite terminus of the group that may have the ability to physically and electronically interact with the metal center, active site, substrate, reaction intermediates and/or product, for example, by forming a ligand-metal or ligand-substrate bond.

"Optional" or "optionally" means that the subsequently described circumstance may or may not occur, so that the description includes embodiments where the circumstance occurs as well as instances where it does not. For example, the phrase "optionally substituted" means that a non-hydrogen substituent may or may not be present on a given atom, and, thus, the description includes structures in which a non-hydrogen substituent is present and structures in which a non-hydrogen substituent is not present. For example, the term "optionally substituted" and like terms, for instance, when used in a list, may be read as "substituted alkyl and unsubstituted alkyl." It is to be understood that the various pendant groups (including the 2-thiophenyl groups) are intended to include both substituted and unsubstituted moieties. It is also to be understood that, in some embodiments, the term "optionally substituted" applies to the terms alkyl, alkylene, alkenyl, alkenylene, alkynyl, alkynylene, alkoxy, aromatic, aryl, heteraryl, aryloxy, alkaryl, and aralkyl (including their specific exemplars, e.g., phenyl), even if not explicitly stated as such (for example, in provided structure depictions)—i.e., the structures include the range of substituted and unsubstituted moieties.

As used herein, the term "active catalyst" refers to the compound or combination of compounds that actively catalyzes a reaction, e.g., by interacting with substrates or reactants to thereby lower the energy requirements for chemical transformation. As used herein, the term "pre-catalyst" refers to a compound that does not itself actively catalyze a reaction, but undergoes an initial reaction to thereby produce the active catalyst.

Ligands

One or more embodiments of the present disclosure provide ligands having a structure represented by Formula (I), Formula (II), Formula (III), or Formula (IV):

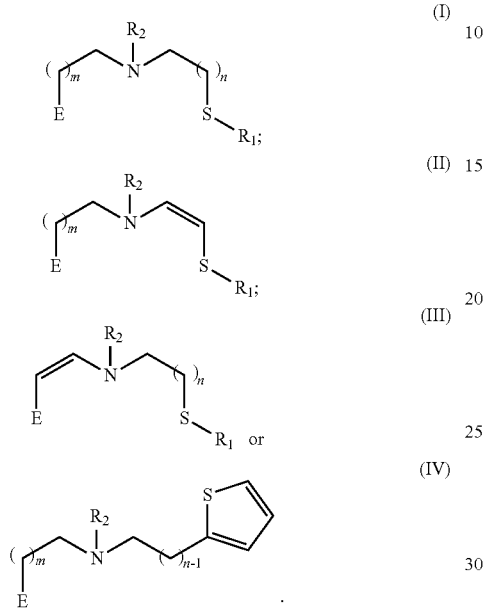

In Formulae I through IV, E may be:

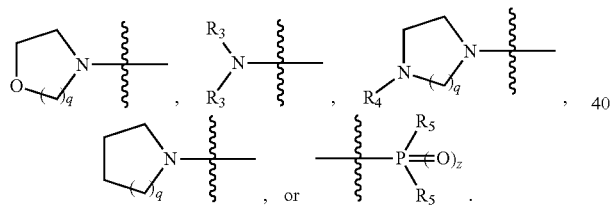

Additionally $R_1$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group.

$R_2$, $R_3$, and $R_4$ may independently at each occurrence be a hydrogen atom (H), a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group.

$R_5$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, a substituted or unsubstituted arylalkyl group, a substituted or unsubstituted alkoxy group, or a substituted or unsubstituted aryloxy group.

Also, in Formulae I through IV, m may be 1, 2, 3, 4, or 5; n may be 1, 2, 3, 4, or 5; q may be 1, 2, 3, or 4; and z may be 0 or 1. See also FIG. 1.

In some embodiments, any one or more (i.e., any subset) of the following compounds may be excluded from the scope of Formula(I):

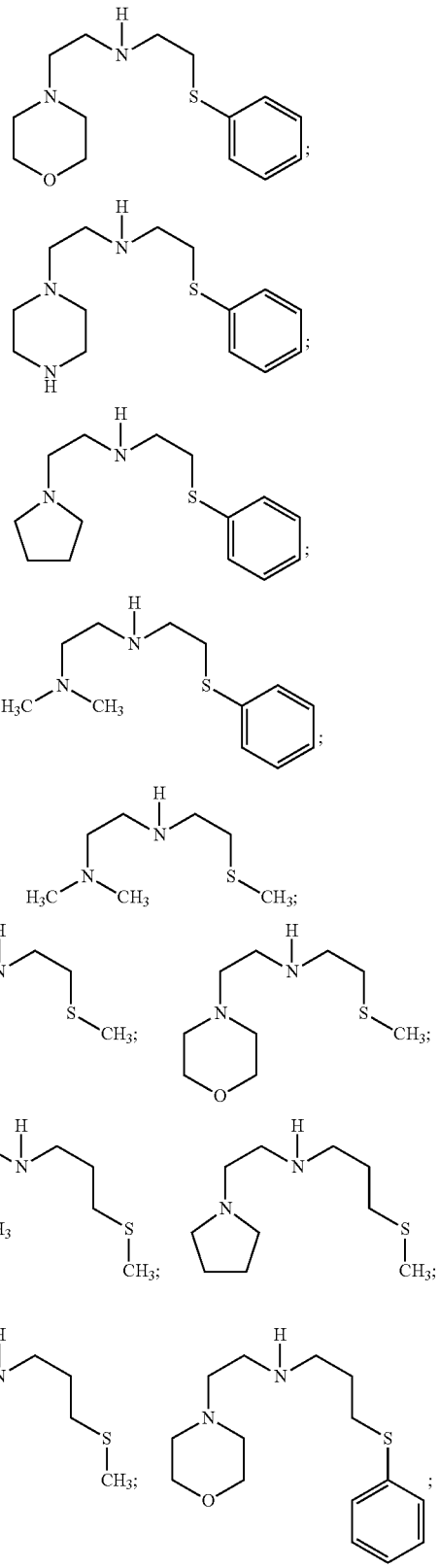

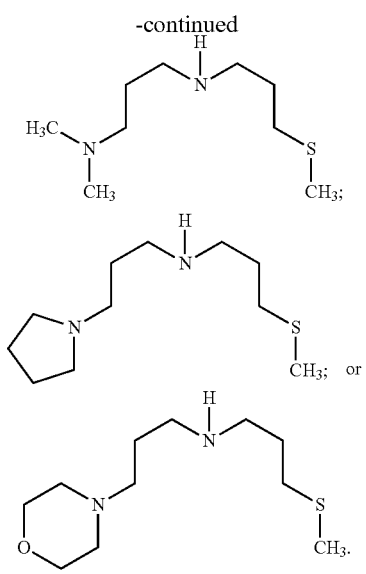

In some embodiments, the compounds represented by Formula (I) in which m=n=1, $R_1$ is phenyl, and E is morpholinyl, piperazinyl, pyrrolidinyl, or dimethylamino are excluded from the scope of embodiments of the present disclosure. In some embodiments, the compounds represented by Formula (I) in which m=n=1 and $R_1$ is phenyl are excluded from the scope of embodiments of the present disclosure.

In some embodiments of the compounds represented by Formula (I), when m=1 or 2 and n=1 or 2, then E is

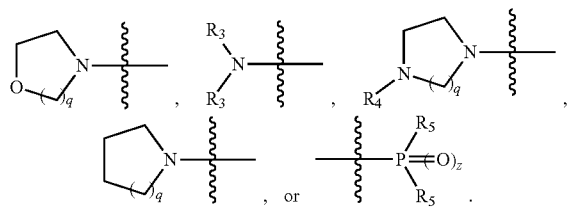

In some embodiments of the compounds represented by Formula (I), when m=1 or 2, n=1 or 2, $R_1$ is methyl or phenyl, and E is morpholinyl, piperazinyl, pyrrolidinyl, or dimethylamino, then $R_2$ is not H.

In general, it will be understood that any compound (ligand or coordination complex/catalyst) known at the time of the invention is to be considered a separate exclusion to the more general descriptions provided here. However, even when a ligand by itself is excluded, as in the example above, a coordination complex/catalyst including the ligand may still be included within the scope of embodiments of the disclosure. For example, whereas various described compounds, genera, or subgenera may be excluded as ligands or discrete compounds from the scope of embodiments of the present disclosure, catalysts (including those of ruthenium and iridium) that comprise these ligands may still be within the scope of embodiments of the present disclosure. That is, embodiments in which the descriptions of catalysts include the specific genera, subgenera, or complexes comprising these ligand compounds and embodiments in which the descriptions of catalysts exclude the specific genera, subgenera, or complexes comprising these ligand compounds are both considered to be within the scope of embodiments of the present disclosure.

In some embodiments, when the ligand includes a substituted group, the substituent on that group may be the same as described herein in connection with the Terms, or may be an amino group, an alkyl group, an alkoxy group, an alkoxycarbonyl group, an aryl group, an aryloxy group, a carboxylate group, a $C_{3-6}$ cycloalkyl group, a halogen, a hydroxy group, a hydroxycarbonyl group, a thioalkyl group, or a thiolaryl group. In some embodiments, the term "substituted or unsubstituted $C_{1-6}$ alkyl", at least with respect to $R_2$, includes alkyls substituted with the following example substituents:

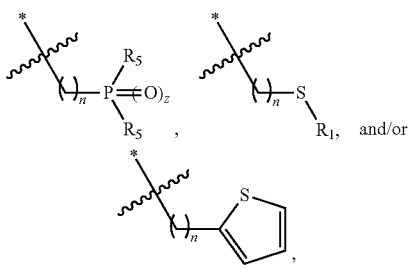

where each of the various permutations of n, z, and $R_5$ (as defined herein) are included as embodiments of the present disclosure. In some embodiments, n is 1, 2, or 3 (for example, 2), z is 0 or 1, and $R_1$ and $R_5$ are phenyl.

One or more embodiments of the present disclosure provide ligands having a structure represented by Formula (V), Formula (VI), Formula (VII), Formula (VIII), Formula (IX), or Formula (X):

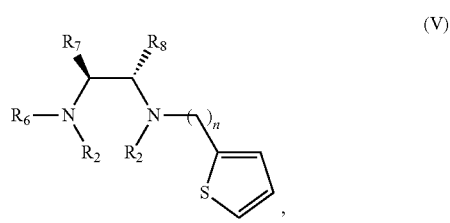

(V)

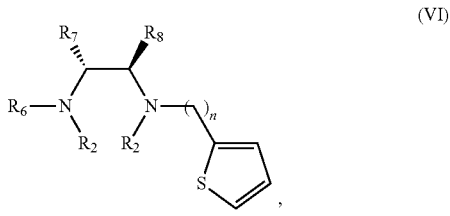

(VI)

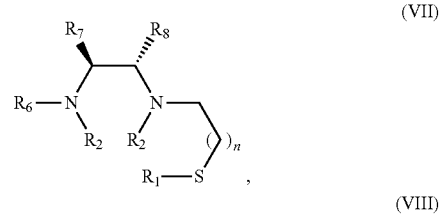

(VII)

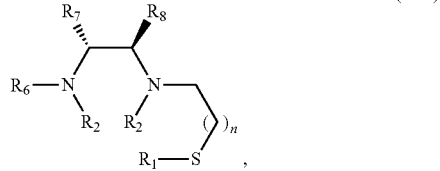

(VIII)

-continued

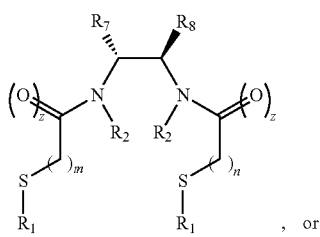

(IX)

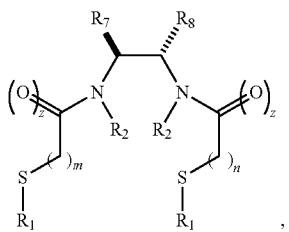

(X)

or an achiral isomer, enantiomer, diastereomer, isomeric mixture, and/or salt thereof.

In Formulae V through X, $R_1$, $R_2$, q, and z may each be the same as defined above in connection with the ligands represented by Formulae (I) to (IV). Additionally, m may be 1, 2, 3, 4, or 5; n may be 1, 2, 3, 4, or 5; and z may be 0 or 1.

Also, in Formulae V through X, $R_6$ may be H, $-(CH_2)_n-S-R_1$, $-(CH_2)_n-(2\text{-thiophenyl})$, or $-(CH_2)_n-P(O)_z(R_5)_2$.

$R_7$ and $R_8$ may each independently be H, a substituted or unsubstituted $C_{1-6}$ alkyl group, a substituted or unsubstituted aryl or heteroaryl group, or a substituted or unsubstituted arylalkyl group. In some embodiments, $R_7$ and $R_8$ are connected via a bridging group to form a 5-7 membered cyclic or heterocyclic ring including the carbons to which they are bound. In some embodiments, only one of $R_7$ and $R_8$ is H. Note that in the structures represented by Formulae (IX) and (X), when z is 0, the carbonyl group is a methylene group.

In some embodiments, when $R_7$ and $R_8$ are a heteroaryl group or are connected via a bridging group to form a 5-7 membered cyclic or heterocyclic ring, the heteroaryl group or heterocyclic ring may comprise 1 or 2 oxygen (O) or nitrogen (N) atoms. In some embodiments, $R_7$ and $R_8$ are connected via a bridging group to form an substituted or unsubstituted cyclopentyl, cyclohexyl, [1,4]dioxanyl, or [1,3]dioxolanyl ring including the carbons to which they are bound. For example, in some embodiments, the resulting structure may be:

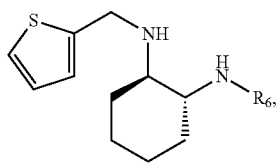

in which $R_6$ is $-H$, $-CH_2CH_2S(\text{phenyl})$, $-CH_2CH_2P(=O)(\text{phenyl})_2$, or $-CH_2CH_2P(\text{phenyl})_2$; or

Figure 2:
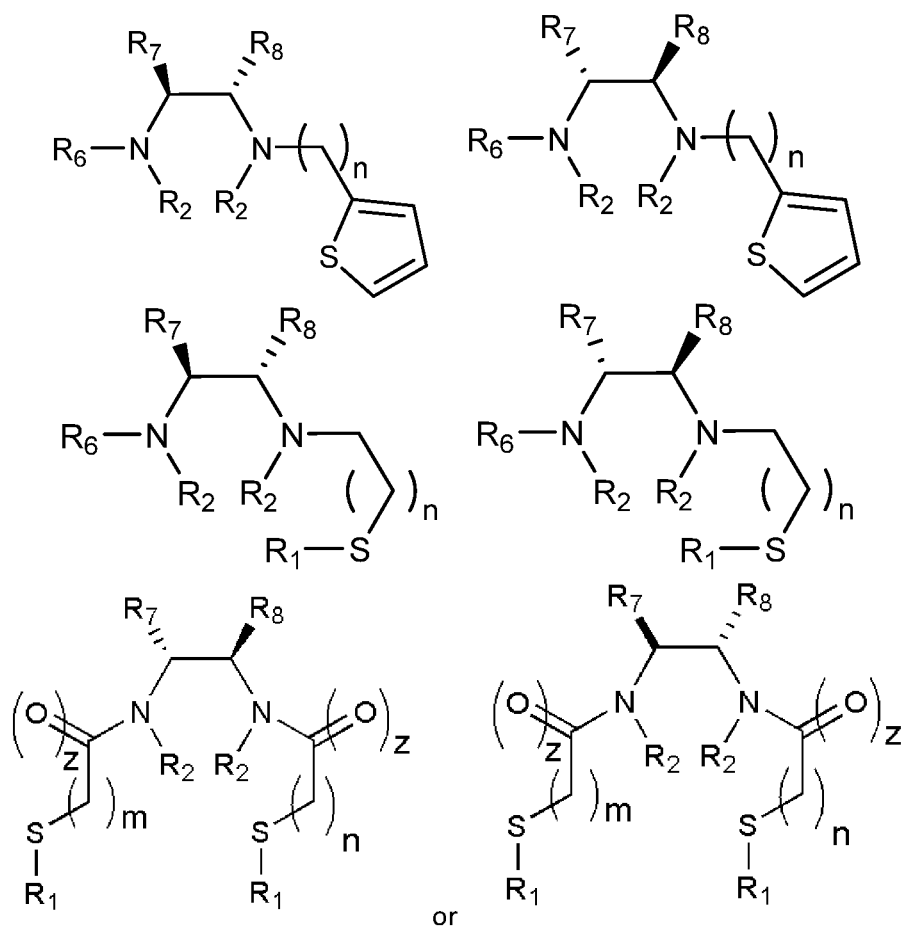

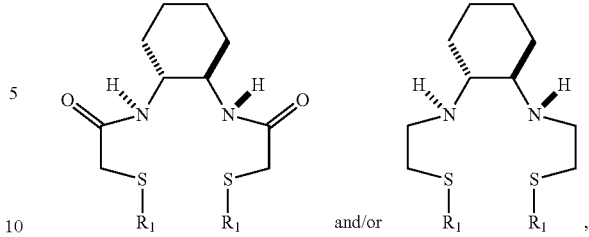

in which each $R_1$ may independently be a phenyl, benzyl, methyl, or tert-butyl. See also FIG. 2.

Some embodiments include ligands represented by Formulae (I) to (X), in which $R_1$ is independently methyl, phenyl, or benzyl.

Some embodiments include ligands represented by Formulae (I) to (X), in which each $R_2$ is independently H, benzyl, methyl, naphthyl, phenyl, propyl, ethylenediphenyl phosphine, or ethylenediphenyl phosphine oxide.

Some embodiments include ligands represented by Formulae (I) to (X), in which each $R_3$ is independently methyl, ethyl, propyl, isopropyl, n-butyl, isobutyl, tert-butyl, cyclopropylmethyl, cyclobutylmethyl, cyclopentylmethyl, cyclohexylmethyl, benzyl (-Bn), phenyl (-Ph), or any subset thereof (e.g., H, methyl, phenyl, or benzyl; or H or methyl).

The ligands represented by Formulae (I) to (X) may also independently comprise ligands in which $R_5$ is independently lower alkyl, cycloalkyl, or phenyl.

To this point, the substituent E has been described in terms of structures in which q is 1, 2, 3, or 4, or any combination thereof. However, in some embodiments, n is 1 or 2, such that E may be oxazolidinyl, morpholinyl, imidazolidinyl, N-methyl-imidazolidinyl, piperazinyl, N-methyl-piperazinyl, aziridinyl, azetidinyl, pyrrolidinyl, piperidinyl, dimethylamino, diethylamino, or ethylmethylamino. In some embodiments, E may be diarylphosphine or diarylphosphine oxide, dialkylphosphine or dialkylphosphine oxide, alkylarylphosphine or alkylarylphosphine oxide, diarylphosphite, diarylphosphate, dialkylphosphite, dialkylphosphate, alkylarylphosphite, or alkylarylphosphate.

Similarly, m and n have been described in terms of being 1, 2, 3, 4, or 5, or any subset thereof. In some embodiments of Formulae (I) to (X), m=n=1, provided that the ligand/compound is not excluded as described herein. In some embodiments, m is 1 and n is 1, 2, 3, 4, or 5, or a subset thereof. Some embodiments of Formulae (I) to (X) provide that n is 1 and m is 1, 2, 3, 4, or 5, or a subset thereof. Similarly, m and n may be independently 2, 3, 4, or 5, or any subset thereof, as applied to any of the compounds represented by Formulae (I) to (X).

It should also be appreciated that each of the embodiments described in terms of the ligands represented by Formulae (I) to (X) may be applied in combination with any other described embodiment(s).

In some non-limiting examples, the ligands have a structure:

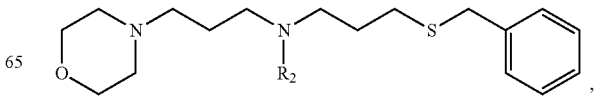

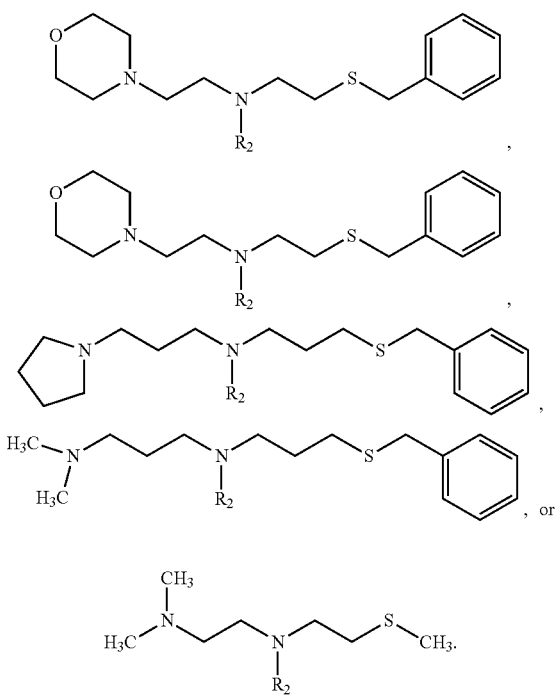
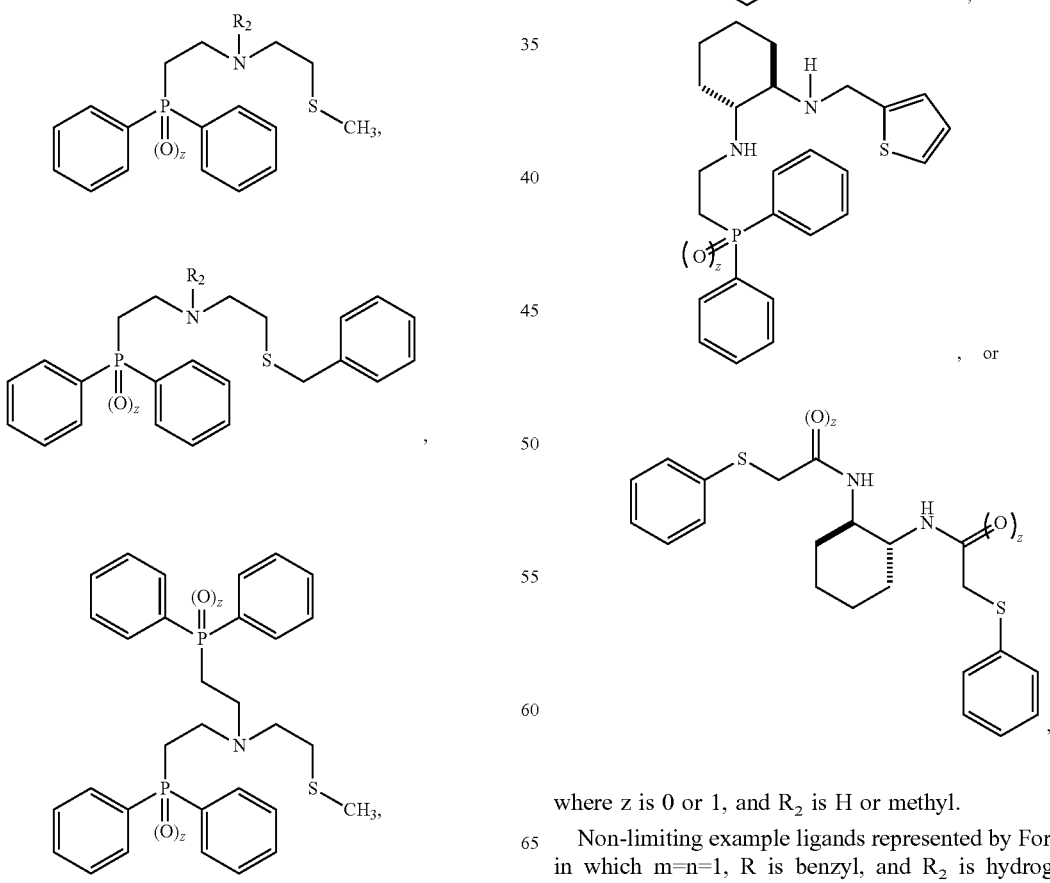
In some non-limiting examples, the ligands have a structure:
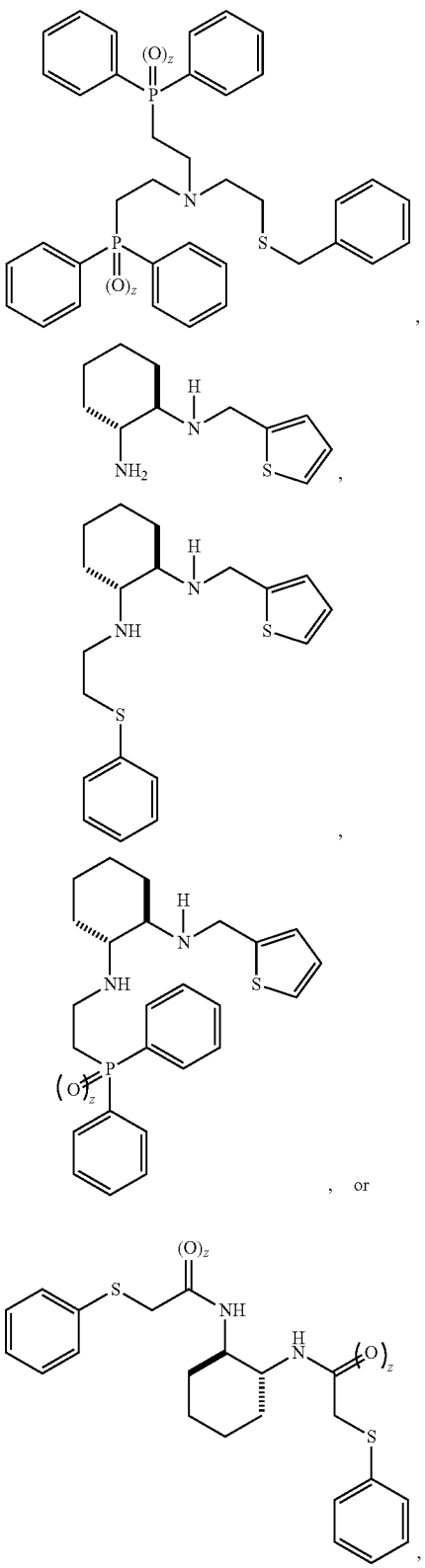
where z is 0 or 1, and $R_2$ is H or methyl.
Non-limiting example ligands represented by Formula (I) in which m=n=1, R is benzyl, and $R_2$ is hydrogen may include:

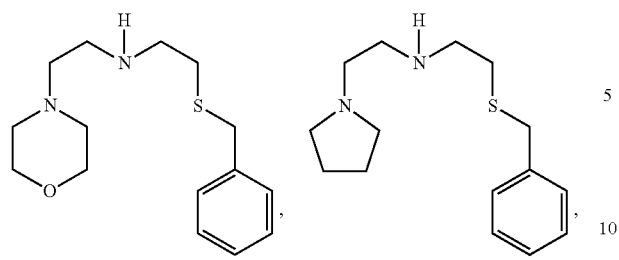
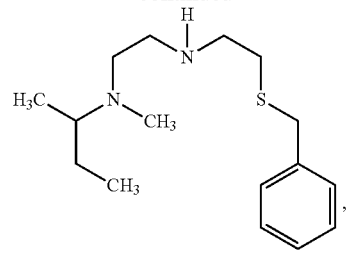
-continued
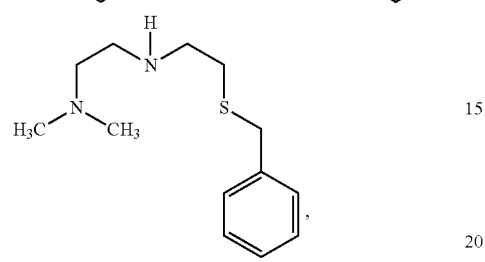
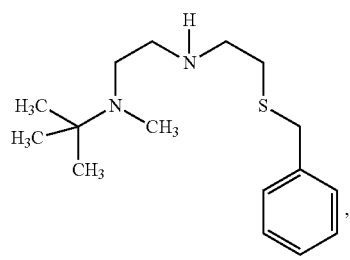 [SMILES: CN(CCNCCSCc1ccccc1)C(C)(C)C]
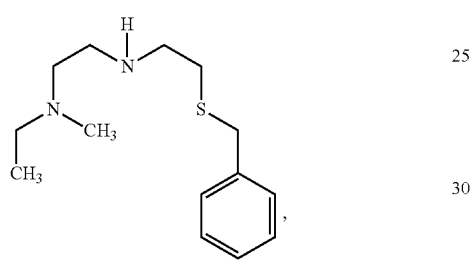
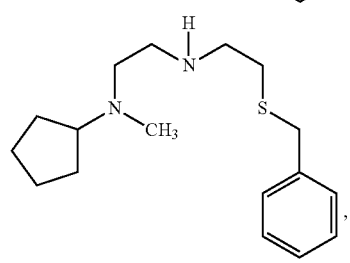
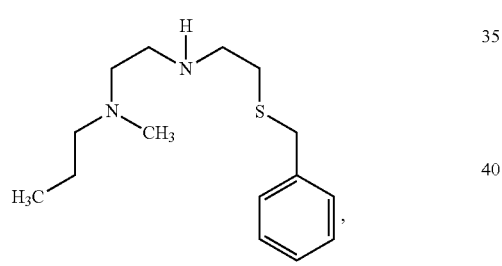
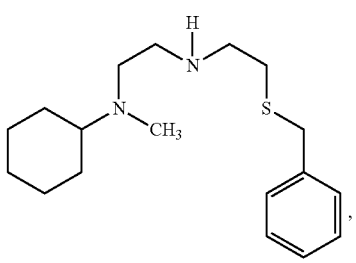
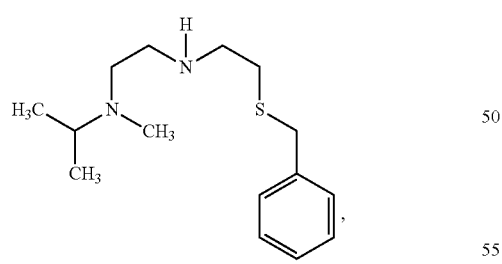
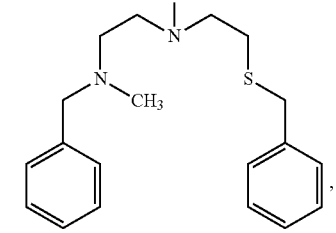
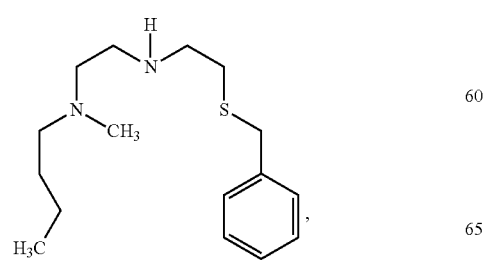
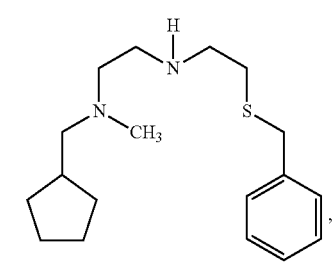

-continued
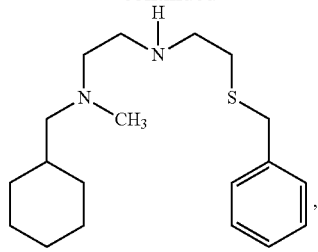,
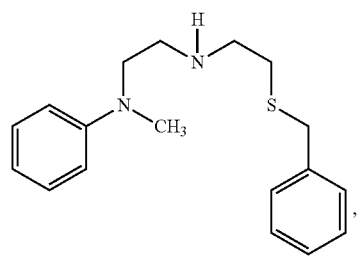,
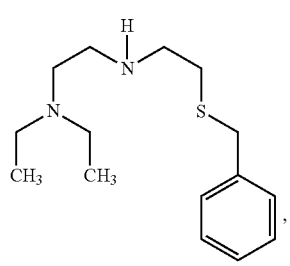,
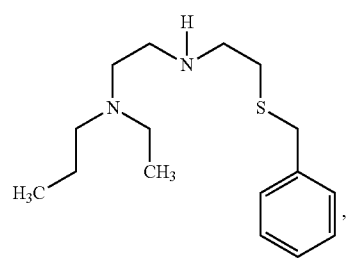,
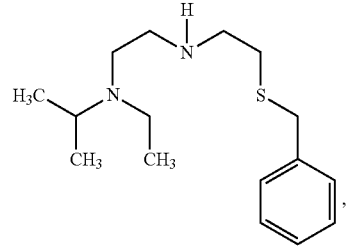,
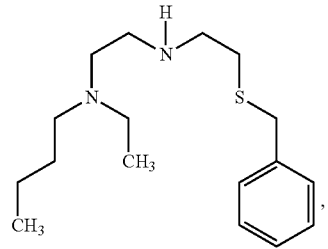,
-continued
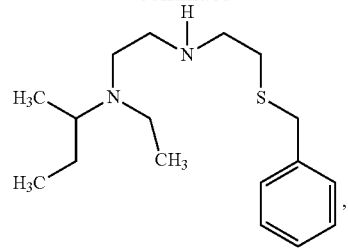,
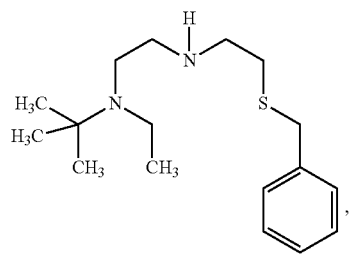,
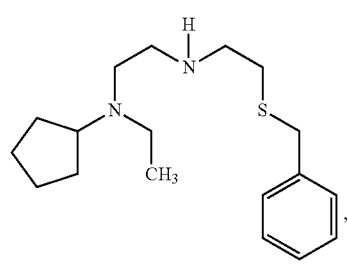,
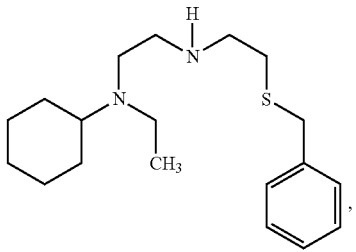,
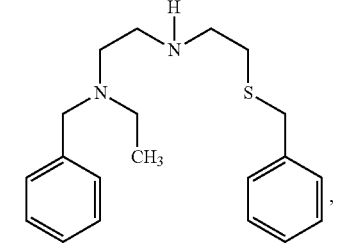,
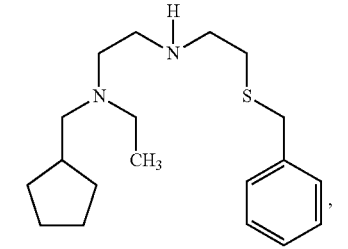, -continued
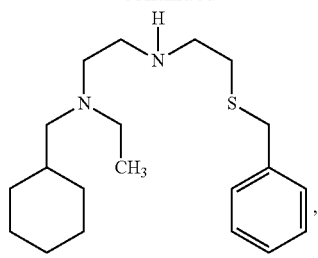
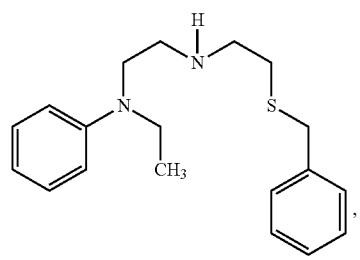
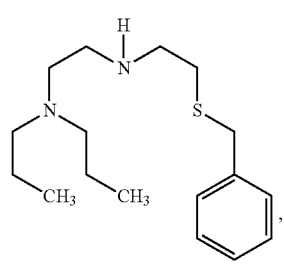
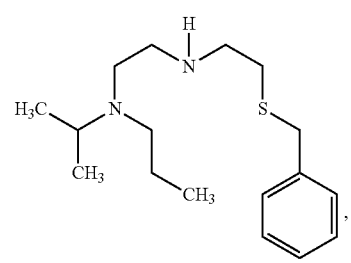
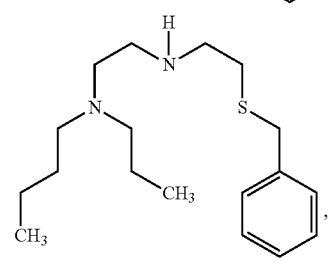
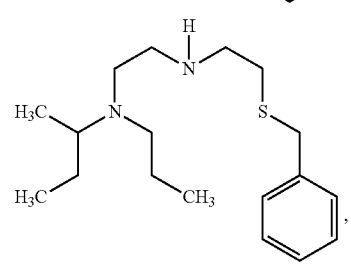
-continued
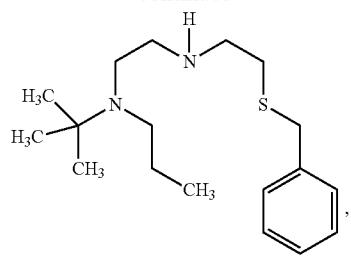
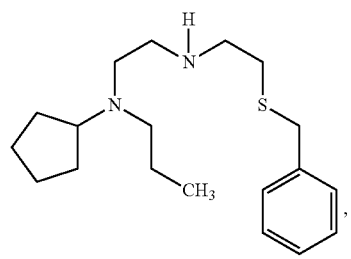
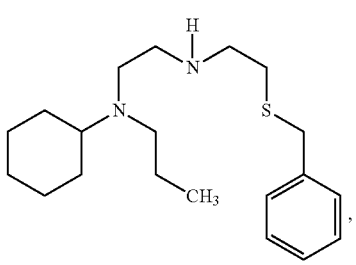
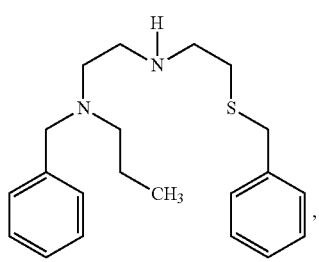
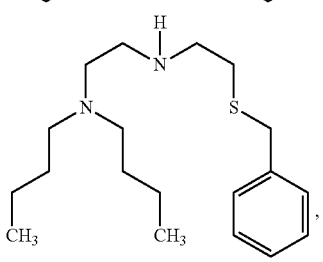
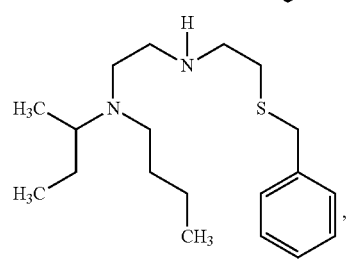

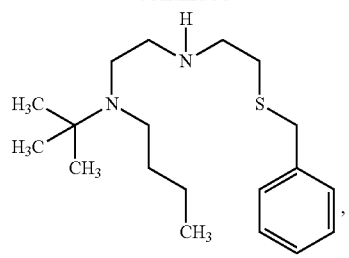
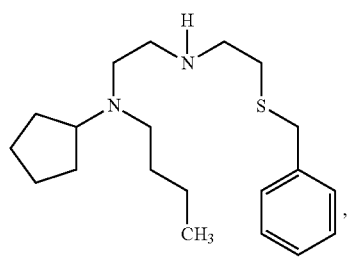
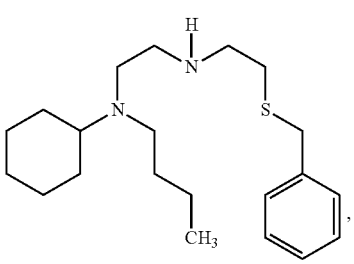
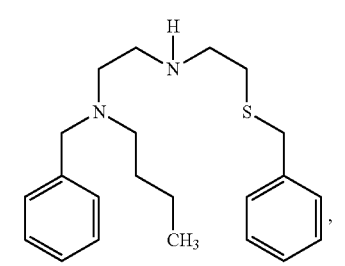
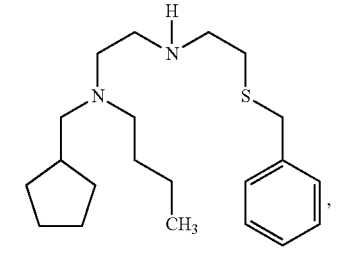
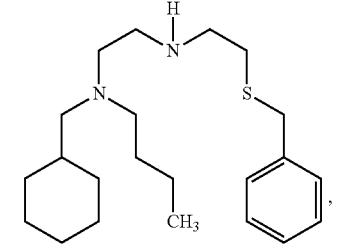
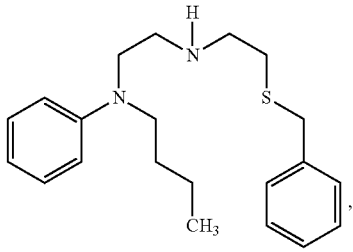
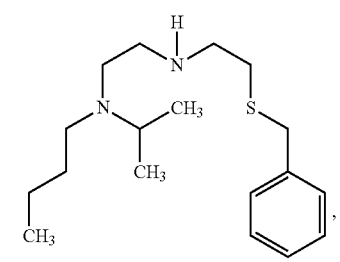
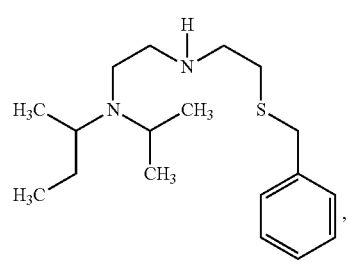
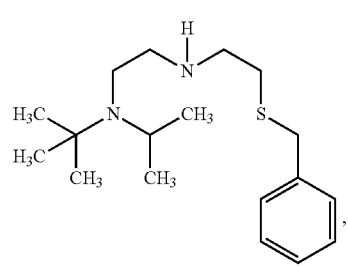
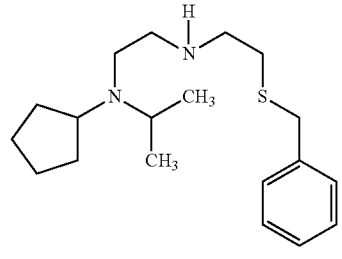
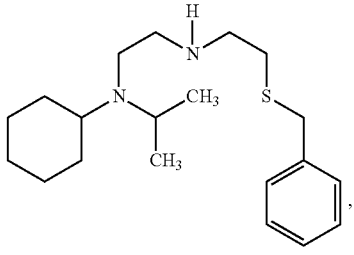

29
-continued
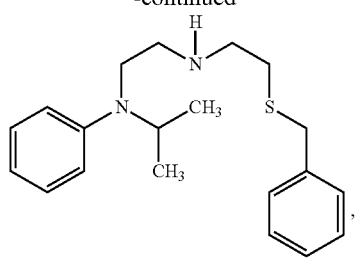
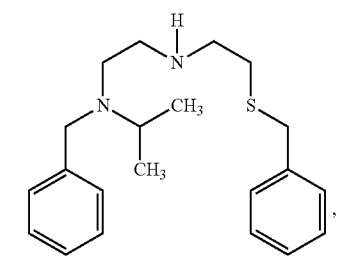
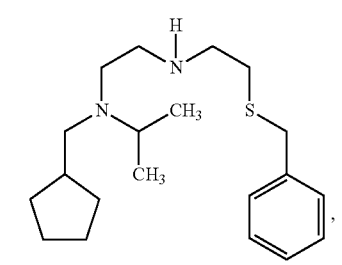
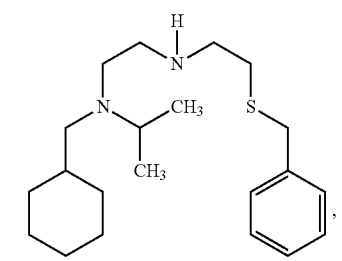
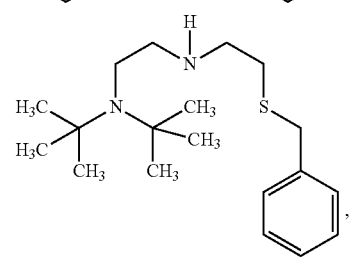
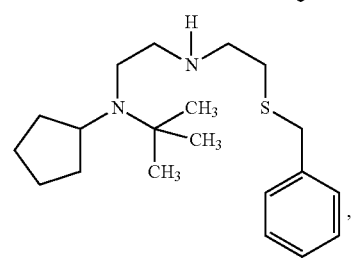
30
-continued
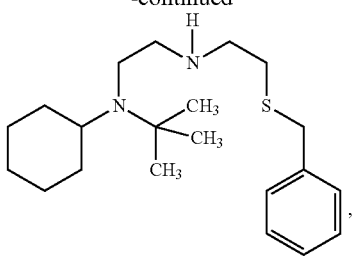
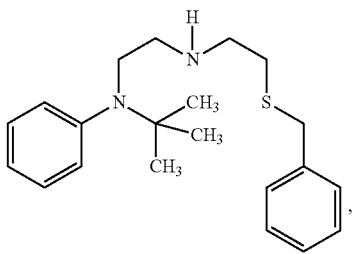
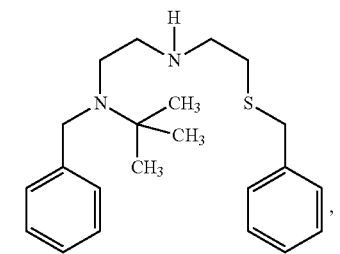
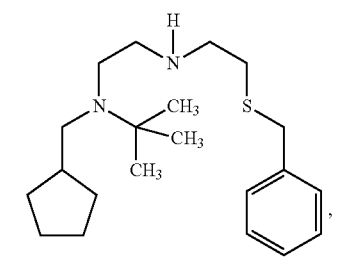
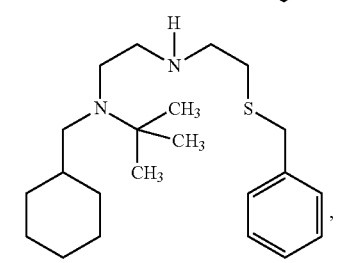
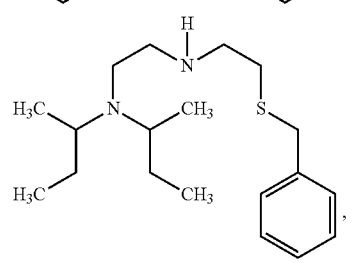

31
-continued
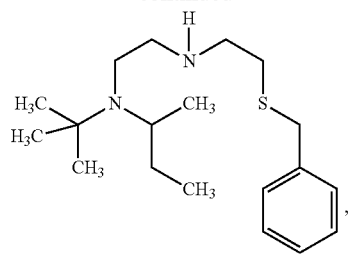
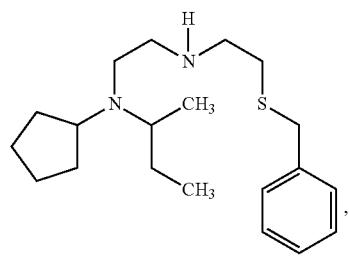
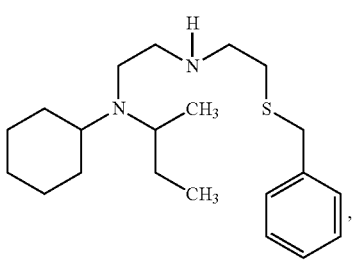
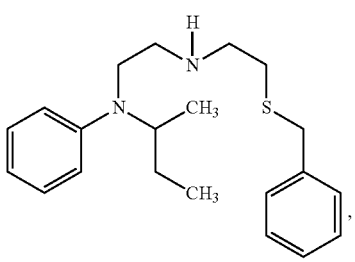
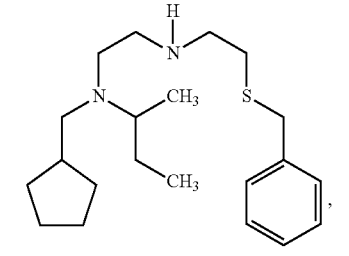
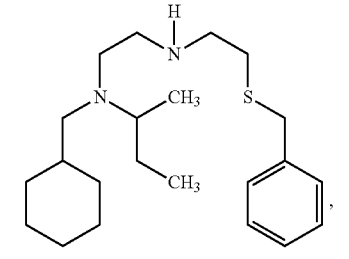
32
-continued
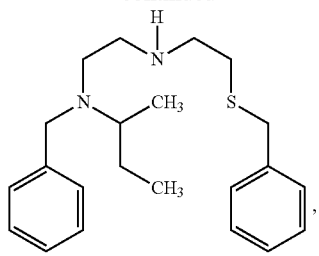
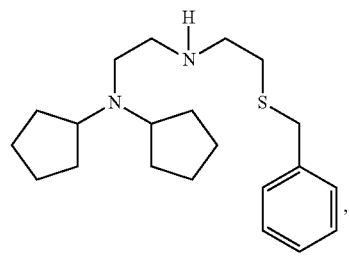
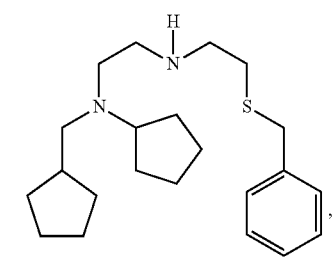
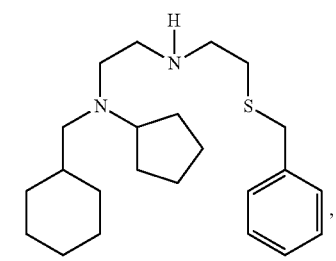
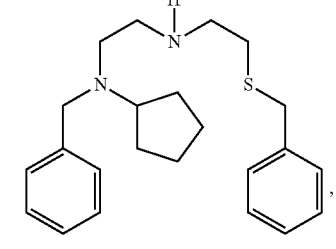
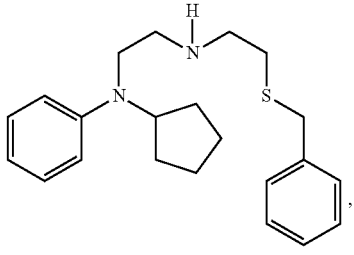

33
-continued
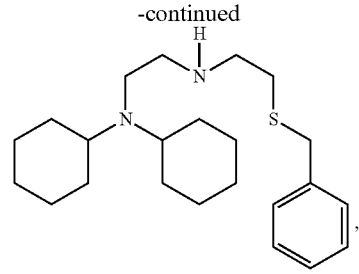
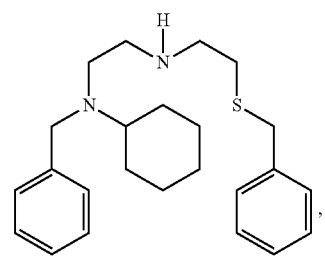
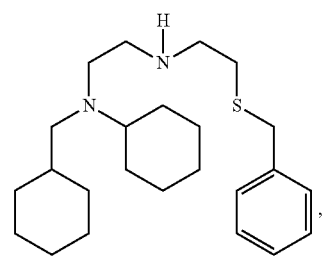
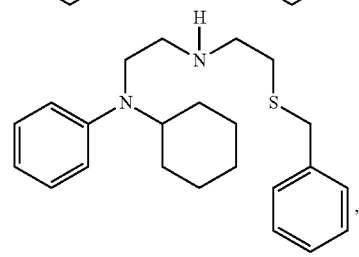
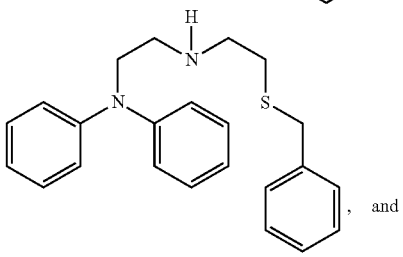, and
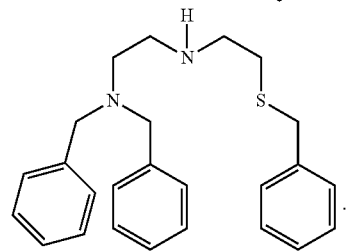.
Non-limiting example ligands represented by Formula (I) in which m=n=1, R₁ is methyl, and R₂ is hydrogen may include:
34
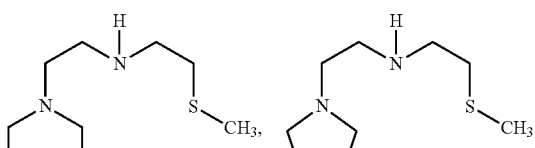
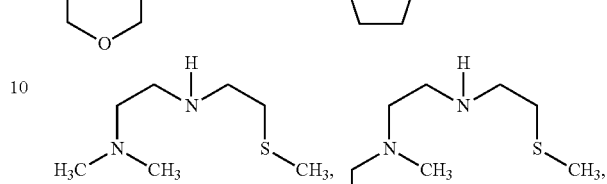
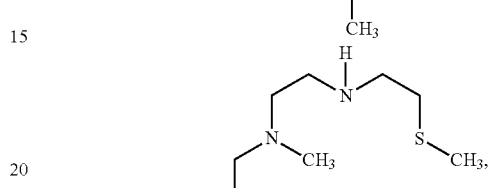
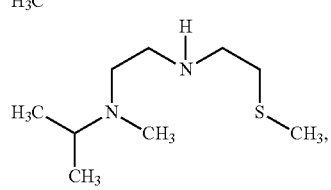
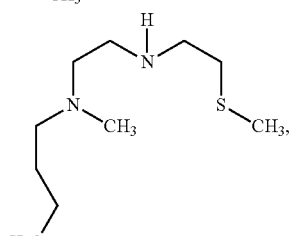
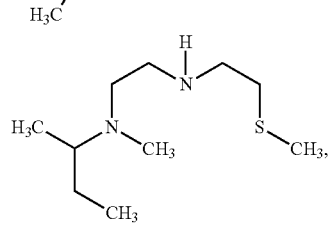
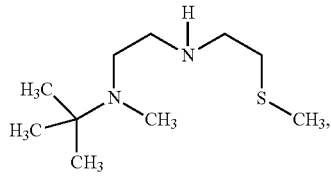
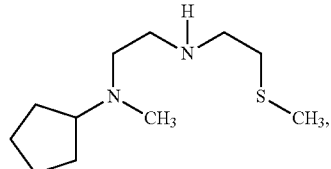
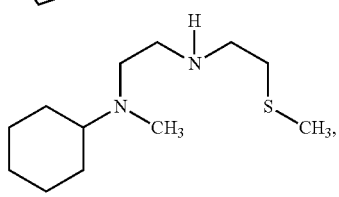

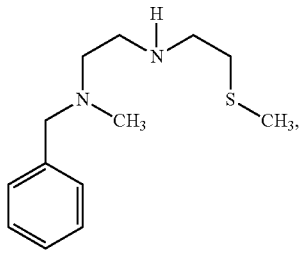
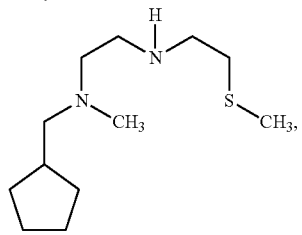
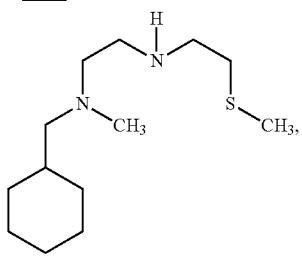
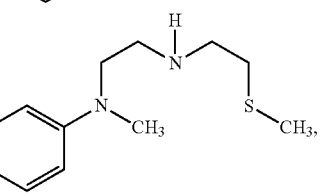
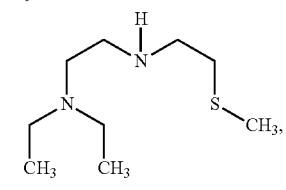
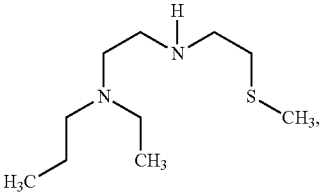
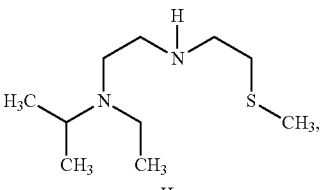
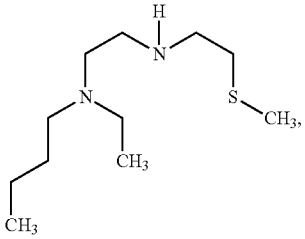
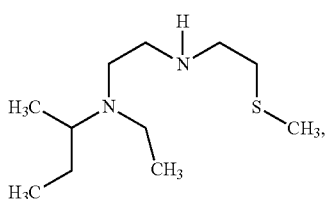
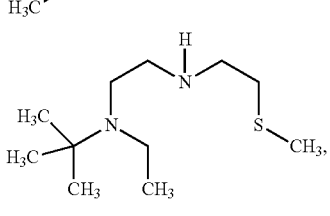
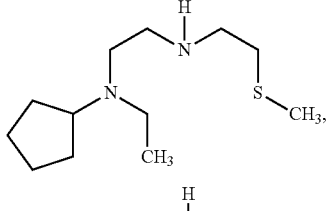
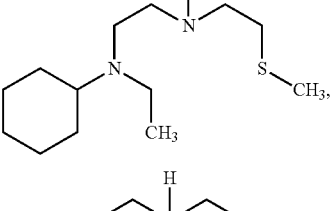
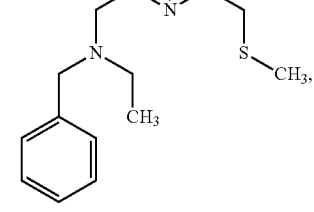
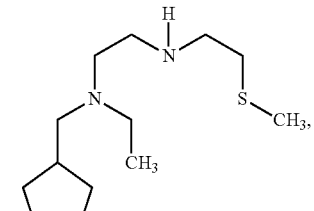
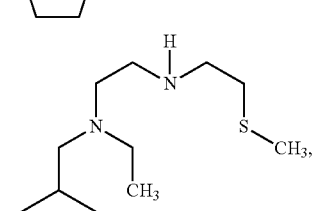
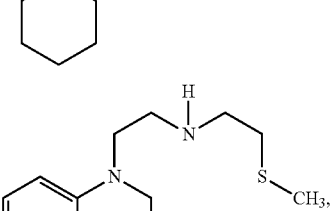

-continued
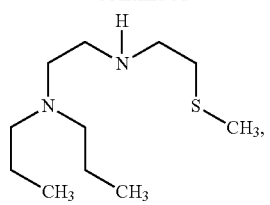
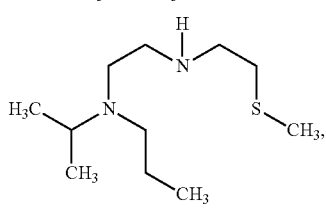
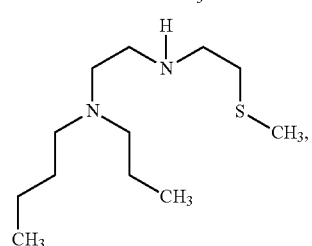
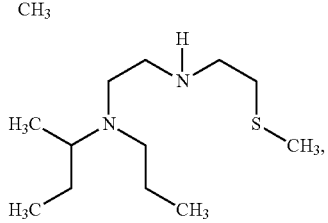
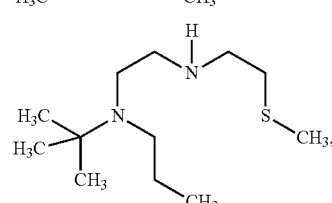
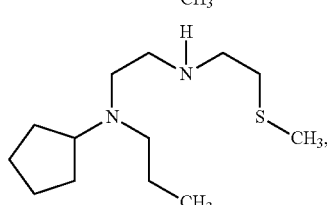
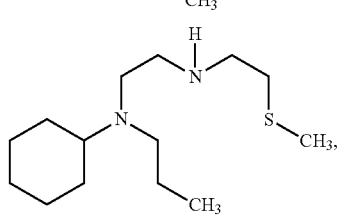
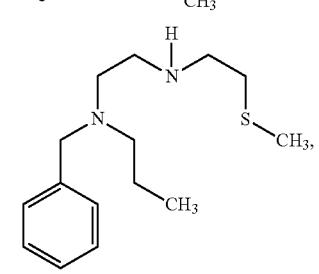
-continued
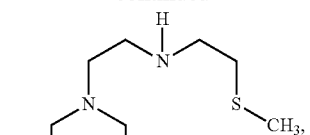
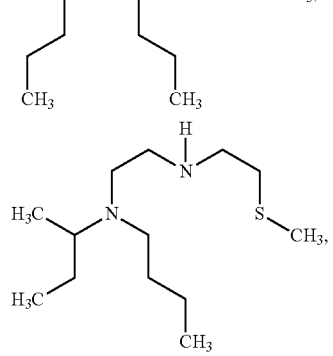
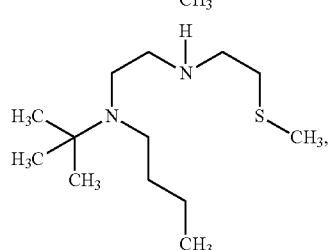
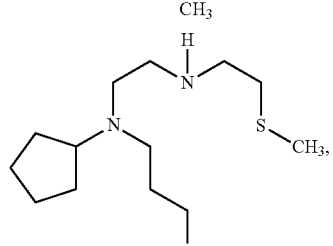
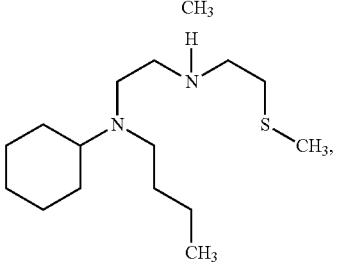
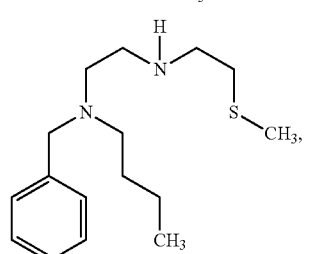
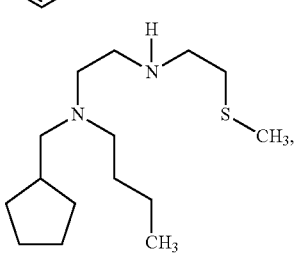

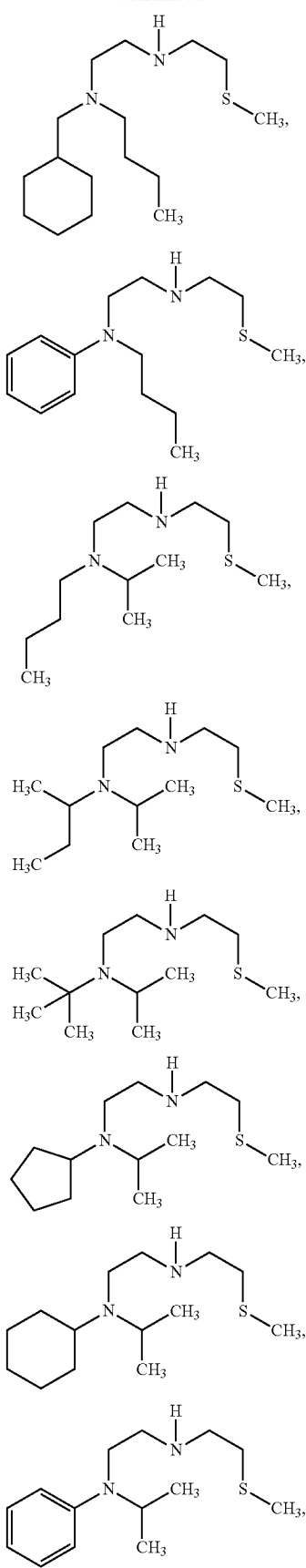
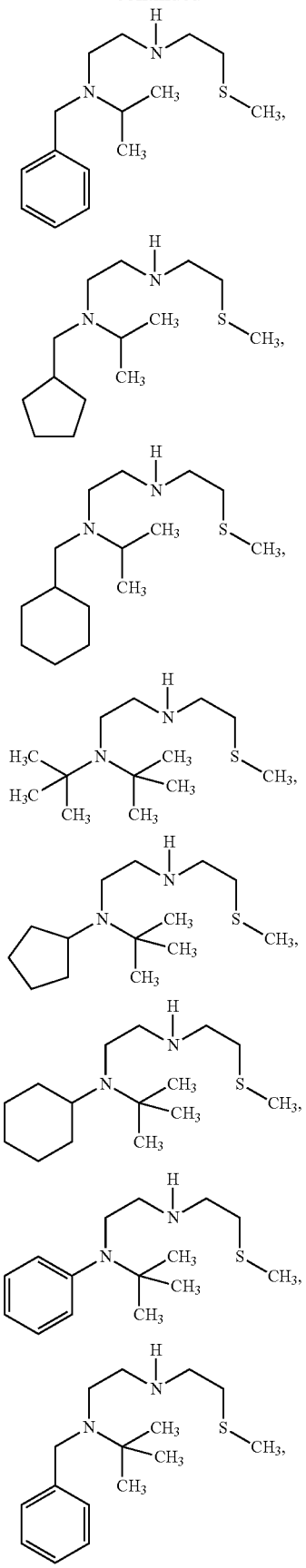

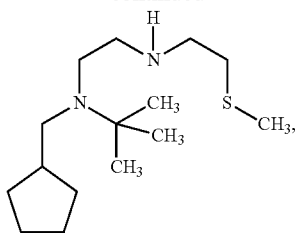
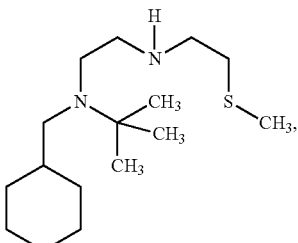
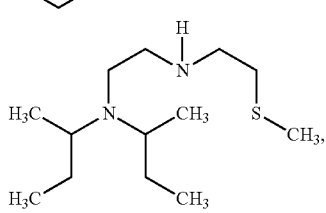
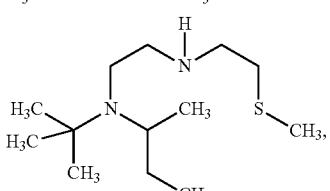
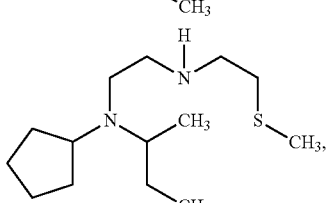
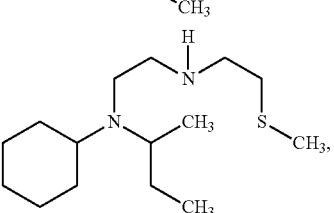
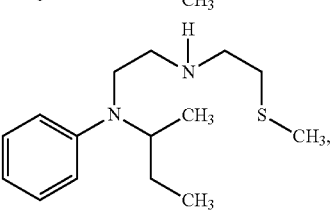
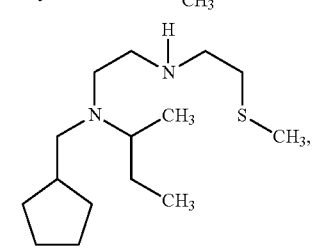
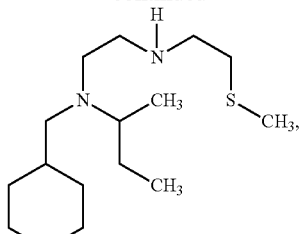
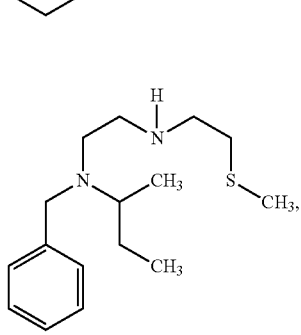
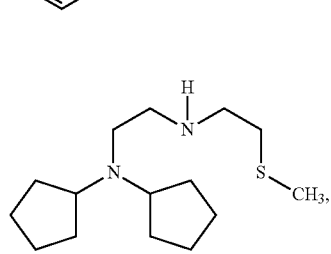
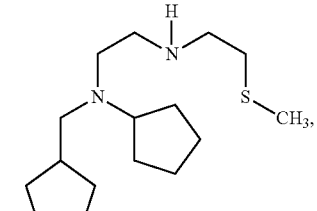
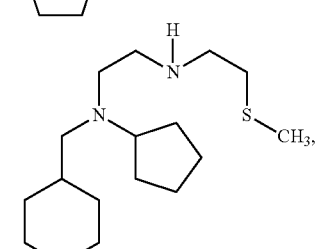
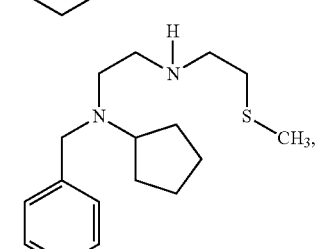
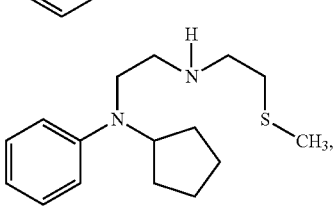

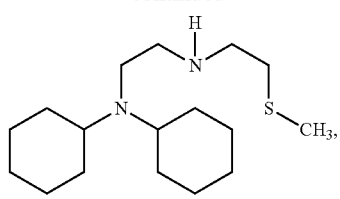
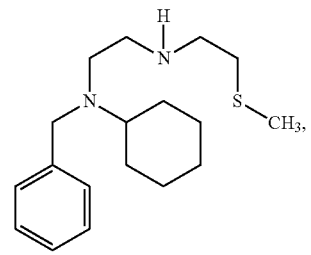
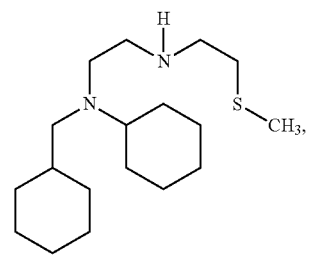
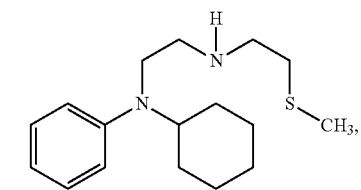
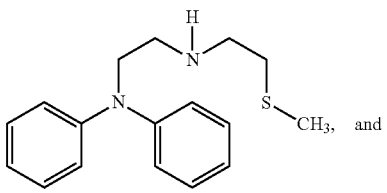
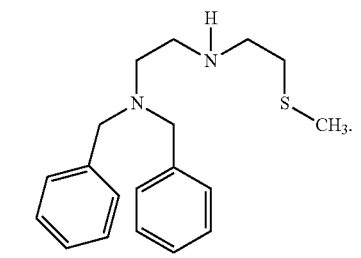
Non-limiting example ligands represented by Formula (I) in which m=n=1 and $R_2$ is alkyl or aryl may include:
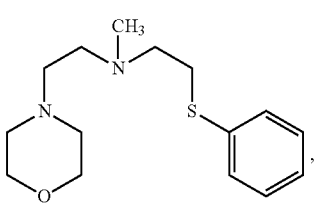
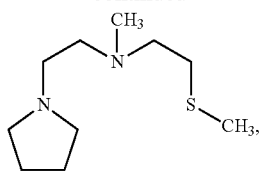
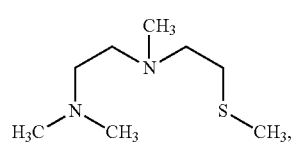
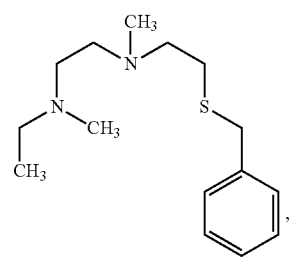
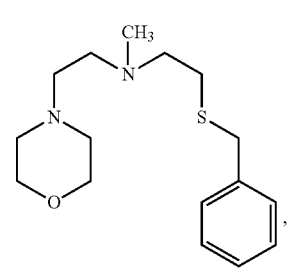
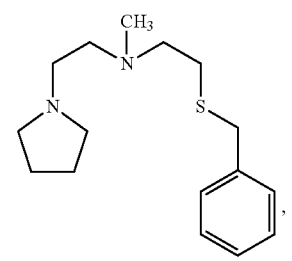
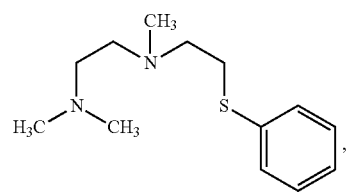
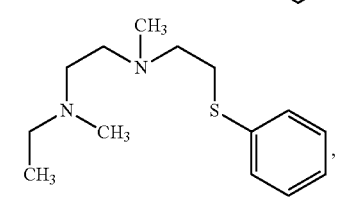

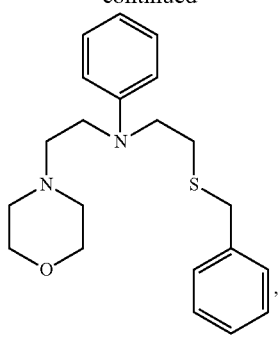
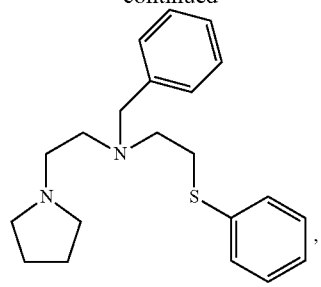
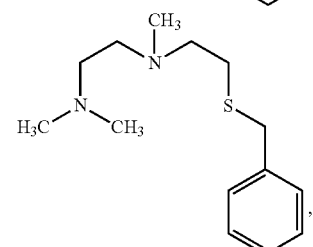
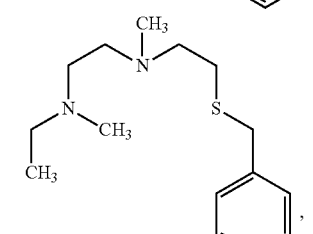
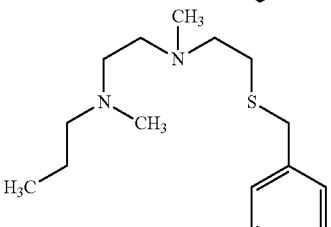
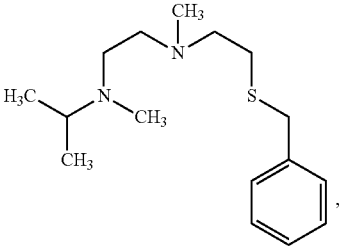
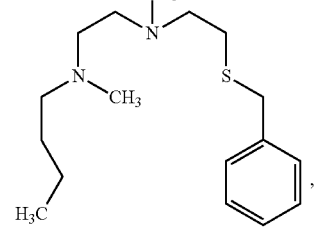
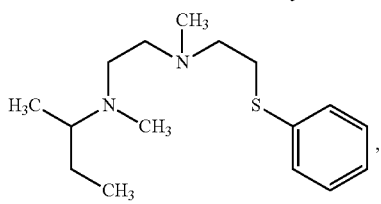

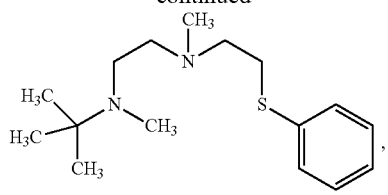
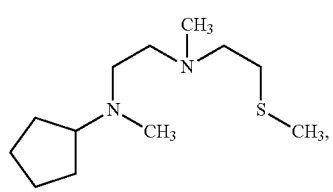
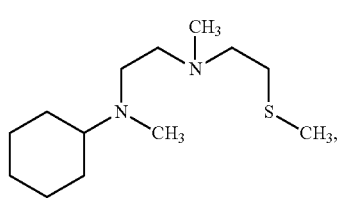
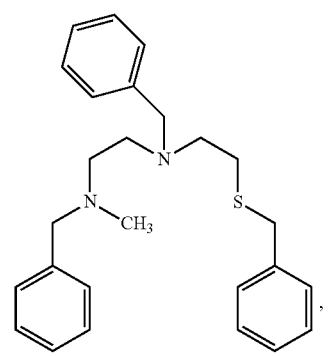
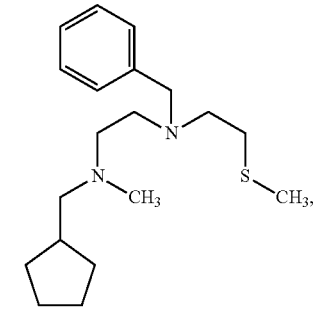
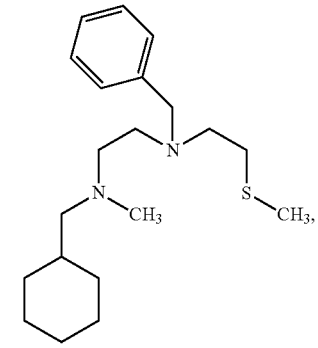
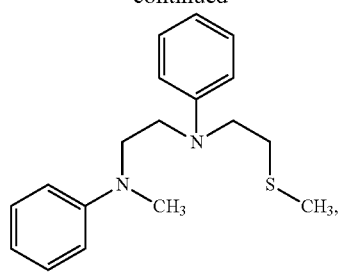
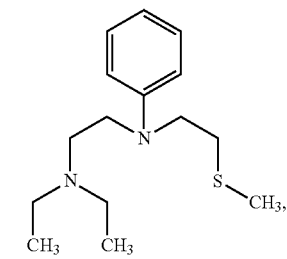
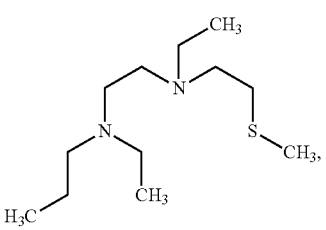
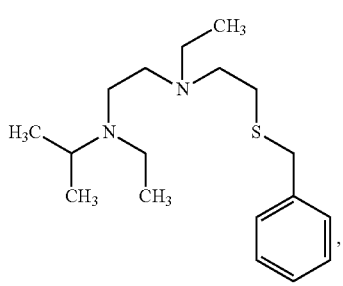
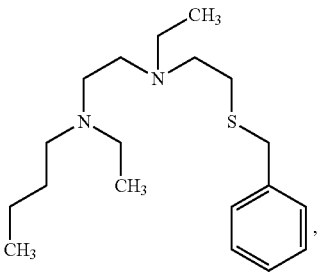
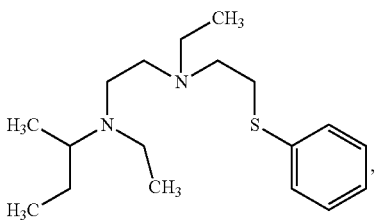

-continued
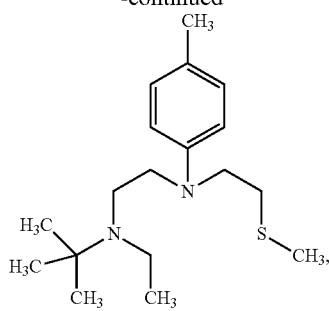
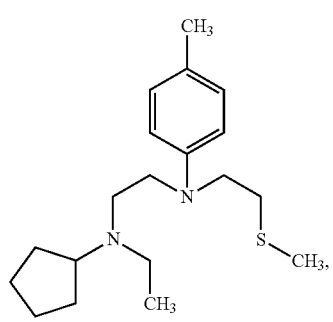
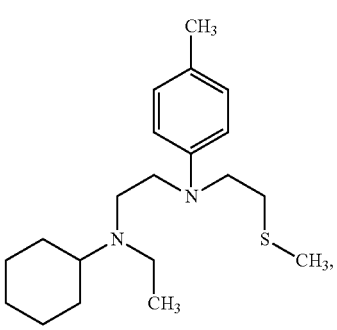
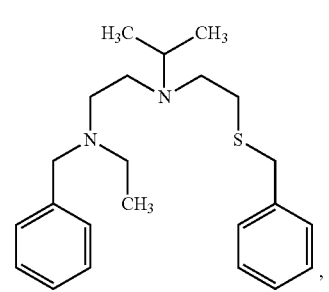
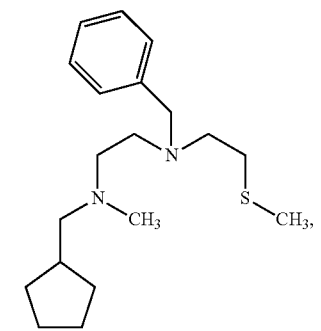
-continued
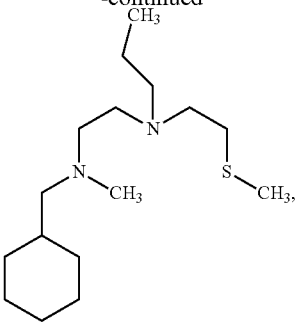
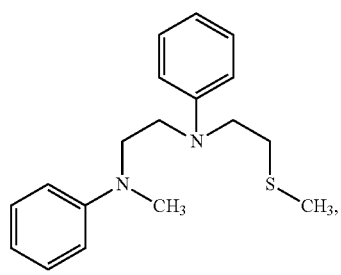
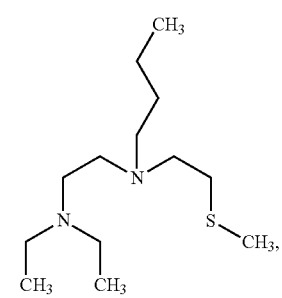
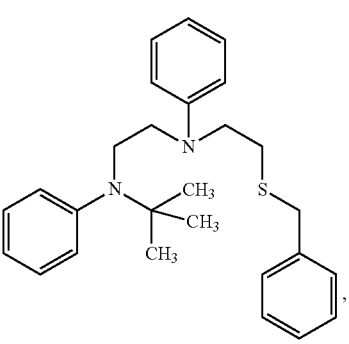
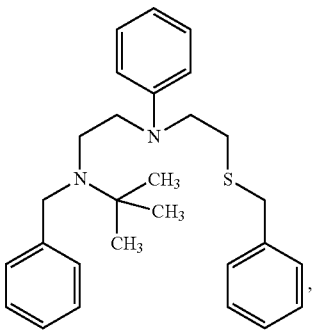

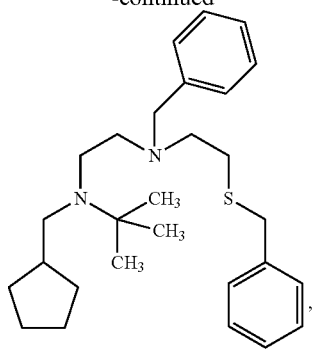,
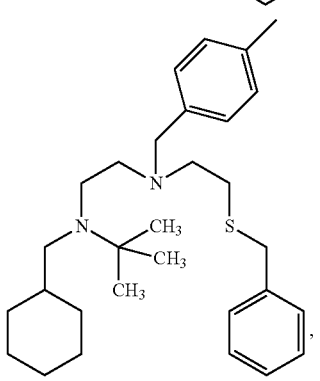,
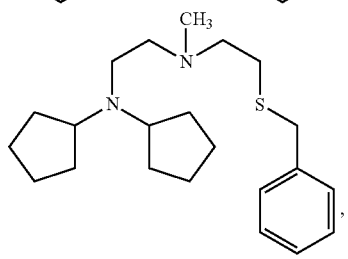,
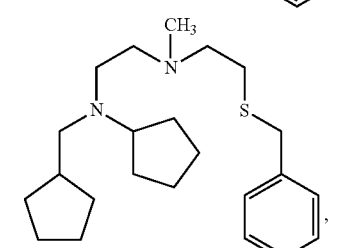,
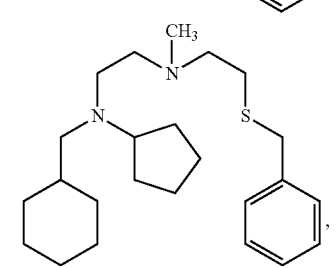,
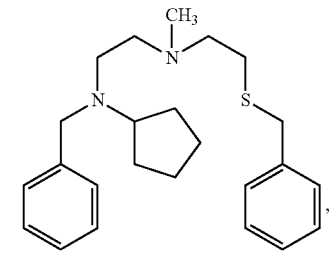,
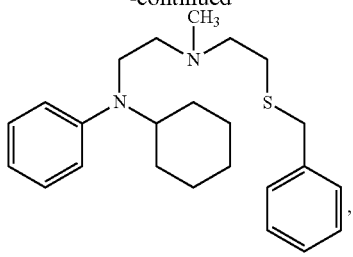,
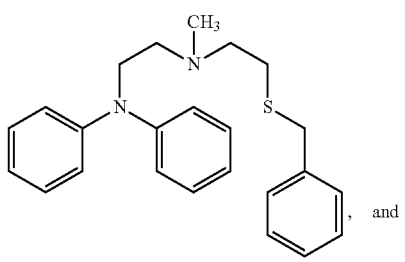, and
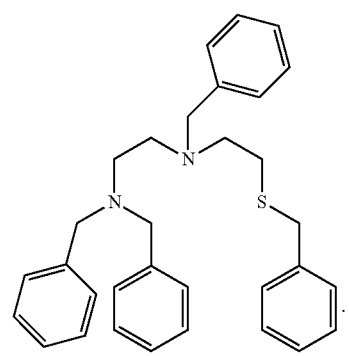.
Non-limiting example ligands represented by Formula (I) in which m=1, n=2, $R_1$ is phenyl, and $R_2$ is hydrogen may include:
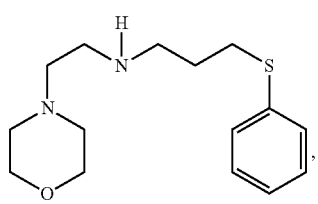,
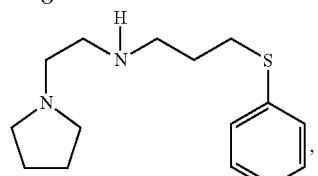,
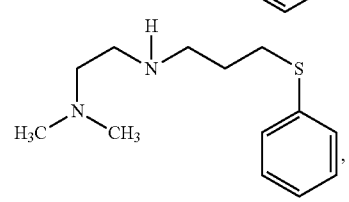, -continued
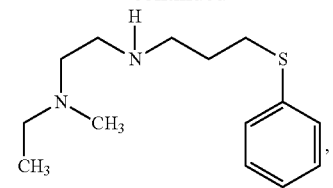
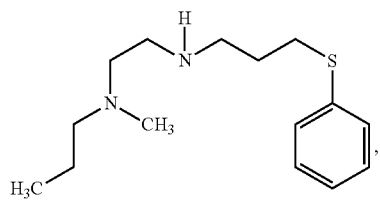
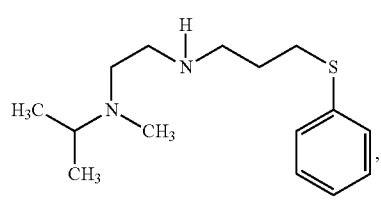
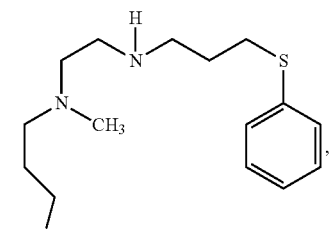
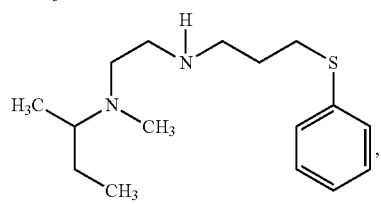
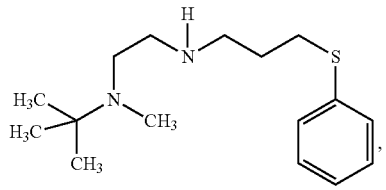
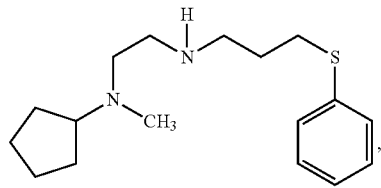
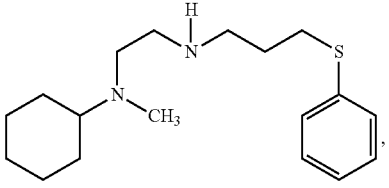
-continued
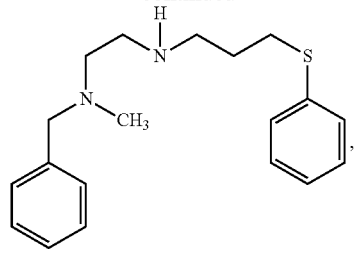
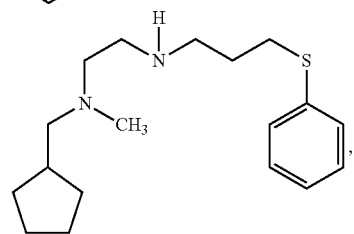
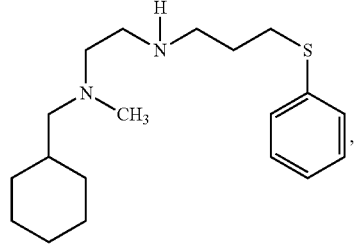
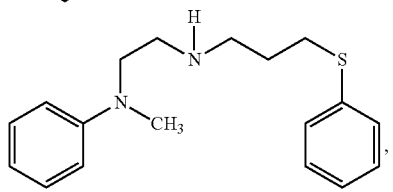
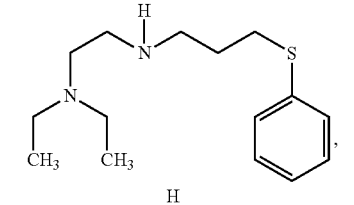
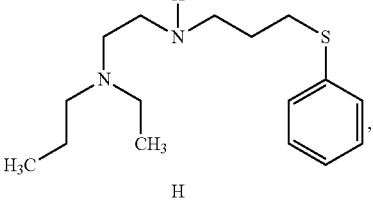
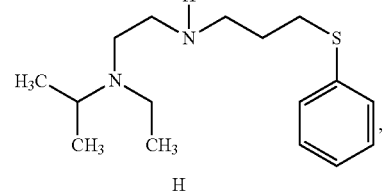
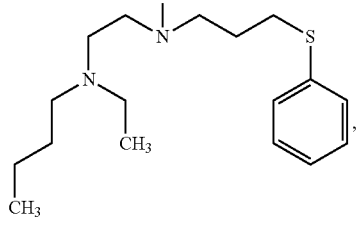

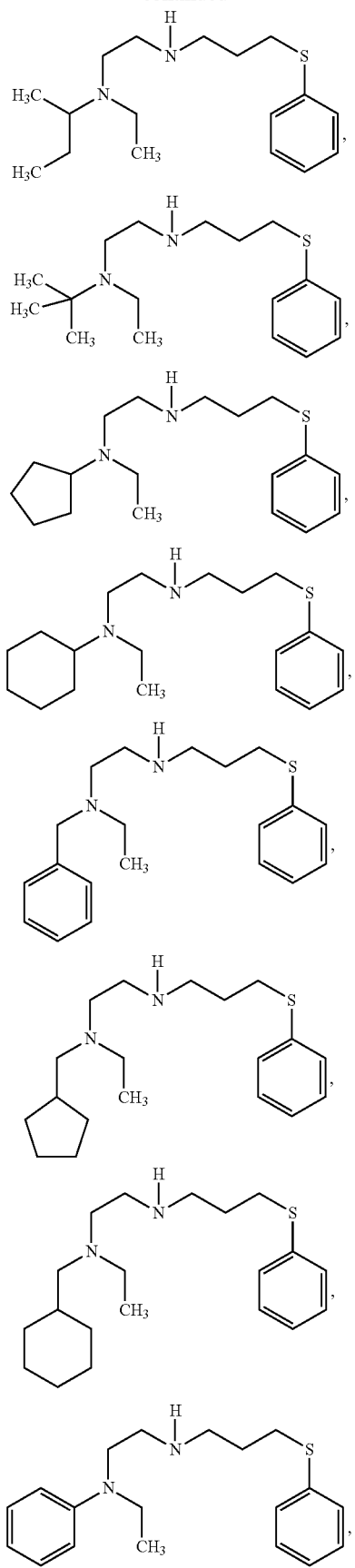
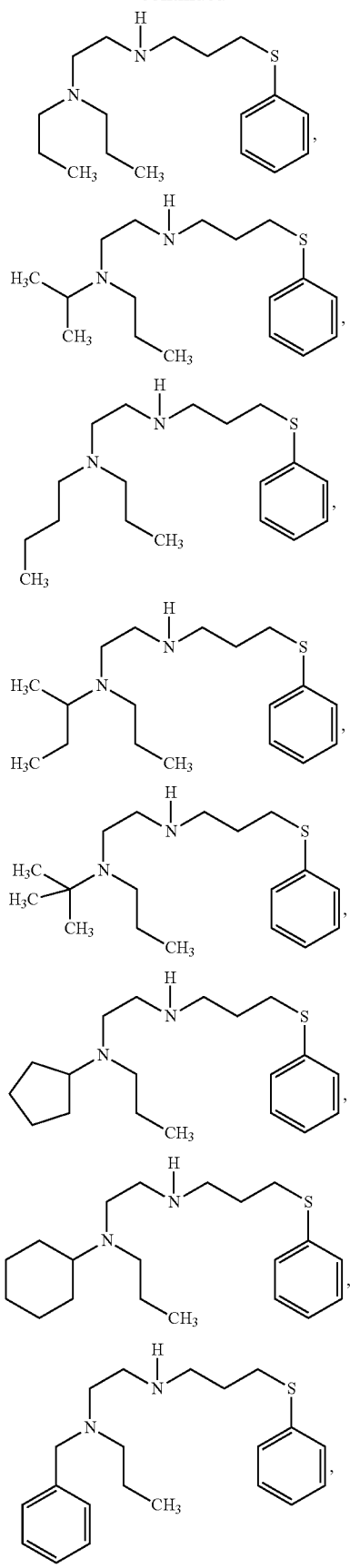

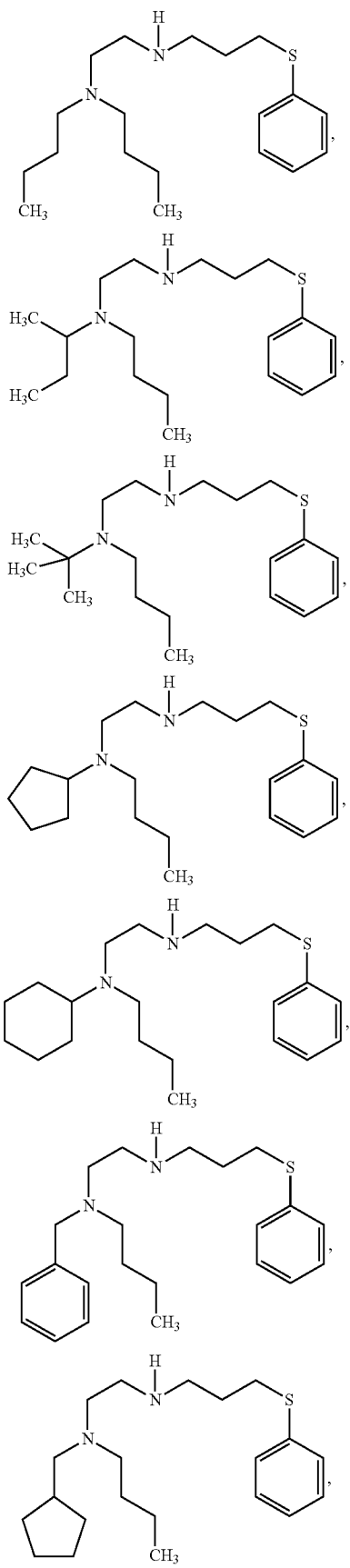
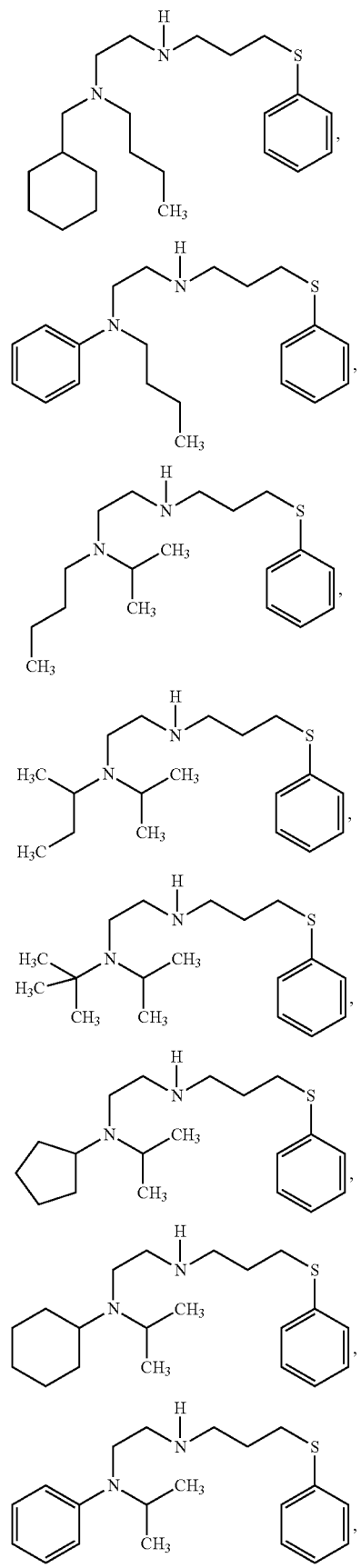

-continued
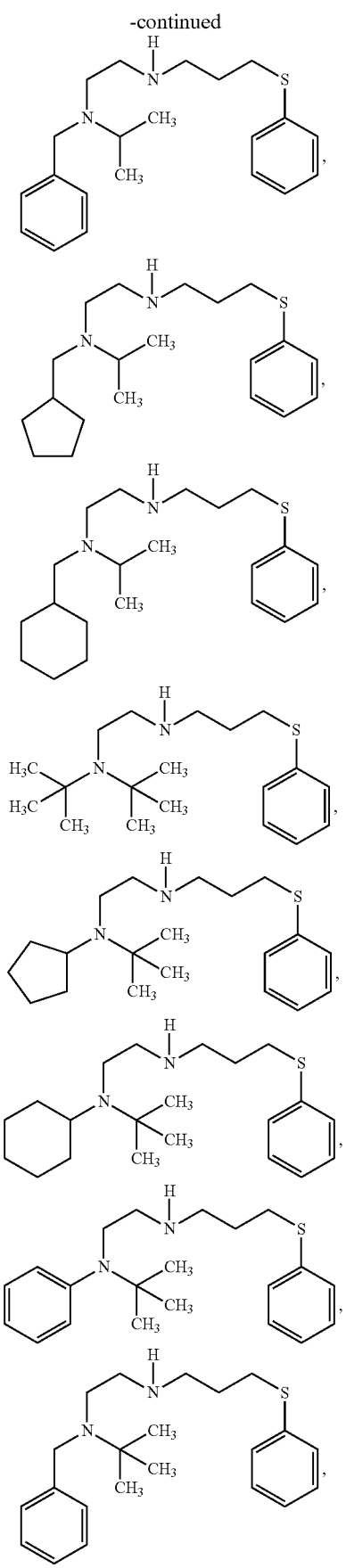
-continued
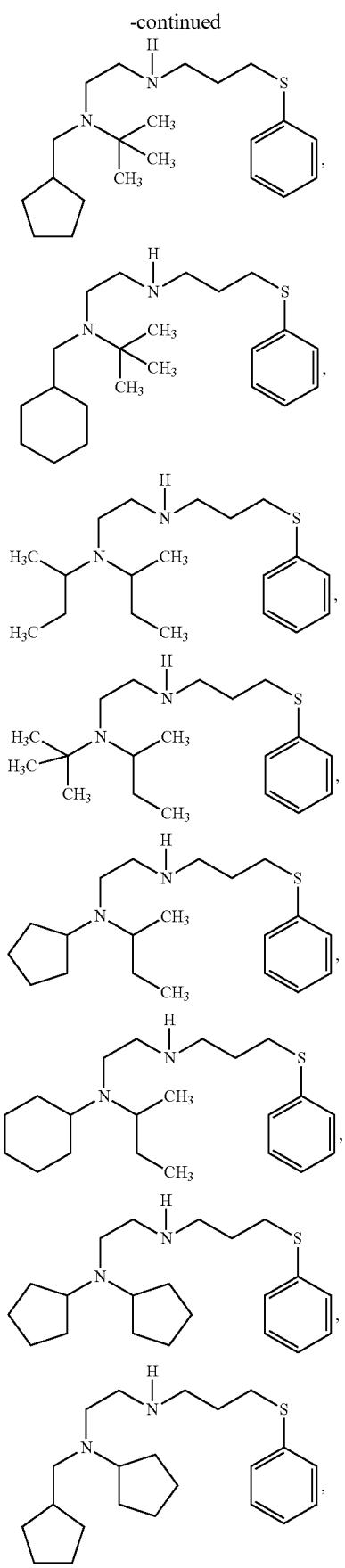

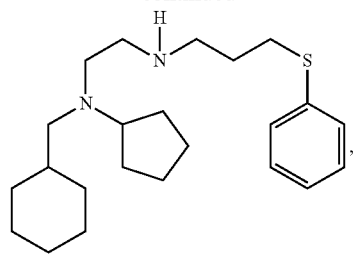
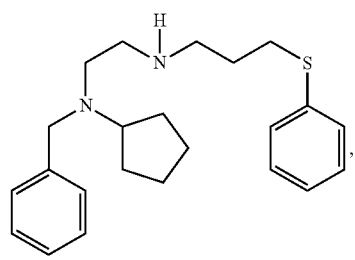
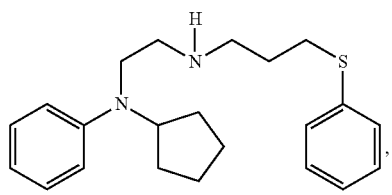
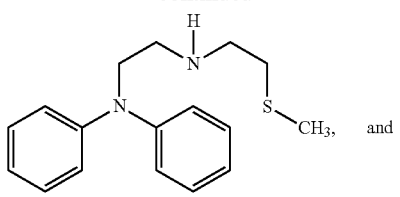
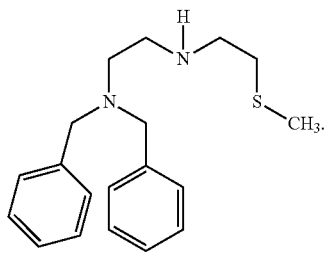 [SMILES: CSCCNCCN(Cc1ccccc1)Cc1ccccc1]
Non-limiting example ligands represented by Formula (I) in which m=1, n=2, $R_1$ is phenyl, and $R_2$ is alkyl or aryl may include:
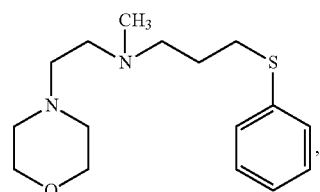
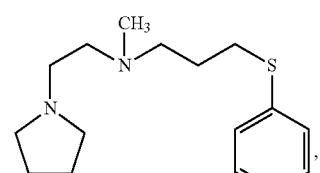
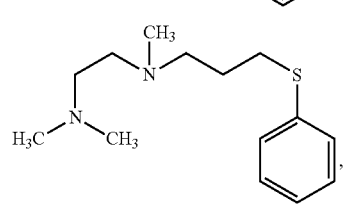
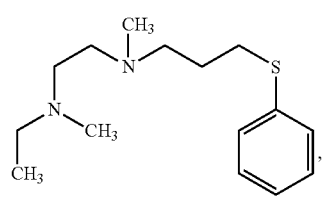
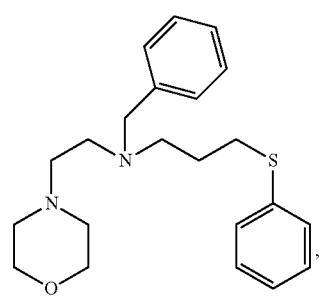

-continued
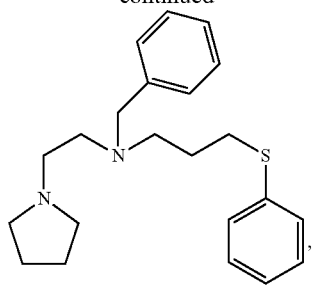
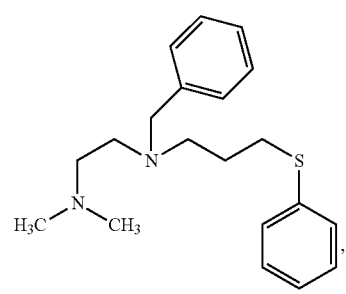
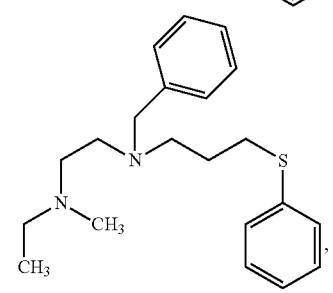
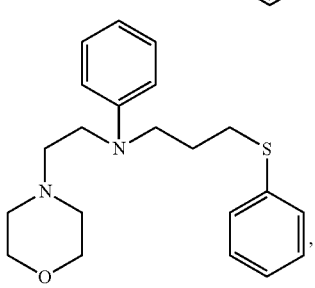
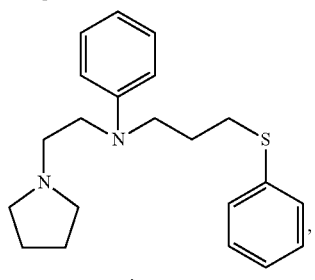
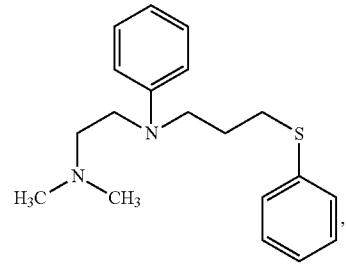
-continued
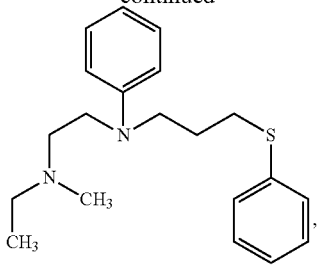
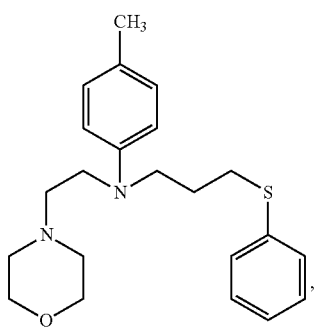
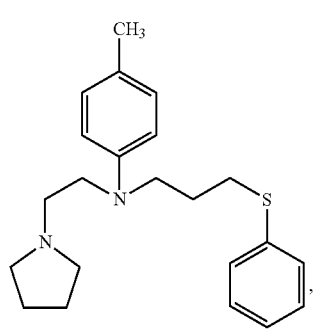
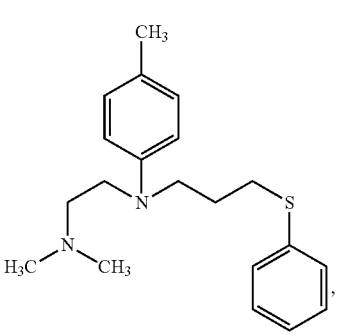
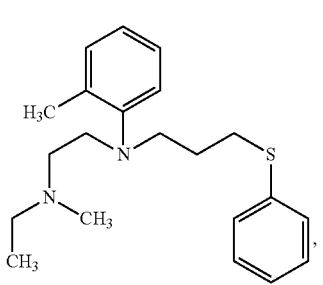

-continued
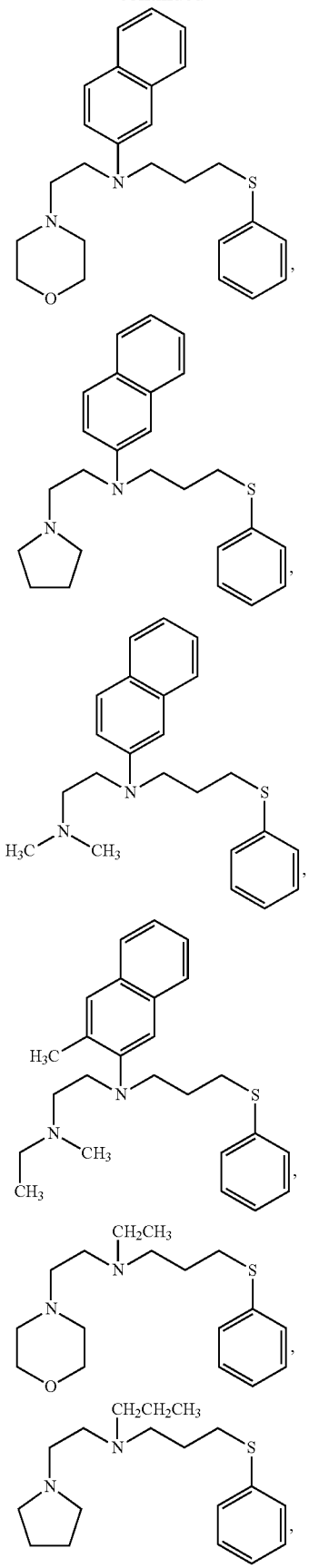
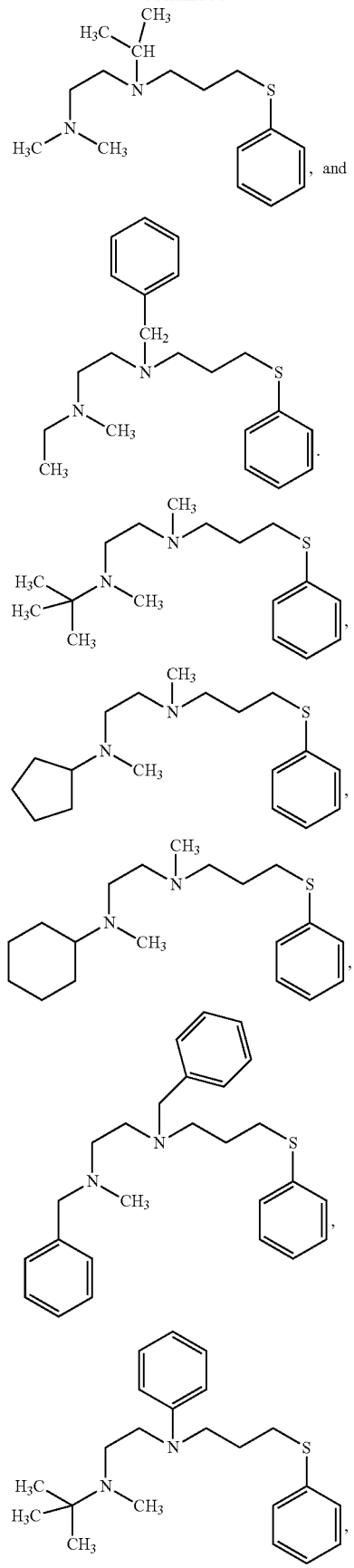
, and

67
-continued
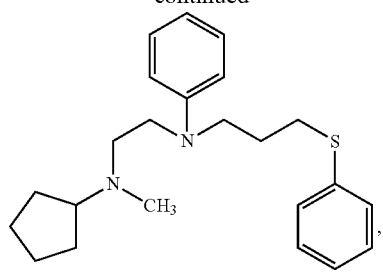
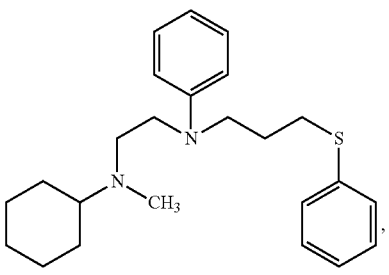
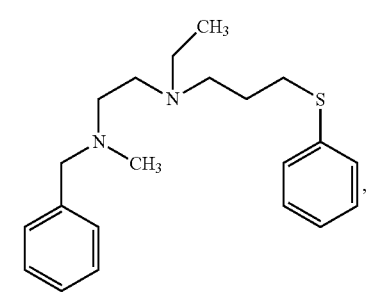
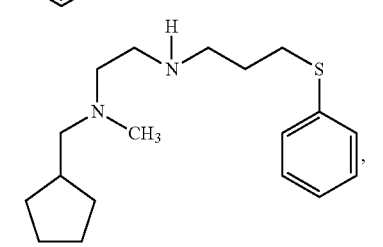
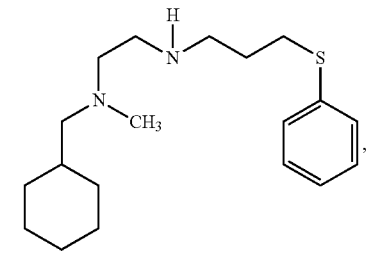
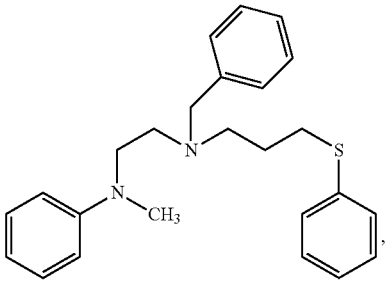
68
-continued
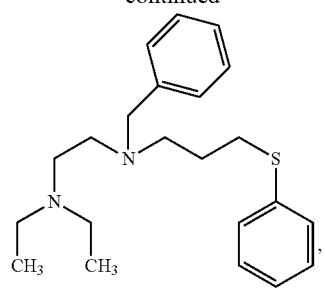
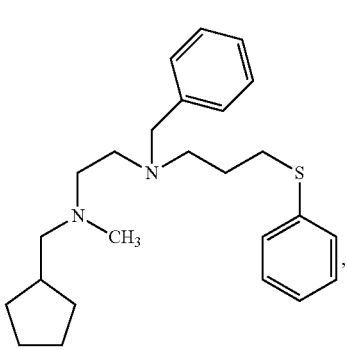
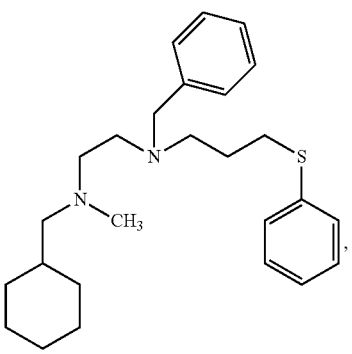
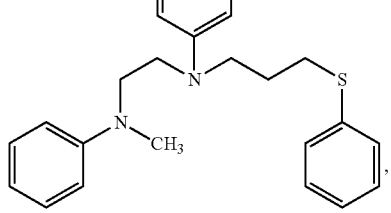
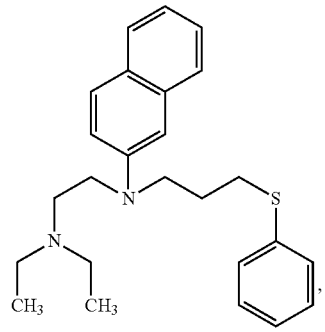

69
-continued
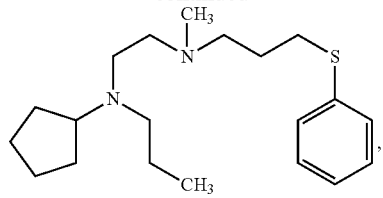
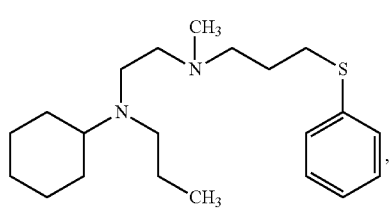
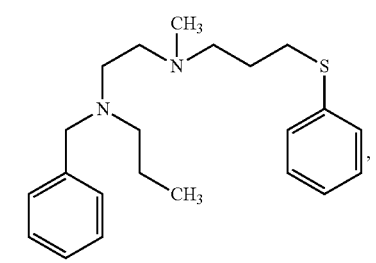
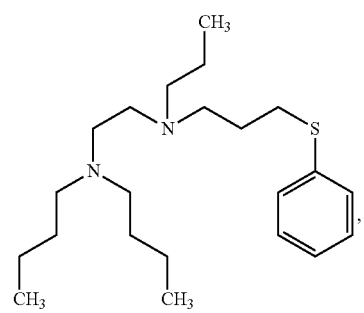
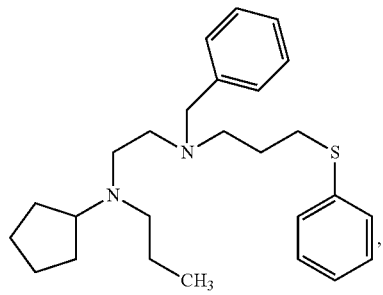
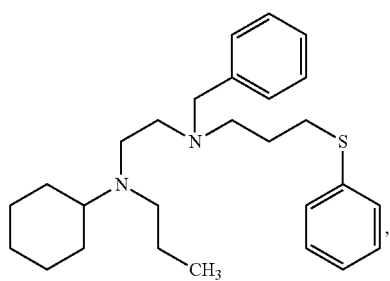
70
-continued
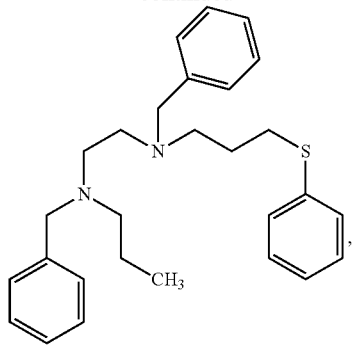
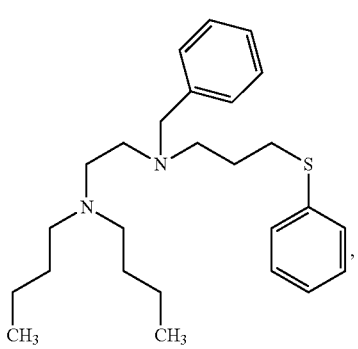
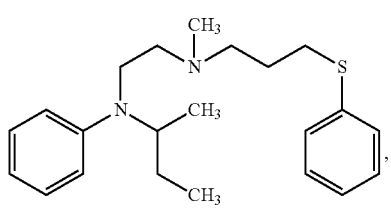
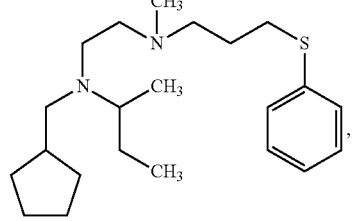
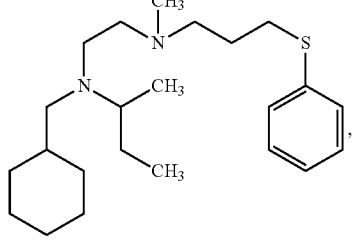
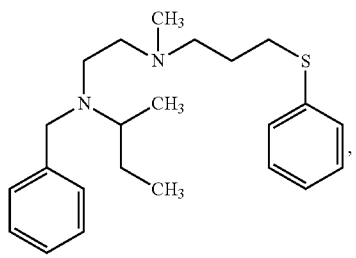

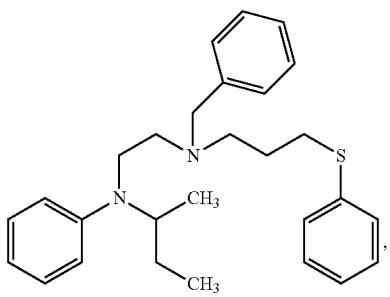
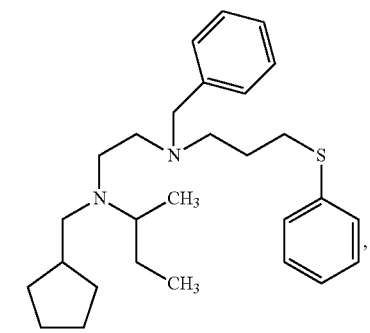
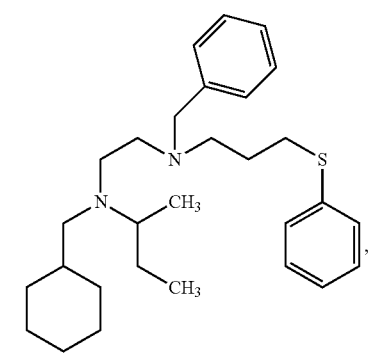
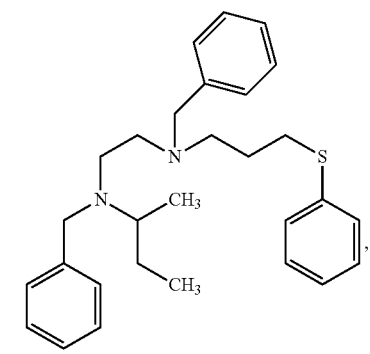
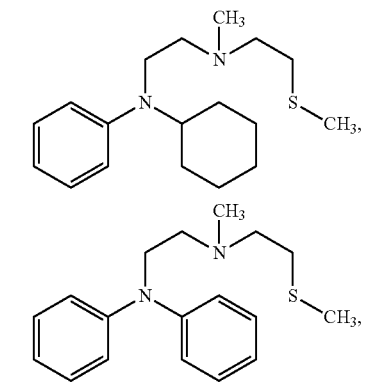
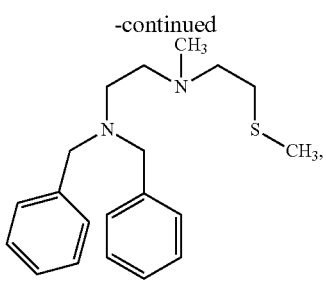
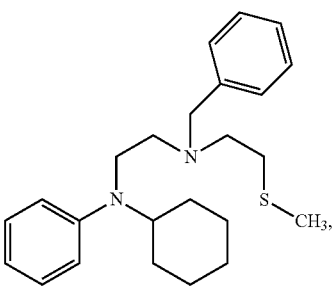
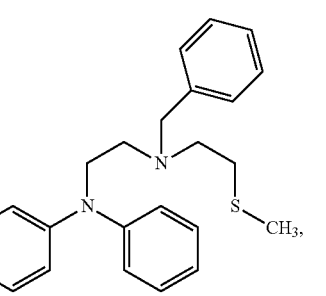
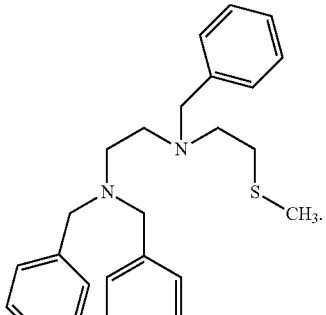
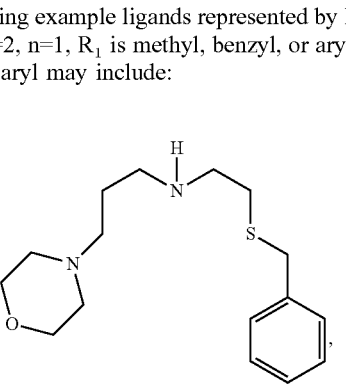
Non-limiting example ligands represented by Formula (I) in which m=2, n=1, R₁ is methyl, benzyl, or aryl, and R₂ is H, alkyl, or aryl may include:
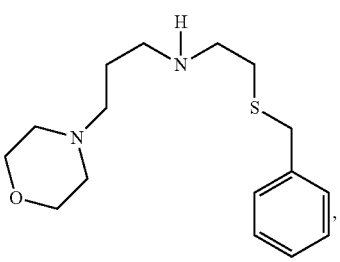

73
-continued

74
-continued

75
-continued
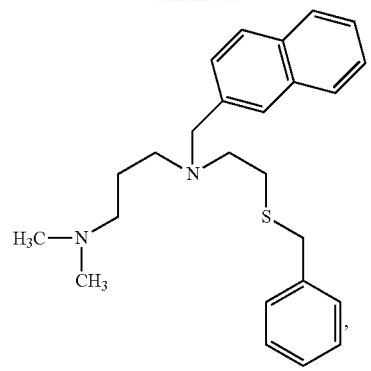
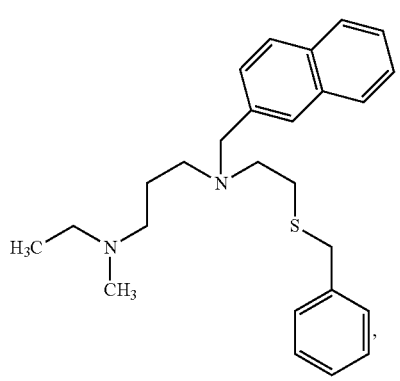
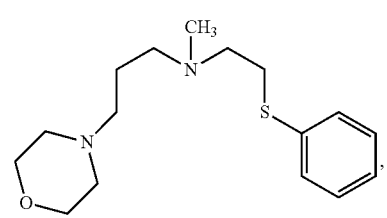
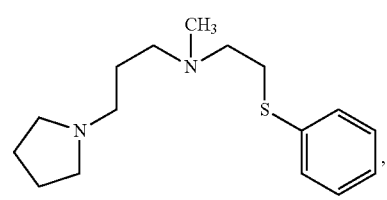
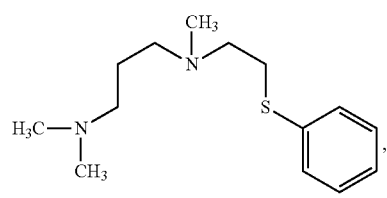
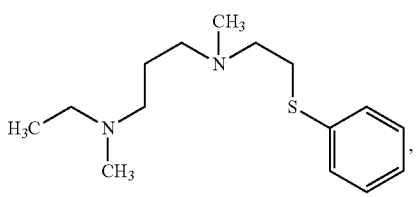
76
-continued
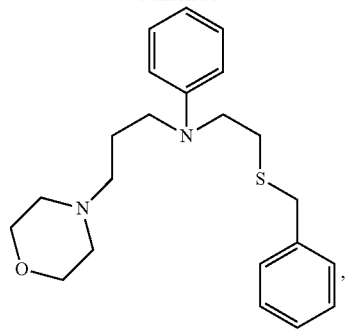
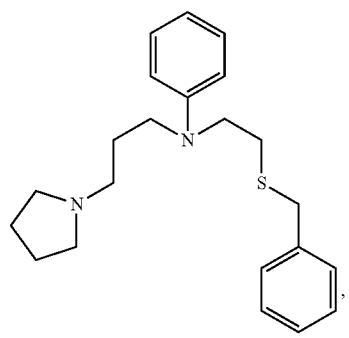
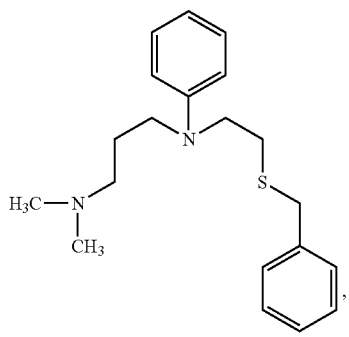
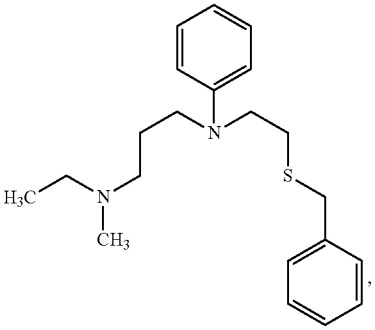
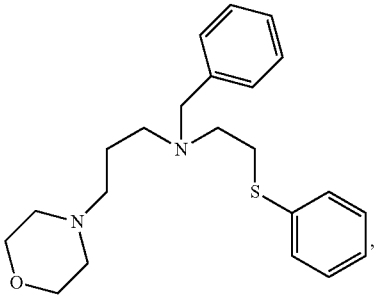

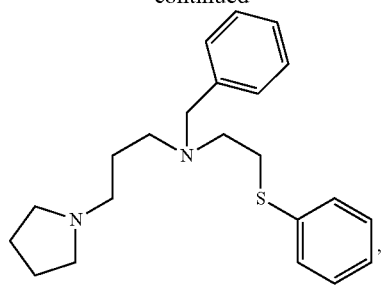
,
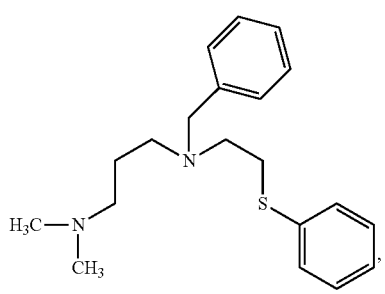
,
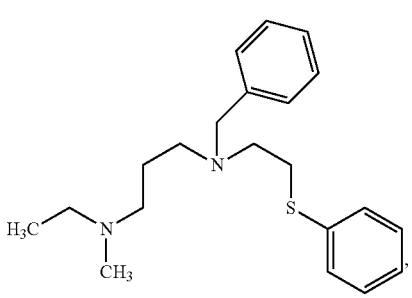
,
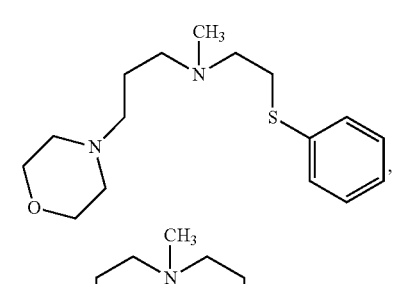
,
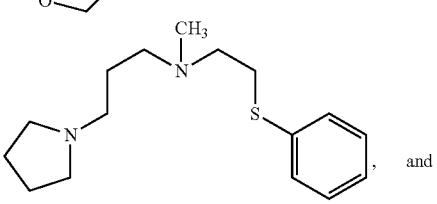
, and
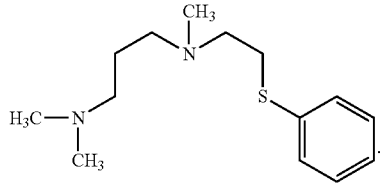
.
Non-limiting example ligands represented by Formula (I) in which m=n=2, $R_1$ is alkyl or aryl, and $R_2$ is H may include the following:
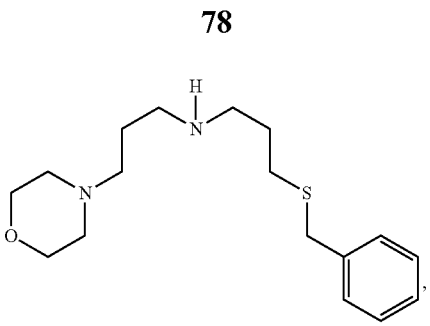
,
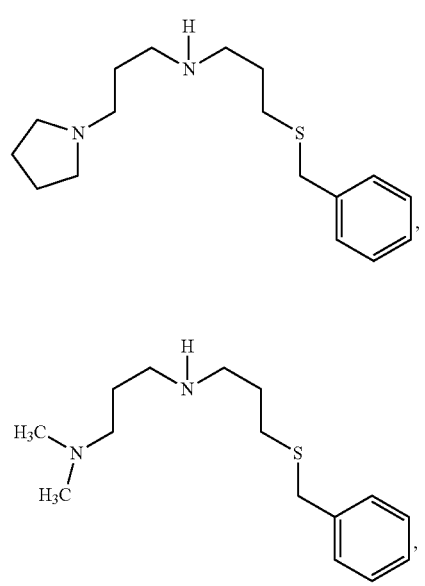
,
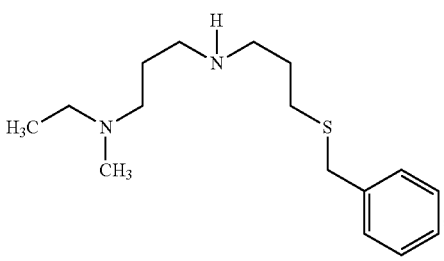
,
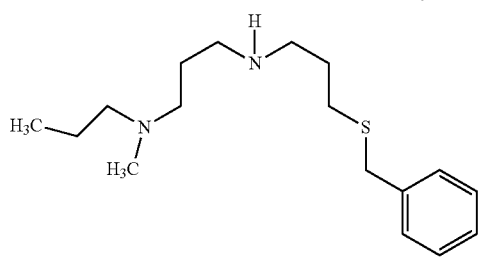
,
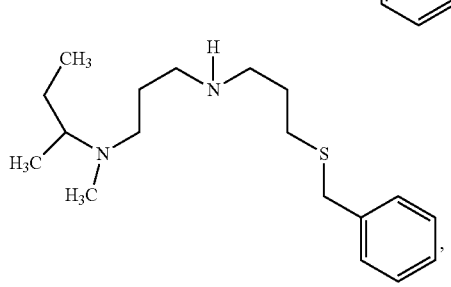
, -continued
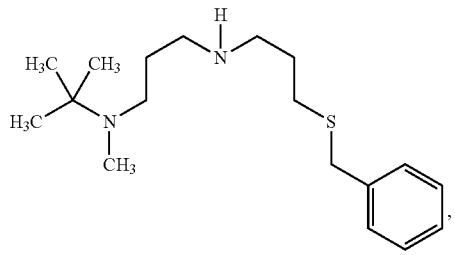
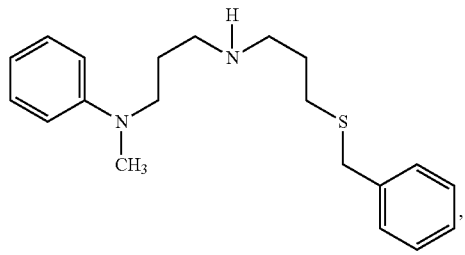
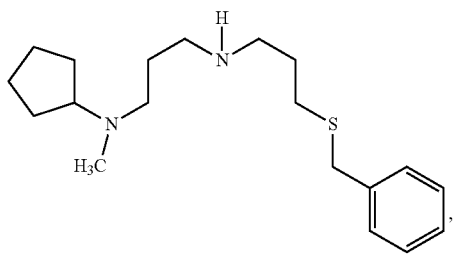
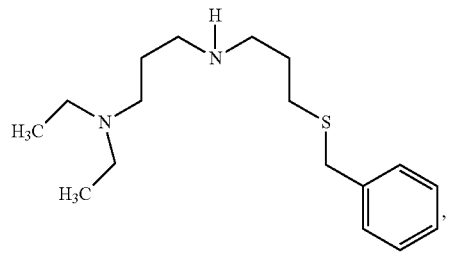
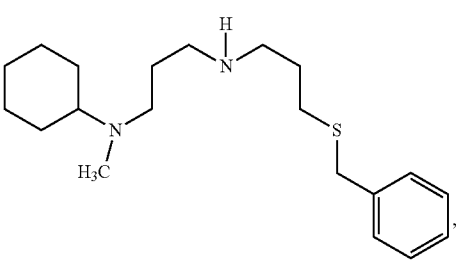
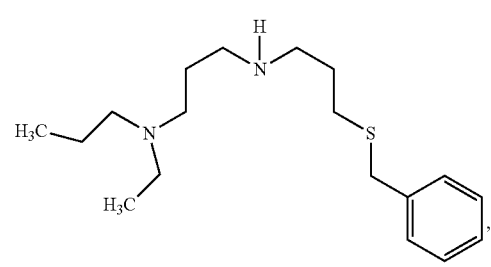
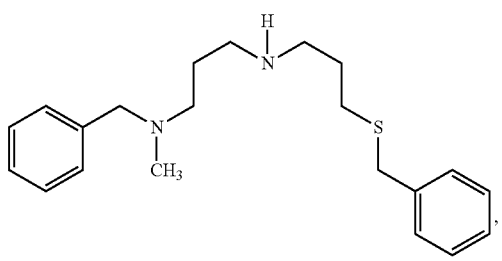
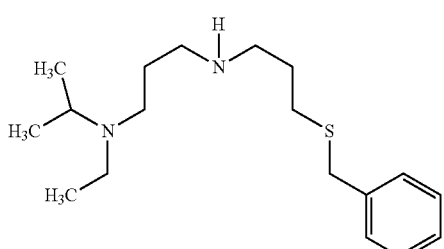
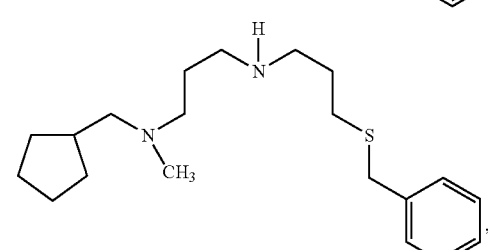
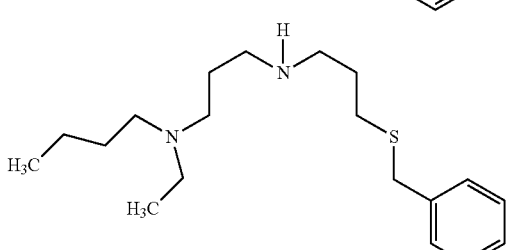
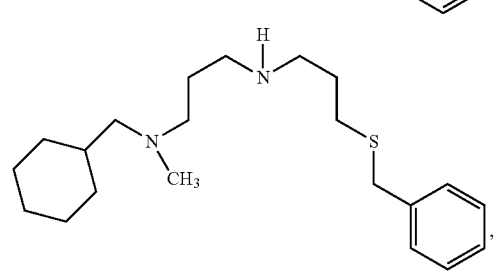
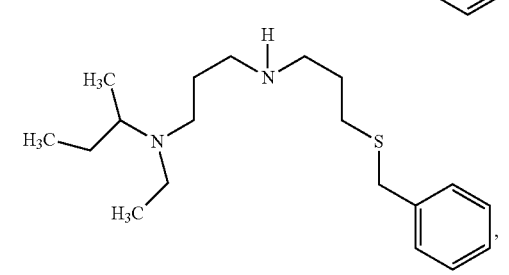

81
-continued
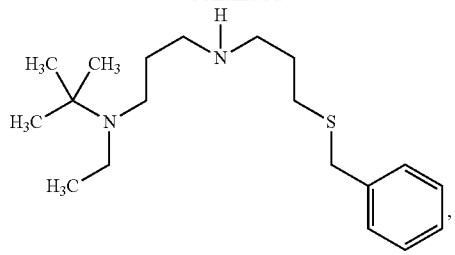
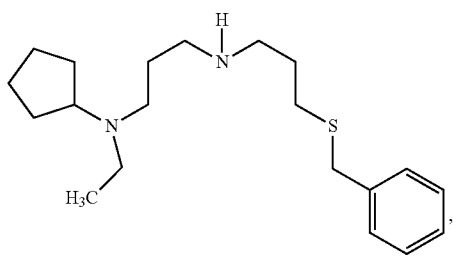
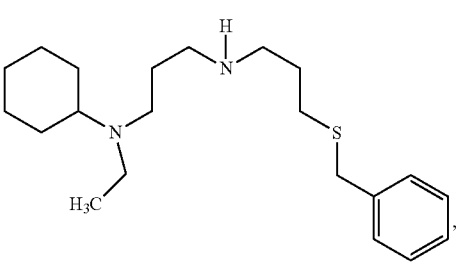
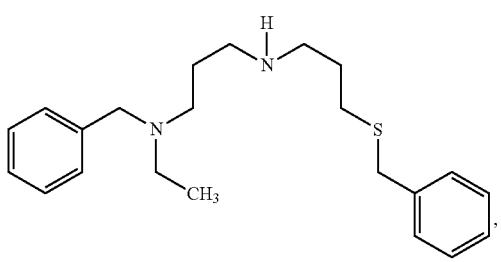
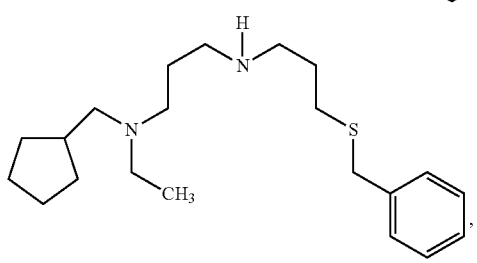
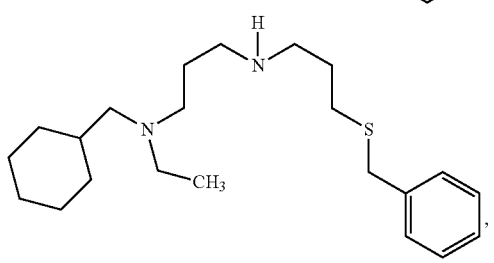
82
-continued
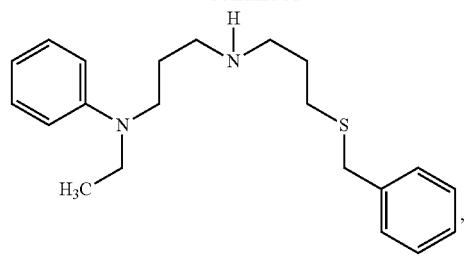
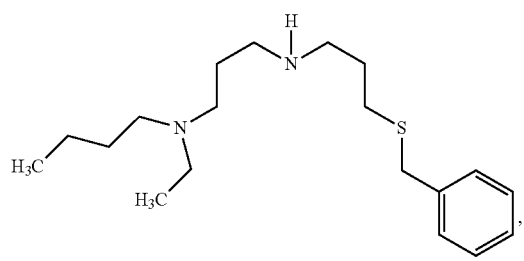
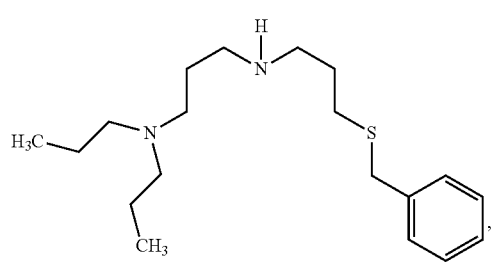
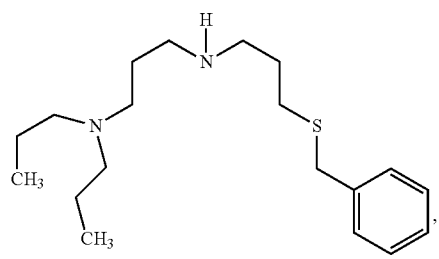
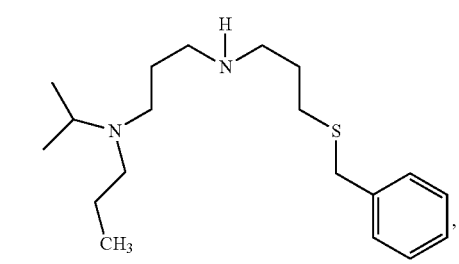
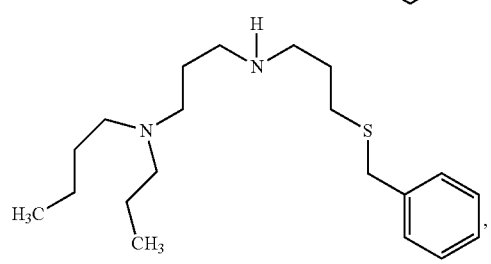

-continued
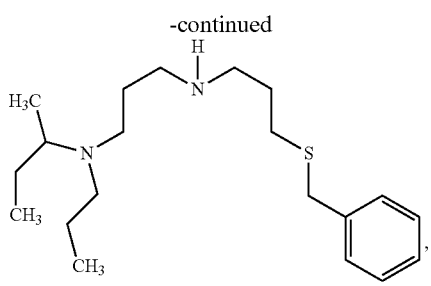
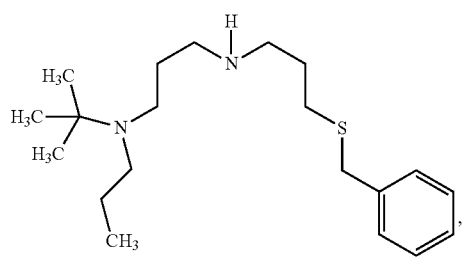
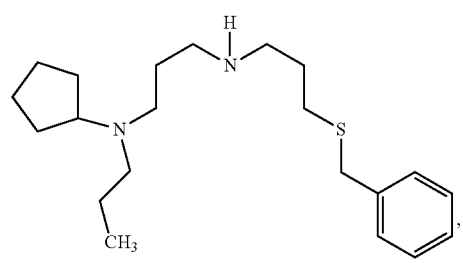
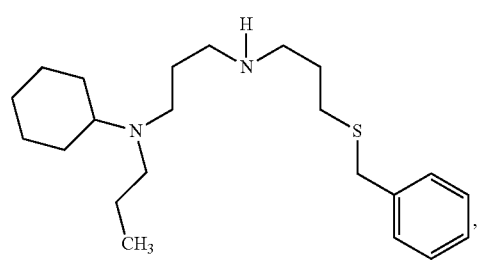
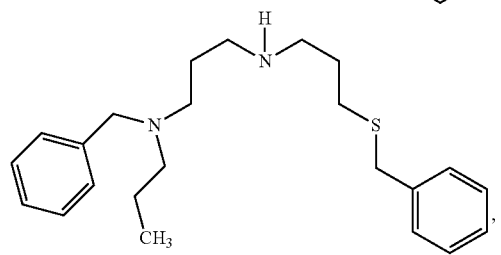
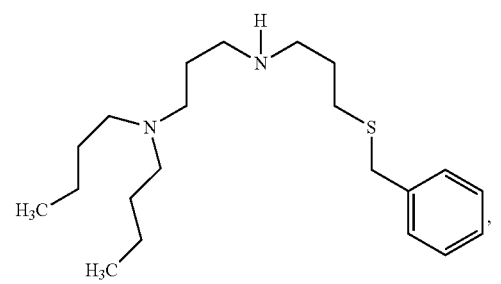
-continued
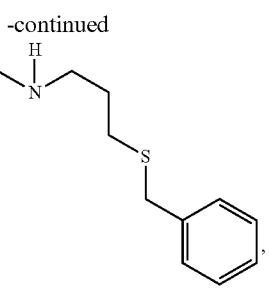
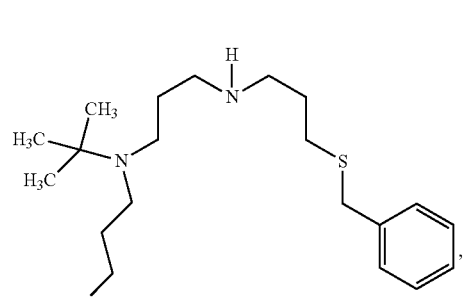
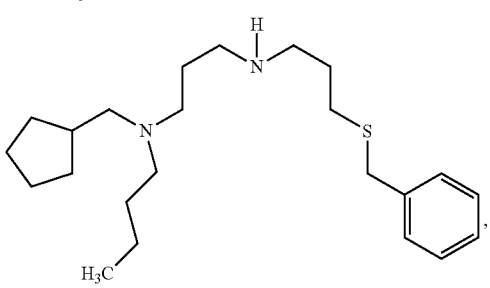
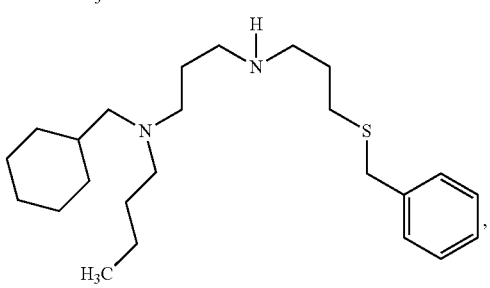
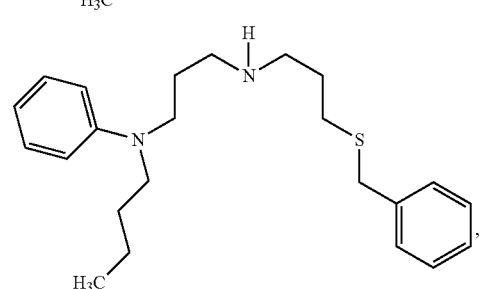
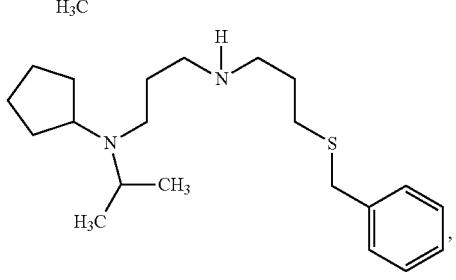

85
-continued
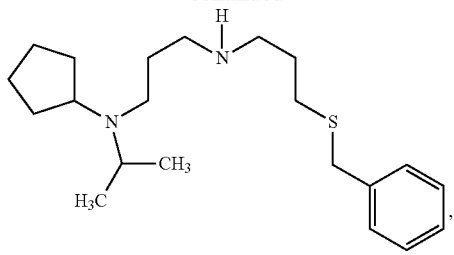
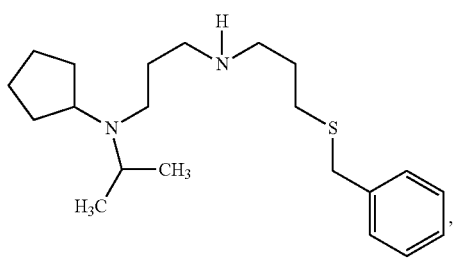
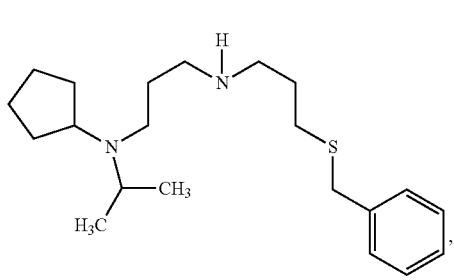
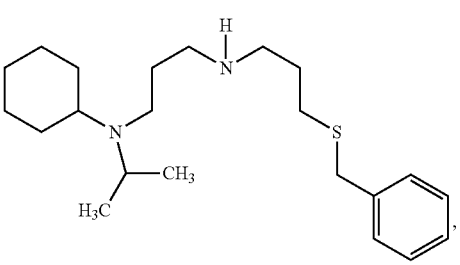
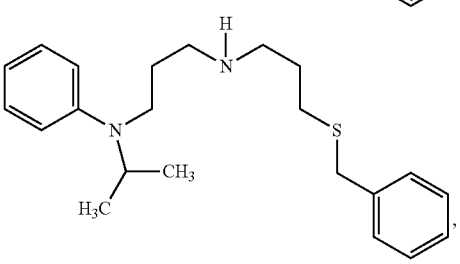
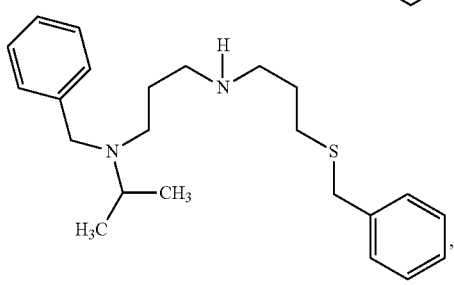
86
-continued
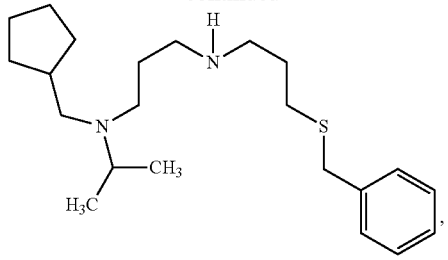
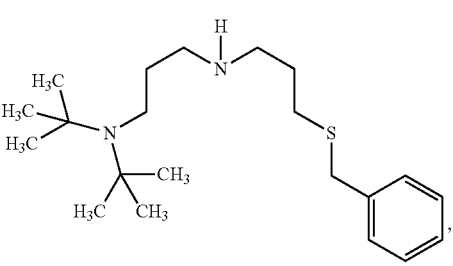
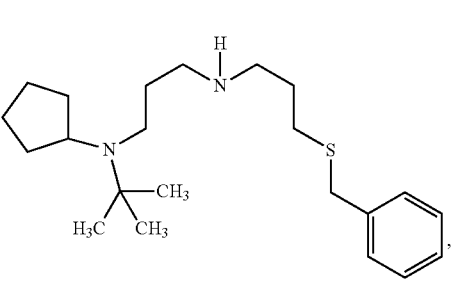
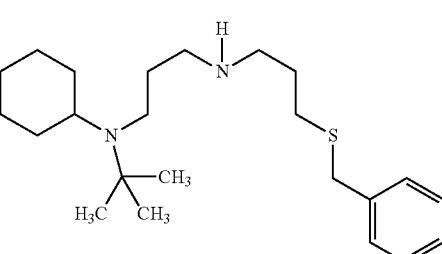
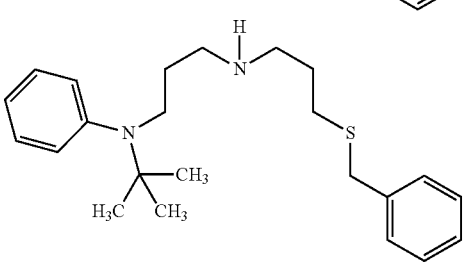
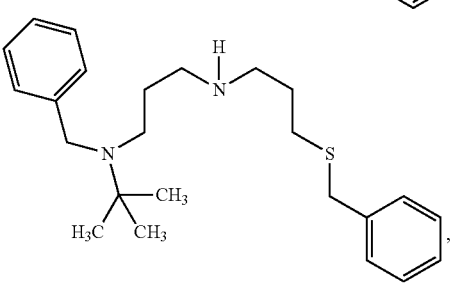

87
-continued
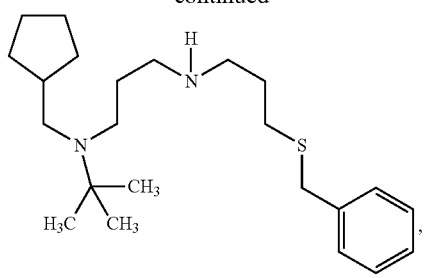
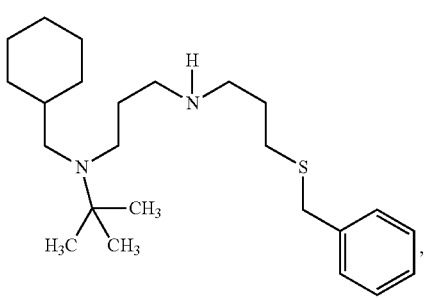
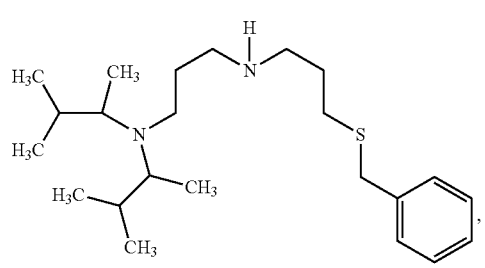
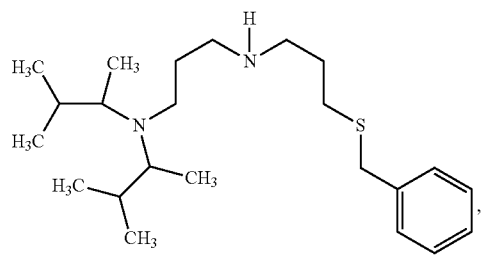
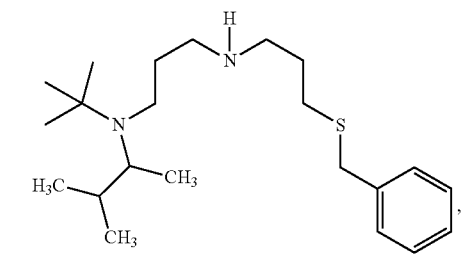
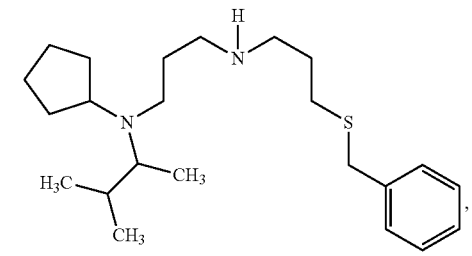
88
-continued
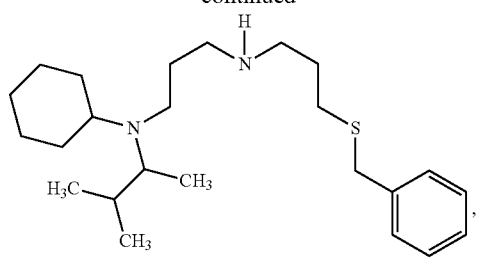
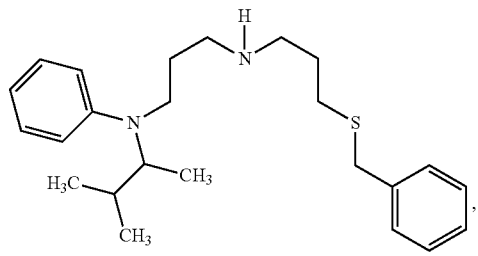
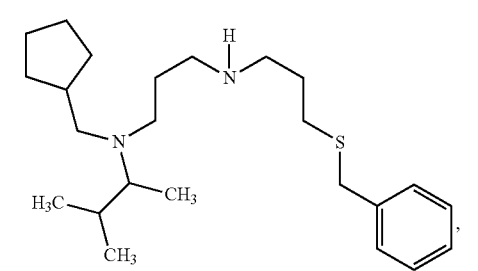
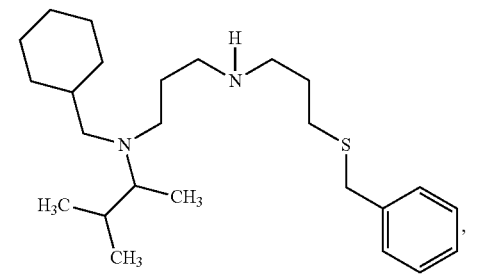
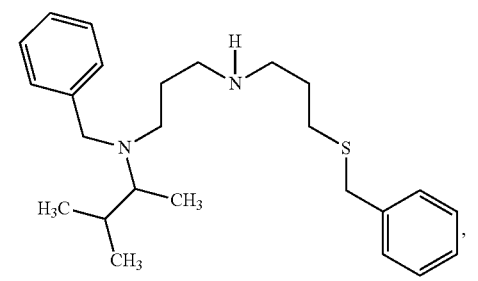
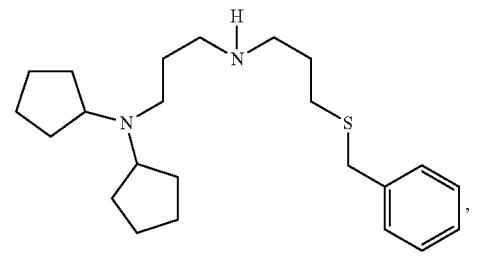

-continued
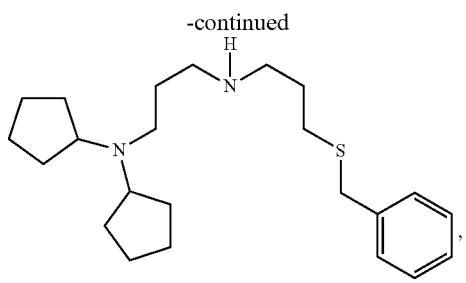
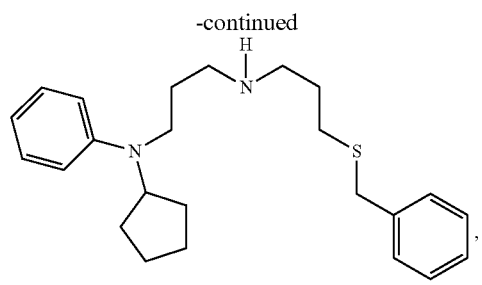
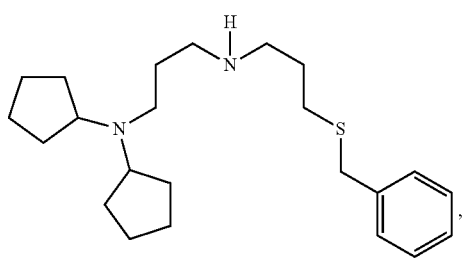
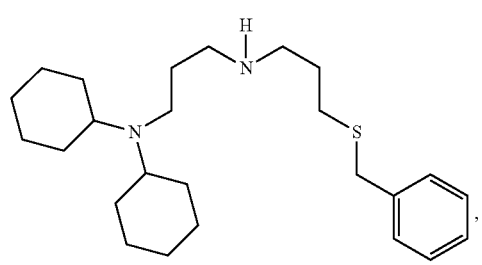
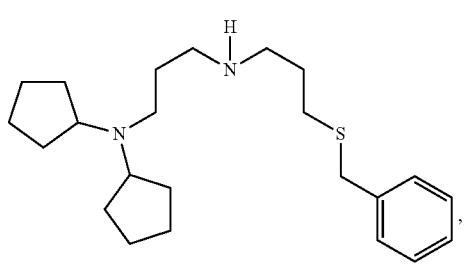
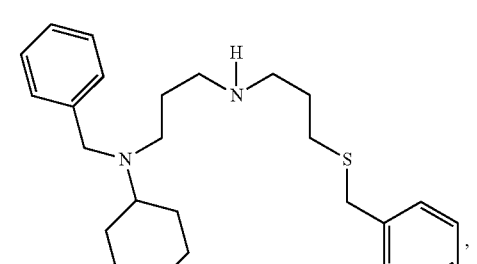
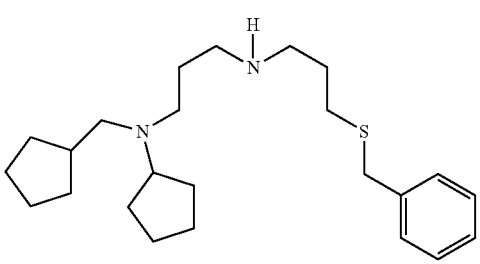
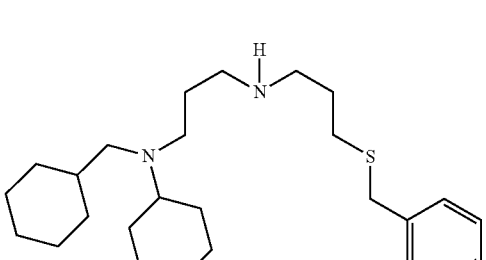
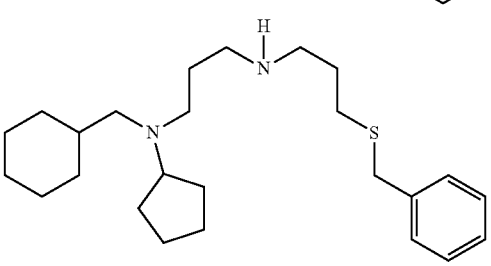
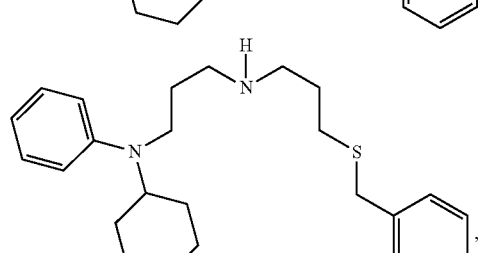
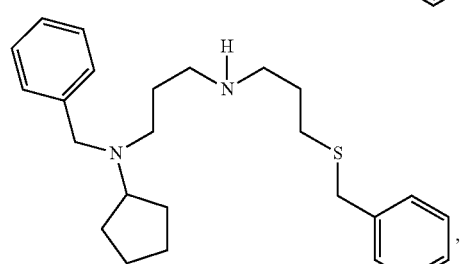
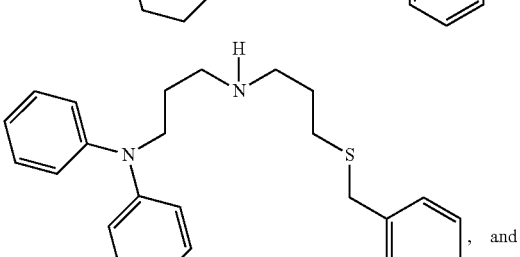, and

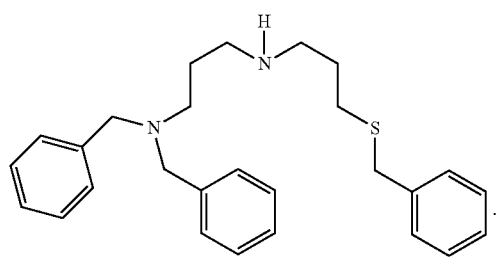
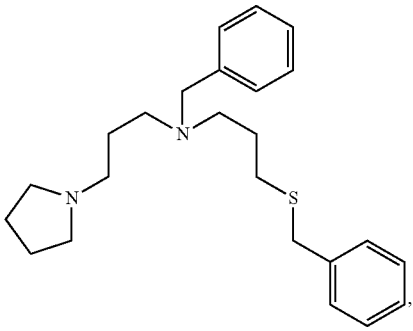
Non-limiting example ligands represented by Formula (I) in which m=n=2, $R_1$ is alkyl or aryl, and $R_2$ is alkyl or aryl may include:
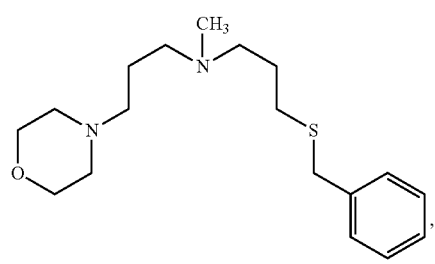
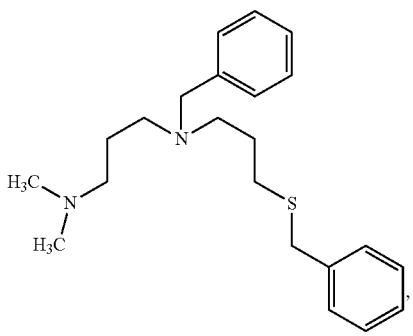
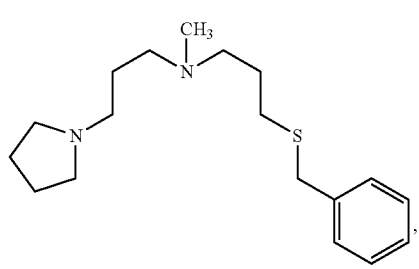
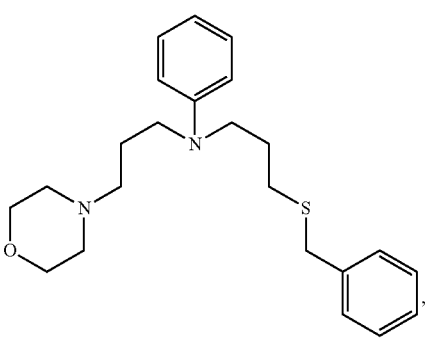
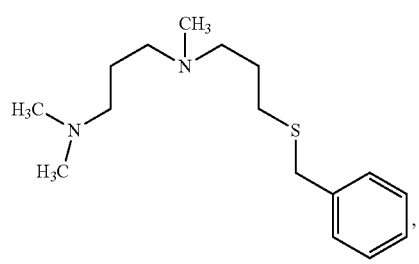
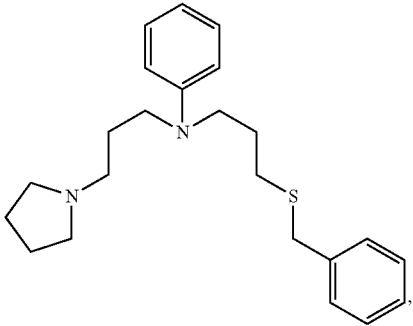
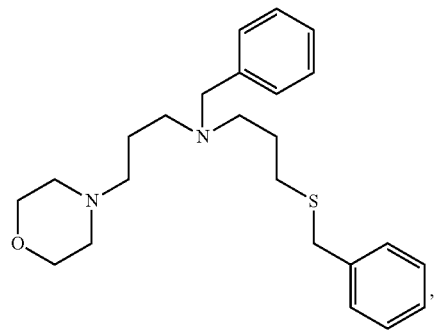
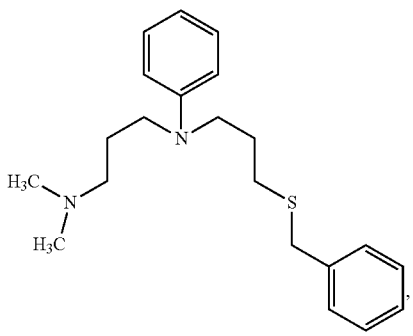

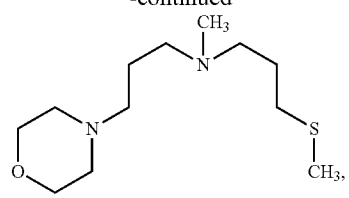
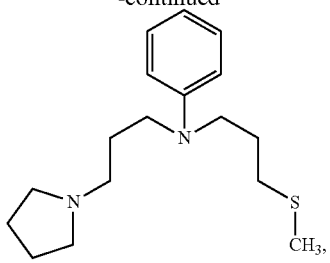

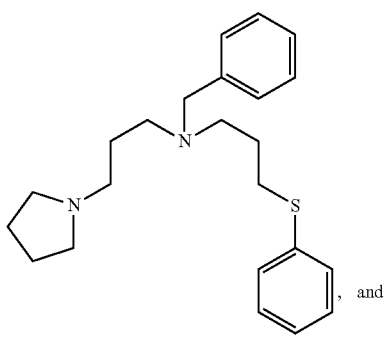
, and
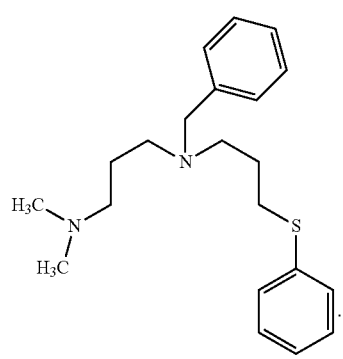
.
Non-limiting example ligands represented by Formula (I) in which m=n=1 may include the following:
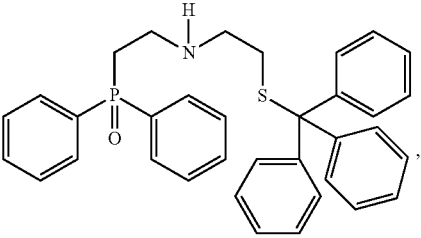
,
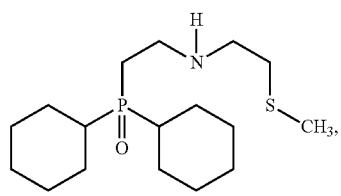
,
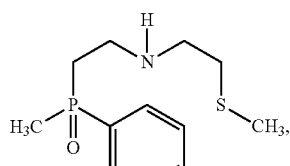
,
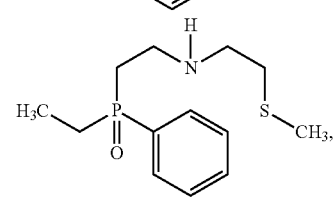
,
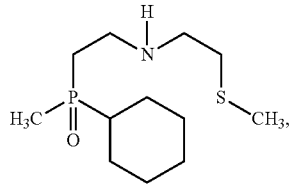
,
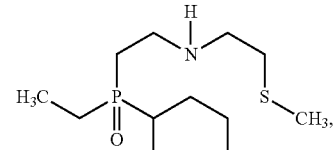
,
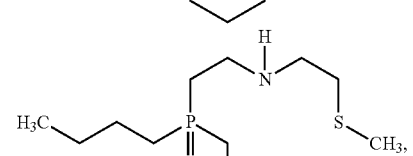
,
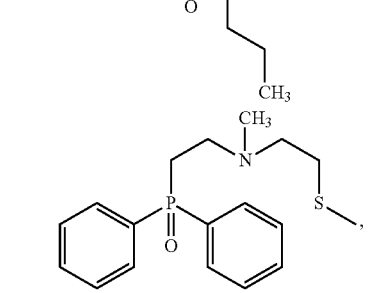
,

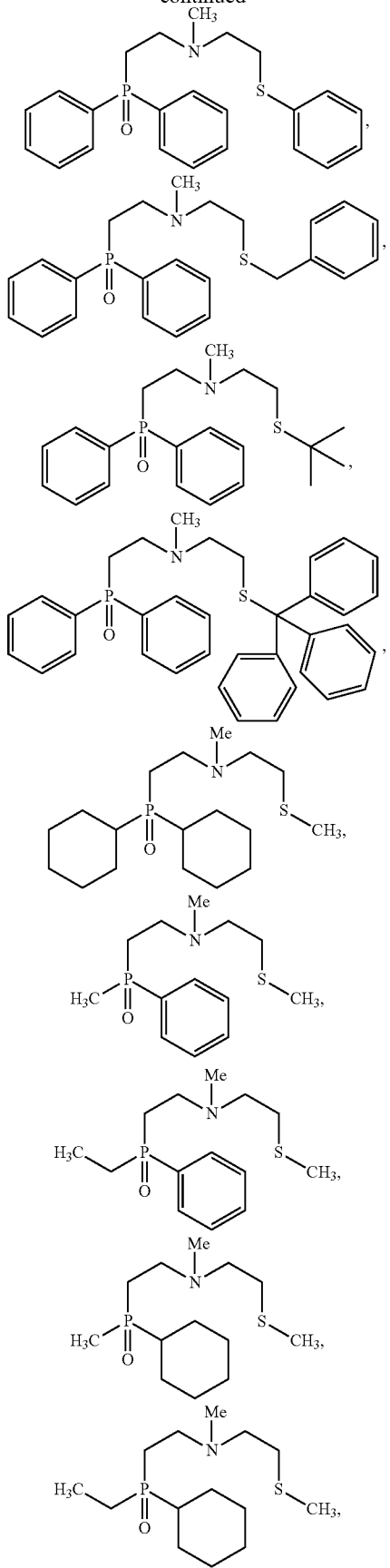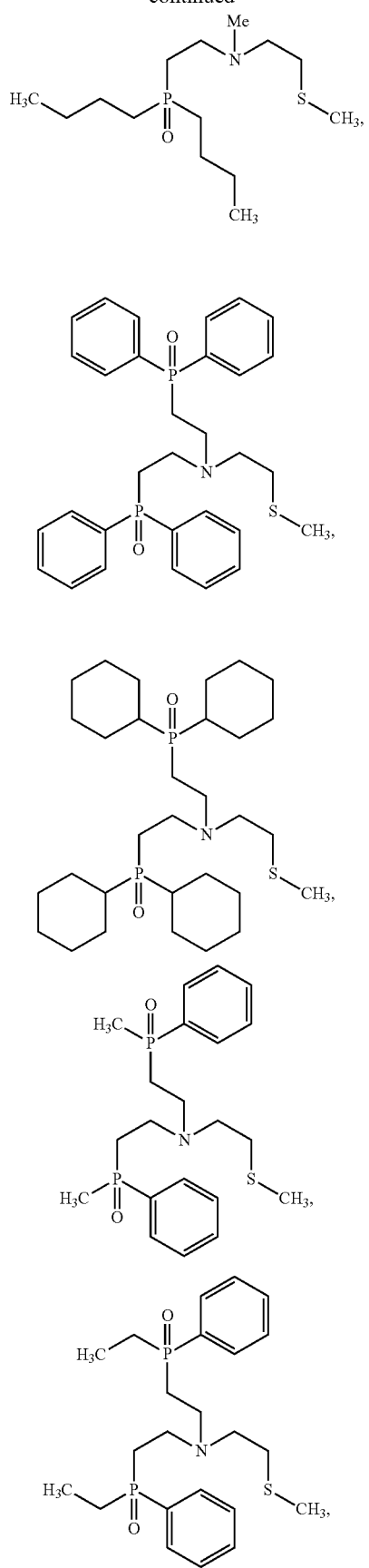

99
-continued
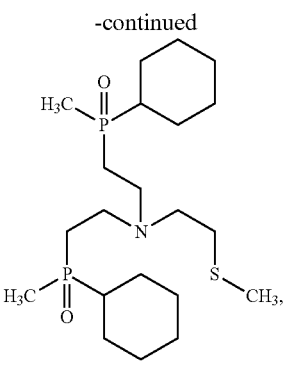
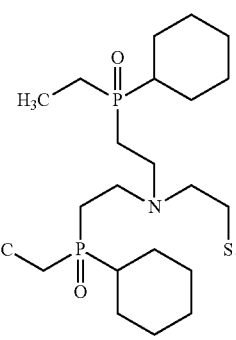
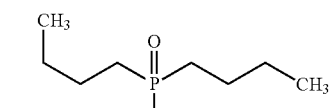
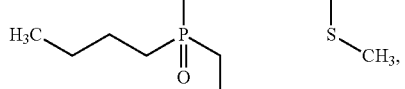
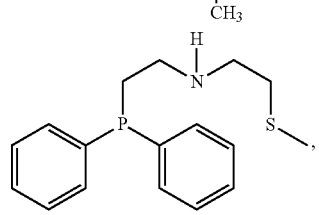
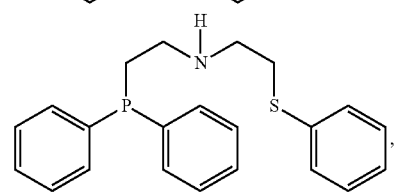
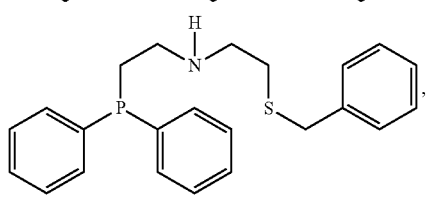
100
-continued
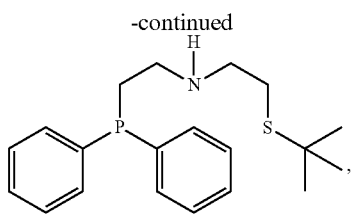
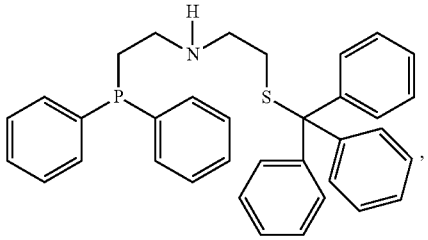
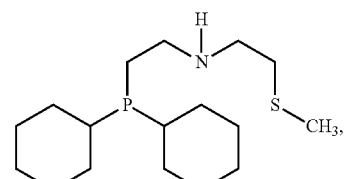
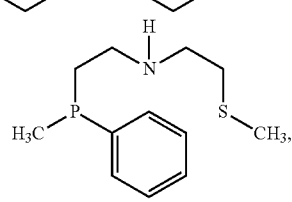
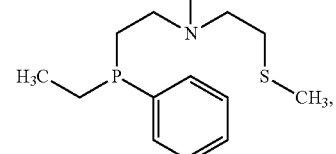
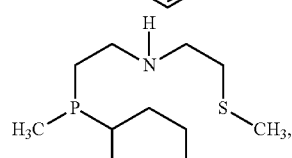
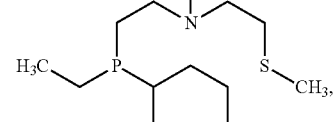
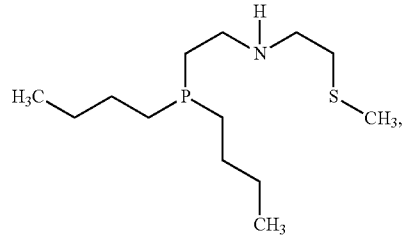

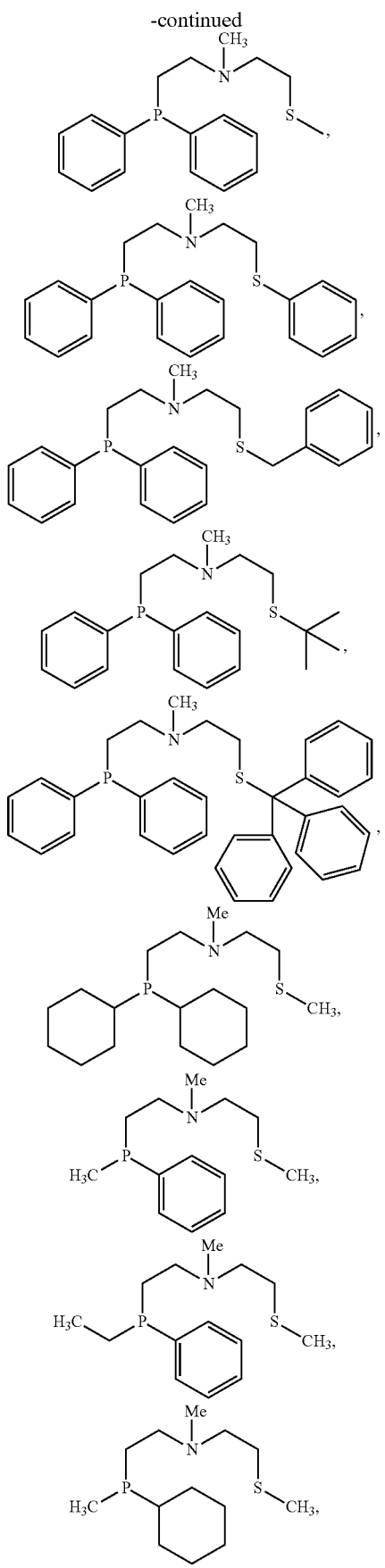
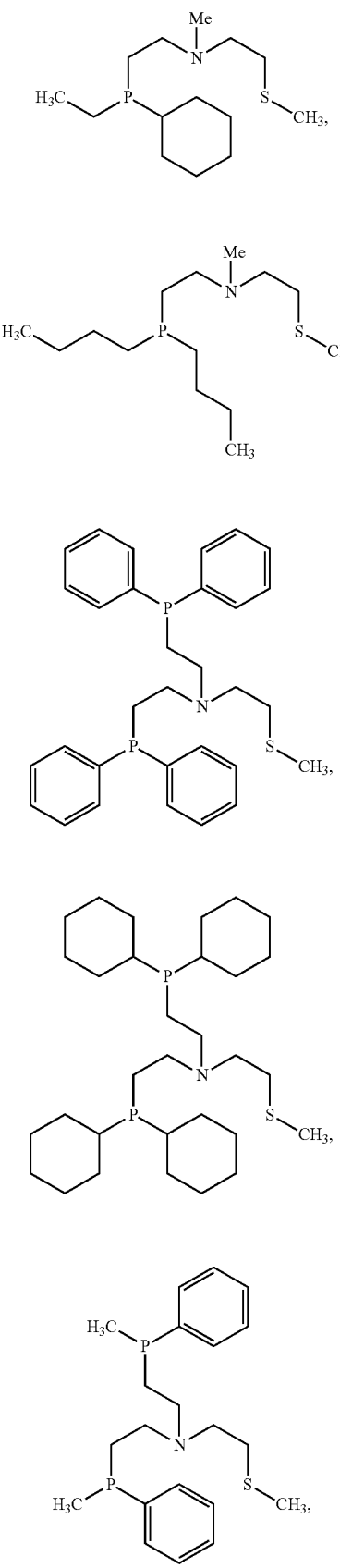

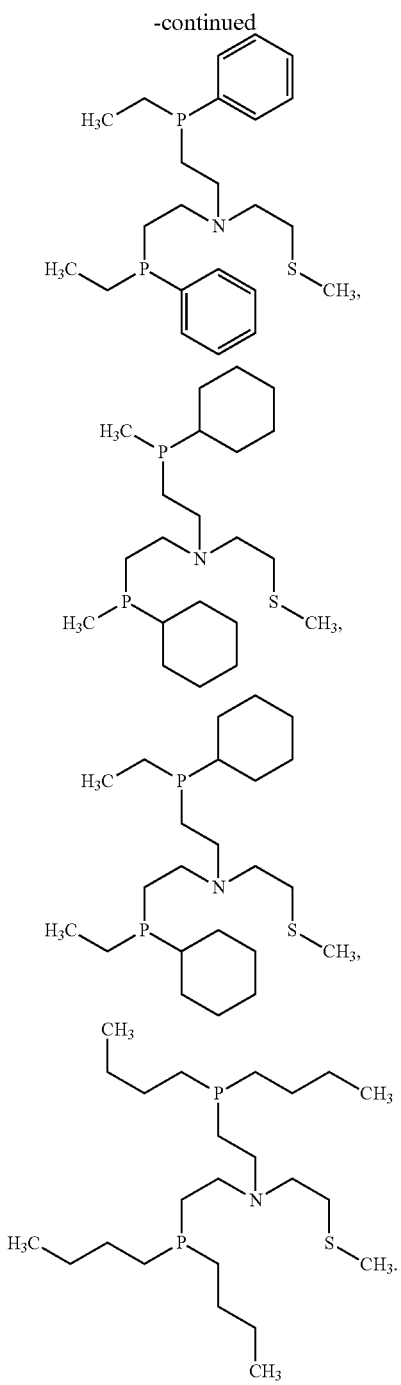

A comparable diversity of structures is available for (e.g., represented by) each of the other ligands of Formulae (II) to (X).

For ease of description, the ligands represented by Formulae (I) to (XII) may be described in terms of their heteroatom functionalities (e.g., content) as NNS-type, P(O) NS-type, PNS-type, SNNS-type, SNNP(O)-type, or SNNP-type ligands, depending on the specific nature (e.g., groups) of E and $R_6$. As used herein, these descriptions are used in their art-recognized form to refer to the specific atoms within the ligand that are formally bound to the metal, where the term "(O)" is intended to indicate that an oxygen atom (e.g., oxo group) is directly attached to the preceding atom.

Catalysts

One or more embodiments of the present disclosure are also directed to coordination complexes or catalysts comprising at least one of the inventive ligands described herein. Again, the terms "coordination complex" and "catalyst" may be used interchangeably and are intended to refer to an organometallic entity, as understood by those of skill in the art. While the complexes may be useful as catalysts, the use of the term "catalyst" should not be interpreted in a way that limits the scope of utility for these complexes.

In some embodiments, the catalysts may comprise at least one ligand represented by Formulae (I) to (X), including an NNS-type, P(O)NS-type, PNS-type, SNNS-type, SNNP(O)-type, SNNP-type ligand, or any described permutations thereof, coordinated to at least one transition metal. As described in the Examples, such catalysts may be formed by reacting a suitable transition metal precursor with at least one of the ligands described herein. In some embodiments, this involves the reaction of a suitable metal chloride or metal olefin complex with the appropriate ligand.

While the ligands have been described, in some embodiments, in terms of exclusions, for example, as excluding:

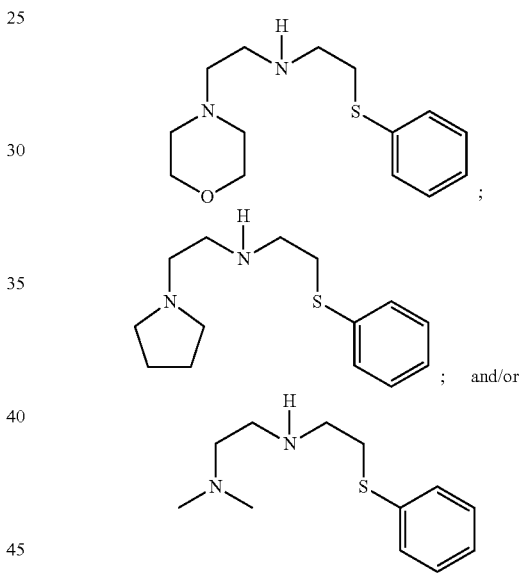

from other specific and generic ligand embodiments, it will be understood that such descriptions do not automatically exclude catalysts including such ligands from the scope of embodiments of the present disclosure. In some embodiments, the catalysts may be free of any excluded ligand or combination of excluded ligands; and in some embodiments, the catalysts may include all such ligands or ligand embodiments described herein.

Figure 6:
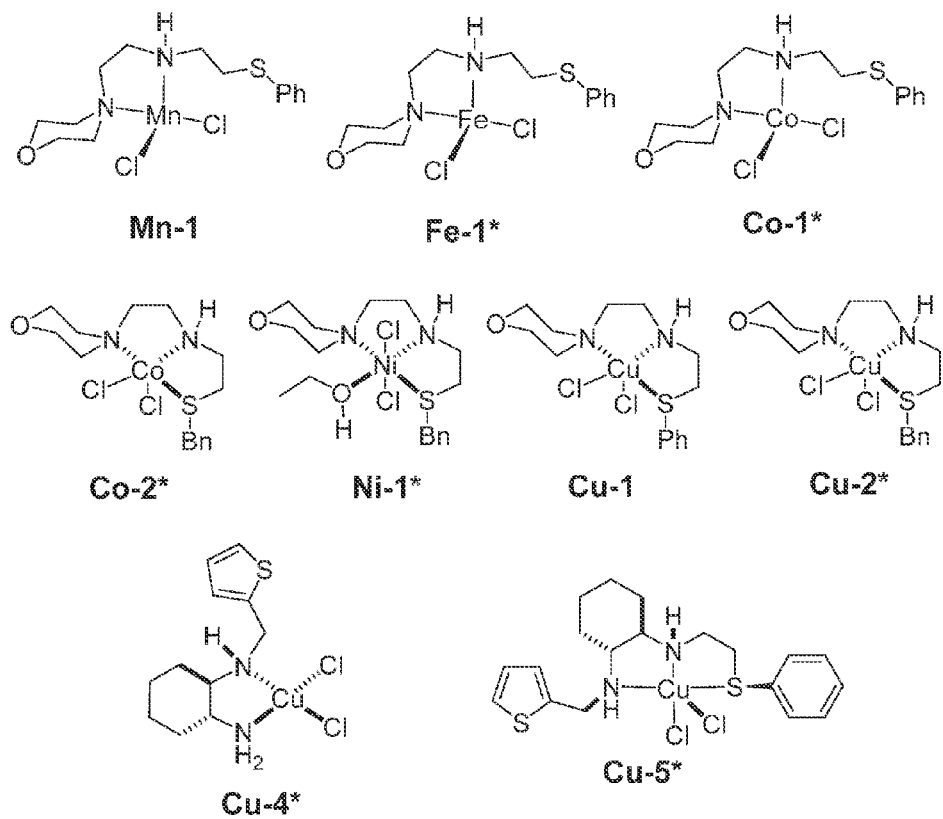
Figure 7:
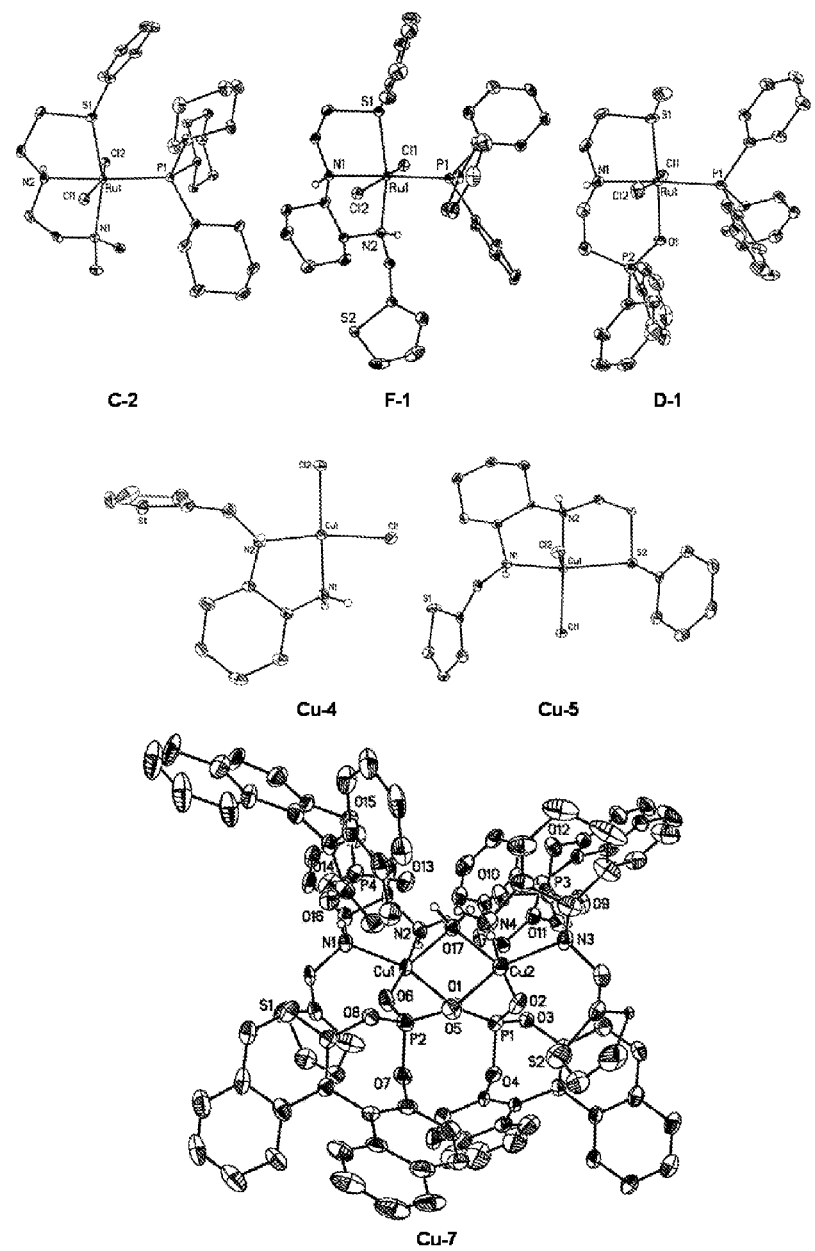
FIG. 7 shows selected X-Ray molecular structures for complexes C-2, F-1, D-1.CH$_2$Cl$_2$, Cu-4, Cu-5 and Cu-8.4MeCN-pentane (thermal ellipsoids showing 50% level of probability). Hydrogen atoms (except those bound to nitrogen and oxygen, i.e., NH and OH groups) are omitted for clarity.

As used herein, the term "transition metal" includes any metal of Group 4 to Group 12, including the lanthanides and actinides. In some embodiments, the transition metal may refer to one of the Group 6 to Group 11 transition metals. Such transition metals include, but are not limited to titanium (Ti), vanadium (V), zirconium (Zr), hafnium (Hf), chromium (Cr), molybdenum (Mo), tungsten (W), manganese (Mn), rhenium (Re), iron (Fe), ruthenium (Ru), osmium (Os), cobalt (Co), rhodium (Rh), iridium (Ir), lanthanum (La), nickel (Ni), palladium (Pd), platinum (Pt), copper (Cu), silver (Ag), gold (Au), zinc (Zn), and samarium (Sm). In some embodiments, the catalysts may include Cr, Co, Cu, Fe, Mn, Mo, Ni, Os, Pd, Rh, Sm, or W, or any subset combination thereof. In some embodiments, the catalysts may include Fe, Ru, Os, Co, Rh, or Ir, or any subset combination thereof. See also FIG. 6. In some embodiments, the catalysts may include ruthenium, iridium, or a combination thereof.

The catalysts may be described in terms of their stoichiometries. For example, in some embodiments, the ratio of the ligand to transition metal is 1 to 1. Further, the catalysts may contain one, two, or more transition metals per molecule. The ligands may bridge multiple transition metal centers, or may be monodentate, bidentate, tridentate, or tetradentate with respect to any individual transition metal center.

Depending on the nature of the transition metal and ligand combination, other ligands, including formally anionic ligands, neutral ligands, or cationic ligands may be coordinated to the transition metal. Non-limiting examples of anionic ligands may include substituted or unsubstituted alkyl groups, substituted or unsubstituted aryl groups, substituted or unsubstituted alkoxy groups (e.g., methoxy or benzyloxy), substituted or unsubstituted aryloxy groups (e.g., phenoxy), optionally fluorinated carboxylate groups (e.g., mono-, di-, or trifluoroacetic acid), halides (including fluoride, chloride, bromide, iodide), hydride, hydroxy, NO⁻, OTf⁻ (triflate), OTs⁻ (tosylate), phosphate, or $BH_4$. In some embodiments, at least one of the formally anionic ligands is a chloride anion.

When the transition metal complex includes one or more neutral ligands, the neutral ligands may include suitable C, N, O, P, or S-bonded ligands as are known in the art for transition metal complexes. Non-limiting examples of neutral ligands may include nitriles (including alkyl or aryl nitriles), amines (including alkyl, aryl, or unsubstituted primary, secondary, or tertiary amines), carbonyl, carbenes, alkyl or aryl ethers (including cyclic ethers, such as tetrahydrofuran), olefins, phosphines, phosphine oxides, phosphites, alkyl or aryl sulfoxides, and other solvent molecules (including lower alcohols and water). The phosphine, phosphine oxide, and phosphite ligands may include substituted or unsubstituted alkyl groups, substituted or unsubstituted cycloalkyl groups, substituted or unsubstituted aryl groups, substituted or unsubstituted arylalkyl moieties groups, or combinations thereof, again as are known in the art.

In some embodiments, the catalysts may comprise ruthenium having an empirical formula represented by $Ru(NNS)X_1X_2L$, $Ru[P(O)NS]X_1X_2L$, $Ru(PNS)X_1X_2L$, $Ru(SNNS)X_1X_2L$, $Ru[SNNP(O)]X_1X_2L$, or $Ru(SNNP)X_1X_2L$, in which:

NNS, P(O)NS, PNS, SNNS, SNNP(O), or SNNP is a NNS-type, P(O)NS-type, PNS-type, SNNS-type, SNNP(O)-type, or SNNP-type ligand, respectively;

$X_1$ and $X_2$ are formally anionic ligands; and

L is absent or a neutral ligand. L may be absent, for example, when the coordination sphere of the Ru is satisfied without the need for another neutral ligand, when a suitable neutral ligand is not available or is unable to access the binding site, or when a neutral ligand temporarily or permanently dissociates from the metal center.

In some embodiments, the catalysts comprise ruthenium having an empirical formula $Ru(NNS)X_1X_2L$, where NNS, $X_1$, $X_2$, and L are the same as described herein. The catalyst may be mononuclear or dinuclear with respect to the ruthenium.

When the catalysts comprise Ru, non-limiting examples of the ruthenium complexes may include catalysts represented as:

(A)
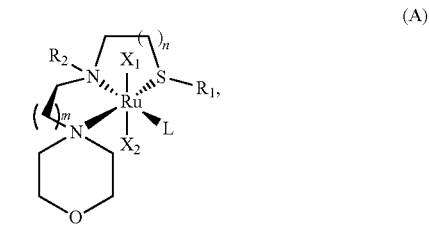

(B)
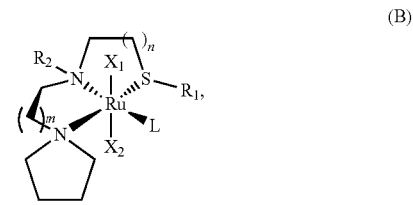

(C)
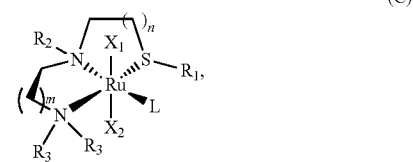

(D)
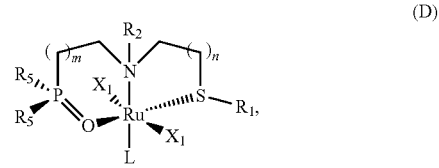

(E)
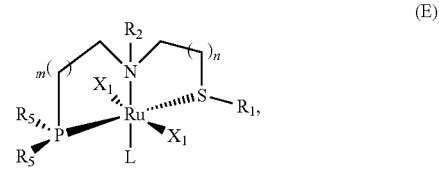

(F)
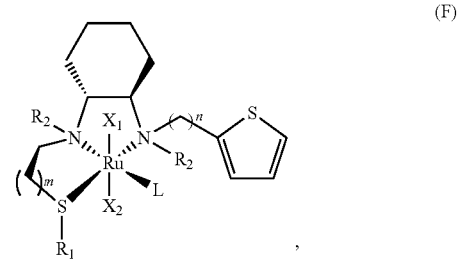

, (G)
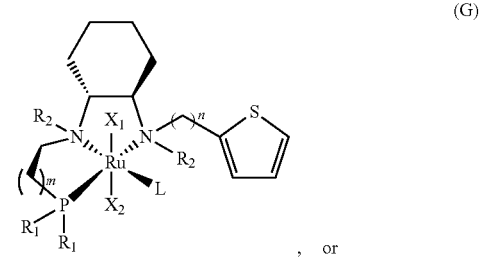

, or

-continued

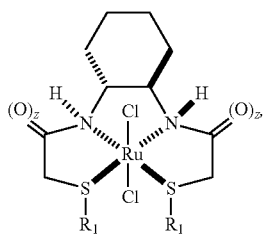
(H)

or isomers thereof. In Ru complexes (A) to (H), $R_1$, $R_2$, $R_3$, $X_1$, $X_2$, m, n, z, and E may each be the same as defined above. See also FIGS. 3A and 5.

In some embodiments, the catalysts may be represented by structures (A) to (H), in which:

$X_1$ and $X_2$ may independently be a halide (such as Cl), H, OTf, or $BH_4$, m and n may independently be 1, 2, 3, 4, or 5, or a subset thereof;

z may independently be 0 or 1;

L may independently be $-S(=O)(CH_3)_2$, $-CO$, $-PPh_3$, $-PCy_3$, $-PMe_3$, $-P^iPr_3$, $-P^tBu_3$, or $-PPh_3$;

$R_1$ may be alkyl, aryl, or arylalkyl (e.g., methyl, phenyl, and benzyl);

$R_2$ may be H, alkyl, aryl, or arylalkyl (e.g., methyl, ethyl, propyl, isopropyl, 1-butyl, 2-butyl, isobutyl, tert-butyl, benzyl, or phenyl); and $R_3$ may be alkyl, aryl, or arylalkyl (e.g., methyl ($-CH_3$), cyclohexyl ($-Cy$), benzyl (-Bn, $-CH_2Ph$), phenyl (-Ph) or naphthyl).

The catalysts represented by structure (A) in which:

(i) m=n=1, $X_1=X_2=Cl$, $R_1$ is methyl, benzyl, or phenyl, and L is $PPh_3$; (ii) m=n=1, $X_1=X_2=Cl$, $R_1$ is phenyl, and L is $CH_3S(O)CH_3$; and (iii) m=1, n=2, $X_1=X_2=Cl$, $R_1$ is benzyl, and L is $PPh_3$; structures (B) and (C) in which (i) $R_1$ is phenyl, $R_2$ is H, $R_3$ is methyl, and L is $PPh_3$; structure (D) in which m=n=1, $R_1$ is methyl, $R_2$ is H, $R_5$ is phenyl, and $X_1$ is Cl; and structure (F) where m=n=1, $R_1$ is phenyl, and $R_2$ is H, have all been characterized crystallographically in the depicted conformations.

Further non-limiting example embodiments of the inventive ruthenium complexes include those in which the structures may be represented as:

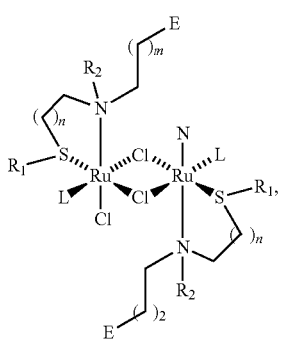
(J)

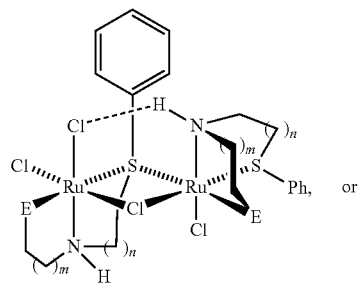
(K)

or (L)

or isomers thereof.

In Ru complexes (I) through (L), $R_2$, $R_3$, m, n, and E may each be the same as defined herein for the structures of other compounds. See also FIGS. 3B and 5.

In some embodiments, the catalysts may be represented by structures (J), (K), or (L), in which:

m and n are independently 1, 2, 3, 4, or 5; or a subset thereof;

$R_1$ is alkyl, aryl, or arylalkyl (e.g., methyl, phenyl, and/or benzyl);

$R_2$ is H, alkyl, aryl, or arylalkyl (e.g., methyl, ethyl, propyl, isopropyl, 1-butyl, 2-butyl, isobutyl, tert-butyl, benzyl, and/or phenyl);

each L is independently $-S(=O)(CH_3)_2$, CO, or $-PPh_3$, $-PCy_3$, $-PMe_3$, $-P^iPr_3$, $-P^tBu_3$, or $-PPh_3$;

E is:

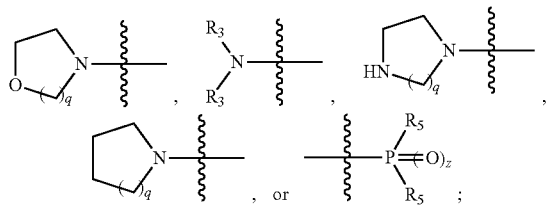

each $R_3$ is independently methyl, ethyl, propyl, isopropyl, 1-butyl, 2-butyl, isobutyl, tert-butyl, benzyl (-Bn), or phenyl (-Ph), and q is 1, 2, 3, or 4.

Figure 3A:
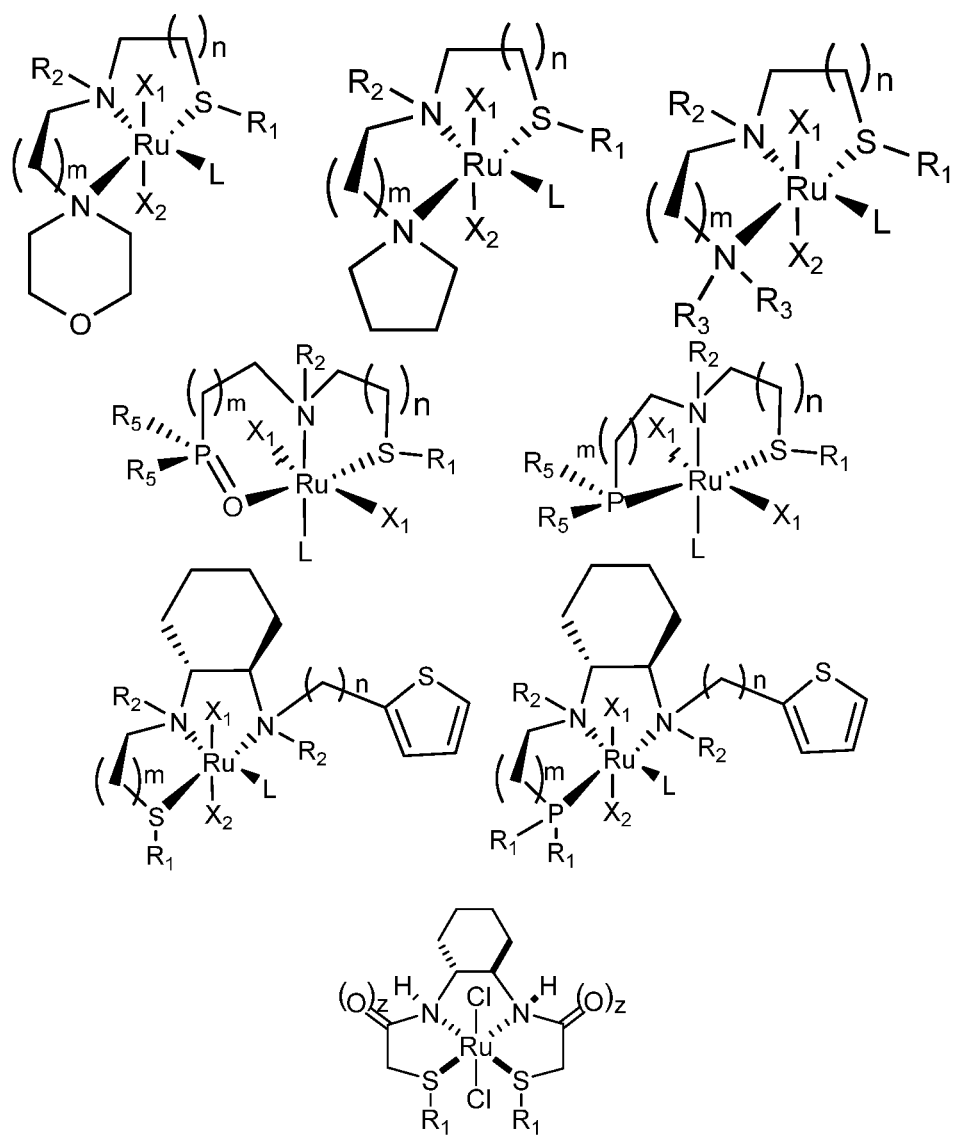
FIG. 3A and FIG. 3B show generic structures of several of the inventive ruthenium catalysts.
Figure 3B:
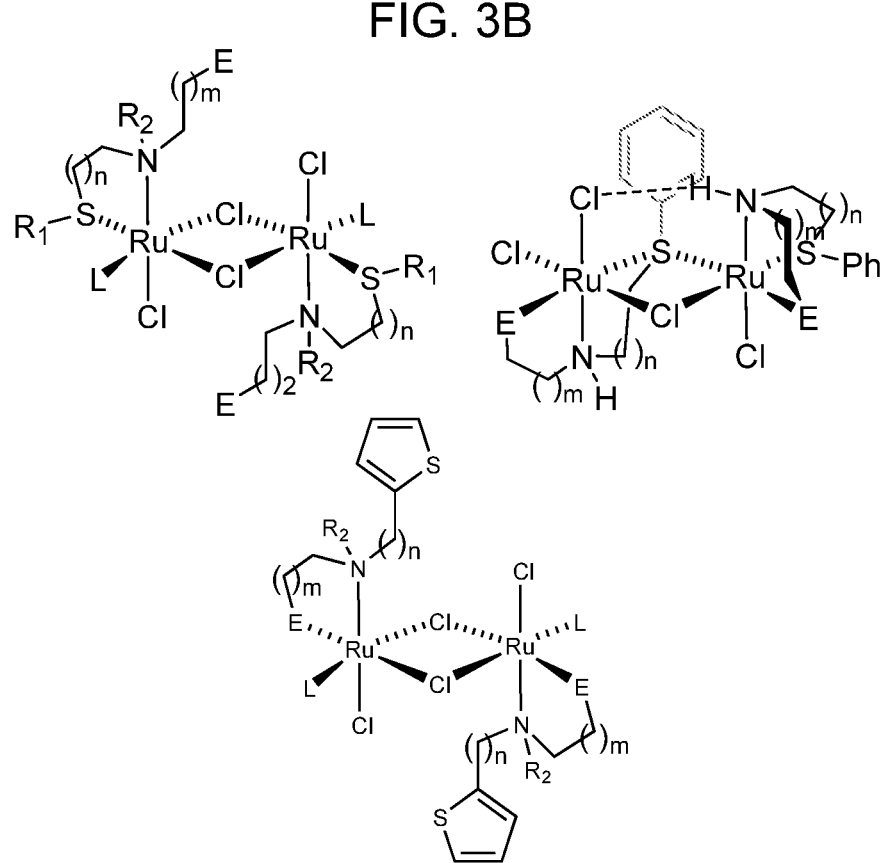
Figure 5:
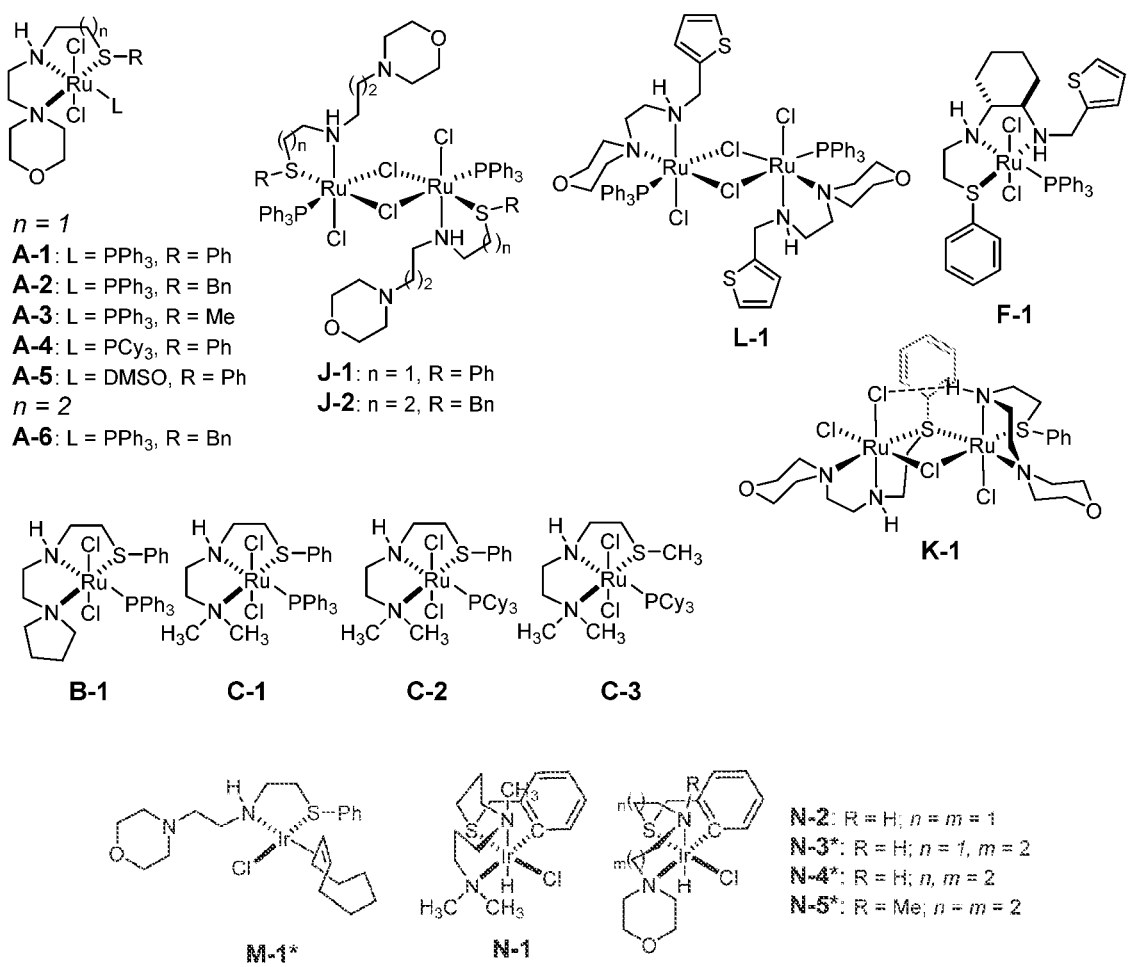
FIG. 5 and FIG. 6 show example structures prepared during the course of this work. An asterisk (*) indicates that the structure has been determined by X-ray crystallography.

Non-limiting examples of related structures are shown in FIGS. 3A, 3B, and 5.

The catalysts represented by structure (J) in which m=2, n=1, L=$PPh_3$, and E is morpholinyl, and structure (K) in which m=n=1 and E is morpholinyl have been characterized crystallographically in the depicted conformations, though other conformers, isomers, or tautomers may exist in solution.

In some embodiments, when the $R_1$ or $R_2$ groups are alkyl or aryl groups and are held in a conformation that places at least one C—H bond near the metal center when the ligand is bound in the metal, the ligand may undergo C—H activation at that C—H bond. As used herein, the term "C—H activation" is used in its art-recognized sense to refer to an organometallic reaction in which the C—H bond is broken in the presence of the metal, and a metal-H and a metal-C bond are formed in its place. In some embodiments, when the $R_1$ or $R_2$ group is an aryl group, the C—H activation may occur at a position ortho- to the heteroatom substituted by the $R_1$ or $R_2$ group, and may be referred to as ortho-metallation. The metal may be any transition metal or post-transition metal capable of this type of reaction, including the second and third row transition metals, for example, ruthenium (Ru), tungsten (W), iridium (Ir), rhodium (Rh), zirconium (Zr), rhenium (Re), osmium (Os), and platinum (Pt).

In some embodiments, the ortho-metallated complex may be seen as (e.g., observed or considered to be) a tautomer of the un-metallated complex. In some embodiments, the ortho-metallated complex and the un-metallated complex may co-exist and their amounts may be related by a chemical equilibrium. It will be understood that unless otherwise stated, descriptions of embodiments including ortho-metallated complexes encompass the corresponding un-metallated complex tautomers as well as mixtures of the two, and vice versa.

In some embodiments, the catalysts may comprise iridium having an empirical formula of $Ir(NNS)X_1L$, $Ir[P(O)NS]X_1L$, $Ir(PNS)X_1L$, $Ir(SNNS)X_1L$, $Ir[SNNP(O)]X_1L$, or $Ir(SNNP)X_1L$, where:

NNS, P(O)NS, PNS, SNNS, SNNP(O), or SNNP refers to a NNS-type, P(O)NS-type, PNS-type, SNNS-type, SNNP(O)-type, or SNNP-type ligand, respectively;

$X_1$ is a formally anionic ligand; and

L is an absent or neutral ligand.

In some embodiments, suitable catalysts for the chemoselective hydrogenation of α,β-unsaturated alcohols may have a structure represented by:

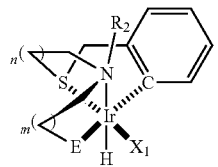

In this embodiment, E may be:

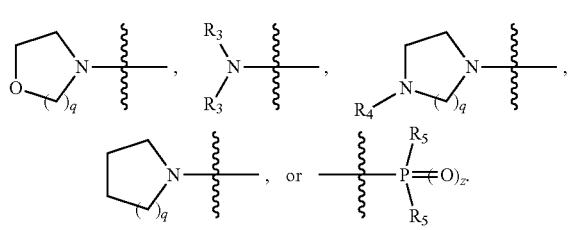

In addition, $R_2$ may be H, Me, Et, BN, or an alkyl group;

$R_3$ and $R_4$ may independently at each occurrence be H, a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, or a substituted or unsubstituted arylalkyl group;

$R_5$ may independently at each occurrence be a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, a substituted or unsubstituted arylalkyl group, a substituted or unsubstituted alkoxy group, or a substituted or unsubstituted aryloxy group;

m may be 1, 2, 3, 4, or 5; n may be 1, 2, 3, 4, or 5; q may be 1, 2, 3, or 4; z may be 0 or 1; and $X_1$ and $X_2$ may each independently be a halide (such as Cl), H, OTf, or $BH_4$.

In some embodiments, the catalysts comprise iridium having an empirical formula $Ir(NNS)X_1L$, where NNS, $X_1$, $X_2$, and L may each be the same as described herein.

In this regard, some non-limiting example embodiments of the structures of the inventive iridium complexes may be represented as:

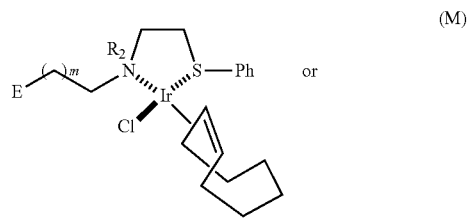

(M)

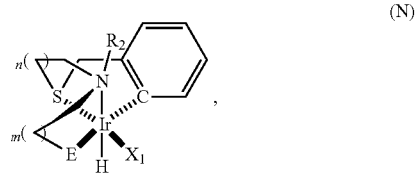

(N)

or isomers thereof, where $R_2$, $X_1$, m, n, and E may each be the same as defined herein. Non-limiting examples of structures may include, for example:

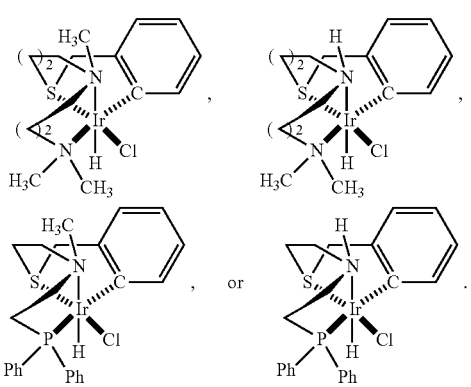

Non-limiting examples of complexes suitable for the chemoselective hydrogenation of α,β-unsaturated alcohols that have been previously isolated include:

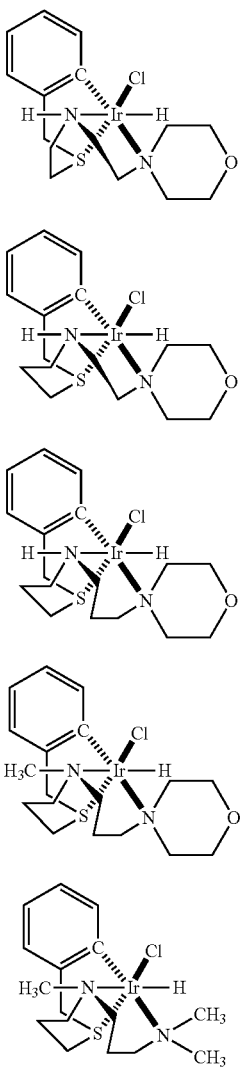

N-2

N-3

N-4

N-5

N-6

Figure 4:
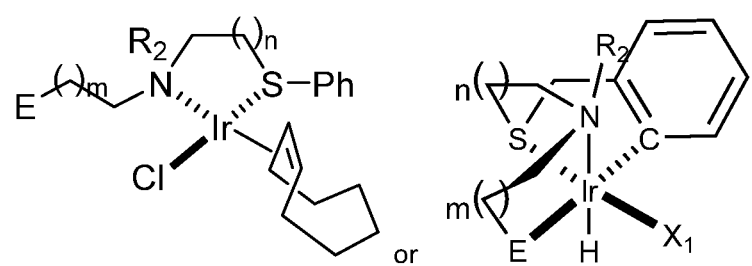
FIG. 4 shows generic structures of several of the inventive iridium catalysts. The various terms are described in the specification.

Additional related structures are shown in FIGS. 4 and 5. In some embodiments, the isomers of these N-structures may include ortho-metallated complexes that are tautomers of the un-metallated complexes and vice versa, as described above, and geometric isomers, for example, structures having ligands positioned differently than shown herein.

In some embodiments in which the organometallic complexes contain PN(H)P-type ligands, the saturated ethylene bridges between the N and P moieties may reversibly hydrogenate/dehydrogenate, converting these bridges to unsaturated ethenylene linkages. See, e.g., Käβ et al., *Angew. Chem. Int. Ed.* 2009, 48, 905, the entire content of which is incorporated herein by reference. Such structures having unsaturated ethenylene linkages would be considered to be tautomers of embodiments of the present disclosure, and are included within the scope of embodiments of the present disclosure.

In some embodiments, m and n may independently be 1, 2, 3, 4, or 5; or a subset thereof;

$X_1$ may be a halide (e.g., chloride), an optionally fluorinated carboxylate group (including trifluoroacetate), H, OTf, or $BH_4$;

$R_2$ may be H, alkyl, arylalkyl, or aryl;

E may be:

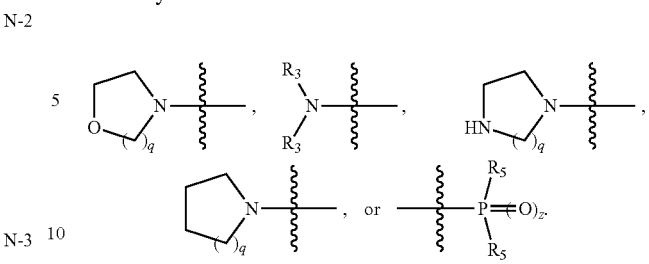

(each of these representing independent embodiments);
each $R_3$ may independently be methyl, ethyl, propyl, isopropyl, 1-butyl, 2-butyl, isobutyl, tert-butyl, benzyl (-Bn), or phenyl (-Ph); and
q may be 1, 2, 3, or 4.

Catalysts represented by structure (M) in which m=n=1 and E is morpholinyl, as well as catalysts represented by structure (N) in which (i) m=2, n=1, $R_2$ is H, and E is morpholinyl, and (ii) m=n=2, E is morpholinyl, and $R_2$ is separately H or methyl, have been characterized crystallographically in the depicted conformations.

In some iridium complexes, as shown above, the species described by these empirical formulae may comprise ortho-metallated ligands. While such complexes are chemically distinct from their non-ortho-metallated conformers, they may also be described as isomers or tautomers of one another.

In the case of at least these ruthenium and iridium complexes, embodiments have been prepared in which L is $-S(=O)(CH_3)_2$, CO, nitrile, or a phosphine such as $-PPh_3$, $-PCy_3$, $-PMe_3$, $-P^iPr_3$, $-P^tBu_3$, or $-PPh_3$. In some embodiments, when the catalyst is an iridium complex, L is an olefin or a cycloolefin, for example, cyclooctene.

In addition to the ortho-metallation described above, in some embodiments, the transition metal coordination complex may be capable of oxidatively adding $H_2$, a dihalogen (e.g., $Cl_2$, $Br_2$, $I_2$), a carboxylic acid (e.g., acetic acid, trifluoroacetic acid, or benzoic acid), a hydrogen halide (e.g., HCl, HBr, or HI), an alkyl or benzyl halide (e.g., MeI), and dioxygen, as such reactions are known in the art, and the resulting oxidative adducts are considered to be within the scope of embodiments of the present disclosure.

All of the catalysts described elsewhere herein (including in the Examples), including isomers, tautomers, or N-alkylated, N-arylated, and N-aralkylated derivatives thereof, are to be considered as being included within the scope of embodiments of the present disclosure.

Catalytic Reactions

One or more embodiments of present disclosure are also directed to the use of these coordination complexes or catalysts for the hydrogenation of selected substrates, and to methods of affecting (e.g., controlling) these transformations. These hydrogenation reactions may use dihydrogen or formic acid as the source of the hydrogen in these transformations, and the catalyst may be present in the corresponding reaction mixture either as delivered to (e.g., in the reactant form provided to) the reaction or as derived in situ under the reaction conditions.

In some embodiments, the methods comprise reacting an organic substrate having at least one unsaturated bond with a source of hydrogen (e.g., dihydrogen, a secondary alcohol, formic acid, or a combination thereof) in the presence of one of the inventive catalysts, under reaction conditions sufficient or suitable for hydrogenating one or more of the unsaturated bond(s). The unsaturated bond(s) of the organic substrate may independently be at least one of an >C=C< (alkenyl), —C≡C— (alkynyl), >C=O (carbonyl), >C=N— (imino), —C≡N (nitrile), —N=O (nitroso), or —N=N— (azo) bond. In such cases, the organic substrate having the unsaturated C=C, C=O, or C=N bond may comprise an aldehyde, ketone, an imine, an imide, a carboxylic acid, an acid anhydride, an ester, an amide (carboxamide), a carbonic anhydride ester (carbonate), a carbamic acid ester (carbamate), and/or a urea functional group. Organic carbonyl and/or imine double bonds may be attractive substrates for these catalysts. The unsaturated bonds may be functionalized or non-functionalized, conjugated or non-conjugated. Other bifunctional catalysts have been shown to exhibit exceptionally high C=O/C=C chemoselectivity, and similar selectivity can reasonably be expected with the inventive catalysts described herein. As used herein, the term "C=O/C=C chemoselectivity" is used in its art-recognized sense to refer to an ability to preferentially and selectivity react with the C=O bond but not the C=C bond of a substrate.

In some embodiments, such as those in which the catalysts are bifunctional (e.g., include ligands with NH functionalities), the catalysts independently catalyze the hydrogenation of ketones and imines. In some embodiments when the catalysts include chiral ligands, the catalysts may be used for asymmetric ketone hydrogenation and stereoselective catalytic C—N_ENREF_42 and C—C bond-forming reactions (e.g., aziridination of alkenes). In some embodiments, the catalysts may be used for the asymmetric transfer hydrogenation of ketones and imines, asymmetric hydrogenation of polar functionalities (functional groups), asymmetric Michael reaction of 1,3-dicarbonyl compounds with cyclic enones and nitroalkenes, aerobic oxidative kinetic resolution of racemic secondary alcohols (e.g., stereoselective synthesis of secondary alcohols), and asymmetric hydration of nitriles. In some embodiments, the catalysts may also be useful for reactions of $CO_2$, carbonates, ester hydrogenation, and various acceptorless dehydrogenations. Under suitable conditions, these catalysts may act as pre-catalysts for $CO_2$ hydrogenation and electroreduction, ester hydrogenation, ketone transfer hydrogenations, the solvolysis of ammonia borane, and the amination of aliphatic alcohols. ENREF 67

In some embodiments, the methods comprise reacting carbon dioxide, an adduct thereof, or a hydration or alcoholic product thereof (e.g., a carbonate) with a source of hydrogen (typically dihydrogen) in the presence of one of the inventive catalysts, under reaction conditions sufficient to hydrogenate the unsaturated bond.

In some embodiments, these reactions may be conducted in polar or non-polar solvents in the presence of base co-catalysts. Non-limiting examples of such solvents may include aromatic hydrocarbons (aryl or heteroaryl solvents), alcohols, nitriles, ethers, or even water (see Examples for additional non-limiting examples). The solvents may be selected so as to provide a system (e.g., reaction environment) in which at least a portion, and in some embodiments all of the catalyst, the co-catalyst, the source of hydrogen, and/or the substrate are dissolved to thus form a solution capable of affecting the desired transformation on an appropriate timescale. The reactions may be conducted in such solvents at even mild temperatures and moderate pressures. Example operating temperature ranges include ranges from about 10° C. to about 15° C., from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., from about 85° C. to about 90° C., from about 90° C. to about 95° C., from about 95° C. to about 100° C., from about 100° C. to about 120° C., from about 120° C. to about 140° C., from about 140° C. to about 160° C., from about 160° C. to about 180° C., from about 180° C. to about 200° C., or any combination of these ranges, for example, from about 20° C. to about 100° C., from about 25° C. to about 60° C., and from about 35° C. to about 50° C. Example operating pressure ranges include those ranges from about 1 bar to about 2 bar, from about 2 bar to about 3 bar, from about 3 bar to about 4 bar, from about 4 bar to about 5 bar, from about 5 bar to about 10 bar, from about 10 bar to about 15 bar, from about 15 bar to about 20 bar, from about 20 bar to about 25 bar, from about 25 bar to about 30 bar, from about 30 bar to about 40 bar, from about 40 bar to about 50 bar, or any combination of these ranges, for example, from about 2 bar to about 50 bar, and from about 5 bar to about 25 bar, where "bar" expresses units of absolute pressure. In the case of hydrogen (e.g., when the reaction includes hydrogen at the above pressures), these conditions may provide sufficient dissolution or concentration of hydrogen in most solvents to provide a reaction mixture having convenient turnover rates.

Figure 8:
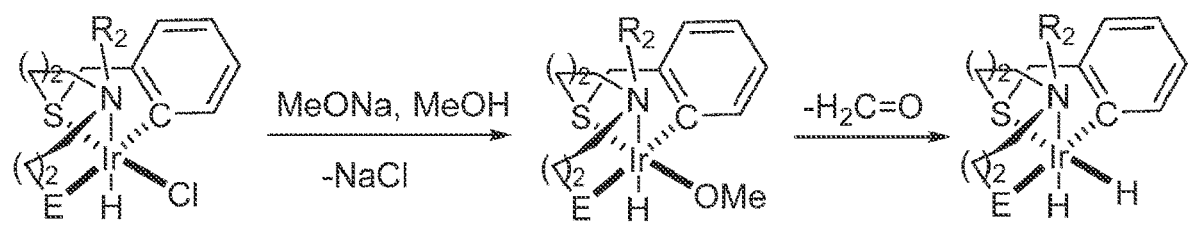
FIG. 8 shows a potential mechanism for the conversion of iridium chloride catalysts to a proposed iridium dihydride intermediate generated under hydrogenation conditions.

A basic co-catalyst may be useful in imparting catalytic activity. In some embodiments, a basic co-catalyst may be used with the bifunctional complexes. Good success has been achieved using alkoxide bases, for example sodium methoxide, though it will be understood that other alkali metal and alkaline earth metal alkoxides, including isopropoxides and tert-butoxides may also work. Without intending to be bound by the correctness or incorrectness of any particular theory, the alkoxide anion may activate the transition metal catalyst by displacing other anionic ligands. (see, e.g., FIG. 8).

The catalysts appear to be usefully active, especially those based on ruthenium and iridium, and good success has been achieved under these conditions where the substrate to catalyst ratio is in a range of from about 1000:1 to about 50,000:1, though embodiments of the present disclosure are not necessarily limited to these conditions.

The following listing of embodiments is intended to complement, rather than displace or supersede, the previous descriptions.

Embodiment 1

A ligand having a structure of Formula (I), Formula (II), Formula (III), or Formula (IV):

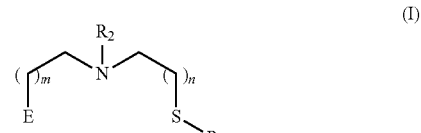

(I)

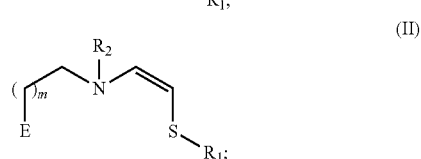

(II)

-continued

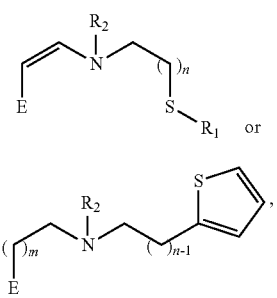

in which E is:

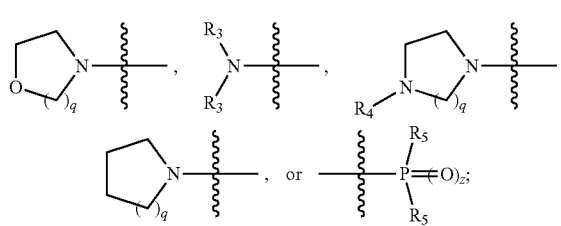

R$_1$ is independently at each occurrence a substituted or unsubstituted C$_{1-6}$ alkyl group, a substituted or unsubstituted C$_{3-6}$ cycloalkyl group, a substituted or unsubstituted aryl group, a substituted or unsubstituted heteroaryl group, or a substituted or unsubstituted arylalkyl group;

R$_2$, R$_3$, and R$_4$ are independently at each occurrence H, a substituted or unsubstituted C$_{1-6}$ alkyl group, a substituted or unsubstituted C$_{3-6}$ cycloalkyl group, a substituted or unsubstituted aryl group, a substituted or unsubstituted heteroaryl group, or a substituted or unsubstituted arylalkyl group;

R$_5$ is independently at each occurrence a substituted or unsubstituted C$_{1-6}$ alkyl group, a substituted or unsubstituted C$_{3-6}$ cycloalkyl group, a substituted or unsubstituted aryl group, a substituted or unsubstituted heteroaryl group, a substituted or unsubstituted arylalkyl group, a substituted or unsubstituted alkoxy group, or a substituted or unsubstituted aryloxy group;

m is 1, 2, 3, 4, or 5; n is 1, 2, 3, 4, or 5; q is 1, 2, 3, or 4; and z is independently 0 or 1.

In some embodiments, R$_2$ is not H.

In some embodiments, one or more of the following compounds may be individually or collectively, in any subset permutation, excluded from the genus of Formula (I):

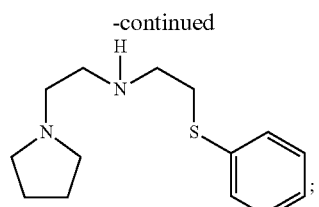

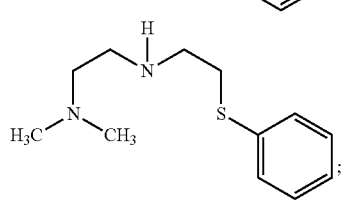

-continued

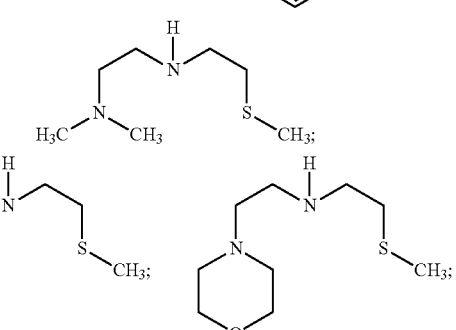

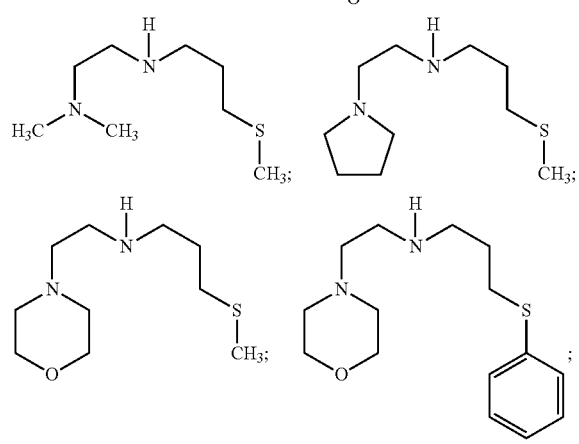

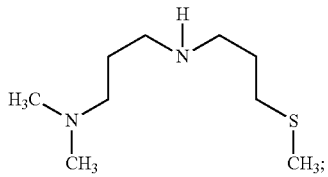

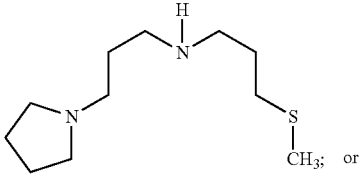

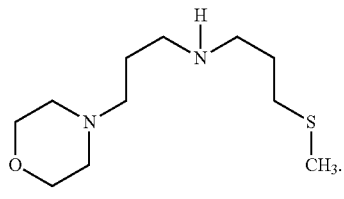

Aspects of this embodiment exclude the independent compounds of Formula (I) in which m=n=1, $R_1$ is phenyl, and E is morpholinyl, piperazinyl, pyrrolidinyl, or dimethylamino.

In some embodiments, the compounds of Formula (I) in which m is independently 1 or 2, n is independently 1 or 2, and $R_1$ is independently phenyl or methyl are excluded from the scope of embodiments of the present disclosure.

In some embodiments of the compounds of Formula (I), when m=1 or 2, n=1 or 2, then E is

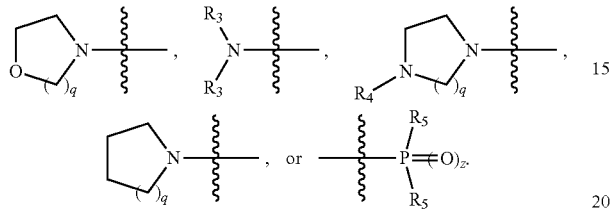

In some embodiments of the compounds of Formula (I), when m is independently 1 or 2, n is independently 1 or 2, R is independently methyl or phenyl, and E is independently morpholinyl, piperazinyl, and pyrrolidinyl, or dimethylamino, then $R_2$ is not H. The scope of the above embodiments includes the salts of these compounds.

Embodiment 2

A ligand having a structure of Formula (V), Formula (VI), Formula (VII), Formula (VIII), Formula (IX), or Formula (X):

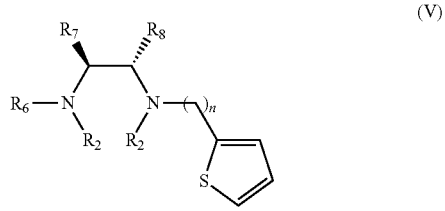

(V)

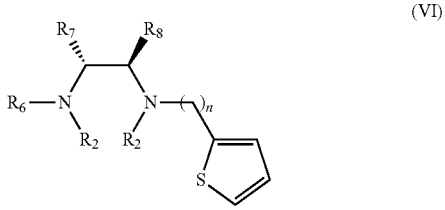

(VI)

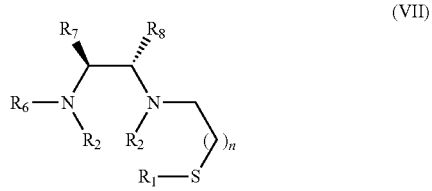

(VII)

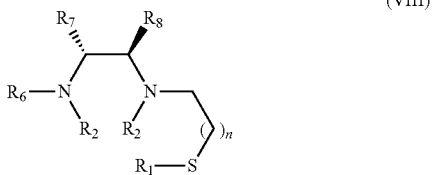

(VIII)

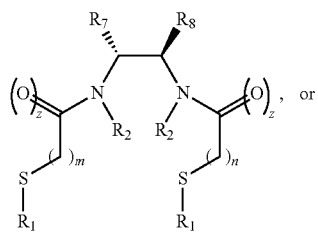

(IX)

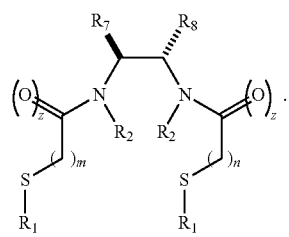

(X)

or an achiral isomer, enantiomer, diastereomer, isomeric mixture, and/or salt thereof, in which:

$R_1$, $R_2$, $R_5$, n, and z are the same as defined in Embodiment 1;

$R_6$ is H, $-(CH_2)_n-S-R_1$, $-(CH_2)_n$-(2-thiophenyl), or $-(CH_2)_n-P(O)_z(R_5)_2$; and $R_7$ and $R_8$ are independently H, a substituted or unsubstituted $C_{1-6}$ alkyl group, a substituted or unsubstituted aryl or heteroaryl group, or a substituted or unsubstituted arylalkyl group, or are connected via a bridging group to form a 5-7 membered cyclic or heterocyclic ring including the carbons to which they are bound, provided that only one of $R_7$ and $R_8$ is H.

Embodiment 3

The ligand of Embodiment 2, in which $R_7$ and $R_8$ are connected via a bridging group to form an substituted or unsubstituted cyclopentyl, cyclohexyl, [1,4]dioxanyl, or [1,3]dioxolanyl ring, each including the carbons to which $R_7$ and $R_8$ are bound.

Embodiment 4

The ligand of any one of Embodiments 1 to 3, in which $R_1$ is methyl, phenyl, or benzyl.

Embodiment 5

The ligand of any one of Embodiments 1 to 4, in which $R_2$ is H, methyl, phenyl, or benzyl.

Embodiment 6

The ligand of any one of Embodiments 1 to 5, in which $R_2$ is H.

Embodiment 7

The ligand of any one of Embodiments 1 to 5, in which $R_2$ is not H. In some aspects of this Embodiment, $R_2$ is methyl.

Embodiment 8

The ligand of any one of Embodiments 1 to 7, in which $R_3$ is independently methyl, ethyl, propyl, isopropyl, 1-butyl, 2-butyl, isobutyl, tert-butyl, benzyl (-Bn), or phenyl (-Ph).

Embodiment 9

The ligand of any one of Embodiments 1 to 8, in which $R_5$ is a substituted or unsubstituted phenyl group. In some aspects of this Embodiment, $R_5$ is an unsubstituted phenyl.

Embodiment 10

The ligand of any one of Embodiments 1 to 9, in which E is oxazolidinyl, morpholinyl, imidazolidinyl, N-methyl-imidazolidinyl, piperazinyl, N-methyl-piperazinyl, aziridinyl, azetidinyl, pyrrolidinyl, piperidinyl, dimethylamino, diethylamino, ethylmethylamino, diarylphosphine or diarylphosphine oxide, dialkylphosphine or dialkylphosphine oxide, alkylarylphosphine or alkylarylphosphine oxide, diarylphosphite or diarylphosphate, dialkylphosphite or dialkylphosphate, or alkylarylphosphite or alkylarylphosphate.

Embodiment 11

The ligand of any one of Embodiments 1 to 10, in which m and n are 1.

Embodiment 12

The ligand of Embodiment 11, in which $R_1$ is methyl or benzyl.

Embodiment 13

The ligand of any one of Embodiments 1 to 10 or 12, in which m is 2, 3, 4, or 5 and n is 1.

Embodiment 14

The ligand of any one of Embodiments 1 to 10, in which m and n are independently 2, 3, 4, or 5.

Embodiment 15

The ligand of Embodiment 1 or any one of Embodiments 4 to 10, as applied to claim 1, having a structure of Formula (IV).

Embodiment 16

The ligand of Embodiment 1 or 15, or any one of Embodiments 4 to 10, as applied to claim 1, having a structure of Formula (IV), in which n is 2.

Embodiment 17

The ligand of Embodiment 1 having a structure of:

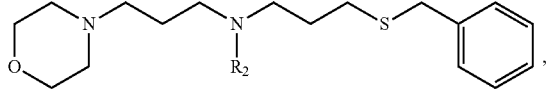

-continued

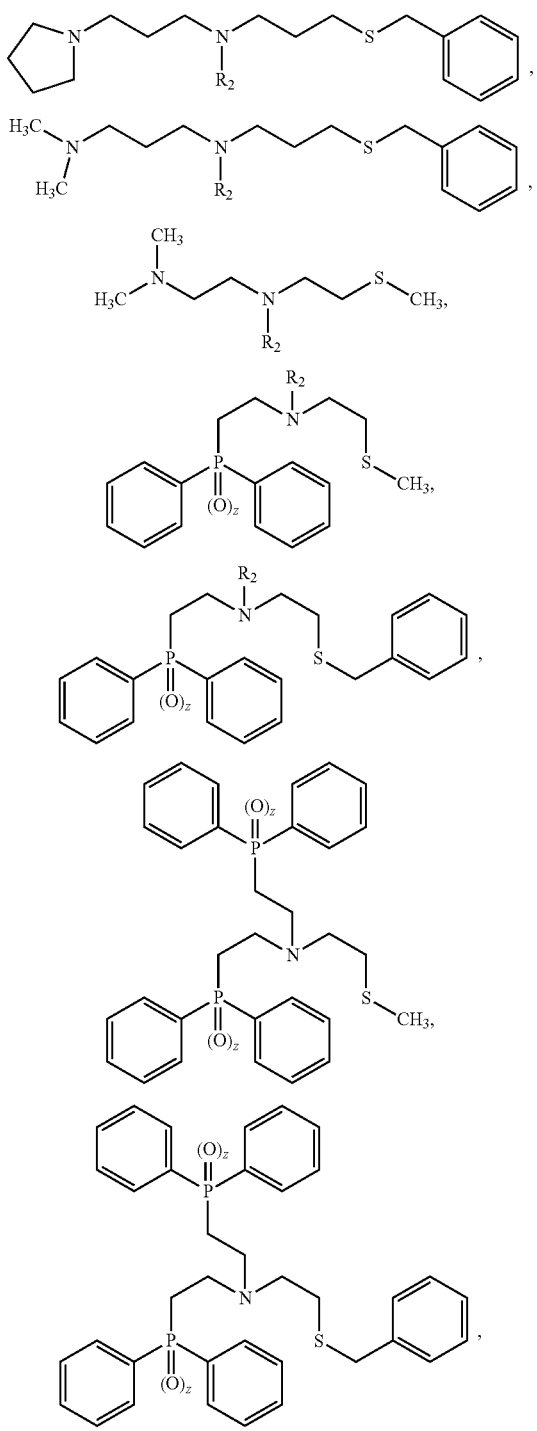

or the ligand of Embodiment 2 having a structure of:

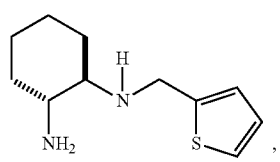

-continued

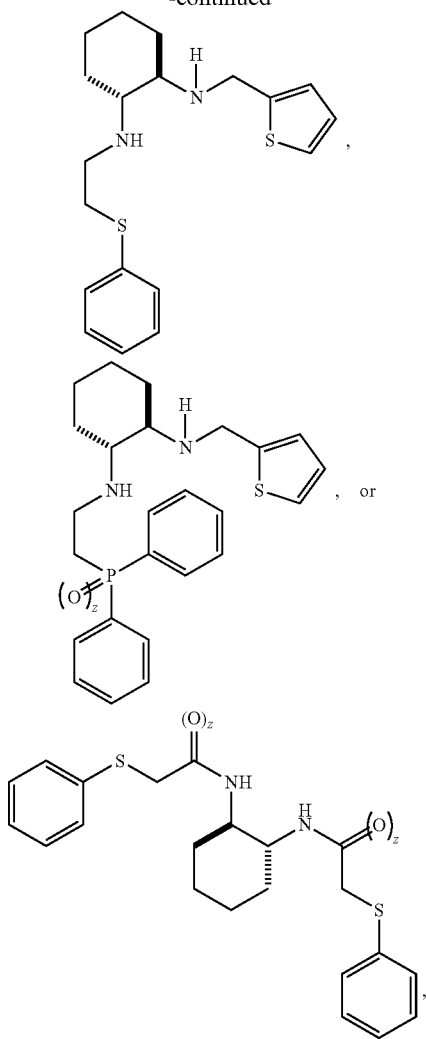

in which z is 0 or 1. In some aspects, $R_2$ may independently be H or methyl.

Embodiment 18

A coordination complex comprising a ligand coordinated to at least one transition metal, in which the ligand is at least one compound of Formulae (I) to (IV) of Embodiment 1 or any one of Embodiments 4 to 17, as applied to Embodiment 1.

Embodiment 19

A coordination complex comprising a ligand coordinated to at least one transition metal, in which the ligand is at least one compound of Formulae (V) to (X) of Embodiment 2, or any one of Embodiments 3 to 17, as applied to Embodiment 2.

Embodiment 20

The coordination complex of Embodiment 18 or 19, in which the transition metal comprises at least one of the Group 4 to Group 12 transition metals, for example, one of the Group 6 to Group 11 transition metals]

Embodiment 21

The coordination complex of Embodiment 18 or 19, in which the transition metal comprises at least one of Ti, V, Zr, Hf, Cr, Mo, W, Mn, Re, Fe, Ru, Os, Co, Rh, Ir, La, Ni, Pd, Pt, Cu, Ag, Au, or Zn, for example, Cr, Co, Cu, Fe, Mn, Mo, Ni, Os, Pd, Rh, Sm, or W.

Embodiment 22

The coordination complex of Embodiment 18 or 19, in which the transition metal is ruthenium or iridium.

Embodiment 23

The coordination complex of Embodiment 22, in which the transition metal is ruthenium, the complex having an empirical formula $Ru(NNS)X_1X_2L$, $Ru[P(O)NS]X_1X_2L$, $Ru(PNS)X_1X_2L$, $Ru(SNNS)X_1X_2L$, $Ru[SNNP(O)]X_1X_2L$, or $Ru(SNNP)X_1X_2L$, where NNS, P(O)NS, PNS, SNNS, SNNP(O), or SNNP is a NNS-type, P(O)NS-type, PNS-type, SNNS-type, SNNP(O)-type, or SNNP-type, respectively;

$X_1$ and $X_2$ are independently formally anionic ligands; and

L is absent or a neutral ligand. In specific aspects of this Embodiment, the complex has an empirical formula of $Ru(NNS)X_1X_2L$.

Embodiment 24

The coordination complex of Embodiment 22, in which the transition metal is iridium, the complex having an empirical formula $Ir(NNS)X_1L$, $Ir[P(O)NS]X_1L$, $Ir(PNS)X_1L$, $Ir(SNNS)X_1L$, $Ir[SNNP(O)]X_1L$, or $Ir(SNNP)X_1L$, where NNS, P(O)NS, PNS, SNNS, SNNP(O), or SNNP is a NNS-type, P(O)NS-type, PNS-type, SNNS-type, SNNP(O)-type, or SNNP-type, respectively;

$X_1$ is a formally anionic ligand; and

L is a neutral ligand. In specific aspects of this Embodiment, the complex has an empirical formula of $Ir(NNS)X_1L$.

Embodiment 25

The coordination complex of Embodiment 23 or 24, in which $X_1$ and $X_2$ are independently a substituted or unsubstituted alkyl group, a substituted or unsubstituted aryl group, a substituted or unsubstituted alkoxy group, substituted or unsubstituted aryloxy group, a carboxylate group, a fluorinated carboxylate group, a halide (including fluoride, chloride, bromide, iodide), a hydride, a hydroxide, NO, OTf (triflate), OTs (tosylate), phosphate, or $BH_4$. In some aspects of this embodiment, $X_1$ and $X_2$ are independently alkoxy, fluorinated carboxylate, halide, hydride, NO, OTf (triflate), OTs (tosylate), or $BH_4$.

Embodiment 26

The coordination complex of any one of Embodiments 23 to 25, in which at least one of $X_1$ and $X_2$ is chloro.

Embodiment 27

The coordination complex of any one of Embodiments 23 to 26, in which L is absent, an alkyl or aryl nitrile, an alkyl or aryl amine, carbonyl, an alkyl or aryl ether, an alkyl or aryl phosphine, an alkyl or aryl phosphine oxide, an alkyl or aryl phosphite, an alkyl or aryl phosphate or an alkyl or aryl sulfoxide.

Embodiment 28

The coordination complex of any one of Embodiments 23 to 27, in which L is —S(=O)(CH$_3$)$_2$, CO, —PPh$_3$, —PCy$_3$, —PMe$_3$, —P$^r$Pr$_3$, —P$^r$Bu$_3$, or —PPh$_3$.

Embodiment 29

The coordination complex of Embodiment 22 or any one of Embodiments 25 to 28 as applied to claim 18, in which the coordination complex is a dinuclear complex of ruthenium.

Embodiment 30

The coordination complex of any one of Embodiments 24 to 26, in which L is an olefin.

Embodiment 31

The coordination complex of Embodiment 30, in which L is cyclooctene.

Embodiment 32

An oxidative addition product of the coordination complex of any one of Embodiments 23 to 29.

Embodiment 33

The oxidative addition product of Embodiment 32, derived from the addition of H$_2$, dihalogen, hydrogen carboxylate (e.g., carboxylic acid), hydrogen halide, and/or alkyl halide to a corresponding precursor coordination complex. In some aspects of this Embodiment, the oxidative addition product is derived from the addition of HCl, HBr, HI, Cl$_2$, Br$_2$, I$_2$, MeI, acetic acid, benzoic acid, and/or trifluoroacetic acid to the complex.

Embodiment 34

The coordination complex of Embodiment 18 or 19, characterized as having a structure of any one of the compounds of FIG. 3A, FIG. 3B, or FIGS. 4-8, or an isomer or tautomer thereof.

Embodiment 35

A method comprising reacting an organic substrate having at least one unsaturated >C=C< (alkenyl), —C≡C— (alkynyl), >C=O (carbonyl), >C=N— (imino), —C≡N (nitrile), —N=O (nitroso), or —N=N— (azo) bond with dihydrogen in the presence of a catalyst under reaction conditions sufficient or suitable to reduce the unsaturated bond by the addition of dihydrogen across the unsaturated bond, the catalyst being derived in situ from the presence of coordination complex of any one of Embodiments 18 to 34 under the reaction conditions.

Embodiment 36

A method comprising reacting an organic substrate having at least one unsaturated >C=C< (alkenyl), —C≡C— (alkynyl), >C=O (carbonyl), >C=N— (imino), —C≡N (nitrile), —N=O (nitroso), or —N=N— (azo) bond with formic acid in the presence of a catalyst under reaction conditions sufficient or suitable to reduce the unsaturated bond by the addition of dihydrogen across the unsaturated bond, the catalyst being comprising a coordination complex of any one of Embodiments 18 to 34 or derived in situ from the presence of coordination complex of any one of Embodiments 18 to 34 under the reaction conditions.

Embodiment 37

The method of Embodiment 35 or 36, in which the unsaturated bond is a carbonyl or imine double bond.

Embodiment 38

The method of any one of Embodiments 35 to 37, in which the organic substrate having the unsaturated C=C, C=O, or C=N bond comprises a ketone, an imine, an imide, a carboxylic acid, an acid anhydride, an ester, an amide (carboxamide), a carbonic anhydride ester (carbonate), a carbamic acid ester (carbamate), or a urea functional group.

Embodiment 39

A method comprising reacting carbon dioxide as a substrate with dihydrogen in the presence of a catalyst, the catalyst comprising a coordination complex of any one of Embodiments 18 to 34 or derived in situ from the coordination complex of any one of Embodiments 18 to 34, under reaction conditions sufficient or suitable to reduce the carbon dioxide by the addition of dihydrogen thereto.

Embodiment 40

The method of any one of Embodiments 35 to 39, in which the conditions sufficient or suitable to reduce the carbon dioxide or the unsaturated bond comprise reacting the substrate, the catalyst, and the dihydrogen in the presence of a solvent and a strong base.

Embodiment 41

The method of Embodiment 40, in which the strong base is an alkali metal or alkaline earth metal alkoxide, for example, a methoxide, isopropoxide, or tert-butoxide.

Embodiment 42

A method comprising reacting a primary or secondary alcohol (including but not limited to methanol, ethanol, propanol, or isopropanol) in the presence of a catalyst under reaction conditions sufficient or suitable to dehydrogenate the primary or secondary alcohol, the catalyst comprising a coordination complex of any one of Embodiments 18 to 34 or derived in situ from the coordination complex of any one of Embodiments 18 to 34 under the reaction conditions.

Embodiment 43

A method comprising reacting a primary or secondary alcohol (including but not limited to methanol, ethanol, propanol, or isopropanol) in the presence of a catalyst under reaction conditions sufficient or suitable to dehydrogenate the primary or secondary alcohol, the catalyst comprising a coordination complex of any one of Embodiments 18 to 34 or derived in situ from the coordination complex of any one of Embodiments 18 to 34 under the reaction conditions.

Embodiment 44

A method comprising reacting an alkene substrate and appropriate reactant(s) (as is known in the art), in the presence of a catalyst, under reaction conditions sufficient or suitable to form a cycloalkyl (e.g., cyclopropyl) or aziridine moiety, the catalyst comprising a coordination complex of any one of Embodiments 18 to 34 or derived in situ from the coordination complex of any one of Embodiments 18 to 34 under the reaction conditions.

Embodiment 45

A method comprising reacting a nitrile, a borane, or an aliphatic alcohol, in the presence of a catalyst, under reaction conditions sufficient or suitable to hydrate the nitrile, solvate the borane, or aminate the alcohol, respectively, the catalyst comprising a coordination complex of any one of Embodiments 18 to 34 or derived in situ from the coordination complex of any one of Embodiments 18 to 34 under the reaction conditions.

Embodiment 46

The coordination complex of Embodiment 24, in which the complex is present in an ortho-metallated tautomer form.

Embodiment 47

A method comprising reacting an α,β-unsaturated ketone in the presence of a catalyst, under reaction conditions sufficient or suitable to chemoselectively hydrogenate the ketone C=O bond, the catalyst comprising a coordination complex of any one of Embodiments 23 to 24 or derived in situ from the coordination complex of any one of Embodiments 23 to 24 under the reaction conditions.

Embodiment 48

The method of Embodiment 47, in which the α,β-unsaturated ketone is one of the following:

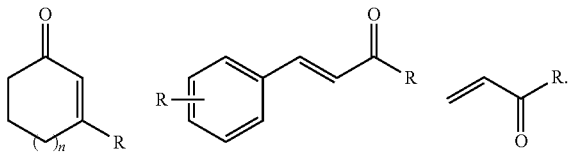

EXAMPLES

The following Examples are provided to illustrate some of the concepts described within this disclosure. While each Example describes specific embodiments regarding the composition, methods of preparation, and methods of use, it will be understood that the Examples do not limit the more general embodiments described herein.

In the following examples, efforts have been made to ensure accuracy with respect to numbers used (e.g. amounts, temperature, etc.), but some experimental error and deviation should be accounted for in the reported values. Unless indicated otherwise, temperature is reported in degrees Celsius, and pressure is assumed to be at or near atmospheric pressure (1 bar).

Example 1. Materials and Methods

Phosphorus tribromide (99%, CAS Number 7789-60-8), 2-(phenylthio)ethanol (99%, CAS Number 699-12-7), 2-(methylthio)ethanol (99%, CAS Number 5271-38-5), ethylene sulfide (98%, CAS Number 420-12-2), trimethylene sulfide (≥96.0%, CAS Number 287-27-4), 2-(4-morpholinyl)ethanamine (99%, CAS Number 2038-03-1), 3-morpholinopropylamine (CAS Number 123-00-2), 1-(2-aminoethyl)pyrrolidine (98%, CAS Number 7154-73-6), 1-(2-aminoethyl)piperazine (99%, CAS Number 140-31-8), 2-chloroethyl methyl sulfide (97%, CAS Number 542-81-4), 2-thiophenecarbaldehyde (98%, CAS Number 98-03-3), (1R,2R)-(−)-1,2-diaminocyclohexane ((R,R)-DACH, 98%, CAS Number 20439-47-8), diphenylvinylphosphine (95%, CAS Number 2155-96-6), $H_2O_2$ (30 wt. % in $H_2O$, CAS Number 7722-84-1), and (2-methylthio)ethylamine (97%, CAS Number 18542-42-2) were purchased from Sigma Aldrich and used as received or purified by distillation in the case of selected liquids (see experimental procedures). Benzyl bromide (99%, CAS Number 100-39-0) was purchased from Alfa Aesar. N,N-dimethylethylenediamine (>97.0%, CAS Number 108-00-9) was purchased from TCI. Anhydrous potassium carbonate (≥99.0%) was purchased from Fisher Scientific. Sodium methoxide (95%, powder, CAS Number 124-41-4) was purchased from Sigma Aldrich. (Phenylsulfanyl)acetaldehyde (CAS Number 66303-55-7) was synthesized as described in J. Org. Chem. 1995, 60, 1276. All solvents for organic synthesis were purchased from Sigma Aldrich and used as received.

All syntheses of organometallic complexes were performed in an MBraun Labmaster 130 glovebox under an argon atmosphere. Dichloromethane (anhydrous, ≥99.8%, Sigma Aldrich), toluene (anhydrous, 99.8%, Sigma-Aldrich), THF (anhydrous, ≥99.9%%, Sigma Aldrich), diethyl ether (anhydrous, ≥99.7%, Sigma Aldrich), pentane (anhydrous, ≥99%, Sigma Aldrich), methanol (anhydrous, 99.8%, Sigma Aldrich), acetonitrile (anhydrous, 99.8%, Sigma Aldrich), absolute ethanol (≥99.5%, Sigma Aldrich), [$RuCl_2$(PPh$_3$)$_3$] (97%, CAS Number 15529-49-4, Sigma Aldrich), [$RuCl_2$($\eta^4$-COD)], (97%, CAS Number 50982-12-2, STREM), [$RuCl_2$(DMSO)$_4$] (96%, CAS Number 89395-66-4, Sigma Aldrich), [IrCl($\eta^2$-COE)$_2$]$_2$ (97%, CAS Number 12246-51-4, Sigma Aldrich), $MnCl_2$ (≥99%, Sigma Aldrich), $FeCl_2$ (98%, Sigma Aldrich), $CoCl_2$ (97%, Acros Organics), $NiCl_2$ (98%, Acros Organics), $CuCl_2$ (≥99.995%, Sigma Aldrich), Ru-MACHO (739103 Aldrich), Gusev's Ru—SNS (97%, 746339 Aldrich), Milstein's Ru—PNN (735809 Aldrich), (R,R)-Ts-DENEB (T3078, TCI), (R)—RUCY-XylBINAP (R0139, TCI), and Abdur-Rashid's Ir—PNP (min 98%, 77-0500 Strem) were purchased from the above manufacturers and used as received.

Elemental Analyses were performed by Midwest Microlab, LLC (Indianapolis, Ind. 46250) under air or under an inert atmosphere of nitrogen or argon, depending on the sensitivity of the compound being analyzed. All NMR experiments were carried out using a Bruker AV400 MHz spectrometer. $^1H$ and $^{13}C\{^1H\}$ NMR spectra were calibrated using the residual deuterated solvent signal relative to TMS in ppm (δ). $^{19}F$ NMR spectra were measured without lock but properly shimmed in methanol and calibrated relative to 2,2,2-trifluoroethanol (product C), with δ set at −77.0 ppm. Magnetic susceptibility measurements (Gouy balance, Sherwood Scientific, r.t.) were performed with diamagnetic correction. X-Ray data for compound C-2 were collected on a Bruker D8 Quest diffractometer equipped with CMOS detector in shutterless mode. The crystal was cooled to 100 K employing an Oxford Cryostream liquid nitrogen cryostat. Data for compounds F-1, D-1, Cu-4, Cu-5 and Cu-8 were collected on a Bruker D8 diffractometer equipped with an APEX II CCD detector. The crystals were cooled to 140 K using a Bruker Kryoflex liquid nitrogen cryostat. Both instruments employed graphite monochromatized MoKa (A=0.71073 Å) radiation. For Cu-8, disordered acetonitrile and pentane solvent molecules were modeled with Platon/Squeeze (4 acetonitrile and 1 pentane solvent per copper dimer). For D-1, a disordered dichloromethane solvent molecule was refined in two partial occupancy positions. The structures F-1, Cu-4, Cu-5, and Cu-8 had disordered thiophene moieties that were refined in two partial occupancy positions. Cell indexing, data collection, integration, structure solution, and refinement were performed using Bruker and Shelxtl software.

2-Bromoethyl phenyl sulfide ($PhSCH_2CH_2Br$), 2-bromoethyl methyl sulfide ($MeSCH_2CH_2Br$), 2-bromoethyl benzyl sulfide ($BnSCH_2CH_2Br$), and 3-bromopropyl benzyl sulfide ($BnCH_2CH_2CH_2Br$) were prepared as described below, and shown in Scheme 1.

Synthesis of 2-bromoethyl phenyl sulfide (CAS Number 4837-01-8)

2-(phenylthio)ethanol (30 mL, 0.222 mol) was cooled using an ice bath. Phosphorus tribromide (7.1 mL, 0.076 mol) was carefully added dropwise to the now cold 2-(phenylthio)ethanol with stirring over the period of 15 min (the reaction is exothermic). The resulting solution was stirred at room temperature for another 30 min. The reaction was partitioned between 100 mL of ether and 50 mL of water. The organic phase was separated, dried over $MgSO_4$, and filtered, and the solvent was removed by evaporation to give 44.7 g of the crude product, which was then purified by vacuum distillation. Yield: 43.6 g (91%).

Synthesis of 2-bromoethyl methyl sulfide (CAS Number 54187-93-8)

Phosphorus tribromide (6.6 mL, 0.070 mol) was carefully added dropwise to 2-(methylthio)ethanol with stirring (19.39 g, 0.210 mol) over the period of 60 min (the reaction is exothermic, so a 4° C. ice-bath was used). To the resulting viscous mixture was added diethyl ether (75 mL) and then water (15 mL). The ice-bath was removed and the mixture was allowed to stir for approximately 1 min to afford two clear phases. The organic phase was separated (top layer of the separating funnel), dried over $MgSO_4$, and filtered, and solvent was removed by evaporation to give 9.79 g of the crude product, which was then purified by vacuum distillation. Yield: 7.51 g (23%), transparent liquid.

Synthesis of 2-bromoethyl benzyl sulfide (CAS Number 60671-59-2)

A neat mixture of benzyl bromide (25 grams, 17.4 mL, 0.108 mol) and ethylene sulfide (10.96 grams, 10.9 mL, 0.182 mol) was prepared and heated to 50° C. while being monitored by $^1H$ NMR spectroscopy for the disappearance of the benzyl bromide methylene proton signal at δ 4.53 ppm (cf. 3.79 ppm resonance of the product in $CDCl_3$). Less than 7% was present after 24 hours, and less than 2% was present after 48 hours. After reacting for 65 hours, the solution was flushed with dry argon to remove excess ethylene sulfide (70° C., 20 min). The product was purified by distillation under vacuum. The first fraction that boiled at 50° C. was collected. This fraction solidified during the distillation. Yield: 30.49 g (90%). After several weeks, the product solidified under air in the refrigerator. It is therefore recommended that the product be used immediately or within one week for further synthesis.

Synthesis of 3-bromopropyl benzyl sulfide (CAS Number 88738-51-6)

A mixture of trimethylene sulfide (7.09 grams, 0.096 mol) and benzyl bromide (10.4 mL, 0.088 mol) dry acetonitrile (45 mL) was stirred at room temperature for 26 hours. The acetonitrile was evaporated at reduced pressure (55° C., 1 h, 40 mbar) and the residue distilled in vacuo to yield 18.9 g (88%) of a colorless oil containing 3-bromopropyl benzyl sulfide with approximately 6% of BnBr.

Synthesis of diphenylvinylphosphine oxide (CAS Number 2096-78-8)

A solution of $H_2O_2$ (30 mL, 30 wt. % in $H_2O$, reagent) in water (100 mL) was added dropwise overnight under stirring to a solution of 25 g of diphenylvinylphosphine in 1000 mL of dichloromethane. After completion of the reaction (as verified by $^{31}P\{^1H\}$NMR monitoring), 1000 mL water was added to the mixture and the organic phase was separated. The organic phase was washed with water two times (1000 mL), dried over $MgSO_4$, filtered, and evaporated to afford the product in 87% yield (white solid, 23.38 g).

Example 2. Synthesis of NNS-Type Ligands

Chart 1 illustrates NNS-type (e.g., NN(H)S-type) ligands of the general formula $(E)N(CH_2)_mNH(CH_2)_nSR_1$ that were synthesized and subsequently used to make embodiment complexes:

Chart 1

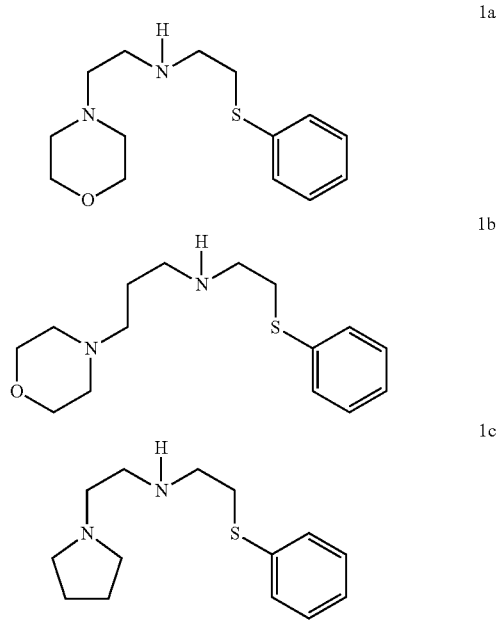

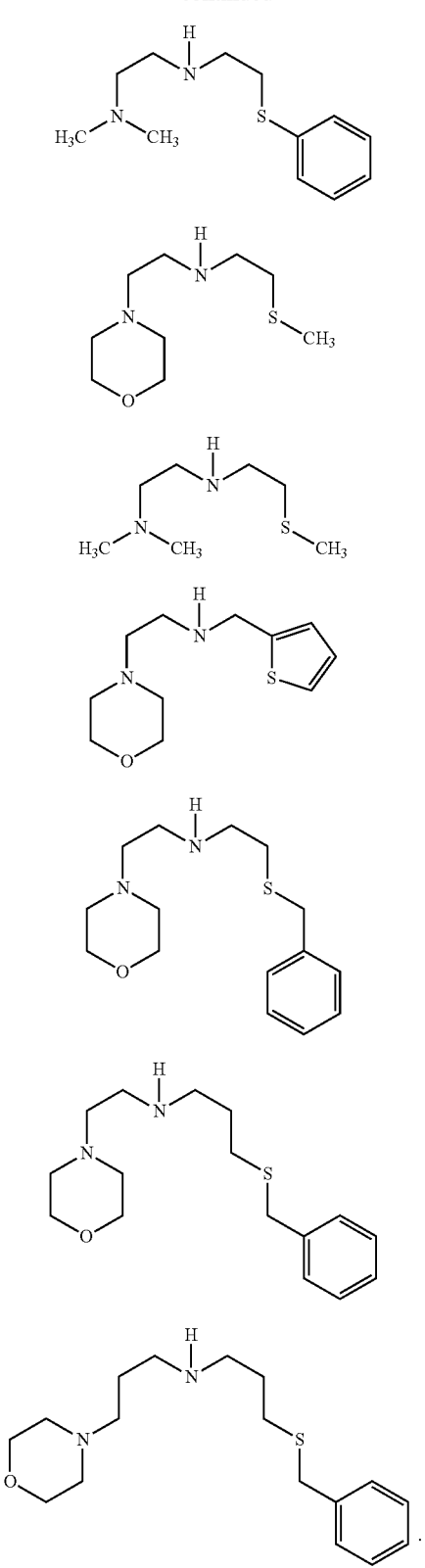

and were characterized via elemental analysis and $^1$H and $^{13}$C{$^1$H} NMR spectroscopy. The ligands are classified as structures 1 through 5 according to the R group on the S moiety of the ligand, and as substructures a through e according to the E group moiety of the ligand. The percentages following the R groups in the lists below each intermediate or final product indicate the Isolated reaction yields after fractional or simple (ligand 5a) vacuum distillations.

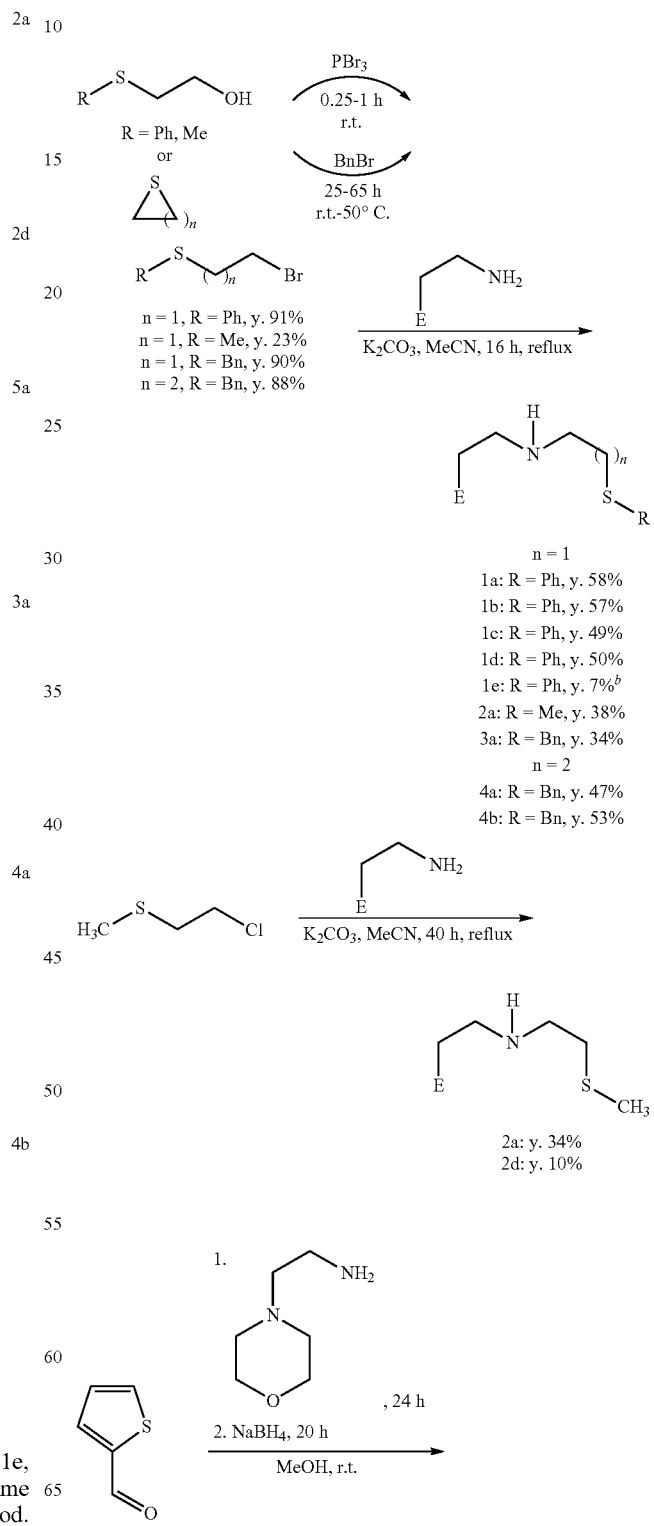

NN(H)S-type ligands, including ligands 1a, 1b, 1c, 1d, 1e, 2a, 3a, 4a, 4b, and 5a, were synthesized according to Scheme 1. The reactions were performed in air inside a fume hood. These ligands were obtained as colorless or yellow liquids, -continued

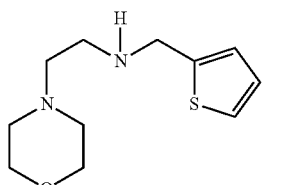

5a: y. 60%

-continued

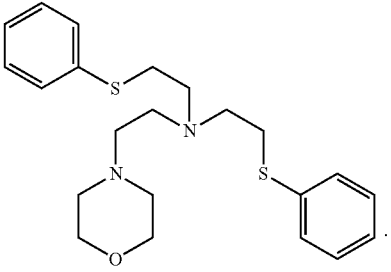

16%

2-bromoethyl phenyl sulfide (15.1 mL, 0.1 mol) and anhydrous potassium carbonate (38.9 g, 0.28 mol) were successively added with stirring to a solution of 2-(4-morpholinyl)ethanamine (13.1 mL, 0.1 mol) in acetonitrile (200 mL). The resulting suspension was refluxed for 16 h, cooled to room temperature, filtered (the residue on the filter was washed with acetonitrile, 2×15 mL), and the solvent was removed by rotary evaporation to afford 24.78 g of a viscous yellow oil (55° C., 1 h, 40 mbar). $^1$H NMR spectroscopy of the oil revealed a mixture of three amines: the starting 2-(4-morpholino)ethylamine (16%), the desired product, 2-morpholino-N-(2-(phenylthio)ethyl)ethylamine (68%), and a side product 2-morpholino-N,N-bis(2-(phenylthio)ethyl)ethylamine (16%), as shown in Scheme 2. The desired product was isolated by fractional vacuum distillation on a simple distillation kit without theoretical plates. The first collected fraction (b.p. 35-39° C.) corresponds to residual 2-(4-morpholinyl)ethylamine starting material (recovery 1.97 g, ~2 mL, transparent liquid). The second collected fraction (b.p. 145-167° C.) corresponds to the desired product. Isolated yield: 15.45 g (58%, based on 2-bromoethyl phenyl sulfide) as a clear yellowish oil. Elem. Anal.: Calcd for $C_{14}H_{22}N_2OS$ (266.40): C, 63.12; H, 8.32; N, 10.52%. Found: C, 63.04; H, 8.22; N, 10.42%. $^1$H NMR (400 MHz, CDCl$_3$, r.t.): δ 1.77 (br s, 1H, NH), 2.43 (vt, $^3J_{H-H}$≈5 Hz, 4H), 2.48 (t, $^3J_{H-H}$≈6 Hz, 2H), 2.70 (t, $^3J_{H-H}$≈6 Hz, 2H), 2.86 (t, $^3J_{H-H}$≈6 Hz, 2H), 3.08 (t, $^3J_{H-H}$≈6 Hz, 2H), 3.70 (t, $^3J_{H-H}$≈5 Hz, 4H), 7.19 (t, $^3J_{H-H}$≈7 Hz, 1H$_{para}$), 7.28 (t, $^3J_{H-H}$≈8 Hz, 2H$_{meta}$), 7.36 (d, $^3J_{H-H}$≈8 Hz, 2H$_{ortho}$). $^{13}$C{$^1$H} (100.5 MHz, CDCl$_3$, r.t.): δ 34.1 (s, 1C), 45.7 (s, 1C), 48.4 (s, 1C), 53.7 (s, 2C), 58.3 (s, 1C), 67.0 (s, 2C), 126.2 (s, 1C$_{para}$, Ph), 128.9 (s, 2C$_{ortho}$, Ph), 130.0 (s, 2C$_{meta}$, Ph), 135.9 (s, 1 C$_{ipso}$).

Example 2.2. Synthesis of Ligand 1b (3-morpholino-N-(2-(phenylthio)ethyl)propan-1-amine)

A solution of 3-morpholinopropylamine (14.6 mL, 0.1 mol) in acetonitrile (200 mL) was prepared. 2-bromoethyl phenyl sulfide (15.1 mL, 0.1 mol) was added to the solution with stirring, followed by addition anhydrous potassium carbonate (38.9 g, 0.28 mol) also with stirring. The resulting suspension was refluxed for 16 hours, cooled to room temperature, and filtered. The residue on the filter was washed with acetonitrile, 2×15 mL, and the solvent was removed by rotary evaporation to afford 27.6 g of a viscous yellow oil (55° C., 1 h, 40 mbar). Ligand 1b was obtained by fractional vacuum distillation on a simple distillation kit containing two theoretical plates. The first collected fraction (b.p. 41-46° C.) corresponds to residual 3-morpholinopropylamine starting material (recovery ~2.8 mL, transparent liquid). The second collected fraction (b.p. 141-156° C.) corresponds to ligand 1b (isolated yield: 15.98 g (57%,

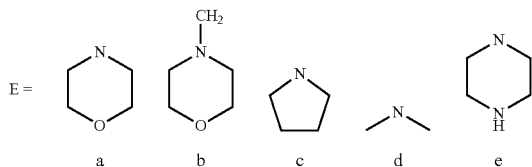

$^a$Contains ~6% BnBr. $^b$Crude yield in the 21:79 mixture with 2-(4-(2-(phenylthio)ethyl)piperazin-1-yl)ethanamine. $^c$Synthesis was performed only one time.

Example 2.1. Synthesis of Ligand 1a
(2-morpholino-N-(2-phenylthio)ethyl)ethylamine)

Scheme 2

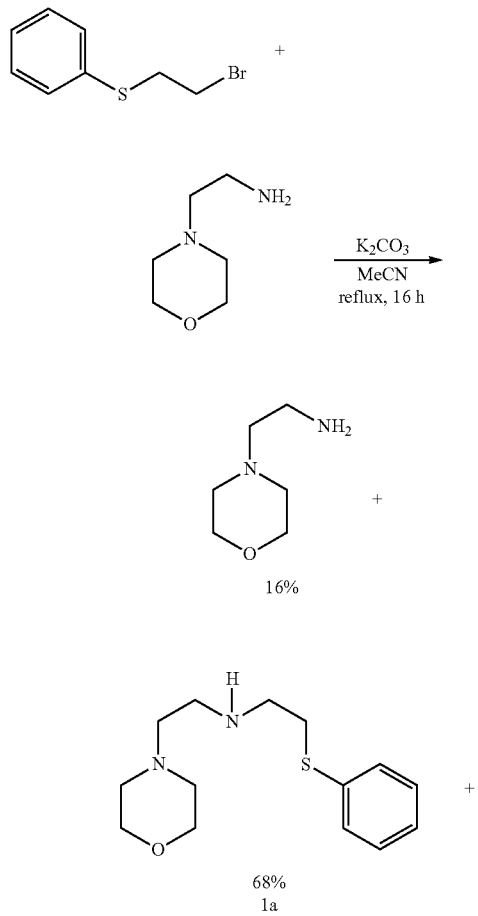

based on 2-bromoethyl phenyl sulfide) as a clear almost transparent (slightly yellowish) oil). Elem. Anal.: Calc'd for $C_{15}H_{24}N_2OS$ (280.43): C, 64.25; H, 8.63; N, 9.99%. Found: C, 64.13; H, 8.88; N, 9.99%. $^1$H NMR (400 MHz, CDCl$_3$, r.t.): δ 1.56 (br s, 1H, NH), 1.64 (q, $^3J_{H-H}$≈7 Hz, 2H), 2.36 (t, $^3J_{H-H}$≈8 Hz, 2H), 2.40 (br s, 4H), 2.63 (t, $^3J_{H-H}$≈7 Hz, 2H), 2.82 (t, $^3J_{H-H}$≈7 Hz, 2H), 3.05 (t, $^3J_{H-H}$≈7 Hz, 2H), 3.69 (t, $^3J_{H-H}$≈4 Hz, 4H), 7.16 (t, $^3J_{H-H}$≈7 Hz, 1H$_{para}$), 7.26 (t, $^3J_{H-H}$≈8 Hz, 2H$_{meta}$), 7.34 (d, $^3J_{H-H}$≈7 Hz, 2H$_{ortho}$). $^{13}$C{$^1$H} (100.5 MHz, CDCl$_3$, r.t.): δ 26.7 (s, 1C), 34.2 (s, 1C), 48.1 (s, 1C), 48.3 (s, 1C), 53.8 (s, 2C), 57.3 (s, 1C), 67.0 (s, 2C), 126.1 (s, 1C$_{para}$, Ph), 128.9 (s, 2C$_{ortho}$, Ph), 129.6 (s, 2C$_{meta}$, Ph), 135.9 (s, 1C$_{ipso}$).).

Example 2.3. Synthesis of Ligand 1c (2-(phenyl-thio)-N-(2-(pyrrolidin-1-yl)ethyl) ethylamine)

A solution of 1-(2-aminoethyl)pyrrolidine (4.57 g, 0.04 mol) in acetonitrile (80 mL) was prepared. 2-bromoethyl phenyl sulfide (8.70 g, 0.04 mol) was added to the solution, followed by anhydrous potassium carbonate (15.20 g, 0.11 mol), with stirring. The resulting suspension was refluxed for 16 hours, cooled to room temperature, filtered (the filter was washed with acetonitrile 2×10 mL) and the solvent was removed by evaporation on a rotavap to afford 9.72 g of a viscous orange-yellow oil (60° C., 1 h). Ligand 1c was obtained by fractional vacuum distillation on a simple distillation kit containing two theoretical plates. The first collected fraction (b.p. 26-28° C.) corresponds to residual 1-(2-aminoethyl)pyrrolidine (recovery approximately 1 mL). The second collected fraction (b.p. 130-142° C.) corresponds to ligand 1c. Isolated yield: 4.94 g (49%, based on 2-bromoethyl phenyl sulfide) of a clear yellowish oil. Elem. Anal.: Calc'd for $C_{14}H_{22}N_2S$ (250.40): C, 67.15; H, 8.86; N, 11.19%. Found: C, 66.88; H, 8.59; N, 10.79%. $^1$H NMR (400 MHz, CDCl$_3$, r.t.): δ 1.67 (br s, 1H, NH), 1.78 (br s, 4H), 2.50 (br s, 4H), 2.59 (t, $^3J_{H-H}$≈6 Hz, 2H), 2.74 (t, $^3J_{H-H}$≈6 Hz, 2H), 2.88 (t, $^3J_{H-H}$≈6 Hz, 2H), 3.08 (t, $^3J_{H-H}$≈6 Hz, 2H), 7.19 (t, $^3J_{H-H}$≈7 Hz, 1H$_{para}$), 7.29 (t, $^3J_{H-H}$≈8 Hz, 2H$_{meta}$), 7.37 (d, $^3J_{H-H}$≈8 Hz, 2H$_{ortho}$). $^{13}$C{$^1$H} (100.5 MHz, CDCl$_3$, r.t.): δ 23.5 (s, 2C), 34.2 (s, 1C), 48.3 (s, 1C), 48.6 (s, 1C), 54.2 (s, 2C), 56.0 (s, 1C), 126.1 (s, 1C$_{para}$, Ph), 128.9 (s, 2C$_{ortho}$, Ph), 130.0 (s, 2C$_{meta}$, Ph), 136.0 (s, 1C$_{ipso}$).

Example 2.4. Synthesis of Ligand 1d (N$^1$,N$^1$-dimethyl-N$^2$-(2-(phenylthio)ethyl) ethane-1,2-diamine)

2-bromoethyl phenyl sulfide (15.08 mL, 0.1 mol) and anhydrous potassium carbonate (38.9 g, 0.28 mol) were successively added to a solution of N,N-dimethylethylene-diamine (10.9 mL, 0.1 mol) in acetonitrile (200 mL) with stirring. The resulting suspension was refluxed for 16 h, cooled to room temperature, filtered (the filter was washed with acetonitrile 2×15 mL) and the solvent was removed by rotary evaporation to afford 18.54 g of the viscous yellowish oil (60° C., 1 h). The desired product was obtained by fractional vacuum distillation on a simple distillation kit containing two theoretical plates. The first collected fraction (b.p. 30-33° C.) corresponds to N,N-dimethylethylenediamine (recovery 2.9 mL). The second collected fraction (b.p. 90-110° C.) corresponds to the desired product. Isolated yield: 11.22 g (50%, based on 2-bromoethyl phenyl sulfide) as a clear, almost transparent (slightly yellowish) oil. Elem. Anal.: Calcd for $C_{12}H_{20}N_2S$ (224.37): C, 64.24; H, 8.99; N, 12.49%. Found: C, 64.19; H, 8.87; N, 12.46%. $^1$H NMR (400 MHz, CDCl$_3$, r.t.): δ 1.83 (brs, 1H, NH), 2.19 (s, 6H), 2.37 (t, $^3J_{H-H}$≈6 Hz, 2H), 2.65 (t, $^3J_{H-H}$≈6 Hz, 2H), 2.83 (t, $^3J_{H-H}$≈7 Hz, 2H), 3.04 (t, $^3J_{H-H}$≈7 Hz, 2H), 7.15 (t, $^3J_{H-H}$≈7 Hz, 1H$_{para}$), 7.25 (t, $^3J_{H-H}$≈8 Hz, 2H$_{meta}$), 7.33 (d, $^3J_{H-H}$≈8 Hz, 2H$_{ortho}$). $^{13}$C{$^1$H} (100.5 MHz, CDCl$_3$, r.t.): δ 34.1 (s, 1C), 45.5 (s, 2C), 47.0 (s, 1C), 48.6 (s, 1C), 59.1 (s, 1C), 126.1 (s, 1C$_{para}$, Ph), 128.9 (s, 2C$_{ortho}$, Ph), 130.0 (s, 2C$_{meta}$, Ph), 136.0 (s, 1C$_{ipso}$).

Example 2.5. Synthesis of Ligand 1e (2-(phenylthio)-N-(2-(piperazin-1-yl)ethyl)ethanamine)

A solution of 1-(2-aminoethyl)piperazine (13.1 mL, 0.1 mol) in acetonitrile (200 mL) was prepared. 2-bromoethyl phenyl sulfide (15.1 mL, 0.1 mol) was added to the solution, followed by anhydrous potassium carbonate (38.9 g, 0.28 mol), each with stirring. The resulting suspension was refluxed for 16 h, cooled to room temperature, and filtered. The residue on the filter was washed with acetonitrile (2×15 mL), and the solvent was removed by rotary evaporation to afford 25.45 g of a viscous orange liquid (55° C., 1 h, 40 mbar). Two fractions were distilled from this mixture. The first collected fraction (b.p. 43-48° C.) corresponds to residual 1-(2-aminoethyl)piperazine (recovery 4.3 mL, transparent liquid). The second collected fraction (b.p. 152-173° C.) corresponds to a mixture of 2-(4-(2-(phenylthio)ethyl)piperazin-1-yl)ethanamine and 2-(phenylthio)-N-(2-(piperazin-1-yl)ethyl)ethanamine in a 1:0.27 ratio (8.36 g, yellow oil) according to $^1$H NMR Analysis. No further purification was performed.

Example 2.6. Synthesis of Ligand 2a (2-(methylthio)-N-(2-morpholinoethyl)ethanamine)

Method A (from MeSCH$_2$CH$_2$Br)

A solution of 2-(4-morpholinyl)ethanamine (5.87 mL, 0.045 mol) in acetonitrile (90 mL) was prepared. 2-bromoethyl methyl sulfide (6.94 g, 0.045 mol) was added to the solution, followed by anhydrous potassium carbonate (17.4 g, 0.13 mol), each with stirring. The resulting suspension was refluxed for 16 h, cooled to room temperature, filtered (the residue on the filter was washed with acetonitrile, 2×10 mL) and the solvent was removed by rotary evaporation to afford 9.06 g of a yellow suspension (55° C., 1 h, 40 mbar). Ligand 2a was obtained by fractional vacuum distillation on a simple distillation kit without theoretical plates. The first collected fraction (b.p. 30-31° C.) presumably corresponds to residual 2-(4-morpholinyl)ethanamine (recovery was approximately 1.6 mL, transparent liquid). The second collected fraction (b.p. 91-115° C.) corresponds to ligand 2a. Isolated yield: 3.50 g (38%, based on 2-bromoethyl methyl sulfide) as a transparent liquid. A note of caution: a higher boiling fraction (>115° C.) contains an admixture of tertiary amine. Elem. Anal.: Calc'd for $C_9H_{20}N_2OS$ (204.33): C, 52.90; H, 9.87; N, 13.71%. Found: C, 52.98; H, 9.90; N, 13.53%. $^1$H NMR (400 MHz, CDCl$_3$, r.t.): δ 2.08 (s, 3H), 2.18 (br s, 1H, NH), 2.42 (m, 4H), 2.48 (t, $^3J_{H-H}$≈6 Hz, 2H), 2.64 (t, $^3J_{H-H}$≈6 Hz, 2H), 2.71 (t, $^3J_{H-H}$≈6 Hz, 2H), 2.82 (t, $^3J_{H-H}$≈6 Hz, 2H), 3.68 (vt, $^3J_{H-H}$≈5 Hz, 4H). $^{13}$C{$^1$H} (100.5 MHz, CDCl$_3$, r.t.): δ 15.3 (s, 1C), 34.3 (s, 1C), 45.7 (s, 1C), 48.0 (s, 1C), 53.7 (s, 2C), 58.2 (s, 1C), 67.0 (s, 2C).

Example 2.7. Synthesis of Ligand 2a (2-(methylthio)-N-(2-morpholinoethyl)ethanamine)

Method B (from MeSCH$_2$CH$_2$Cl)

This method was similar to Method A above, but 2-chloroethyl methyl sulfide was used instead of 2-bromoethyl methyl sulfide and the reaction mixture was refluxed for 40 h instead of 16 h. Isolated yield of ligand 2a: 3.13 g (34% from 5 g of MeSCH$_2$CH$_2$Cl). Elem. Anal.: Calc'd for C$_9$H$_{20}$N$_2$OS (204.33): C, 52.90; H, 9.87; N, 13.71%. Found: C, 52.82; H, 10.03; N, 13.50%.

Example 2.8. Synthesis of Ligand 2d (N$^1$,N$^1$-dimethyl-N$^2$-(2-(methylthio)ethyl)ethane-1,2-diamine)

2-chloroethyl methyl sulfide (5 g, 0.045 mol) and anhydrous potassium carbonate (17.7 g, 0.13 mol) were successively added to a solution of N,N-dimethylethylenediamine (4.94 mL, 0.045 mol) in acetonitrile (90 mL) with stirring. The resulting suspension was refluxed for 40 h, cooled to room temperature, filtered (the filter was washed with acetonitrile 2×10 mL) and the solvent was removed by rotary evaporation to afford 5.5 g of the yellowish liquid (60° C., 1 h). The desired product was obtained by slow fractional vacuum distillation. The first collected fraction (b.p. 25-40° C.) corresponds to the 1:2 mixture of starting N,N-dimethylethylenediamine and the desired product (recovery ~1 mL). The second collected fraction (b.p. 40-70° C.) corresponds to the pure desired product. Isolated yield: 0.75 g (10%, based on 2-chloroethyl methyl sulfide) as a clear, almost transparent (slightly yellowish) oil. The fraction having a b.p. >70° C. corresponds to a mixture of products. $^1$H NMR (400 MHz, CDCl$_3$, r.t.): δ 1.58 (br s, 1H, NH), 2.06 (s, 3H), 2.18 (s, 6H), 2.09 (t, $^3$J$_{H-H}$≈6 Hz, 2H), 2.61 (t, $^3$J$_{H-H}$≈7 Hz, 2H), 2.66 (t, $^3$J$_{H-H}$≈6 Hz, 2H), 2.80 (t, $^3$J$_{H-H}$≈7 Hz, 2H). $^{13}$C{$^1$H}(100.5 MHz, CDCl$_3$, r.t.): δ 15.3 (s, 1C), 34.3 (s, 1C), 45.6 (s, 2C), 47.0 (s, 1C), 48.3 (s, 1C), 59.2 (s, 1C).

Example 2.9. Synthesis of Ligand 3a (2-morpholino-N-(2-(benzylthio)ethyl)ethylamine)

A solution of 2-morpholinoethylamine (6.56 mL, 0.05 mol) in acetonitrile (100 mL) was prepared. 2-bromoethyl benzyl sulfide (11.56 g, 0.05 mol) was added to the solution, followed by anhydrous potassium carbonate (19.35 g, 0.14 mol), each with stirring. The resulting suspension was refluxed for 16 h, cooled to room temperature, and filtered. The residue on the filter was washed with acetonitrile (2×10 mL), and the solvent was removed by rotary evaporation to afford 13.75 g of a viscous orange-yellow suspension (55° C., 1 h, 40 mbar). Ligand 3a was obtained by fractional vacuum distillation on a Vigreux column composed of two theoretical plates. The first collected fraction (b.p. 34-38° C.) corresponds to the residual 2-(4-morpholinyl)ethanamine (recovery 1.64 g, approximately 1.7 mL). The second collected fraction (b.p. 132-158° C.) corresponds to ligand 3a. Isolated yield: 4.81 g (34%, based on 2-bromoethyl benzyl sulfide) of a clear dark-yellowish oil. Elem. Anal.: Calc'd for C$_{15}$H$_{24}$N$_2$OS (280.43): C, 64.25; H, 8.63; N, 9.99%. Found: C, 64.44; H, 8.33; N, 10.23%. $^1$H NMR (400 MHz, CDCl$_3$, r.t.): δ 1.88 (br s, 1H, NH), 2.43 (br m, 4H), 2.46 (t, $^3$J$_{H-H}$≈6 Hz, 2H), 2.59 (t, $^3$J$_{H-H}$≈6 Hz, 2H), 2.66 (t, $^3$J$_{H-H}$≈7 Hz, 2H), 2.77 (t, $^3$J$_{H-H}$≈7 Hz, 2H), 3.70 (t, $^3$J$_{H-H}$≈7 Hz, 4H), 3.72 (s, 2H), 7.20-7.31 (m, 5H). $^{13}$C{$^1$H} (100.5 MHz, CDCl$_3$, r.t.): δ 31.7 (s, 1C), 36.2 (s, 1C), 45.7 (s, 1C), 48.4 (s, 1C), 53.8 (s, 2C), 58.3 (s, 1C), 67.0 (s, 2C), 127.0 (s, 1C$_{para}$, Ph), 128.5 (s, 2C$_{meta}$, Ph), 128.8 (s, 2C$_{ortho}$, Ph), 138.5 (s, 1C$_{ipso}$).

Example 2.10. Synthesis of Ligand 4a (3-(benzylthio)-N-(2-morpholinoethyl)propan-1-amine)

A solution of 2-(4-morpholinyl)ethanamine (3.4 mL, 0.026 mol) in acetonitrile (50 mL) was prepared. 3-bromopropyl benzyl sulfide (6.36 g, 0.026 mol) was added to the solution, followed by anhydrous potassium carbonate (10 g, 0.072 mol), with stirring. The resulting suspension was refluxed for 16 h, cooled to room temperature, and filtered. The residue on the filter was washed with acetonitrile (2×10 mL), and the solvent was removed by rotary evaporation to afford 7.15 g of a viscous orange-yellow liquid (55° C., 1 h, 40 mbar). Ligand 4a was obtained by fractional vacuum distillation on a Vigreux column composed of two theoretical plates. The first collected fraction (b.p 25-26° C.) corresponds to residual 2-(4-morpholinyl)ethanamine (recovery approximately 0.5 mL). The second collected fraction (b.p. 145-176° C.) corresponds to the analytically pure ligand 4a (3.57 g, 47%, based on 3-bromopropyl benzyl sulfide). Elem. Anal.: Calc'd for C$_{16}$H$_{26}$N$_2$OS (294.46): C, 65.26; H, 8.90; N, 9.51%. Found: C, 65.56; H, 9.08; N, 9.75%. $^1$H NMR (400 MHz, CDCl$_3$, r.t.): δ 1.42 (br s, 1H, NH), 1.75 (q, J≈7 Hz, 2H), 2.35-2.53 (overlapped m, 8H), 2.66 (t, $^3$J$_{H-H}$≈7 Hz, 4H), 3.65-3.73 (overlapped m, 6H), 7.23 (m, 1H), 7.26-7.35 (overlapped m, 4H). $^{13}$C{$^1$H} (100.5 MHz, CDCl$_3$, r.t.): δ 29.2 (s, 1C), 29.5 (s, 1C), 36.3 (s, 1C), 46.1 (s, 1C), 48.9 (s, 2C), 53.8 (s, 1C), 58.3 (s, 2C), 67.0 (S, 1C), 126.9 (s, 1C$_{para}$, Ph), 128.4 (s, 2C$_{meta}$, Ph), 128.8 (s, 2C$_{ortho}$, Ph), 138.5 (s, 1C$_{ipso}$).

Example 2.11. Synthesis of Ligand 4b (3-(benzylthio)-N-(3-morpholinopropyl)propan-1-amine)

3-bromopropyl benzyl sulfide (7.78 g, 0.03 mol) and anhydrous potassium carbonate (12.40 g, 0.09 mol) were successively added to a solution of 3-morpholinopropylamine (4.64 mL, 0.03 mol) in acetonitrile (65 mL) with stirring. The resulting suspension was refluxed for 16 h, cooled to room temperature, filtered (the residue on the filter was washed with acetonitrile 2×10 mL) and the solvent was removed by rotary evaporation to afford 9.49 g of a yellow solution containing a small amount of a yellow solid (55° C., 1 h, 40 mbar). The desired product was obtained by fractional vacuum distillation on a small Vigreux column composed of two theoretical plates. The first collected fraction (b.p. 33-35° C.) corresponds to the residual 3-morpholinopropylamine (recovery ~0.8 mL). The second collected slightly yellowish fraction (b.p. 148-173° C.) corresponds to the desired product (4.22 g). A yellow fraction (b.p. 173-185° C.) was also collected and corresponds to the desired product according to NMR analysis (0.68 g). Combined isolated yield: 4.9 g (53%, based on 3-bromopropyl benzyl sulfide) of a clear yellowish oil. Elem. Anal.: Calcd for C$_{17}$H$_{28}$N$_2$OS (308.48): C, 66.19; H, 9.15; N, 9.08%. Found: C, 65.79; H, 9.19; N, 9.13%. $^1$H NMR (400 MHz, CDCl$_3$, r.t.): δ 1.56 (br s, 1H, NH), 1.64 (q, $^3$J$_{H-H}$≈7 Hz, 2H), 1.72 (q, $^3$J$_{H-H}$≈7 Hz, 2H), 2.32-2.47 (overlapped m, 8H), 2.57-2.68 (overlapped m, 4H), 3.67 (overlapped m, 6H), 7.21 (m, 1H), 7.24-7.32 (overlapped m, 4H). $^{13}$C{$^1$H} (100.5 MHz, CDCl$_3$, r.t.): δ 26.7 (s, 1C), 29.2 (s, 1C), 29.4 (s, 1C), 36.3 (s, 1C), 48.5 (s, 1C), 48.8 (s, 1C), 53.8 (s, 2C), 57.4 (s, 1C), 67.0 (s, 2C), 126.9 (s, 1C$_{para}$, Ph), 128.4 (s, 2C$_{meta}$, Ph), 128.8 (s, 2C$_{ortho}$, Ph), 138.5 (s, 1C$_{ipso}$).

Example 2.12. Synthesis of Ligand 5a (2-morpholino-N-(thiophen-2-ylmethyl)ethanamine)

Freshly distilled thiophene carbaldehyde (3.6 mL, 0.038 mol) was added to a solution of 2-(4-morpholinyl)ethanamine (5 g, 5.1 mL, 0.038 mol) in methanol (80 mL). The obtained mixture was stirred for 24 h to afford a yellow solution, to which was slowly added NaBH$_4$ (4 equiv, 5.8 g, 20 min), resulting in hydrogen evolution. Subsequently, 10 mL of methanol was added to transfer the remaining NaBH$_4$ from the funnel into the solution) and the system was stirred for 20 h at room temperature. 30 mL H$_2$O and then 100 mL CH$_2$Cl$_2$ were slowly added to the white suspension. The organic phase was extracted, and the residual inorganic phase was washed with 100 mL CH$_2$Cl$_2$. The combined organic phases afforded the crude product as a yellow liquid after solvent evaporation (7.08 g). The product was purified by vacuum distillation (109-113° C.). Isolated yield: 5.20 g (60%), transparent oil. Elem. Anal.: Calcd for C$_{11}$H$_{18}$N$_2$OS (226.34): C, 58.37; H, 8.02; N, 12.38%. Found: C, 58.13; H, 8.20; N, 12.41%. $^1$H NMR (400 MHz, CDCl$_3$, r.t.): δ 2.11 (brs, 1H, NH), 2.40 (m, 4H), 2.49 (t, $^3J_{H-H}$≈6 Hz, 2H), 2.73 (t, $^3J_{H-H}$≈6 Hz, 2H), 3.68 (m, 4H), 4.01 (s, 2H), 6.89-6.96 (m, 2H), 7.20 (dd, $^3J_{H-H}$≈5 Hz, $^4J_{H-H}$≈1 Hz, 1H). $^{13}$C{$^1$H} (100.5 MHz, CDCl$_3$, r.t.): δ 44.9 (s, 1C), 48.3 (s, 1C), 53.7 (s, 2C), 58.1 (s, 1C), 67.0 (s, 2C), 124.4 (s, 1C), 125.0 (s, 1C), 126.6 (s, 1C), 144.1 (s, 1C).

Chart 2 illustrates NNS-type ligands 6 and 7, represented by the formula E(CH$_2$)$_3$N(CH$_3$)(CH$_2$)$_3$SBn (E=—NC$_4$H$_8$O and —N(CH$_3$)$_2$) that were synthesized, isolated and subsequently used to make embodiment complexes. Isolated yields are listed below each ligand.

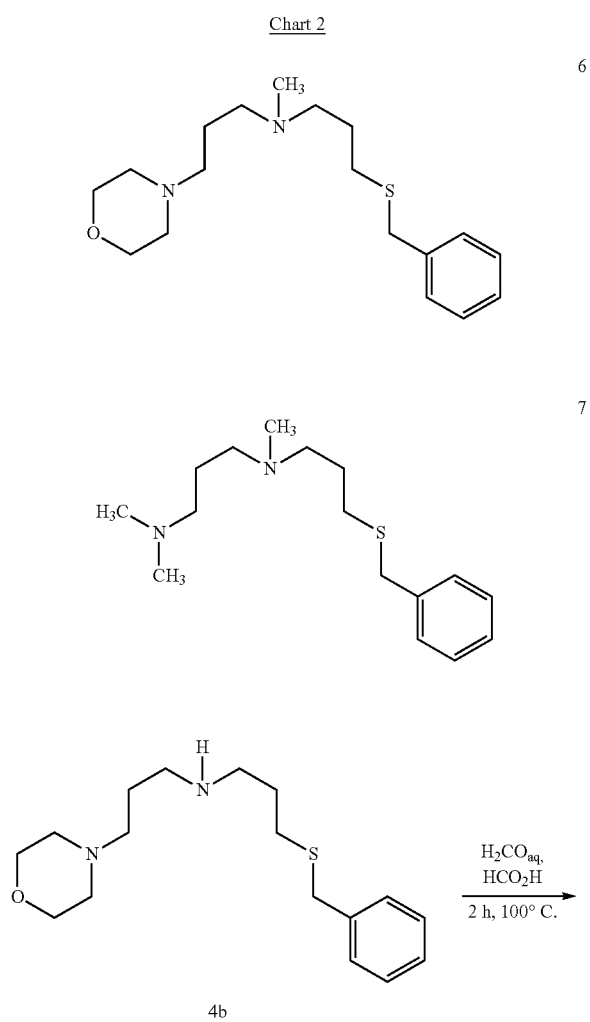

Chart 2

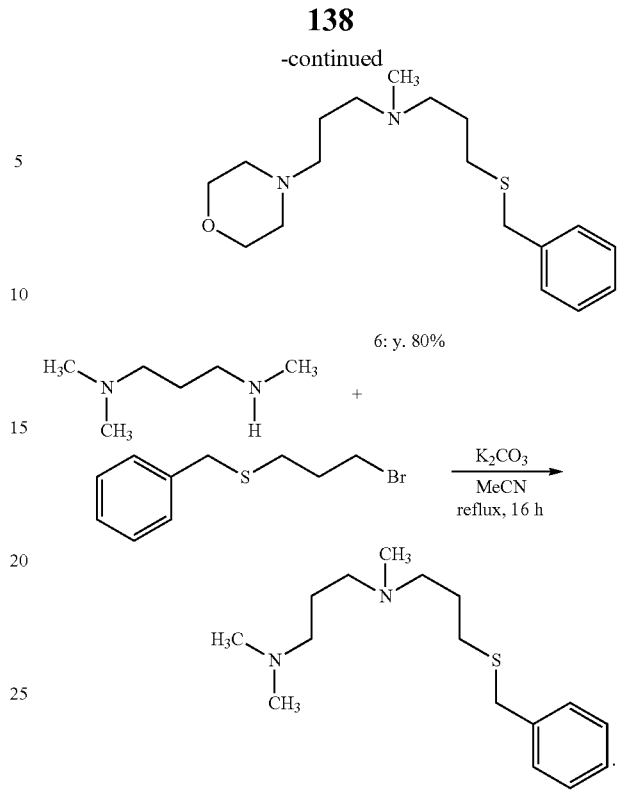

Example 2.13. Synthesis of Ligand 6 (3-(benzylthio)-N-methyl-N-(3-morpholinopropyl)propan-1-amine)

A mixture of 4b (1.19 g, 3.858 mmol), formic acid (712 mg, 4 equiv), and 1.75 mL of formaldehyde solution (37 wt. % in H$_2$O) was stirred for 2 h at 100° C. in a 50 mL Schlenk flask in air. The reaction mixture was cooled, treated with 18 mL of a 20% aqueous solution of NaOH, and extracted with 3×20 mL of Et$_2$O. The combined ether solution was washed with 2×20 mL of water, dried over MgSO$_4$, filtered, and rotary evaporated under vacuum (55° C., 1 h, 40 mbar). Yield: 0.99 g (80%), yellowish liquid. Elem. Anal.: Calcd for C$_{18}$H$_{30}$N$_2$OS (322.51): C, 67.04; H, 9.38; N, 8.68%. Found: C, 67.89; H, 9.45; N, 8.77%. $^1$H NMR (400 MHz, CDCl$_3$, r.t.): δ 1.64 (q, $^3J_{H-H}$≈7 Hz, 2H), 1.71 (q, $^3J_{H-H}$≈7 Hz, 2H), 2.19 (s, 3H), 2.30-2.50 (overlapped m, 12H), 3.71 (overlapped m, 6H), 3.67 (overlapped m, 6H), 7.23 (m, 1H), 7.26-7.34 (overlapped m, 4H). $^{13}$C{$^1$H} (100.5 MHz, CDCl$_3$, r.t.): δ 24.4 (s, 1C), 26.9 (s, 1C), 29.3 (s, 1C), 36.4 (s, 1C), 42.2 (s, 1C), 53.8 (s, 2C), 55.6 (s, 1C), 56.5 (s, 1C), 57.0 (s, 1C), 67.0 (s, 2C), 126.9 (s, 1C$_{para}$, Ph), 128.5 (s, 2C$_{meta}$, Ph), 128.8 (s, 2C$_{ortho}$, Ph), 138.5 (s, 1C$_{ipso}$).

Example 2.14. Synthesis of Ligand 7 (3-(benzylthio)-N$^1$-methyl-N$^2$,N$^2$-dimethyl)propan-1-amine)

A solution of N,N,N'-trimethyl-1,3-propanediamine (96% Aldrich, 5 g, 0.043 mol) in acetonitrile (90 mL) was prepared. 3-bromopropyl benzyl sulfide (10.54 g, 0.043 mol) was added to the solution, followed by anhydrous potassium carbonate (16.5 g, 0.12 mol), with stirring. The resulting suspension was refluxed for 16 hours, cooled to room temperature, and filtered. The residue on the filter was washed with acetonitrile (2×10 mL) and the solvent was removed by evaporation on a rotavap to afford 11.89 g of a two-phase yellow liquid (55° C., 1 h, 40 mbar). The desired product was obtained by fractional vacuum distillation on a simple distillation kit without theoretical plates. The first collected transparent fraction (b.p. 75-135° C.) corresponds to the desired product. Isolated yield: 3.25 g (27%) as a clear liquid. Elem. Anal.: Calcd for $C_{16}H_{28}N_2S$ (280.47): C, 68.52; H, 10.06; N, 9.99%. Found: C, 68.15; H, 9.99; N, 9.70%. $^1$H NMR (400 MHz, CDCl3, r.t.): δ 1.60 (q, $^3J_{H-H}$≈7 Hz, 2H), 1.69 (s, $^3J_{H-H}$≈7 Hz, 2H), 2.17 (s, 3H), 2.20 (s, 6H), 2.24 (vt, J≈7 Hz, 2H), 2.32 (vt, J≈7 Hz, 2H), 2.36 (vt, J≈7 Hz, 2H), 2.42 (vt, J≈7 Hz, 2H), 3.69 (s, 2H), 7.21 (m, 1H), 7.24-7.32 (m, 4H). $^{13}C\{^1H\}$ (100.5 MHz, CDCl$_3$, r.t.): δ 25.7 (s, 1C), 27.0 (s, 1C), 29.3 (s, 1C), 36.3 (s, 1C), 42.3 (s, 1C), 45.6 (s, 2C), 55.8 (s, 1C), 56.6 (s, 1C), 57.9 (s, 1C), 126.9 (s, 1C), 128.4 (s, 2C), 128.8 (s, 2C), 138.6 (s, 1C).

Example 3. Synthesis of P(O)NS-type and PNS-Type Ligands

P(O)NS-type and PNS ligands of the type shown in Chart 3 can be or have been prepared and used to make inventive complexes.

Chart 3

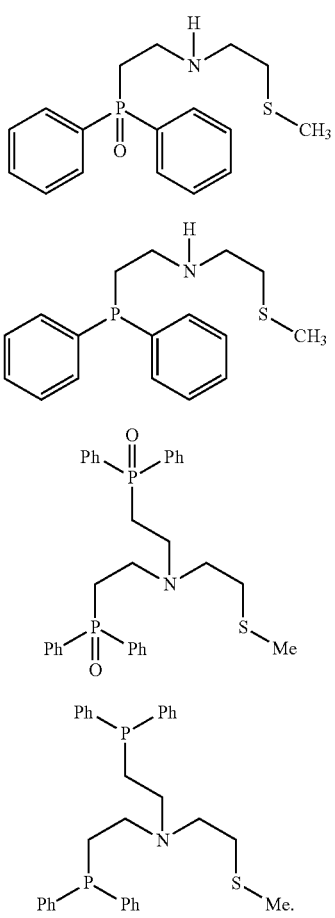

Ligand 8 was synthesized from diphenylvinylphosphine oxide according to Scheme 4. The reaction was performed in air inside a fume hood. Ligand 8* bearing the corresponding phosphine analogue may be prepared by reduction of ligand 8 with any suitable reducing agent, including a silane reducing agent, as shown in Scheme 4 (under argon). Such processes are well-documented in literature (see, e.g., *Curr. Green Chem.*, 2014, 1, 182; *Org. Lett.* 2004, 6, 4675, the entire content of which is incorporated by reference herein). Isolated yields are listed under each of ligands 8, 8*, 9, and 9*.

Scheme 4.

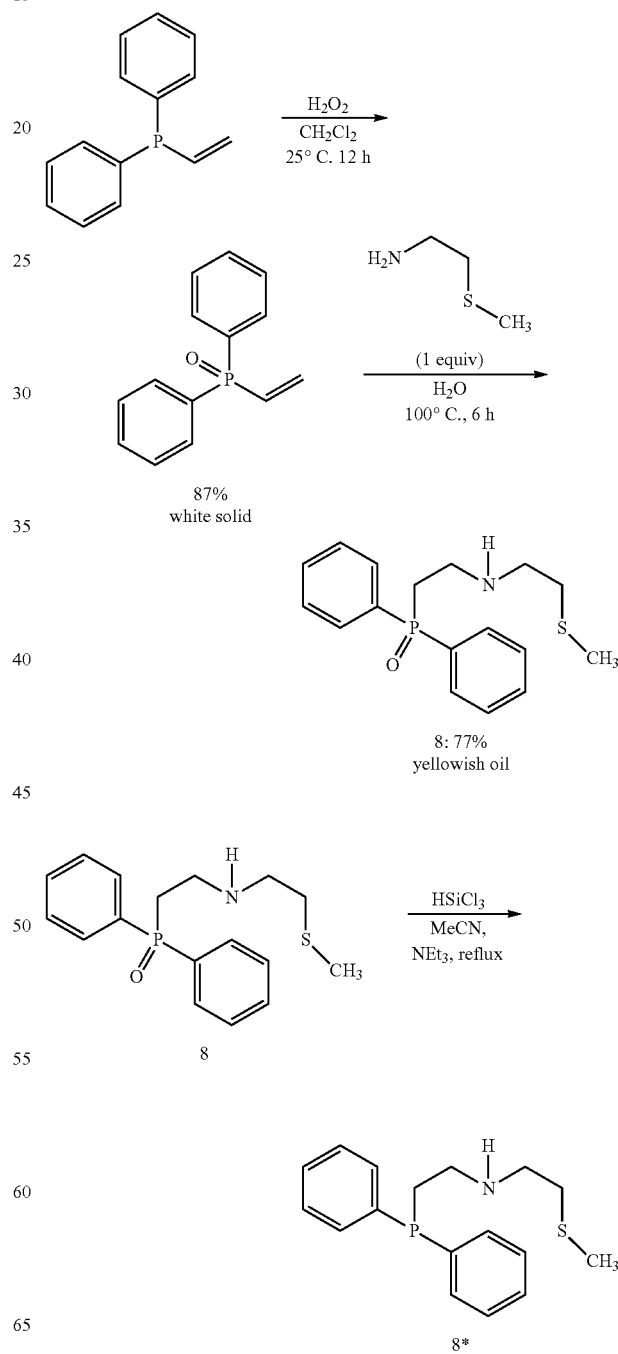

-continued

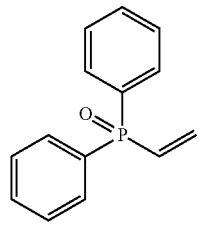 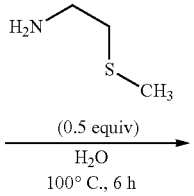

(0.5 equiv)
H₂O
100° C., 6 h

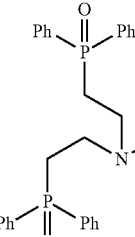

9

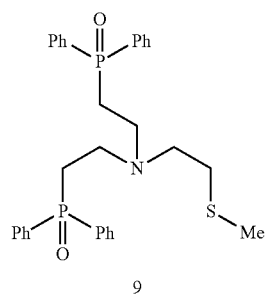

HSiCl₃
MeCN,
NEt₃, reflux

9

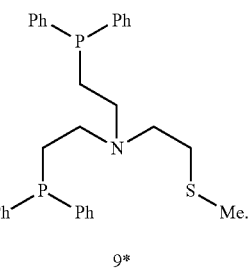

9*

Example 3.1. Synthesis of Ligand 8 [(2-((2-(methylthio)ethyl)amino)ethyl)diphenylphosphine oxide]. Isolation of 8 and 9

Scheme 5

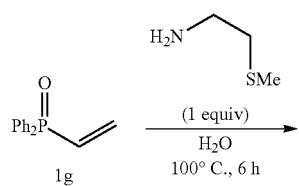

(1 equiv)
H₂O
100° C., 6 h

1g

-continued

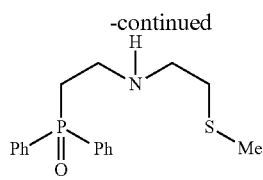

isol.y. 1082 mg (77%)
yellowish oil
8

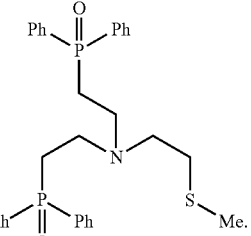

isol.y. 111 mg
white solid
9

A mixture of diphenylvinylphosphine oxide (1 g, 4.38 mmol) and 2-(methylthio)ethylamine (1.1 equiv, 448 μL, 4.82 mmol, 97% Aldrich) were stirred in 10 mL of water at 100° C. for 6 h. When stirring was switched off, two phases were clearly observed: an orange organic phase and a transparent water phase. The organic phase was extracted with dichloromethane (2×15 mL), the combined extracts were dried over MgSO₄, and the solvent was removed via rotary evaporation (1 h, 60° C.) to afford the crude product as a yellow-orange viscous oil primarily comprising a mixture of product 8 (>88%), tertiary amine (>9%) and traces of starting material (δ 28.0 ppm) according to $^{31}P\{^1H\}$ NMR (1250 mg). The crude product could be directly used in the synthesis of trans-[Ru$^{II}$C₂{κ³(S,N',O)-8}(PPh₃)] (D-1), vide infra. Alternatively, the crude product was purified by column (8.5×5 cm) chromatography (separation medium: SiO₂, 230-400 mesh, 40-63μ, av. pore diameter 60 Å, Sigma, ca. 120 g; solvent system: CHCl₃/methanol, 100:13, ca. 500 mL of the binary mixture; thin-layer chromatography analysis: R$_f$=0.31 for the product, R$_f$=0.63 for the tertiary amine, TLC Baker-Flex silicagel IB-F). First fraction: tertiary amine, yield after washing with pentane under stirring (2×10 mL): 111 mg, of an off-white solid as shown in Scheme 5. Second fraction: product yield after solvent evaporation and drying (2 h, 60° C.): 1082 mg (78%), transparent yellowish oil as shown in Scheme 5. Characterization data for ligand 8. Elem. Anal.: Calcd for C₁₇H₂₂NOPS (319.40): C, 63.93; H, 6.94; N, 4.39%. Found: C, 62.41; H, 6.98; N, 4.39%. $^{31}P\{^1H\}$ (162 MHz, CDCl₃, rt): δ 30.8 (s). $^1H$ NMR (400 MHz, CDCl₃, 25° C.): δ 1.83 (br s, 1H, NH), 2.08 (s, 3H, SMe), 2.51-2.57 (m, 2H), 2.60 (vt, J≈7 Hz, 2H), 2.79 (vt, J≈7 Hz, 2H), 2.99 (m, 2H), 7.47-7.56 (m, 6H), 7.74-7.79 (m, 4H). $^{13}C\{^1H\}$ (100.5 MHz, CDCl₃, 25° C.): δ 15.3 (s, 1C), 30.5 (d, J$_{C-P}$=71 Hz, 1C), 34.2 (s, 1C), 42.6 (s, 1C), 47.8 (s, 1C), 128.7 (d, J$_{C-P}$=12 Hz, 4C$_{meta}$, Ph), 130.7 (d, J$_{C-P}$=9 Hz, 4C$_{ortho}$, PPh₃), 131.8 (d, J$_{C-P}$=3 Hz, 2C$_{para}$, Ph), 132.9 (d, J$_{C-P}$=99 Hz, 2C$_{ipso}$). Characterization data for ligand 9. Elem. Anal.: Calcd for C₃₁H₃₅NO₂P₂S (547.63): C, 67.99; H, 6.44; N, 2.56%. Found: C, 67.87; H, 6.32; N, 2.49%. $^{31}P\{^1H\}$ (162 MHz, CDCl₃, rt): δ 30.7 (s). $^{13}C\{^1H\}$ (100.5 MHz, CDCl₃, 25° C.): δ 15.9 (s, 1C), 27.0 (d, J$_{C-P}$=70 Hz, 2C), 31.8 (s, 1C), 45.6 (s, 2C), 56.9 (s, 1C), 128.7 (d, $J_{C-P}$=12 Hz, 8$C_{meta}$, Ph), 130.7 (d, $J_{C-P}$=9 Hz, 8$C_{ortho}$, PPh$_3$), 131.8 (d, $J_{C-P}$=3 Hz, 4$C_{para}$, Ph), 133.0 (d, $J_{C-P}$=99 Hz, 4$C_{ipso}$).

Example 4. Synthesis of NNS-type and SNNS-Type Chiral Ligands

Chart 4 illustrates the NNS-type (C$_1$-symmetry, ligands 10 and 11) and SNNS-Type (C$_2$-symmetry, ligands 12 and 12*) chiral ligands of NNS-type and SNNS-type that were synthesized, isolated and subsequently used to make inventive complexes.

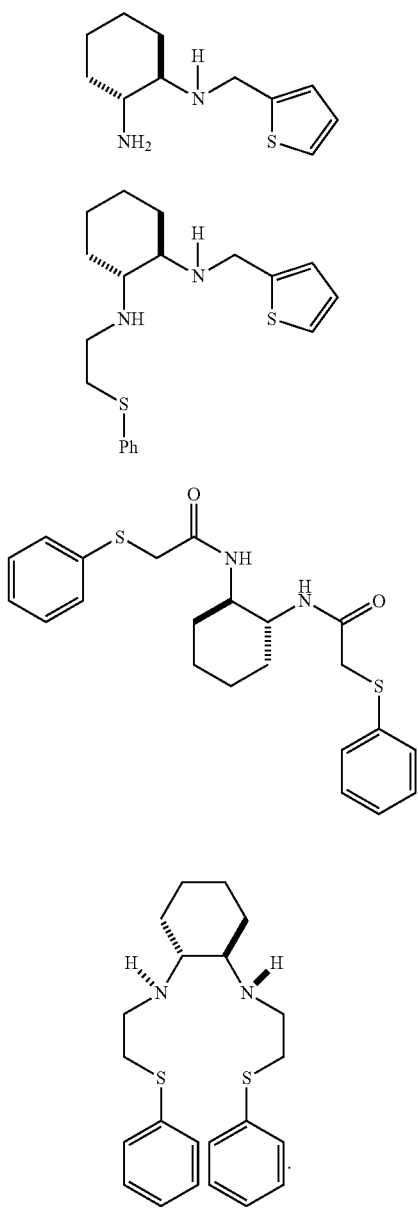

Ligands 10, 11 and 12 were synthesized according to Scheme 6. The reactions were performed in air inside a fume hood. Ligand 11* may be synthesized by reacting ligand 11 with a suitable reducing agent, for example, LiAlH$_4$ as shown in Scheme 6. Isolated yields after fractional vacuum distillation (ligand 10), column chromatography (ligand 11) or precipitation (ligand 12, crude) are listed below each ligand.

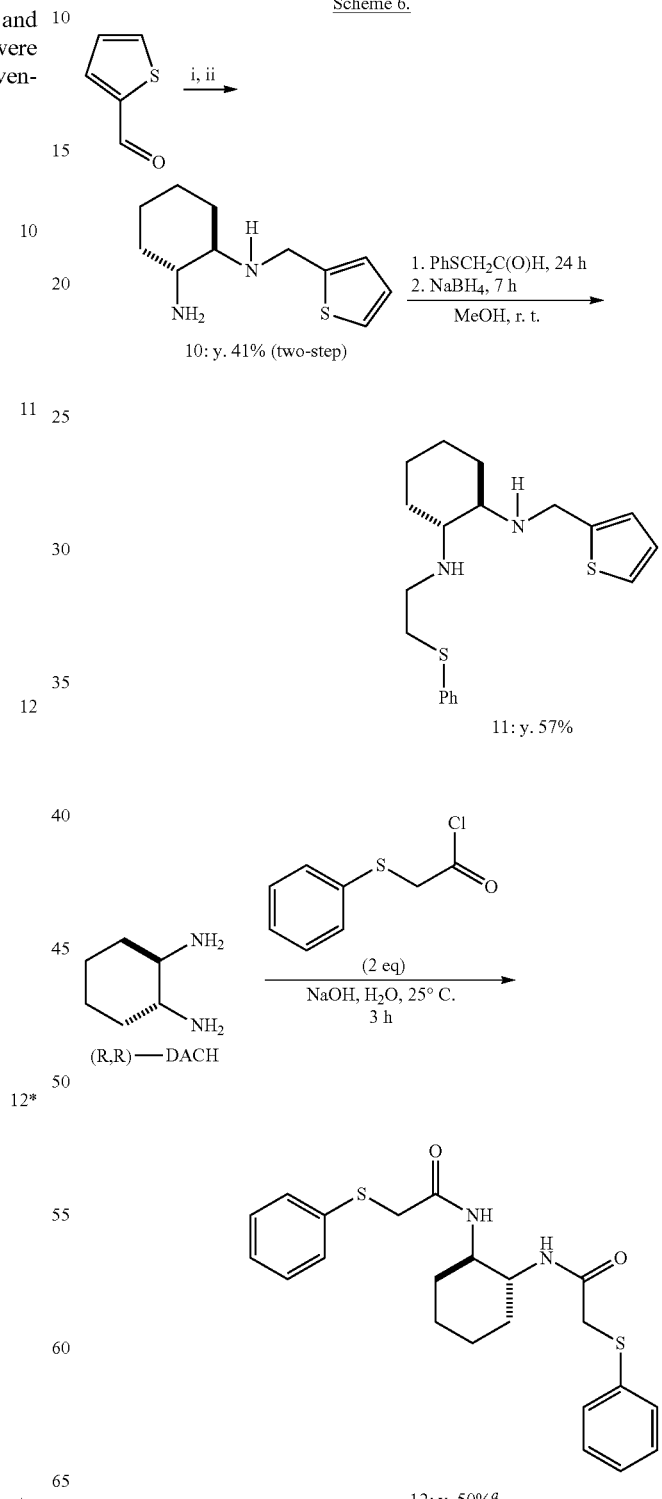

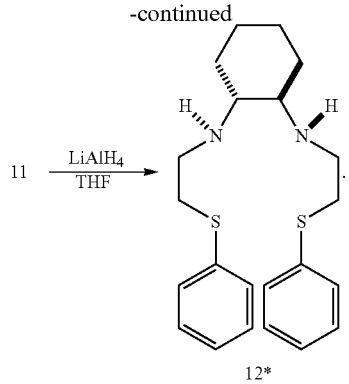

i: (R,R)—DACH (1 equiv) in H₂O, r. t., 2 h;
ii: NaBH₄ (excess), dry EtOH, reflux, 24 h.

Example 4.1. Synthesis of Ligand 10 ((1R,2R)—N1-(thiophen-2-ylmethyl)cyclohexane-1,2-diamine)

A yellow solution of (R,R)-DACH (5 g, 43.79 mmol) in 20 mL of H₂O was added to 4.91 g (43.79 mmol) of freshly distilled 2-thiophenecarbaldehyde in one portion. The obtained mixture was vigorously stirred for 2 h. After this, the obtained white precipitate was filtered on a Buchner funnel, washed with water (5×10 mL) and then pentane (5×20 mL) and dried overnight under vacuum to afford a 7:3 mixture of (1R,2R)—N1-(thiophen-2-ylmethylene)cyclohexane-1,2-diamine ($^1$H NMR: δ 8.47 (1H), 7.41 (d, $^3J_{H-H}$=4 Hz, 1H), 7.32 (d, $^3J_{H-H}$=4 Hz, 1H), 7.09 (t, $^3J_{H-H}$=4 Hz, 1H), 2.91 (m, 1H), 2.78 (m, 1H), 1.94 (d, $^3J_{H-H}$=11 Hz, 1H), 1.79 (m, 2H), 1.68 (m, 2H), 1.43-1.30 (m, 2H), 1.30-1.02 (m, 3H); $^{13}$C{$^1$H} NMR: δ 154.0, 142.5, 130.5, 128.7, 127.4, 77.9, 54.5, 33.7, 33.0, 25.1, 24.8) and (1R,2R)—N1,N2-bis(thiophen-2-ylmethylene)cyclohexane-1,2-diamine (characteristic imine CH resonances at δ 8.29, 2H) containing traces of starting (R,R)-DACH (<6%, characteristic CH resonances at δ 2.27, 2H) according to $^1$H NMR analysis (total 7.6 g). The obtained mixture was refluxed with NaBH₄ (7.7 g, ~5 equiv based on one C=N group) in 150 mL of dry EtOH for 24 h. The suspension was cooled to room temperature and H₂O (20 mL) was added to destroy excess NaBH₄. To the obtained mixture was added 80 mL of brine and 100 mL of CH₂Cl₂. The system was shaken, and the organic phase was separated on a separation funnel, washed with brine (3×80 mL), dried over anhydrous MgSO₄, filtered, then concentrated via rotary evaporation to give 6.88 g of a yellow-red liquid (1 h, 50° C., 40 mbar). The final product was obtained after vacuum distillation from this liquid. A very small fraction corresponding to traces of (R,R)-DACH (b.p. 58° C.) was precollected and solidified during distillation. The second fraction (b.p. 100-135° C.) corresponds to the desired product (bath temperature 180-225° C. under a fully opened vacuum line). Isolated yield: 3.75 g of a clear, slightly yellowish oil (41% two-steps yield, based on (R,R)-DACH). Alternatively, if desired, the final product could be purified by column chromatography on silica gel (eluent CH₂Cl₂-MeOH—NH₃ 10:1:0.5; $R_f$=0.36 for the desired product 9, $R_f$=0.69 for the C₂-symmetric (1R,2R)—N1,N2-bis(thiophen-2-ylmethyl)cyclohexane-1,2-diamine). Elem. Anal.: Calcd for C₁₁H₁₈N₂S (210.34): C, 62.81; H, 8.63; N, 13.32%. Found: C, 62.51; H, 8.43; N, 13.56%. $^1$H NMR (400 MHz, CDCl₃, 25° C.): δ 0.95-1.32 (series of m, 4H), 1.55 (br s, 3H, NH), 1.70 (m, 2H), 1.89 (d, $J_{H-H}$=12 Hz, 1H), 2.13 (m, 2H), 2.37 (m, 1H), 3.92 (d, $^2J_{H-H}$=14 Hz, 1H), 4.13 (d, $^2J_{H-H}$=14 Hz, 2H), 6.94 (m, 2H), 7.18 (m, 1H). $^{13}$C{$^1$H} (100.5 MHz, CDCl₃, 25° C.): δ 25.2 (s, 1C), 31.4 (s, 1C), 35.9 (s, 1C), 45.7 (s, 1C), 55.4 (s, 1C), 124.1 (s, 1C), 124.3 (s, 1C), 126.5 (s, 1C), 145.3 (s, 1C).

Example 4.2. Synthesis of Ligand 11 ((1R,2R)—N1-(2-(phenylthio)ethyl)-N2-(thiophen-2-ylmethyl)cyclohexane-1,2-diamine)

A solution of freshly prepared (phenylsulfanyl)acetaldehyde (668 mg, 4.39 mmol) in 7 mL of MeOH was added to a solution of 10 (922 mg, 4.38 mmol) in 5 mL of MeOH. The obtained mixture was stirred for 20 h to afford an orange (deep-red) solution. To this solution was slowly added NaBH₄ (4 equiv, 663 mg) and the system was stirred for 7 h at room temperature. To this mixture was added 5 mL H₂O and then 20 mL CH₂Cl₂. The organic phase was extracted. To the residual inorganic phase was added again 20 mL CH₂Cl₂ and brine (ca. 10 mL). The organic phase was extracted. The combined organic phases afforded the crude product as a yellow liquid after solvent evaporation. The product was purified by column chromatography (9×5 cm) on silica gel (Sigma, 230-400 mesh, 40-63µ, average pore diameter 60 Å, ~120 g); eluent: hexane-ethyl acetate 7:3 (4 eluent fractions), followed by CH₂Cl₂-MeOH—NH₃ 10:1:0.5 (dried over Na₂SO₄ overnight prior to use); Two fractions were collected at the end, corresponding to the desired product and the starting material 10). Yield 861 mg (57%), yellow-dark oil. Elem. Anal.: Calcd for C₁₉H₂₆N₂S₂ (346.55): C, 65.85; H, 7.56; N, 8.08%. Found: C, 65.77; H, 7.34; N, 8.05%. $^1$H NMR (400 MHz, CDCl₃, 25° C.): δ 1.02 (m, 2H), 1.23 (m, 2H, NH), 1.73 (br s, 2H), 1.93 (br s, 2H), 2.03 (m, 1H), 2.10-2.23 (m, 2H), 2.27 (m, 1H), 2.71 (m, 1H), 2.96 (m, 1H), 3.08 (t, $^3J_{H-H}$≈6 Hz, 2H), 3.90 (vd, $^2J_{H-H}$≈14 Hz, 1H), 4.16 (vd, $^2J_{H-H}$≈6 Hz, 1H), 6.95 (m, 2H), 7.20 (m, 2H), 7.29 (m, 2H), 7.38 (m, 2H). $^{13}$C{$^1$H} (100.5 MHz, CDCl₃, 25° C.): δ 24.9 (s, 1C), 25.0 (s, 1C), 31.5 (s, 1C), 31.8 (s, 1C), 34.7 (s, 1C), 45.5 (s, 1C), 45.6 (s, 1C), 60.6 (s, 1C), 61.4 (s, 1C), 124.1 (s, 1C), 124.4 (s, 1C), 126.0 (s, 1C), 126.5 (s, 1C), 128.9 (s, 1C), 130.0 (s, 1C), 136.2 (s, 1C), 145.1 (s, 1C).

Example 4.3. Synthesis of Ligand 12

(Phenylthio)acetyl chloride (5 g, 26.8 mmol, 97% Aldrich) was added dropwise to a stirred solution of (R,R)-DACH (1.53 g, 13.4 mmol, 98% Aldrich) in 25 mL water containing 2.68 g NaOH (5 equiv, 67 mmol). The reaction mixture was stirred 3 h, after which the white precipitate was filtered, washed with water (2×15 mL, 2×50 mL), ethanol (2×10 mL), and diethyl ether (3×15 mL) and dried under vacuum (jet pump, ~2 h) to afford 2.75 g (50% yield) of product as a white solid. Elem. Anal.: Calcd for C₂₂H₂₆N₂O₂S₂ (414.58): C, 63.74; H, 6.32; N, 6.76%. Found: C, 63.42; H, 6.22; N, 6.59%. $^1$H NMR (400 MHz, CDCl₃, r.t.): δ 1.12 (br m, 2H), 1.26 (br m, 2H), 1.68 (br m, 2H), 1.90 (d, J≈12 Hz, 2H), 3.25 (d, J≈17 Hz, 2H), 3.93 (d, J≈17 Hz, 2H), 3.63 (brs, 2H), 6.92 (brs, 2H), 7.13-7.45 (m, 10H). $^{13}$C{$^1$H} (100.5 MHz, CDCl₃, r.t.): δ 24.5 (s, 2C), 32.0 (s, 2C), 37.1 (s, 2C), 53.6 (s, 2C), 126.5 (s, 2C), 128.1 (s, 4C), 129.2 (s, 4C), 135.0 (s, 2C), 168.4 (s, 2C).

Example 5. Synthesis of P(O)NNS-type and PNNS-Type Chiral Ligands

Non-limiting examples of P(O)NNS-type and PNNS chiral ligands of C₁-symmetry are shown in Chart 5:

Chart 5.

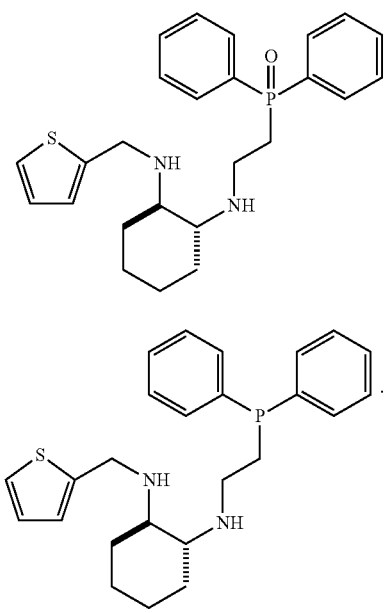

13

13*

Air-stable ligand 13 was synthesized according to Scheme 7. The reaction was performed in air inside a fume hood. Ligand 13* may be prepared by reduction of 13 with any suitable reducing agent under an inert atmosphere, for example, a silane, as shown in Scheme 7 (under argon).

Scheme 7.

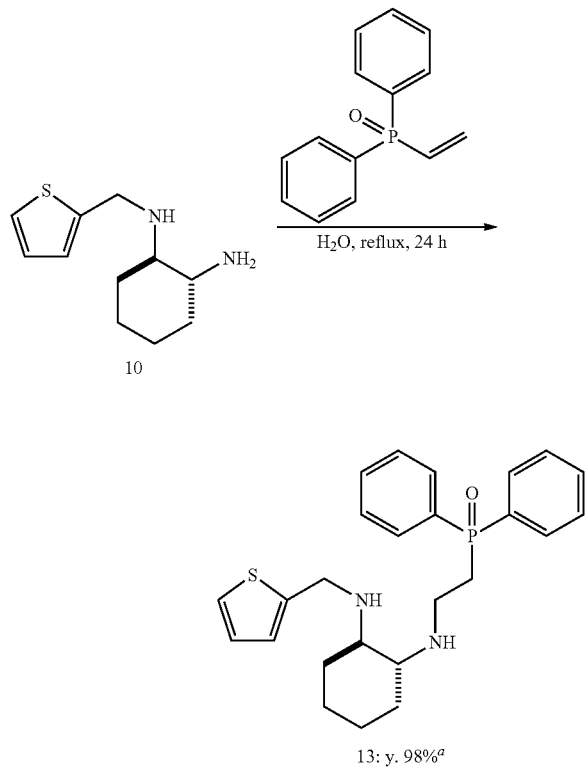

13: y. 98%[a]

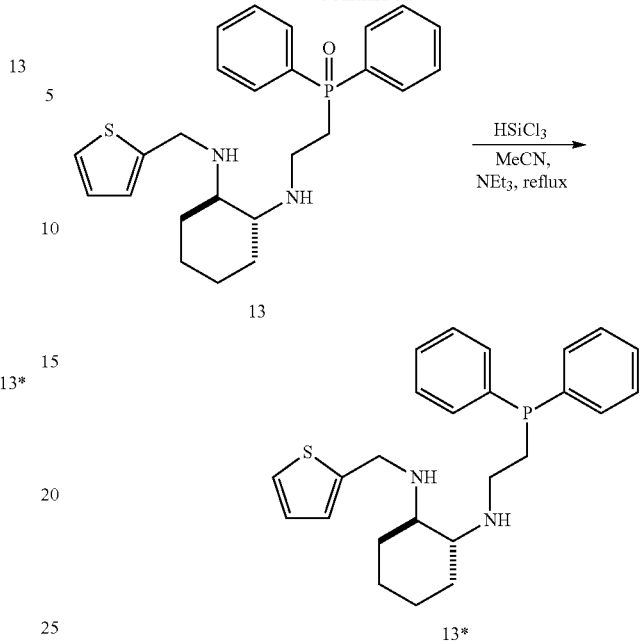

13

13*

[a]Crude yield.

Example 5.1. Synthesis of Ligand 13

A mixture of 10 (547 mg. 2.60 mmol) and diphenylvinylphosphine oxide (593 mg, 2.60 mmol) in 3 mL of water was refluxed for 24 h. The organic product was extracted with dichloromethane (3×5 mL), dried over anhydrous $MgSO_4$, filtered, and then concentrated to give a yellow-red oily material (1120 g, 98% crude yield). The oily material crystallizes as a white powder upon passing through a chromatography column (silica gel or alumina) or upon standing to afford white-orange crystals. In the latter case, the crystals were washed with $Et_2O$ (3×15 mL) and binary $Et_2O$-pentane (1:1, 25 mL each), and vacuum dried to afford a white precipitate. A portion of the crystals were recrystallized from hexane-dichloromethane to afford a white crystalline material. Elem. Anal.: Calcd for $C_{25}H_{31}N_2OPS$ (438.57): C, 68.47; H, 7.12; N, 6.39%. Found: C, 68.49; H, 7.13; N, 6.30%. $^{31}P\{^1H\}$ (162 MHz, $CDCl_3$, r.t.): δ 31.0 (s). $^1H$ NMR (400 MHz, $CDCl_3$, r.t.): δ 0.83-1.07 (m, overlapped, 2H), 1.72 (br t, 2H), 1.68 (br t, 2H), 1.91 (br s, 2H), 2.00 (d, J≈13 Hz, 1H), 2.05-2.24 (m, overlapped, 3H), 2.44-2.62 (m, 2H), 2.80 (vq, J≈10 Hz, 1H), 3.06 (vq, J≈10 Hz, 1H), 3.86 (d, J≈14 Hz, 1H), 4.08 (d, J≈14 Hz, 1H), 6.90 (s, 1H), 6.95 (vt, J≈3 Hz, 1H), 7.19 (d, J≈5 Hz, 1H), 7.40-7.56 (m, 6H), 7.69-7.84 (m, 4H). $^{13}C\{^1H\}$ (100.5 MHz, $CDCl_3$, r.t.): δ 24.9 (two s, overlapped, 2C), 31.1 (d, $J_{C-P}$=65 Hz, 1C), 31.5 (s, 1C), 40.0 (s, 1C), 45.5 (s, 1C), 53.5 (s, 1C), 60.5 (s, 1C), 61.5 (s, 1C), 124.1 (s, 1C), 124.4 (s, 1C), 126.6 (s, 1C), 128.7 (d, $J_{C-P}$=12 Hz, $4C_{meta}$, Ph), 130.7 (d, $J_{C-P}$=9 Hz, $4C_{ortho}$, $PPh_3$), 131.7 (d, $J_{C-P}$=3 Hz, $2C_{para}$, Ph), 133.0 (d, $J_{C-P}$=99 Hz, $2C_{ipso}$), 145.1 (s, 1C).

Example 6. Preparation of Catalyst Complexes

Complexes of ruthenium, iridium, manganese, iron, cobalt, nickel or copper comprising the inventive ligands were prepared from the NNS-type, P(O)NS-type, PNS-type, SNNS-type, SNNP(O)-type, and SNNP-type polydentate ligands and suitable precursors of transition metals under inert atmosphere. Syntheses of ruthenium(II) complexes of the general formula [RuCl$_2$(ligand)L] were typically performed by reacting the ligand with a suitable ruthenium precursor such as [RuCl$_2$(PPh$_3$)$_3$], [RuCl$_2$($\eta^4$-COD)]$_n$/L or [RuCl$_2$(DMSO)$_4$] in a solvent at room temperature or reflux. Syntheses of iridium(I) or iridium(III) complexes were typically performed by reacting the ligand with a suitable iridium precursor such as [IrCl($\eta^2$-COE)$_2$]$_2$ in a solvent at room temperature. Syntheses of [MCl$_2$(ligand)] (M=Mn, Fe, Co, Cu) or [NiCl$_2$(ligand)(EtOH)] were typically performed by reacting the ligand with a suitable metal precursor such as MnCl$_2$, FeCl$_2$, CoCl$_2$, CuCl$_2$ or NiCl$_2$ in a solvent at room temperature.

Example 6.1. Synthesis and Characterization of Ruthenium Complexes Using NNS-Type Ligands Chart 6 illustrates non-limiting examples of ruthenium complexes including NNS-type ligands that were synthesized, isolated and subsequently used as precatalysts in catalytic reactions.

Chart 6

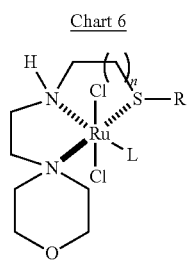

n = 1
A-1: L = PPh$_3$, R = Ph
A-2: L = PPh$_3$, R = Bn
A-3: L = PPh$_3$, R = Me
A-4: L = PCy$_3$, R = Ph
A-5: L = DMSO, R = Ph
n = 2
A-6: L = PPh$_3$, R = Bn

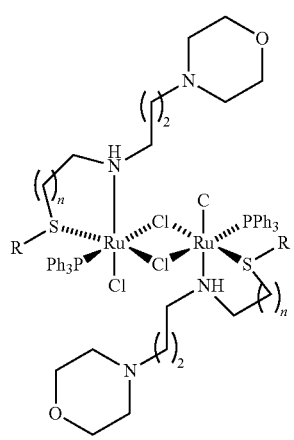

J-1: n = 1, R = Ph
J-2: n = 2, R = Bn

-continued

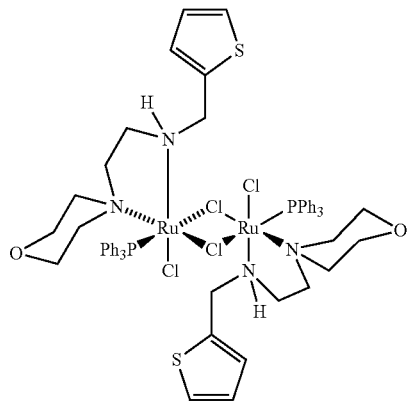
L-1

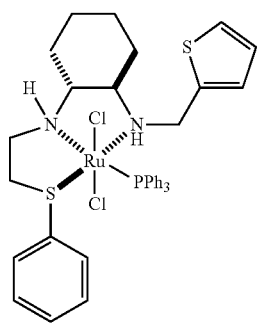
F-1

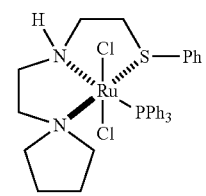
B-1

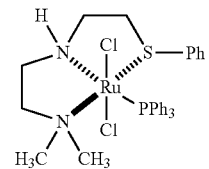
C-1

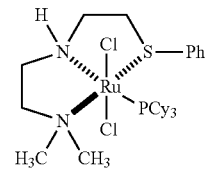
C-2

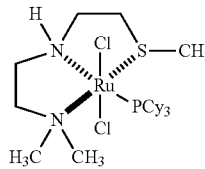
C-3

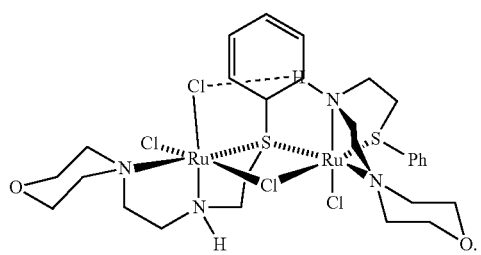

Schemes 8 and 9 illustrate several example ruthenium complexes including NNS-type ligands ("Morph-ENENES" ligands) that were synthesized, isolated and subsequently used as precatalysts in catalytic reactions, including hydrogenation reactions. [RuCl$_2$(PPh$_3$)$_3$], [RuCl$_2$($\eta^4$-COD)]n/PR$_3$, [RuCl$_2$($\eta^4$-COD)]n and [RuCl$_2$(DMSO)$_4$] were used to prepare the various precatalysts. Isolated yields are listed below each product. Stability information refers to the stability of the compound when stored in the solid-state.

Scheme 8

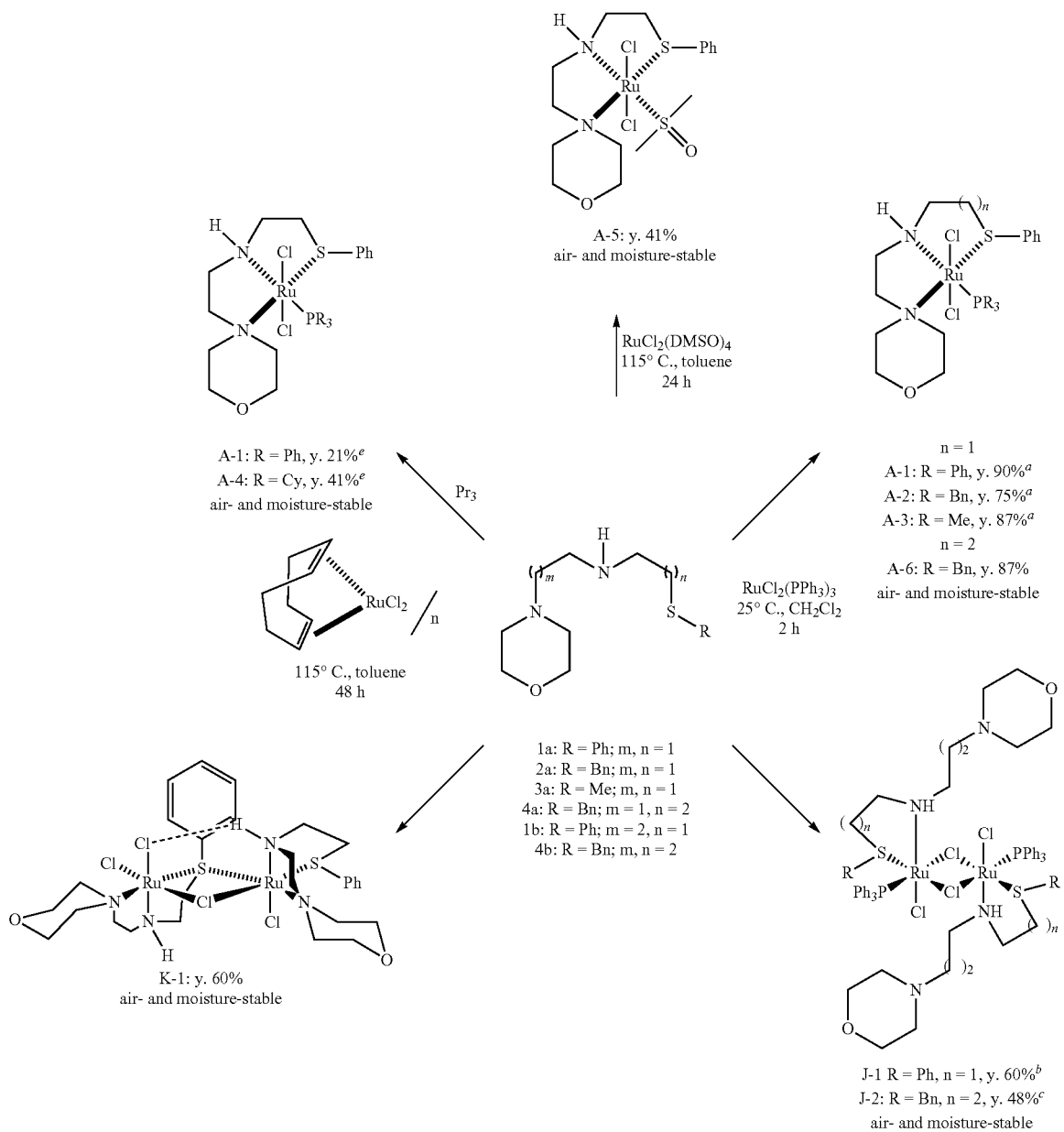

-continued
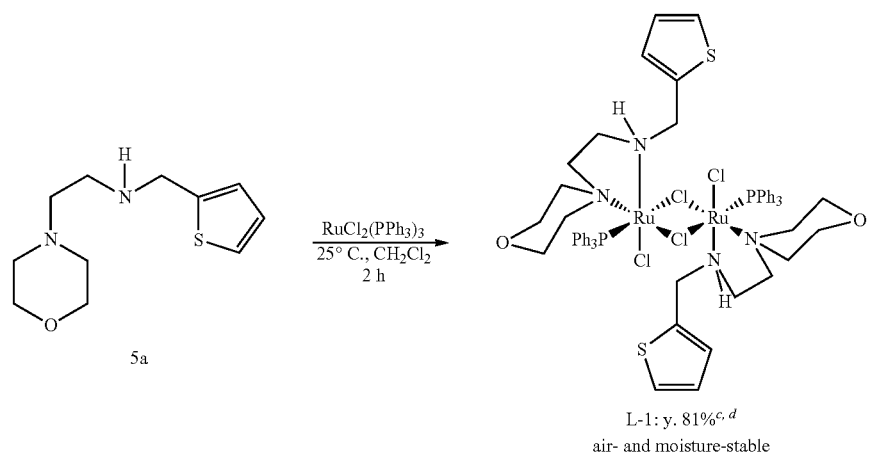
L-1: y. 81%[c, d]
air- and moisture-stable
[a]100% 31P{1H} NMR yield after 1 h.
[b]Reaction affords cis-[RuCl2{K2(N',S)-1b}(PPh3)2] (100% in 1 h, in situ 31P{1H} NMR) prior to crystallization.
[c]Complicated mixture as observed by in situ 31P{1H} NMR spectroscopy prior to crystallization.
[d]Possible structure.
[e]The yield was not optimized.
Scheme 9
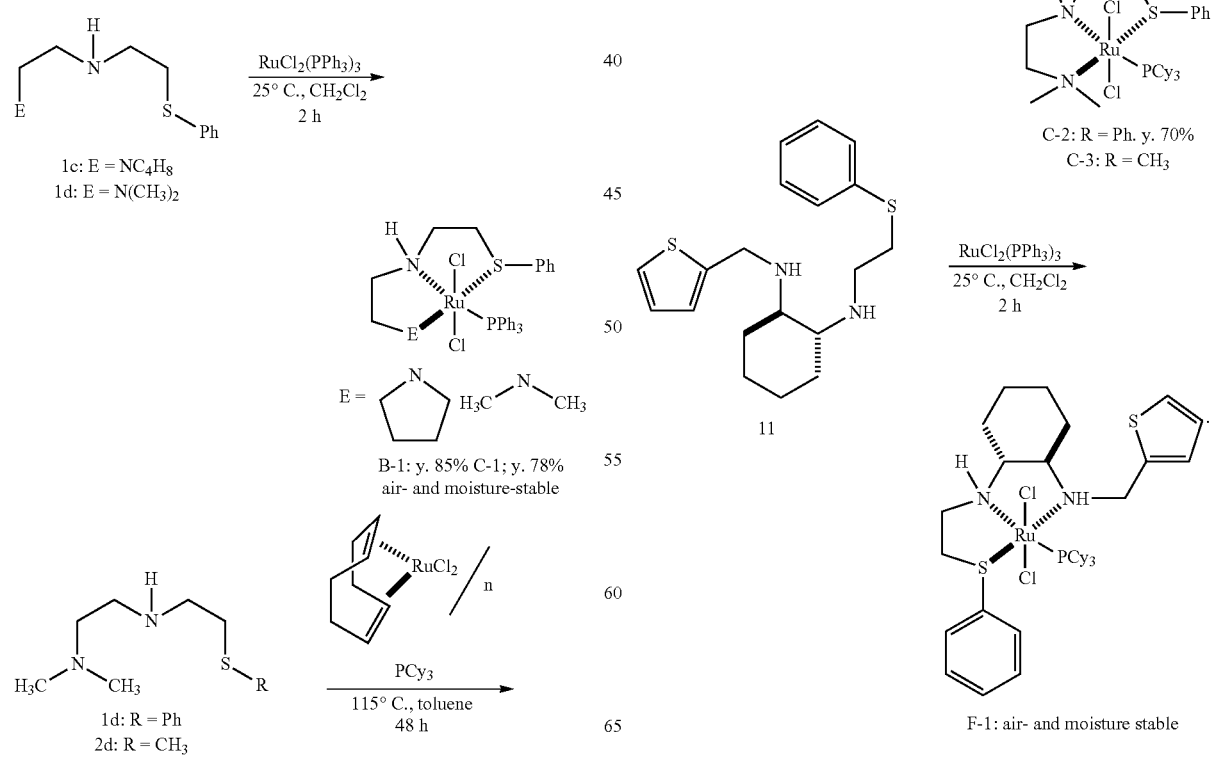

Non-limiting examples of suitable transition metal precursors useful for preparing embodiment complexes include [RuCl$_2$(PPh$_3$)$_3$], [RuCl$_2$($\eta^4$-COD)]$_n$/PR$_3$ (COD=cyclo-octa-1,5-diene, PR$_3$=PPh$_3$, PCy$_3$), [RuCl$_2$($\eta^4$-COD)]$_n$, [RuCl$_2$(DMSO)$_4$] (DMSO=dimethylsulfoxide) and [IrCl($\eta^2$-COE)$_2$]$_2$ (COE=cyclooctene).

In some embodiments, the complexes of Ruthenium were prepared by reacting a ligand selected from 1a, 2a, 3a, 4a, 1b, 4b and 5a (in which E=morpholine) with either [RuCl$_2$(PPh$_3$)$_3$] or [RuCl$_2$($\eta^4$-COD)]$_n$.

Example 6.1.1. Synthesis of Complex A-1. Method A

A solution of 1a (100 mg, 0.375 mmol) in 5 mL of CH$_2$Cl$_2$ was added to [RuCl$_2$(PPh$_3$)$_3$] (360 mg, 0.375 mmol) with stirring. The resulting burgundy solution was stirred at room temperature. An analysis of the reaction mixture by $^{31}$P NMR spectroscopy after 1 hour revealed complete conversion of the starting material into the product, indicated by a resonance at δ 40.9 ppm, and the presence of free PPh$_3$, (6-5.5 ppm). After reacting for a total of 2 hours, the burgundy solution was concentrated to approximately 40% of its original volume, followed by layering with diethyl ether (22 mL) to induce slow crystallization via diffusion. After six days, the mother liquor was decanted, leaving a light pink powder. This powder was transferred to a filter frit, washed with diethyl ether (3×10 mL) and vacuum dried overnight. Isolated yield of complex A-1: 236 mg (90%). Elem. Anal.: Calc'd for C$_{32}$H$_{37}$Cl$_2$N$_2$OPRuS (700.66): C, 54.86; H, 5.32; N, 4.00%. Found: C, 54.96; H, 5.19; N, 4.03%. $^{31}$P{$^1$H} (162 MHz, CD$_2$Cl$_2$, r.t.): δ 41.0 (s). $^1$H NMR (400 MHz, CD$_2$Cl$_2$, r.t.): δ 2.81 (vt, J≈14 Hz, 1H), 2.93-3.07 (m, 2H), 3.16-3.39 (m, 7H), 3.46-3.58 (m, 2H), 3.62-3.68 (m, 3H), 3.81 (vt, J≈13 Hz, 1H), 5.88 (br s, NH, 1H), 6.98 (t, J≈8 Hz, 2H), 7.20-7.33 (m, 12H), 7.72 (vt, J≈9 Hz, 6H). $^{13}$C{$^1$H} (100.5 MHz, CD$_2$Cl$_2$, r.t.): δ 44.9 (s, 1C), 47.0 (s, 1C), 48.4 (s, 1C), 52.9 (s, 1C), 54.7 (s, 1C), 59.3 (s, 1C), 60.2 (s, 1C), 61.6 (s, 1C), 127.1 (d, J$_{C-P}$=8.7 Hz, 6C$_{meta}$, PPh$_3$), 127.9 (s, 2C$_{meta}$, Ph), 128.5 (d, J$_{C-P}$=1.5 Hz, 3C$_{para}$, PPh$_3$), 128.6 (s, 1C$_{para}$, Ph), 133.1 (s, 2C$_{ortho}$, Ph), 134.5 (d, J$_{C-P}$=9.5 Hz, 6C$_{ortho}$, PPh$_3$), 134.8 (s, 1C$_{ipso}$, Ph), 137.7 (d, J=36 Hz, 3C$_{ipso}$); $^{31}$P{$^1$H} (162 MHz, CDCl$_3$, r.t.): δ 40.3 (s). $^1$H NMR (400 MHz, CDCl$_3$, r.t.): δ 2.74 (vt, J≈14 Hz, 1H), 2.94-3.02 (m, 2H), 3.11-3.45 (m, 9H), 3.51-3.70 (m, 5H), 3.78 (vt, J≈13 Hz, 1H), 5.87 (br s, NH, 1H), 6.95 (t, J≈8 Hz, 2H), 7.15-7.32 (m, 12H), 7.72 (t, J≈9 Hz, 6H). $^{13}$C{$^1$H} (100.5 MHz, CDCl$_3$, r.t.): δ 45.2 (s, 1C), 47.2 (s, 1C), 48.5 (s, 1C), 52.8 (s, 1C), 54.8 (s, 1C), 58.9 (s, 1C), 60.2 (s, 1C), 61.6 (s, 1C), 127.3 (d, J$_{C-P}$=8.7 Hz, 6C$_{meta}$, PPh$_3$), 128.1 (s, 2C$_{meta}$, Ph), 128.7 (d, J$_{C-P}$=1.5 Hz, 3C$_{para}$, PPh$_3$), 128.8 (s, 1C$_{para}$, Ph), 133.2 (s, 2C$_{ortho}$, Ph), 134.6 (d, J$_{C-P}$=9.5 Hz, 6C$_{ortho}$, PPh$_3$), 134.5 (s, 1C$_{ipso}$, Ph), 137.1 (d, J=36 Hz, 3C$_{ipso}$).

Example 6.1.2. Synthesis of Complex A-1. Method B

A mixture of [RuCl$_2$(COD)]n (359 mg, 1.281 mmol), PPh$_3$ (336 mg, 1.281 mmol) and ligand 1a (341 mg, 1.281 mmol) was stirred in THF (15 mL) at 75° C. for 39 h in a KONTES® pressure tube. After cooling down, the resulting brick precipitate was collected on a filter frit, washed with diethyl ether (3×5 mL), and vacuum dried. Recrystallization from hot dichloromethane followed by layering with diethyl ether afforded analytically pure complex A-1 in 29% yield (260 mg).

Example 6.1.3. Synthesis of Complex A-2

Complex A-2 was prepared similarly to complex I in Method A (vide supra), with the exception that ligand 2a was used instead of ligand 1a. After decantation of the mother liquor, the obtained red rhombic crystals were washed with diethyl ether (3×10 mL) and vacuum dried overnight. Isolated yield of complex A-2: 225 mg (75%) of C$_{33}$H$_{39}$Cl$_2$N$_2$OPRuS—CH$_2$Cl$_2$ (based on $^1$H NMR. Elem. Anal.: Calc'd for C$_{33}$H$_{39}$Cl$_2$N$_2$OPRuS—CH$_2$Cl$_2$ (768.20): C, 51.07; H, 5.17; N, 3.50%. Found: C, 52.53; H, 5.38; N, 3.54%. The elemental analysis better fits the C$_{33}$H$_{39}$Cl$_2$N$_2$OPRuS.0.63CH$_2$Cl$_2$ (768.20) formulation, Calc'd: C, 52.58; H, 5.28; N, 3.65%. Some co-crystallized CH$_2$Cl$_2$ appears to have been lost during elemental analysis. Independent experiments showed that the amount of solvate depended on the drying time. The compound existed in CDCl$_3$ or CD$_2$Cl$_2$ as a mixture of presumably two diastereomers (79:21 ratio). $^{31}$P{$^1$H}(162 MHz, CDCl$_3$, r.t.): δ 39.6 (s, major, 79%), 40.3 (s, minor, 21%). $^{31}$P{$^1$H} (162 MHz, CD$_2$Cl$_2$, r.t.): δ 40.6 (s, major, 79%), 40.9 (s, minor, 21%).

Example 6.1.4. Synthesis of Complex A-3

Complex A-3 was prepared similarly to complex I, following method A (vide supra), with the exception that ligand 3a was used instead of ligand 1a. After decantation of the mother liquor, the obtained red crystals were washed with diethyl ether (3×10 mL) and vacuum dried overnight. Isolated yield: 209 mg (87%). Elem. Anal.: Calc'd for C$_{27}$H$_{35}$Cl$_2$N$_2$OPRuS (638.59): C, 50.78; H, 5.52; N, 4.39%. Found: C, 50.77; H, 5.51; N, 4.29%. The compound exists in CD$_2$Cl$_2$ as a mixture of presumably two diastereomers (74:26 ratio). $^{31}$P{$^1$H} (162 MHz, CD$_2$Cl$_2$, r.t.): δ 40.9 (s, minor, 24%), 41.9 (s, major, 76%).

Example 6.1.5. Synthesis of Complex A-6

Complex A-6 was prepared similarly to complex A-1 in method A (vide supra), with the exception that ligand 4a was used instead of ligand 1a. After decantation of the mother liquor, a large (>1 cm) red crystal was transferred onto a filter frit, washed with diethyl ether (3×10 mL), dried under vacuum, broken, and vacuum dried overnight. Isolated yield: 238 mg (87%). Elem. Anal.: Calc'd for C$_{34}$H$_{41}$Cl$_2$N$_2$OPRuS (728.72): C, 56.04; H, 5.67; N, 3.84%. Found (under nitrogen): C, 56.32; H, 5.75; N, 3.85%. The compound exists in CD$_2$Cl$_2$ as a mixture of presumably two diastereomers (99:1 ratio). $^{31}$P{$^1$H} (162 MHz, CD$_2$Cl$_2$, r.t.): δ 42.9 (s, minor, 1%), 46.0 (s, major, 99%). $^1$H NMR (400 MHz, CD$_2$Cl$_2$, r.t., major): δ 2.03 (d, J≈13 Hz, 1H), 2.17 (t, J≈13 Hz, 1H), 2.25 (q, J≈13 Hz, 1H), 2.25 (d, J≈14 Hz, 2H), 2.92-3.23 (overlapped m, 10H), 3.52 (d, J≈19 Hz, 1H), 3.58-3.83 (overlapped m, 4H), 4.78 (br s, 1H, NH), 6.87 (br s, 2H), 7.20 (br s, 3H), 7.39 (br s, 9H), 7.93 (br s, 6H). $^{13}$C{$^1$H} (100.5 MHz, CD$_2$Cl$_2$, r.t., major): δ 24.4 (s, 1C), 25.2 (s, 1C), 37.2 (s, 1C), 49.6 (s, 1C), 50.1 (s, 1C), 51.5 (s, 1C), 51.7 (s, 1C), 58.0 (s, 1C), 60.1 (s, 1C), 61.2 (s, 1C), 127.0 (s, 1C$_{para}$, Ph), 127.2 (d, J$_{C-P}$=9 Hz, 6C$_{meta}$, PPh$_3$), 128.3 (s, 2C$_{meta}$, Ph), 128.7 (br s, 3C$_{para}$, PPh$_3$), 129.2 (s, 2C$_{ortho}$, Ph), 135.2 (d, J$_{C-P}$=9 Hz, 6C$_{ortho}$, PPh$_3$), 136.6 (s, 1C$_{ipso}$, Ph), 136.9 (d, J=36 Hz, 3C$_{ipso}$).

Complexes A-1, A-2, A-3, and A-6 were air-stable and moisture stable. After they were prepared, they were all handled in air, and all were characterized by elemental analysis and NMR ($^1$H, $^{13}$C, $^{31}$P) spectroscopy (vide supra).

In addition, X-Ray crystal structures of complexes A-1, A-2, A-3, and A-6 were obtained. and shown to be isostructural κ³[N,N',S]-tridentate trans-[Ru^{II}Cl₂{κ³(N,N',S)—NNS-type ligand}(PPh₃)] complexes.

It may also be worth making some comparisons about the solution phase behavior of complexes A-1, A-2, A-3, and A-6. A second isomer (presumably diastereomer) was not detected for complex A-1 in CD₂Cl₂ by NMR spectroscopy at ambient temperature. For complexes A-2 and A-3, the quantity of a second isomer slightly increases with a decrease in bulkiness of the substituent on the sulfur donor atom (21% for A-2 and 24% for A-3. For complex A-1, which is a 5,6-metallacycle, the second isomer was present at only 1% of the total amount (compared to 21% for complex II, a 5,5-metallacycle). The X-ray structures of these complexes were all similar, being 5,5 or 5,6-ruthenacycles in which the three heteroatoms (N, N and S) are located in a single plane. The chlorine atoms are located in trans-orientation to each other, and the PPh₃ moiety is located trans to the NH group. These structures resemble those of known Ru—PNN complexes and other pincer Ru complexes that include P/N tridentate ligands. Upon dissolution of X-Ray quality crystals of A-1, A-2, A-3, and A-6 in NMR solvents, two isomers (presumably diastereomers) were observed in their respective solution NMR spectra.

Example 6.1.6. Synthesis of Complex J-1

Complex J-1 was prepared similarly to complex A-1 in method A, with the exception that ligand 1b was used instead of ligand 1a. ³¹P NMR analysis of the reaction mixture revealed full conversion of the starting material over 1 hr, presumably into cis-[Ru(PPh₃)₂Cl₂(N,S-ligand)], δ 26.8 ppm (br s, 1P), 36.7 ppm (d, ²J_{P—P}=31 Hz, 1P), and free PPh₃, δ −5.5 ppm. The air-sensitive mixture was stirred for 2 hours and then concentrated to approximately 40% of the original volume, and then layered with diethyl ether (22 mL) to induce crystallization and left for eight days. After decantation of the mother liquor, the obtained red needle crystals were transferred onto a filter frit, washed with diethyl ether (3×10 mL) and vacuum dried overnight. Isolated yield: 162 mg (60%). Elem. Anal.: Calc'd for C₆₆H₇₈C₁₄N₄O₂P₂Ru₂S₂ (1429.38): C, 55.46; H, 5.50; N, 3.92%. Found: C, 55.68; H, 5.49; N, 3.79%. The compound is air-stable at least in the solid-state. The obtained needle-like crystals were sparingly soluble in CD₂Cl₂, CDCl₃, CD₃OD, acetone-d₆ and DMF-d₇. Saturated solutions of small concentrations exhibited complicated ³¹P NMR spectra.

Example 6.1.7. Synthesis of Complex J-2

Complex J-2 was prepared similarly to complex J-1 with the exception that ligand 4b was used instead of ligand 1b. After decantation of the mother liquor, the resulting orange solid was transferred to a filter frit, washed with diethyl ether (3×10 mL) and vacuum dried overnight. Isolated yield: 134 mg (48%), orange solid. Elem. Anal.: Calc'd for C₇₀H₈₆C₁₄N₄O₂P₂Ru₂S₂ (1485.49): C, 56.60; H, 5.84; N, 3.77%. Found: C, 56.42; H, 5.85; N, 3.73%. Similarly to J-1, dimeric J-2 is sparingly soluble in CD₂Cl₂, CDCl₃, CD₃OD, acetone-d₆ and DMF-d₇. Upon standing, the mother liquor produced red crystals after about 1 week (not quantified). X-Ray structural analysis identified the red crystalline product as an unsymmetrical, trichloro-bridged bimetallic complex containing a κ²[N',S]-bidentate ligand, [Ru{κ²(N',S)-4b}(PPh₃)(μ-Cl)₃RuCl(PPh₃)₂] (J-3). This could formally be viewed as the product of an association reaction involving a 16 electron monomer of J-2, (i.e. complex [RuCl₂{κ²(N',S)-4b}(PPh₃)]) and a 14 electron unsaturated fragment, [RuCl₂(PPh₃)₂], that intercept each other within the reaction mixture. Thus, this product is an intermediate or a by-product formed as a result of this complicated reaction. Similarly to J-1, the compound J-2 is sparingly soluble in CD₂Cl₂, CDCl₃, CD₃OD, acetone-d₆ and DMF-d₇. Saturated solutions (low concentrations) exhibit complicated ³¹P{¹H} NMR spectra.

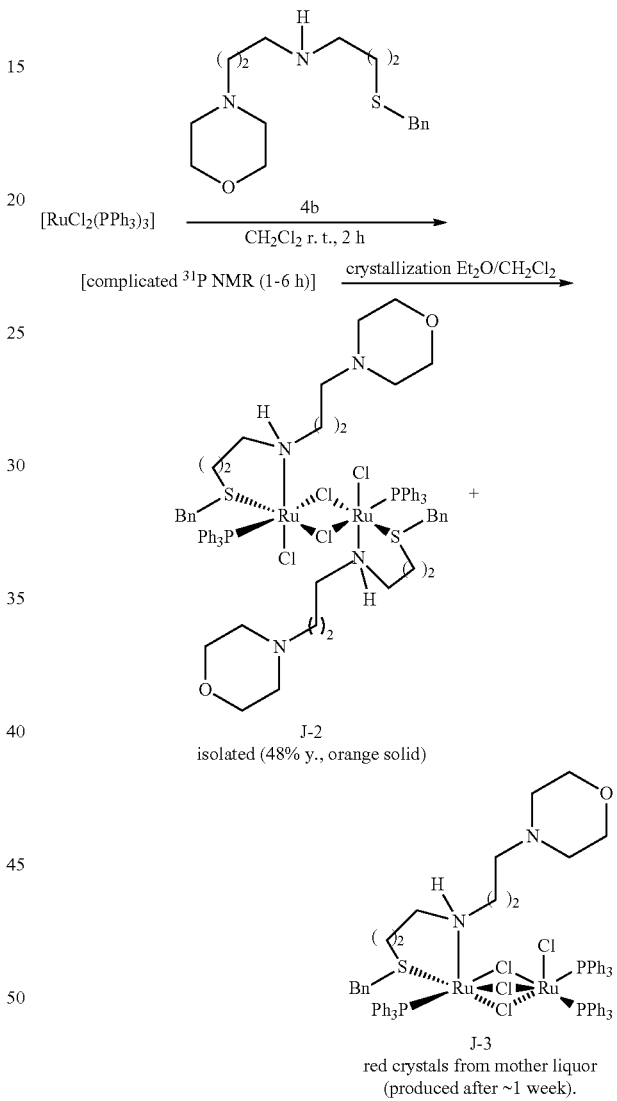

The identity of embodiment complexes J-1 and J-2 were supported by elemental analysis, and the mode of ligand coordination in J-1 was determined from single-crystal X-Ray structural analysis. The crystallographic data show that ligand 1b binds to each Ru atom in a bidentate κ²[N', S]-fashion, affording a five-membered NS ring. The morpholine moieties are directed away from the metal centers. The Ru atoms are connected via two bridging chlorine (Cl) atoms. Each terminal Cl atom is believed to participate in hydrogen bonding with the NH group of the ligand coordinated to the other Ru atom. It may be worth noting that compared to the formation of complexes using ligands 1a, 2a, and 3a, in situ $^{31}$P NMR spectroscopic monitoring of the reactions with ligands 1b and 4b in $CD_2Cl_2$ solvent indicated more complicated mixtures prior to crystallization.

Example 6.1.8. Synthesis of Complex L-1

Complex L-1 was prepared similarly to complex A-1 following method A with the exception that ligand 5a was used instead of ligand 1a. The in situ $^{31}$P NMR monitoring of the reaction of ligand 5a with [RuCl$_2$(PPh$_3$)$_3$] revealed a complicated reaction mixture (in a separate experiment, the composition remained unchanged after 5 h). After 2 hours, the solution was concentrated to approximately 40% of the original volume and was then layered with diethyl ether (22 mL). After 20 days, the mother liquor was decanted and the resulting scarlet powder was transferred to a filter frit, washed with diethyl ether (3×10 mL), and vacuum dried overnight. Isolated yield: 201 mg (81%). Elem. Anal.: Calc'd for $C_{58}H_{66}C_{14}N_4O_2P_2Ru_2S_2$ (1321.20): C, 52.73; H, 5.04; N, 4.24%. Found: C, 51.70; H, 4.85; N, 4.24%. $^1$H NMR (400 MHz, CD$_2$Cl$_2$, r.t., major): δ 1.42 (d, J≈14 Hz, 1H), 1.84 (dd, J≈5 Hz, J≈14 Hz, 1H), 2.16 (t, J≈14 Hz, 1H), 2.47 (d, J≈13 Hz, 1H), 2.63 (d, J≈16 Hz, 1H), 2.85 (br s, 1H), 3.28 (d, J≈13 Hz, 1H), 3.45 (d, J≈13 Hz, 1H), 3.54-3.79 (overlapped m, 4H), 3.84-4.06 (overlapped, 2H), 4.29 (dt, J≈3 Hz, J≈14 Hz, 1H), 6.87 (br s, 1H), 7.02 (m, 1H), 7.39 (brs, 10H), 7.83 (d, J≈5 Hz, 2H), 8.07 (br s, 5H). The NMR ($^1$H, $^{31}$P) spectroscopic analysis and elemental analysis are consistent with the formula shown for complex L-1. Complex L-1 is air-stable at least in the solid-state. It is sparingly soluble in CD$_2$Cl$_2$ and CDCl$_3$ and almost insoluble in THF-d$_8$, MeOD, and acetone-d$_6$. These solutions were air-sensitive. It should be noted that if the scarlet precipitated powder was collected after 10 days, the yield dropped to 14%. An X-ray structure was obtained of a red crystal produced from the mother liquor of L-1; this X-Ray structure revealed an ion-pair complex [Ru$_2$(μ$_2$-Cl)$_3$Cl$_2$(PPh$_3$)$_4$]$^-$ 5aH$^+$ (L-2), which consists of a binuclear trichloro-bridged anion [Ru$_2$(μ$_2$-Cl)$_3$Cl$_2$(PPh$_3$)$_4$]$^-$ and protonated 5a_EN-REF_124.

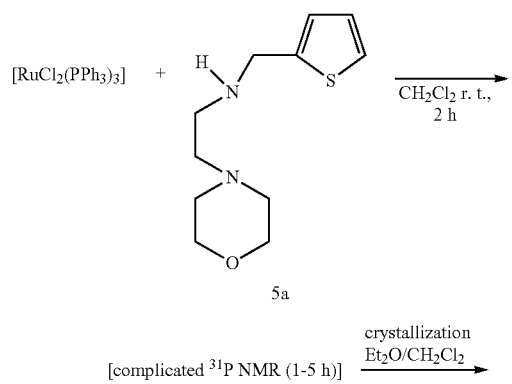

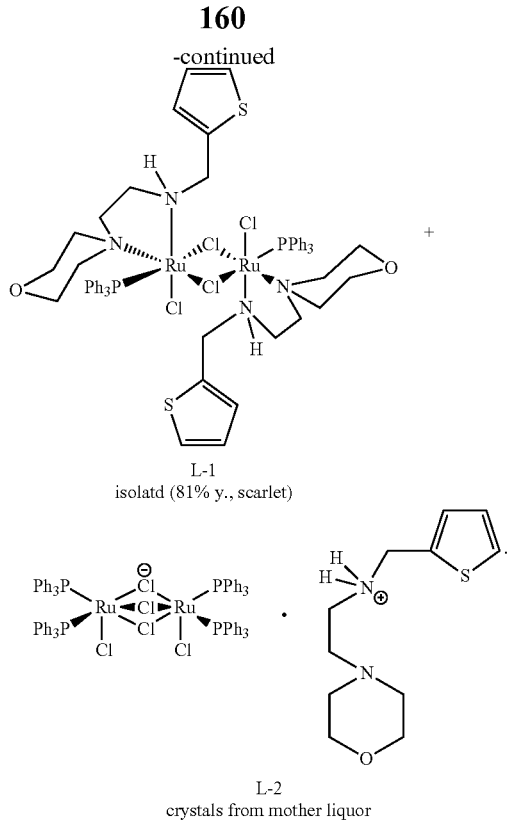

L-1
isolatd (81% y., scarlet)

L-2
crystals from mother liquor

Example 6.1.9. Synthesis of Complex B-1

The procedure for preparing complex B-1 was similar to that for preparing complex A-1, method A, with the exception that ligand 1c was used instead of ligand 1a. After the decantation of the mother liquor, the obtained light pink precipitate was collected on a filter frit, washed with diethyl ether (3×10 mL), and vacuum dried overnight. Isolated yield: 218 mg (85%). Elem. Anal.: Calc'd for $C_{32}H_{37}Cl_2N_2PRuS$ (684.67): C, 56.14; H, 5.45; N, 4.09%. Found: C, 56.33; H, 5.36; N, 3.79%. [31]P{[1]H} (162 MHz, CDCl$_3$, r.t.): δ 42.2 (s). $^1$H NMR (400 MHz, CD$_2$Cl$_2$, r.t.): δ 1.15 (vq, J≈8 Hz, 1H), 1.35 (vq, J≈8 Hz, 1H), 1.60 (m, 2H), 2.41 (vq, J≈12 Hz, 1H), 2.53 (d, J≈12 Hz, 1H), 2.93 (t, J≈13 Hz, 1H), 3.05 (m, 3H), 3.15 (d, J≈9 Hz, 1H), 3.29 (d, J≈9 Hz, 1H), 3.39 (d, J≈11 Hz, 1H), 3.56 (m, 2H), 3.15 (vq, J≈11 Hz, 1H), 5.85 (br s, NH, 1H), 6.94 (t, J≈8 Hz, 2H), 7.14 (t, J≈7 Hz, 1H), 7.14-7.25 (m overlapped, 6H), 7.26-7.33 (d, J≈8 Hz, 6H), 7.66 (t, J≈9 Hz, 5H). [13]C{[1]H} (100.5 MHz, CD$_2$Cl$_2$, r.t.): δ 20.5 (s, 1C), 22.1 (s, 1C), 45.4 (s, 1C), 47.3 (s, 1C), 49.3 (s, 1C), 57.7 (s, 1C), 61.2 (s, 1C), 62.5 (s, 1C), 127.0 (d, $J_{C-P}$≈8 Hz, 6C$_{meta}$, PPh$_3$), 128.0 (s, 2C$_{meta}$, Ph), 128.4 (d, $J_{C-P}$≈1.5 Hz, 3C$_{para}$, PPh$_3$), 128.5 (s, 1C$_{para}$, Ph), 133.0 (s, 2C$_{ortho}$, Ph), 134.6 (d, $J_{C-P}$≈9 Hz, 6C$_{ortho}$, PPh$_3$), 135.0 (s, 1C$_{ipso}$, Ph), 137.2 (d, J≈36 Hz, 3C$_{ipso}$).

Example 6.1.10. Synthesis of Complex C-1

Complex C-1 was prepared similarly to complex A-1, with the exception that ligand 1d was used instead of ligand 1a. Layering with diethyl ether afforded burgundy colored crystals that were collected on a filter frit, washed with Et$_2$O (3×10 mL), and vacuum dried overnight. The elemental analysis, NMR and X-Ray crystallography revealed that complex C-1 exists as a dichloromethane solvate. Isolated yield: 218 mg (78%). Elem. Anal.: Calc'd for $C_{30}H_{35}Cl_2N_2PRuS$—$CH_2Cl_2$ (743.55): C, 50.08; H, 5.02; N, 3.77%. Found C, 50.33; H, 5.12; N, 3.93%. $^{31}P\{^1H\}$ (162 MHz, $CD_2Cl_2$, r.t.): δ 44.3 (s). $^1H$ NMR (400 MHz, $CD_2Cl_2$, r.t.): δ 2.20 (d, J≈12 Hz, 1H), 2.35 (s, 3H), 2.48 (s, 3H), 3.05 (vd, J≈12 Hz, 1H), 3.17-3.26 (m, 1H), 3.26-3.35 (m, 2H), 3.43 (d, J≈11 Hz, 1H), 3.59 (m, 2H), 5.37 ($CH_2Cl_2$), 5.88 (br s, NH, 1H), 6.99 (t, J≈8 Hz, 2H), 7.19-7.26 (m, 6H), 7.26-7.35 (m, 6H), 7.69 (t, J≈9 Hz, 6H). $^{13}C\{^1H\}$ (100.5 MHz, $CD_2Cl_2$, r.t.): δ 44.9 (s, 1C), 47.1 (s, 1C), 48.5 (s, 1C), 51.2 (s, 1C), 49.3 (s, 1C), 52.8 (s, 1C), 53.8 (S, 1C, $CH_2Cl_2$), 67.0 (s, 1C), 127.1 (d, $J_{C-P}$≈8 Hz, $6C_{meta}$, $PPh_3$), 127.9 (s, $2C_{meta}$, Ph), 128.4 (d, $J_{C-P}$≈1.5 Hz, $3C_{para}$, $PPh_3$), 128.6 (s, $1C_{para}$, Ph), 133.1 (s, $2C_{ortho}$, Ph), 134.3 (d, $J_{C-P}$≈9 Hz, $6C_{ortho}$, $PPh_3$), 135.2 (s, $1C_{ipso}$, Ph), 138.0 (d, J≈37 Hz, $3C_{ipso}$).

Complex C-1 was also prepared using $[RuCl_2(COD)]_n$ as a precursor. Thus, a mixture of $[RuCl_2(COD)]_n$ (309 mg, 1.103 mmol), $PPh_3$ (289 mg, 1.103 mmol) and ligand 1d (248 mg, 1.103 mmol) was stirred in toluene (10 mL) at 115° C. for 24 h in a KONTES® pressure tube. After cooling, the resulting brick colored precipitate was filtered on a filter frit, washed with diethyl ether (3×10 mL), and vacuum dried to afford 494 mg of a light pink crude material (Found C, 53.43; H, 5.26; N, 4.08%). Recrystallization from hot THF by filtering and layering with diethyl ether afforded burgundy crystals (261 mg, 32% yield as a THF solvate). Based on NMR analysis, these crystals represent a THF solvate of complex C-1. The crystals were found to easily lose solvent based on elemental analysis. Elem. Anal.: Calc'd for $C_{30}H_{35}Cl_2N_2PRuS$ (658.63): C, 54.71; H, 5.36; N, 4.25%. Found C, 54.37; H, 5.66; N, 3.87%.

X-ray structures were obtained for both complex B-1 and complex C-1. The complexes B-1 and C-1 are isostructural; their solid state structures are also similar to those of octahedral complexes A-1, A-2, A-3, and A-6. The solution behavior of complexes B-1 and C-1 was similar to that of complex A-1 in that no detectable amount of a second isomer was observed in solution. Complexes B-1 and C-1 were tested as pre-catalysts for hydrogenation.

Example 6.1.11. Synthesis of Complex A-4

A mixture of $[RuCl_2(COD)]n$ (309 mg, 1.103 mmol), $PCy_3$ (309 mg, 1.103 mmol) and 1a (294 mg, 1.103 mmol) was stirred in toluene (10 mL) at 115° C. for 48 h in a KONTES® pressure tube. After cooling down, the brick colored precipitate was collected on a filter frit, washed with $Et_2O$ (3×10 mL), and vacuum dried to afford 642 mg of the crude material. $CH_2Cl_2$ (~32 mL) was added to the crude material and the obtained mixture was brought to reflux and filtered using a Whatman® syringe filter (PTFE membrane, pore size 0.45 μm). Layering the obtained red-brown solution with $Et_2O$ (125 mL) afforded 327 mg (41%) of the product as a pink-brown powder after 5 days. Elem. Anal.: Calcd for $C_{32}H_{55}Cl_2N_2OPRuS$ (718.81): C, 53.47; H, 7.71; N, 3.90%. Found: C, 53.11; H, 8.00; N, 3.86%. $^{31}P\{^1H\}$ (162 MHz, $CD_2Cl_2$, r.t.): δ 24.0 (s). $^1H$ NMR (400 MHz, $CD_2Cl_2$, r.t.): δ 0.09 (br s, 1H), 0.92 (br s, 2H), 1.04-1.63 (m, 15H), 1.63-2.05 (m, 9H), 2.10-2.45 (br s, 3H), 2.45-2.70 (br s, 1H), 2.83-3.28 (overlapped, 7H), 3.31-3.56 (overlapped, 6H), 3.56-3.90 (overlapped, 4H), 3.98 (t, J≈8 Hz, 1H), 5.57 (br s, NH, 1H), 7.31 (t, J≈7 Hz, 2H), 7.38 (t, J≈6 Hz, 1H), 8.15 (d, J≈7 Hz, 2H). $^{13}C\{^1H\}$ selected for the coordinated NNS ligand (100.5 MHz, $CD_2Cl_2$, r.t.): δ 46.6 (s, 1C), 46.8 (s, 1C), 48.3 (s, 1C), 53.9 (s, 1C, overlapped with $CD_2Cl_2$ peak), 54.8 (s, 1C), 60.0 (s, 1C), 60.7 (s, 1C), 61.7 (s, 1C), 128.1 (s, $2C_{meta}$, Ph), 129.3 (s, $1C_{para}$, Ph), 134.9 (s, $2C_{ortho}$, Ph), 138.0 (s, $1C_{ipso}$, Ph).

Example 6.1.12. Synthesis of Complex K-1

A mixture of $[RuCl_2(COD)]n$ (155 mg, 0.552 mmol) and 1a (147 mg, 0.552 mmol) was stirred in toluene (10 mL) at 115° C. for 48 h in Kontes® pressure tube. After cooling, a brick-colored precipitate was collected on a filter frit, washed with $Et_2O$ (3×10 mL), and vacuum dried on the filter. The material was extracted on the filter with 5×3 mL $CH_2Cl_2$ allowing the filtrates to be collected in 5 separate vials. A red solution in each vial was layered with $Et_2O$ (20 mL). In 1 week, the combined precipitates (or red crystals) from each vial were collected, washed with $Et_2O$ (3×10 mL), and vacuum-dried to afford 144 mg of the desired product (60%). Elem. Anal.: Calcd for $C_{28}H_{44}Cl_4N_4O_2Ru_2S_2$ (876.75): C, 38.36; H, 5.06; N, 6.39%. Found C, 38.38; H, 4.99; N, 6.32%. Elem. Anal.: Calcd for $C_{28}H_{44}Cl_4N_4O_2Ru_2S_2$ (876.75): C, 38.36; H, 5.06; N, 6.39%. Found (under nitrogen): C, 38.61; H, 4.99; N, 6.17%. The complex is poorly soluble in $CDCl_3$ and slightly more soluble in $CD_2Cl_2$. $^1H$ NMR (400 MHz, $CD_2Cl_2$, r.t., saturated): δ 2.00 (br s, 1H), 2.15 (d, J≈14 Hz, 1H), 2.37 (t, J≈12 Hz, 1H), 2.15 (m, 4H), 2.75-2.94 (m, 3H), 3.04 (d, J≈14 Hz, 1H), 3.07-3.23 (m, 5H), 3.38 (m, 2H), 3.44-3.62 (m, 3H), 3.61-3.75 (m, 3H), 3.79 (d, J≈12 Hz, 1H), 3.87 (t, J≈14 Hz, 1H), 3.93-4.09 (overlapped m, 3H), 4.06 (br s, 1H), 4.44 (t, J≈11 Hz, 1H), 4.72 (br s, 1H, possibly NH), 5.07 (d, J≈18 Hz, 1H), 6.72-8.85 (overlapped, 10H), 9.19 (br s, 1H, NH . . . Cl). The same compound is obtained if the synthesis is carried out in the presence of $P(C_6F_5)_3$.

An X-ray structure of complex K-1 revealed that one ligand coordinates to one Ru atom via mer-fashion (e.g., the N, N, and S atoms are bound to Ru in mer-isomer geometry). A second ligand coordinates to second Ru atom via fac-fashion (e.g., in fac-isomer geometry). The Ru atoms are connected via one bridging Cl atom and the S(Ph) atom from the mer-coordinated ligand. There appears to be a hydrogen-bonding interaction between one NH group of the fac-coordinated ligand and the terminal Cl atom attached to the first Ru atom. Complex K-1 exists as a single species in solution. The NH hydrogen atom H-bonded to the chloride ligand appears at δ 9.19 ppm in the $^1H$ NMR spectrum. It is shifted to low field by Δδ=4.47 ppm relative to the NH resonance of the non-H bonded NH group.

Example 6.1.13. Synthesis of Complex A-5

A mixture of $[RuCl_2(DMSO)_4]$ (190 mg, 0.392 mmol) and ligand 1a (105 mg, 0.392 mmol) was stirred in toluene (5 mL) at 115° C. for 24 h in a KONTES® pressure tube. After cooling, the red precipitate was collected on a filter frit, washed with $Et_2O$ (3×10 mL), and vacuum dried to afford 116 mg of crude material. The material was dissolved in $CH_2Cl_2$ (3 mL), filtered via a Whatman® syringe filter (PTFE membrane, pore size 0.45 μm), and layered with $Et_2O$ (~20 mL). A red crystalline solid was obtained in 41% yield (84 mg). Elem. Anal.: Calcd for $C_{16}H_{28}C_2N_2O_2RuS_2$ (516.50): C, 37.21; H, 5.46; N, 5.42%. Found: C, 37.37; H, 5.41; N, 5.25%. $^1H$ NMR for major diastereomer (400 MHz, $CD_2Cl_2$, r.t.): δ 2.81 (s, 3H), 2.91 (t, J≈13 Hz, 1H), 3.11 (m, 1H), 3.24 (s, 3H), 3.29-3.74 (m, 11H), 3.79 (t, J≈12 Hz, 1H), 3.93 (t, J≈13 Hz, 1H), 4.05 (t, J≈13 Hz, 1H), 5.40 (br s, NH, 1H), 7.37 (t, J≈7 Hz, 2H), 7.46 (t, J≈6 Hz, 1H), 7.98 (d, J≈7 Hz, 2H). $^{13}C\{^1H\}$ for major diastereomer (100.5 MHz, CD$_2$Cl$_2$, r.t.): δ 45.0 (s, 1C), 47.5 (s, 1C), 47.6 (s, 1C), 48.3 (s, 1C), 49.1 (s, 1C), 54.0 (s, 1C, overlapped with CD$_2$Cl$_2$ peak), 55.4 (s, 1C), 58.4 (s, 1C), 60.7 (s, 1C, CH$_3$), 61.7 (s, 1C, CH$_3$), 128.9 (s, 2C$_{meta}$, Ph), 130.1 (s, 1C$_{para}$, Ph), 133.3 (s, 2C$_{ortho}$, Ph), 133.6 (s, 1C$_{ipso}$, Ph).

The X-Ray structure of A-5 showed a solid state structure that was similar to the structures of complexes A-1, A-2, A-3, and A-6. Complex A-5 crystallized as four independent diastereomers due to the presence of asymmetric centers at the N'-nitrogen and sulfur atoms, respectively. In solution, the concentration of one of the diastereomers was observed to be higher than the others (approximately 90% of the total amount).

Example 6.1.14. Synthesis of Complex C-2

A mixture of [RuCl$_2$(COD)]$_n$ (309 mg, 1.103 mmol), PCy$_3$ (309 mg, 1.103 mmol) and 1d (248 mg, 1.103 mmol) was stirred in toluene (10 mL) at 115° C. for 48 h in a KONTES® pressure tube. After cooling, the brick colored precipitate was filtered on a filter frit, washed with Et$_2$O (3×10 mL), and partially vacuum dried on the filter (vacuum pump). The residue was extracted from the filter frit with dichloromethane (6×3 mL). The obtained solution was layered with Et$_2$O (100 mL). Red-brown crystals were collected after a few days (521 mg, 70% yield). Elem. Anal.: Calcd for C$_{30}$H$_{53}$Cl$_2$N$_2$PRuS (676.77): C, 53.24; H, 7.89; N, 4.14%. Found: C, 53.10; H, 7.95; N, 4.05%. $^{31}$P{$^1$H} (162 MHz, CDCl$_3$, r.t.): δ 27.0 (s). $^1$H NMR (400 MHz, CDCl$_3$, r.t.): δ 0.78-3.90 (overlapped m, 47H), 5.57 (br s, 1H, NH), 7.22-7.53 (m, 3H), 8.10-8.30 (m, 2H). $^{13}$C{$^1$H} (100.5 MHz, CDCl$_3$, r.t., selected without PCy$_3$ carbon atoms): δ 46.7 (s, 1C), 46.8 (s, 1C), 48.5 (s, 1C), 52.3 (s, 1C), 54.2 (s, 1C), 67.2 (s, 1C), 128.2 (s, 2C$_{meta}$, Ph), 129.4 (s, 1 C$_{para}$, Ph), 134.9 (s, 2C$_{ortho}$, Ph), 137.8 (s, 1C$_{ipso}$, Ph).

Example 6.1.15. Synthesis of Complex C-3

Complex C-3 was prepared similarly to Complex C-2, using ligand 2d. The compound exists in CDCl$_3$ as a mixture of presumably two diastereomers (79:21 ratio). $^{31}$P{$^1$H} (162 MHz, CDCl$_3$, r.t.): δ 28.8 (s, minor, 21%), 29.0 (s, major, 79%). $^1$H NMR (400 MHz, CDCl$_3$, r.t., selected): δ 2.09 (CH$_3$, major), 2.59 (CH$_3$, major), 2.83 (CH$_3$, major), 4.80 (vt, NH, minor), 5.09 (vt, NH, major). $^{13}$C{$^1$H} (100.5 MHz, CDCl$_3$, r.t., selected without PCy$_3$ carbon atoms, major): δ 20.9 (s, 1C), 43.3 (s, 1C), 46.6 (s, 1C), 48.1 (s, 1C), 52.0 (s, 1C), 55.1 (s, 1C), 67.2 (s, 1C).

Example 6.1.16. Synthesis of Complex F-1

To [RuCl$_2$(PPh$_3$)$_3$] (556 mg, 0.58 mmol) was added a solution of ligand 11 (201 mg, 0.58 mmol) in 7 mL of CH$_2$Cl$_2$ with stirring. The resulting burgundy solution was stirred at r.t. for 2 hrs and evaporated. Diethyl ether was added to cause precipitation. The light-brown precipitate was collected on a frit filter, washed with Et$_2$O (3×10 mL), vacuum dried, and recrystallized from dichloromethane/Et$_2$O. Elem. Anal.: Calcd for C$_{37}$H$_{41}$Cl$_2$N$_2$PRuS$_2$ (780.81): C, 56.91; H, 5.29; N, 3.59%. Found: C, 57.41; H, 5.52; N, 3.56%. In alternative procedure, [RuCl$_2$(PPh$_3$)$_3$] (310 mg, 0.32 mmol) and ligand 11 (112 mg, 0.32 mmol) were refluxed in 2 mL of toluene with stirring. The product was separated from PPh$_3$ excess on an alumina column (Al$_2$O$_3$ neutral, hexane-ethyl acetate 7:3, R$_f$=0.4, air). $^{31}$P{$^1$H} (162 MHz, CD$_2$Cl$_2$, r.t.): δ 48.5 (s). $^1$H NMR (400 MHz, CD$_2$Cl$_2$, r.t.): δ 0.88-1.84 (overlapped, 3H), 1.21-1.45 (overlapped, 3H), 1.72 (d, J≈11 Hz, 1H), 2.58 (d, J≈11 Hz, 1H), 2.77 (m, 1H), 3.08-3.26 (overlapped m, 2H), 3.45-3.74 (overlapped m, 3H), 3.92 (vt, J≈10 Hz, 1H), 4.34 (d, J≈15 Hz, 1H), 4.49 (vt, J≈10 Hz, 1H), 5.41 (brs, 1H, NH), 6.60 (s, 1H), 6.86 (s, 1H), 7.01 (s, 2H), 7.16-7.28 (m, 11H), 7.42 (d, J≈15 Hz, 2H), 7.46-7.62 (m, 6H). $^{13}$C{$^1$H} (100.5 MHz, CD$_2$Cl$_2$, r.t.,): 624.2 (s, 1C), 25.6 (s, 1C), 32.0 (s, 1C), 34.7 (s, 1C), 44.9 (s, 1C), 45.9 (s, 1C), 52.9 (s, 1C), 63.2 (s, 1C), 71.4 (s, 1C), 125.8 (s, 1C), 126.8 (s, 1C), 127.1 (s, 1C), 127.7 (d, J$_{C-P}$=9 Hz, 6C$_{meta}$, PPh$_3$), 128.2 (s, 2C$_{meta}$, Ph), 128.7 (d, J$_{C-P}$=1.5 Hz, 3C$_{para}$, PPh$_3$), 128.8 (s, 1C$_{para}$, Ph), 133.3 (s, 2C$_{ortho}$, Ph), 133.9 (d, J$_{C-P}$=10 Hz, 6C$_{ortho}$, PPh$_3$), 135.2 (s, 1C$_{ipso}$, Ph), 137.1 (d, J≈36 Hz, 3C$_{ipso}$), 142.9 (s, 1C).

Example 6.2. Synthesis and Characterization of Ruthenium Complexes Using P(O)NS-Type Ligands Scheme 10 illustrates an example ruthenium Complex having a P(O)NS-type ligand that was synthesized, isolated, and subsequently used as a precatalyst in catalytic reactions.

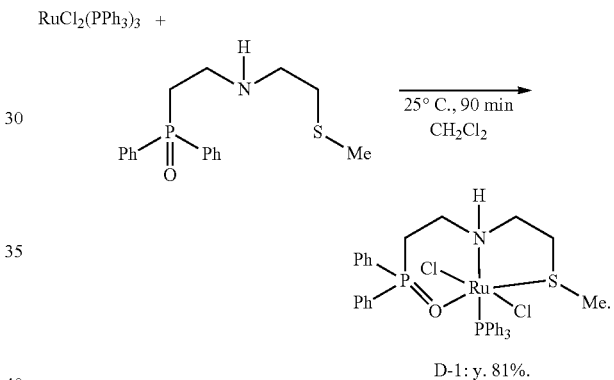

Example 6.2.1. Synthesis of Complex D-1

A solution of crude ligand 8 (140 mg, 0.438 mmol) in 6 mL of CH$_2$Cl$_2$ was added to [RuCl$_2$(PPh$_3$)$_3$] (420 mg, 0.438 mmol) with stirring. The resulting burgundy solution was stirred at r.t. for 90 min ($^{31}$P NMR analysis of the reaction mixture performed after 1 h (CDCl$_3$) reveals full conversion of the starting material into the product (represented by two ~1:1 isomers: δ 43.9 (s, PPh$_3$, 24%), 45.1 (s, PPh$_3$, 26%), 52.7 (s, P(O)Ph$_2$, 24%), 52.8 (s, P(O)Ph$_2$, 26%)) and free PPh$_3$ (6-5.5 ppm)). The reaction mixture was concentrated to ~40% in volume, layered with Et$_2$O (22 mL), and left for six days. After decantation of the mother liquor, the obtained brick-colored precipitate was transferred to a filter frit, washed with Et$_2$O (3×10 mL), and vacuum dried overnight. Isolated yield: 266 mg (81%). Elem. Anal. (%): Calcd. C, 55.78; H, 4.95; N, 1.86. Found: C, 55.62; H, 4.94; N, 1.90. The compound crystallizes from dichloromethane-diethyl ether as a single isomer having four atoms P(O)NS located in one plane, based on X-Ray single crystal analysis. Upon dissolution, two isomers, possibly diastereomers, are observed within the mixing time (e.g., immediately). $^{31}$P{$^1$H}NMR spectroscopy of the isomeric mixture (162 MHz, CD$_2$Cl$_2$, 25° C.): δ 44.2 (s, PPh$_3$, 24%), 45.4 (s, PPh$_3$, 26%), 52.3 (s, P(O)Ph$_2$, 24%), 53.4 (s, P(O)Ph$_2$, 26%). $^1$H NMR of the isomeric mixture (400 MHz, $CD_2Cl_2$, 25° C.): δ 1.22 (s, 3.21H, SMe), 1.24 (s, 3.00H, SMe), 2.13 (dt, J≈13 Hz, J≈4 Hz, 1.00H), 2.27 (d, J≈14 Hz, 1.00H), 2.56 (dt, J≈13 Hz, J≈4 Hz, 1.07H), 2.73-2.99 (m, 5.21H), 3.17 (brt, 2.16H), 2.24-2.42 (m, 4.21H), 3.96 (q, J≈13 Hz, 1.00H), 4.17 (q, J≈13 Hz, 1.07H), 4.87 (vt, J≈11 Hz, 1.07H), 5.13 (vt, J≈11 Hz, 1.00H), 7.25-7.94 (m, 51.75H, Ph). Selected $^{13}C\{^1H\}$ NMR (only sp$^3$ carbon atoms) of the major isomer (100.5 MHz, $CD_2Cl_2$, 25° C.): δ 16.1 (s, 1C), 29.8 (d, $J_{C-P}$≈68 Hz, 1C), 38.7 (s, 1C), 44.3 (d, $J_{C-P}$≈6 Hz, 1C), 49.3 (s, 1C). Selected $^{13}C\{^1H\}$NMR (only sp$^3$ carbon atoms) of the minor isomer (100.5 MHz, $CD_2Cl_2$, 25° C.): δ 19.0 (s, 1C), 29.5 (d, $J_{C-P}$≈67 Hz, 1C), 37.3 (s, 1C), 44.0 (d, $J_{C-P}$≈6 Hz, 1C), 50.7 (s, 1C).

Example 7. Synthesis and Characterization of Iridium Complexes Using NNS-Type Ligands Chart 7 illustrates iridium complexes of NNS-type ligands that were synthesized, isolated and subsequently used as precatalysts in catalytic reactions.

Chart 7

M-1
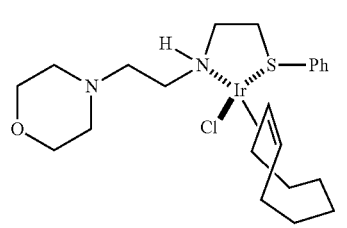

N-2
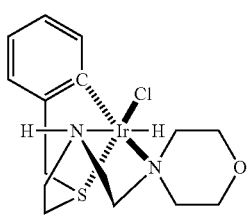

N-3
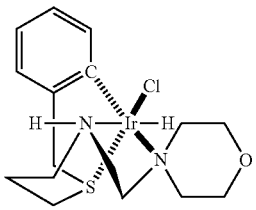

N-4
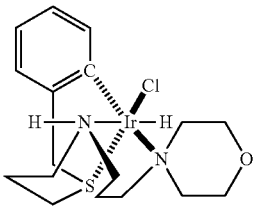

N-5
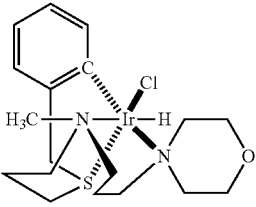

N-1
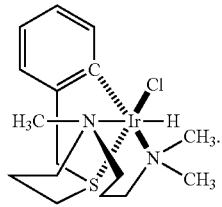

Complexes M-1 and N-1 to N-5 were synthesized according to Scheme 11. Isolated yields are listed below each complex.

Scheme 11

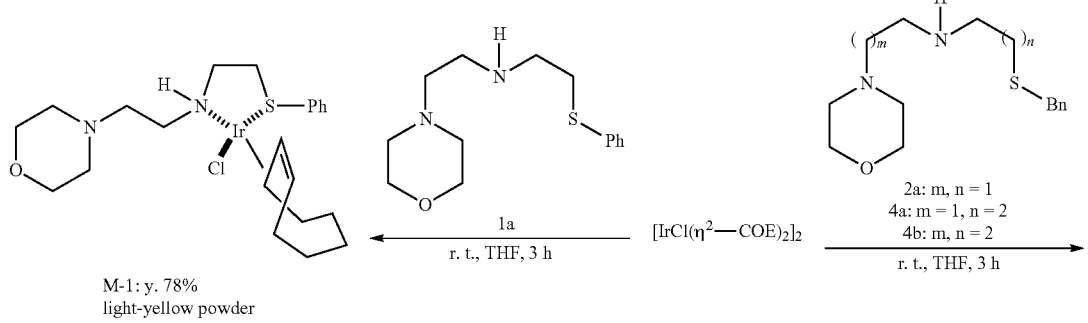

M-1: y. 78%
light-yellow powder

2a: m, n = 1
4a: m = 1, n = 2
4b: m, n = 2

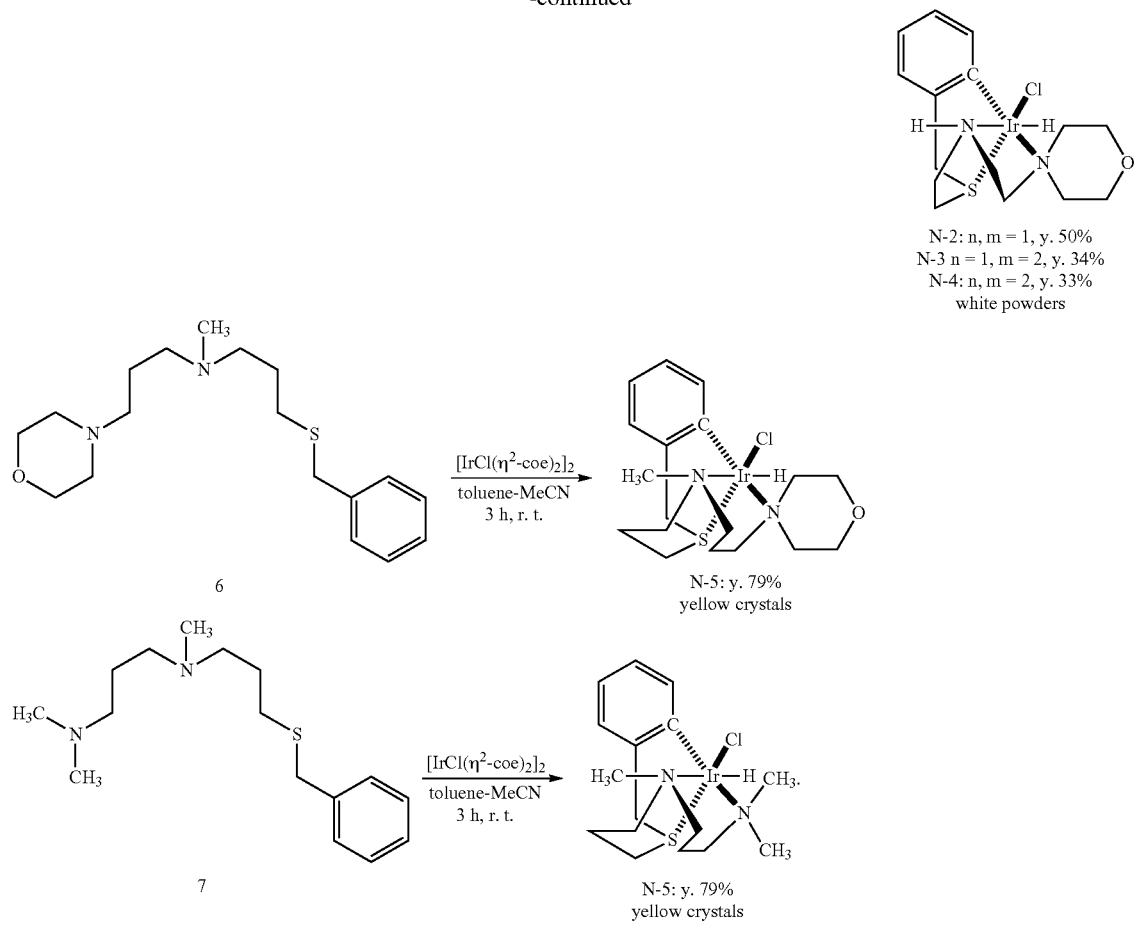

In general, the inventive complexes of iridium were prepared by reacting a ligand with a suitable iridium-containing precursor in a suitable solvent.

Ligands 1a, 2a, 4a, and 4b were reacted with [IrCl($\eta^2$-COE)$_2$]$_2$ in THF (tetrahydrofuran) solvent at room temperature. The outcome of these reactions depended on the nature of the R$_1$ group attached to the S donor atom. Ligands 6 and 7 were reacted with [IrCl($\eta^2$-COE)$_2$]$_2$ in a binary toluene-MeCN solvent at room temperature.

Reaction of ligand 1a with [IrCl($\eta^2$-COE)$_2$]$_2$ in THF solvent at room temperature afforded the yellow, slightly oxygen-sensitive complex [Ir$^I$Cl($\eta^2$-COE){$\kappa^2$(N',S)-1a}] (M-1).

Example 7.1. Synthesis of Complex M-1

In an example preparation, a solution of ligand 1a (86 mg, 0.324 mmol) in THF was added to [IrCl(COE)$_2$]$_2$ (145 mg, 0.162 mmol) (4 mL) with stirring. The initially formed red solution afforded a precipitate after ca. 10 min. The mixture was stirred for 4 h at r.t. and a yellow precipitate was collected on a frit, washed with diethyl ether (3×10 mL) and vacuum dried overnight to afford 152 mg of a yellow product (78%). Elem. Anal.: Calcd. for C$_{22}$H$_{36}$ClIrN$_2$OS (604.27): C, 43.73; H, 6.01; N, 4.64%. Found: C, 43.46; H, 5.93; N, 4.42%. When the same procedure was carried out in 3 mL of THF, the product was isolated in 90% yield. Elemental analysis for this sample, however, was not acceptable for unknown reasons. Found C, 40.85; H, 5.43; N, 3.91%. The compound is oxygen-sensitive in solution. NMR spectra of the are time- and solvent-dependent. The compound was slightly oxygen-sensitive in solution.

In another example procedure, an orange suspension of [IrCl(COE)$_2$]$_2$ (145 mg, 0.162 mmol) in dichloromethane (1 mL) was prepared. A solution of ligand 1a (86 mg, 0.324 mmol) in dichloromethane (3 mL) was also prepared. The solution was added to the suspension. After stirring for less than about 30 seconds, a red solution formed. This was stirred for 3 hours at room temperature, concentrated to about 2 mL, and layered with diethyl ether (20 mL). Yellow crystals and a yellow powder formed after two days. The solids were filtered, washed with diethyl ether (3×5 mL), and dried under vacuum dried to afford 142 mg of a gold-colored material identified as a CH$_2$Cl$_2$ solvate of complex M-1 (one molecule of solvent per 4 molecules of complex based on elemental analysis. Elem. Anal.: Calc'd for 4C$_{22}$H$_{36}$ClIrN$_2$OS.CH$_2$Cl$_2$: C, 42.72; H, 5.88; N, 4.48%. Found: C, 42.55; H, 5.90; N, 4.34%.

Example 7.2. Synthesis of Complex N-2

A solution of ligand 2a (91 mg, 0.324 mmol) in THF (3 mL) was added to [IrCl(COE)$_2$]$_2$ (145 mg, 0.162 mmol) with stirring. The orange-yellow suspension was stirred for 3 h at r.t., and a white precipitate was collected on a frit, washed with diethyl ether (3×10 mL), and vacuum dried overnight to afford 100 mg of the final off-white product (61%). Elem. Anal.: Calcd for C$_{15}$H$_{24}$ClIrN$_2$OS (508.10): C, 35.46; H, 4.76; N, 5.51%. Found (under nitrogen): C, 35.96; H, 4.75; N, 5.09%. The same compound was obtained when the synthesis was carried out in dichloromethane under the same conditions, except 6 mL of the solvent was used; 50% isolated yield (82 mg). The compound is sparingly soluble in $CD_2Cl_2$ (hydride peak is observed at δ −19.49 ppm), DMF-$d_7$.

Example 7.3. Synthesis of Complex N-3

A solution of ligand 4a (95 mg, 0.324 mmol) in THF (3 mL) was added to $[IrCl(COE)_2]_2$ (145 mg, 0.162 mmol) under stirring. The initially formed red solution afforded a precipitate after ca. 2 min. The orange-yellow mixture was stirred for 3 h at r.t., and a white precipitate was collected on a frit, washed with diethyl ether (3×10 mL), and vacuum dried overnight to afford 57 mg of the final off-white product (34%). Elem. Anal.: Calcd. for $C_{16}H_{26}ClIrN_2OS$ (522.12): C, 36.81; H, 5.02; N, 5.37%. Found (under nitrogen): C, 37.71; H, 5.10; N, 5.05%. The compound is stable in $CD_2Cl_2$ at least overnight. $^1H$ NMR (400 MHz, $CD_2Cl_2$, r.t.): 6-21.35 (s, 1H), 1.94 (t, J≈3 Hz, 1H), 2.27 (t, J≈3 Hz, 1H), 2.48 (td, J≈13 Hz, J≈3 Hz, 1H), 2.56 (td, J≈13 Hz, J≈3 Hz, 1H), 2.63-2.84 (overlapped m, 3H), 2.86-3.00 (m, 1H), 3.01-3.11 (m, 1H), 3.53 (d, J≈11 Hz, 1H), 3.61 (t, J≈3 Hz, 1H), 3.68-3.86 (overlapped m, 5H), 3.91 (d, J≈12 Hz, 2H), 4.07 (d, J≈14 Hz, 1H), 4.41 (q, J≈11 Hz, 2H), 6.77-6.92 (overlapped, 2H), 7.13 (d, J≈7 Hz, 1H), 7.94 (d, J≈8 Hz, 1H). $^{13}C\{^1H\}$ (100.5 MHz, $CD_2Cl_2$, r.t.): δ 23.1 (s, 1C), 25.6 (s, 1C), 29.0 (s, 1C), 47.1 (s, 1C), 47.6 (s, 1C), 57.9 (s, 1C), 59.9 (s, 1C), 63.7 (s, 1C), 65.6 (s, 1C), 67.2 (s, 1C), 120.4 (s, 1C), 123.0 (s, 1C), 124.6 (s, 1C), 136.5 (s, 1C), 139.4 (s, 1C), 147.5 (s, 1C).

Example 7.4. Synthesis of Complex N-4

A solution of ligand 4b (100 mg, 0.324 mmol) in THF (3 mL) was added to $[IrCl(COE)_2]_2$ (145 mg, 0.162 mmol) with stirring. The initially formed red solution afforded a precipitate after ca. 10 min. The obtained orange-yellow mixture was stirred for 3 h at r.t., after which a white precipitate was collected on a frit, washed with diethyl ether (3×10 mL), and vacuum dried overnight to afford 58 mg of the final off-white product (33%). Elem. Anal.: Calcd. for $C_{17}H_{28}ClIrN_2OS$ (536.15): C, 38.08; H, 5.26; N, 5.23%. Found (under nitrogen): C, 37.77; H, 5.10; N, 5.27%. The compound is remarkably air-stable in the solid state, but slowly decomposes in $CD_2Cl_2$ under argon (11% decomposition) after 15 h monitoring at room temperature. $^1H$ NMR (400 MHz, $CD_2Cl_2$, r.t.): 6-22.21 (s, 1H), 1.18 (m, 1H), 1.54 (m, 1H), 1.94 (m, 2H), 2.29 (m, 2H), 2.46 (m, 2H), 1.94 (m, 2H), 2.54-2.81 (overlapped m, 4H), 3.34 (br s, 1H, NH), 3.53-4.13 (overlapped m, 8H), 4.39 (t, J≈11 Hz, 1H), 4.50 (t, J≈11 Hz, 1H), 6.83 (t, J≈7 Hz, 1H), 6.93 (t, J≈7 Hz, 1H), 7.12 (d, J≈7 Hz, 1H), 7.82 (d, J≈7 Hz, 1H). $^{13}C\{^1H\}$(100.5 MHz, $CD_2Cl_2$, r.t.): δ 23.5 (s, 1C), 25.9 (s, 1C), 32.3 (s, 1C), 49.7 (s, 1C), 51.1 (s, 1C), 55.1 (s, 1C), 60.3 (s, 1C), 61.6 (s, 1C), 63.7 (s, 1C), 64.0 (s, 1C), 64.4 (s, 1C), 121.0 (s, 1C), 121.5 (s, 1C), 125.3 (s, 1C), 135.5 (s, 1C), 139.2 (s, 1C), 148.9 (s, 1C).

Example 7.5. Synthesis of Complex N-5

A solution of ligand 6 (104 mg, 0.324 mmol) in toluene (2 mL) was added to $[IrCl(COE)_2]_2$ (145 mg, 0.162 mmol), followed by addition acetonitrile (2 mL) with stirring. The initial orange suspension converted into a red solution upon stirring. The mixture was stirred for 3 h at r.t., concentrated to about half volume and layered with pentane (22 mL). After 4 days, the mother liquor was decanted from the residue composed of red-yellow crystalline material (bottom) and well-shaped yellow crystals (wall). The residue was slightly dried, diethyl ether (5 mL) and pentane (5 mL), were successively added, and the resulting suspension was stirred for about 10 min. The binary solvent was decanted, the yellow powder was washed two times with diethyl ether (5 mL), and then dried overnight under vacuum. Isolated yield: 141 mg (79%). Elem. Anal.: Calcd. for $C_{18}H_{30}ClIrN_2OS$ (550.18): C, 39.30; H, 5.50; N, 5.09%. Found (under nitrogen): C, 39.14; H, 5.62; N, 5.29%. $^1H$ NMR (400 MHz, $CDCl_3$, r.t.): 6-25.02 (s, 1H), 1.38-1.51 (m, 1H), 1.60-1.76 (m, 2H), 1.96-2.10 (m, 1H), 2.10-2.19 (m, 1H), 2.19-2.30 (m, 1H), 2.42-2.59 (m, 6H), 2.67-2.81 (m, 2H), 2.81-2.91 (m, 1H), 2.57-2.72 (m, 2H), 3.72-3.88 (m, 4H), 3.88-4.00 (m, 2H), 4.37 (q, J≈10 Hz, 2H), 6.77 (t, J≈7 Hz, 1H), 6.84 (t, J≈7 Hz, 1H), 7.03 (d, J≈7 Hz, 1H), 7.98 (d, J≈7 Hz, 1H). $^{13}C\{^1H\}$ (100.5 MHz, $CDCl_3$, r.t.): δ 15.3 (s, 1C), 22.4 (s, 1C), 24.7 (s, 1C), 36.0 (s, 1C), 50.0 (s, 1C), 54.4 (s, 1C), 59.4 (s, 1C), 60.2 (s, 1C), 61.1 (s, 1C), 61.2 (s, 1C), 64.2 (s, 1C), 64.3 (s, 1C), 120.1 (s, 1C), 120.9 (s, 1C), 124.0 (s, 1C), 133.2 (s, 1C), 138.5 (s, 1C), 149.3 (s, 1C).

Example 7.6. Synthesis of Complex N-1

Complex N-1 was prepared similarly as N-5, except 7 was used as ligand. Isolated yield: 141 mg (79%). Elem. Anal.: Calcd. for $C_{18}H_{30}ClIrN_2OS$ (508.14): C, 37.82; H, 5.55; N, 5.51%. Found (under nitrogen): C, 37.53; H, 5.33; N, 5.47%. Slowly decomposes in $CDCl_3$. $^1H$ NMR (400 MHz, $CDCl_3$, r.t., selected): 6-25.37 (s, 1H), 6.73 (t, J≈7 Hz, 1H), 6.81 (t, J≈7 Hz, 1H), 7.00 (d, J≈7 Hz, 1H), 8.00 (d, J≈7 Hz, 1H). $^{13}C\{^1H\}$ (100.5 MHz, $CDCl_3$, r.t.): δ 23.9 (s, 1C), 24.8 (s, 1C), 36.9 (s, 1C), 50.6 (s, 1C), 53.9 (s, 1C), 54.5 (s, 1C), 59.5 (s, 1C), 59.6 (s, 1C), 60.9 (s, 1C), 61.6 (s, 1C), 119.4 (s, 1C), 120.5 (s, 1C), 123.7 (s, 1C), 135.6 (s, 1C), 138.8 (s, 1C), 149.8 (s, 1C).

The reactivity of $[IrCl(\eta^2\text{-COE})_2]_2$ towards NNS-type ligands 1a, 2a, 4a and 4b was in sharp contrast to its reported reactivity towards PNP-type ligands of the general formula $R_2P(CH_2)_2NH(CH_2)_2PR_2$. The outcome of these PNP ligand reactions also depended on the nature of R and the reaction conditions, including solvent and temperature. For example, when R=$^i$Pr, the complex $[Ir^{III}ClH_2\{(^iPr_2PC_2H4)_2NH\}]$ was isolated when the synthesis was carried out in isopropanol at 80° C., while the complex $[Ir^I(\eta^2\text{-COE})\{(^iPr_2PC_2H4)_2NH\}]$Cl was isolated when the synthesis was carried out at room temperature, and was reported to exhibit fluxional behavior in solution. When R=Cy or Ad, isostructural iridium (III) dihydride complexes $[Ir^{III}ClH_2\{(Cy_2PC_2H4)_2NH\}]$ and $[Ir^{III}ClH_2\{(Ad_2PC_2H4)_2NH\}]$ were isolated when the reaction was carried out at room temperature in toluene and THF, respectively. When R=bulky $^t$Bu, $[IrCl(C_8H_{13})H\{(^tBu_2PC_2H4)_2NH\}]$ was isolated. The $[Ir^{III}ClH_2\{(^iPr_2PC_2H4)_2NH\}]$ ("Ir—PNP") is commercially available and has been reported as (pre)catalyst in ester hydrogenation, ketone transfer hydrogenations, solvolysis of ammonia borane and amination of aliphatic alcohols.

The identities (e.g., compositions) of embodiment complexes M-1 and N-1, N-2, N-3, N-4, and N-5 were supported by elemental analysis. In addition, X-ray structures were obtained for complexes M-1, N-3, N-4, and N-5.

Example 8. Synthesis and Characterization of Other Complexes Using NNS, P(O)NS, SNNS Type Ligands Other transition metal complexes are accessible by reactions of suitable precursors with these inventive ligands. Representative inventive complexes were also prepared using first row transition metals including Mn, Fe, Co, Ni, and Cu. These reactions typically involved reaction of the embodiment ligand with a MCl$_2$ salt (M=transition metal) in a solvent at 25° C. Chart 8 below illustrates other complexes of NNS, P(O)NS, SNNS-type ligands that were synthesized, isolated and subsequently used as precatalysts in catalytic reactions.

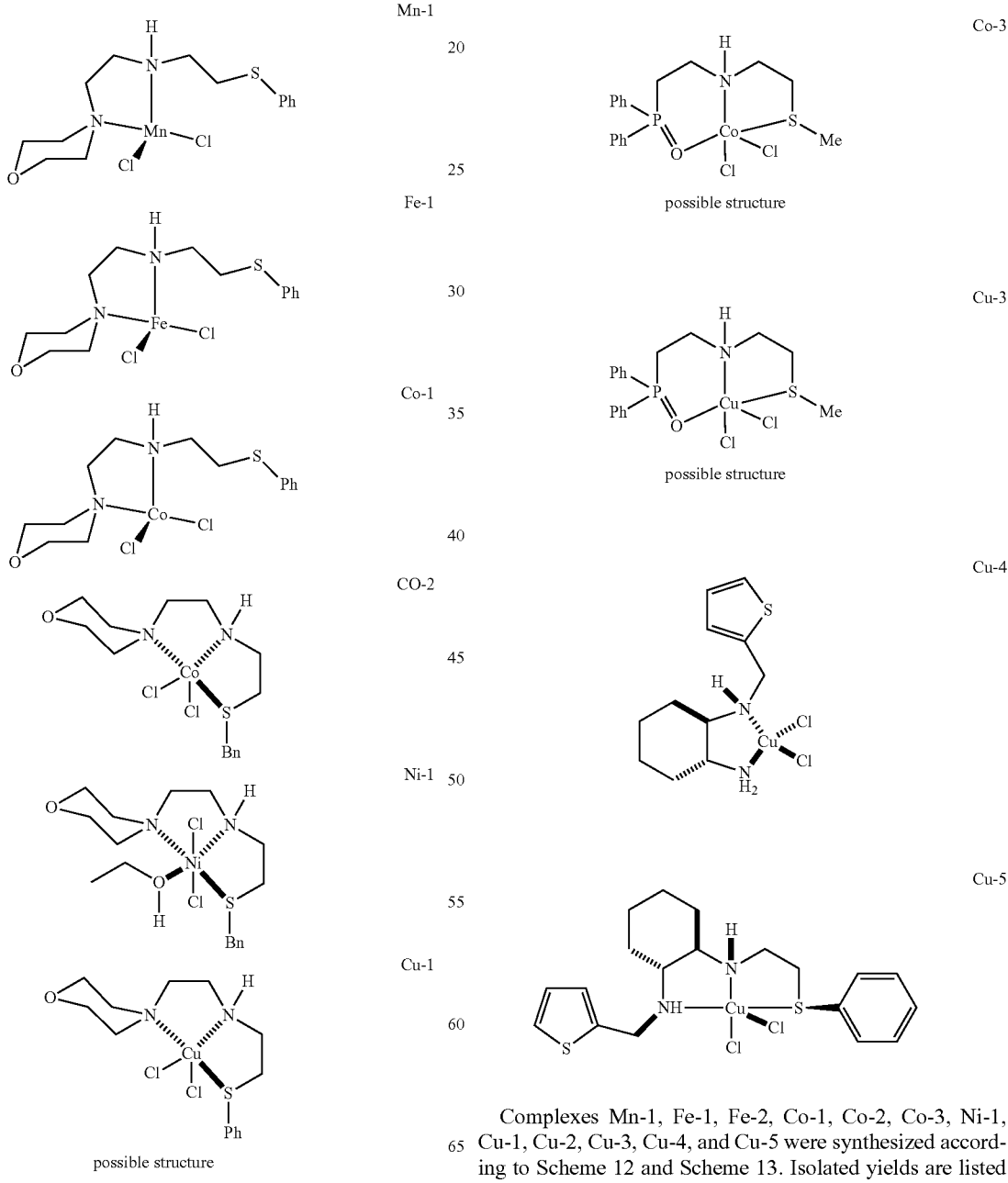

Complexes Mn-1, Fe-1, Fe-2, Co-1, Co-2, Co-3, Ni-1, Cu-1, Cu-2, Cu-3, Cu-4, and Cu-5 were synthesized according to Scheme 12 and Scheme 13. Isolated yields are listed below each complex.

Scheme 12
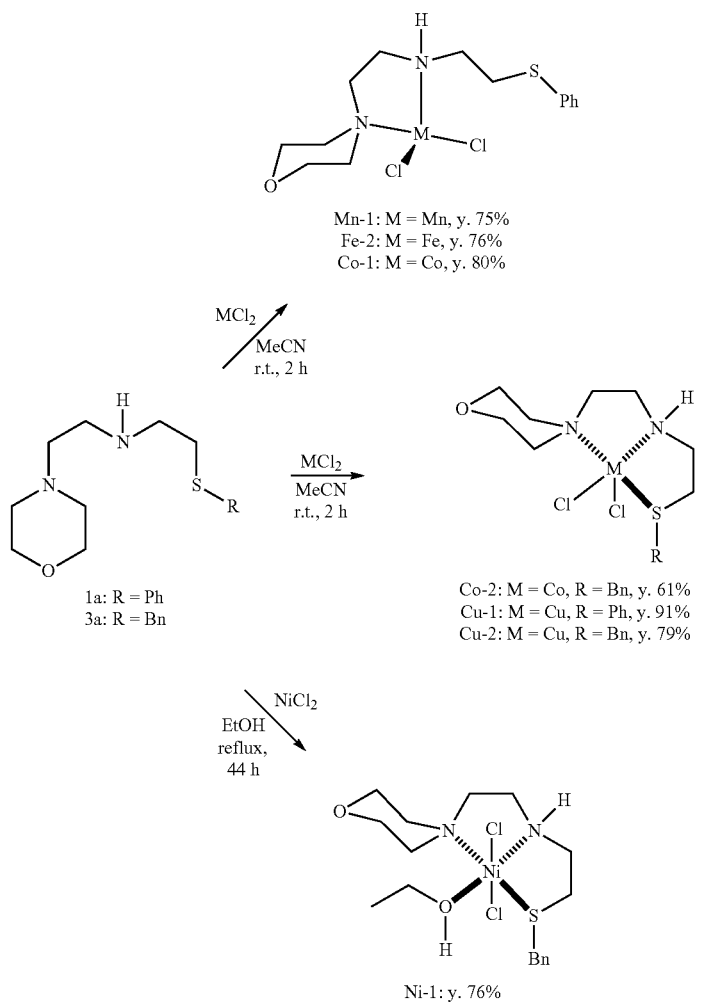
Scheme 13
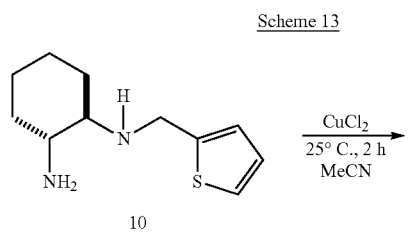
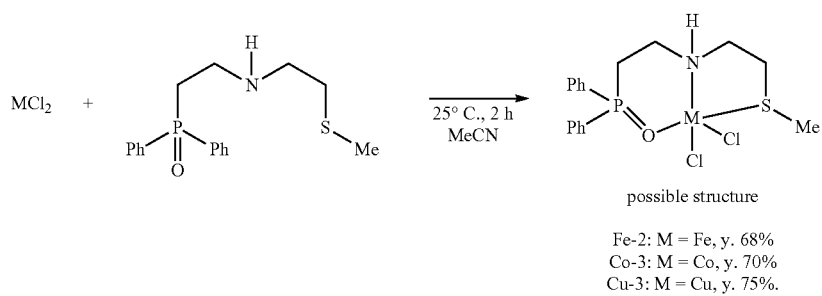
-continued
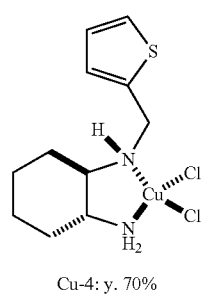
Cu-4: y. 70%

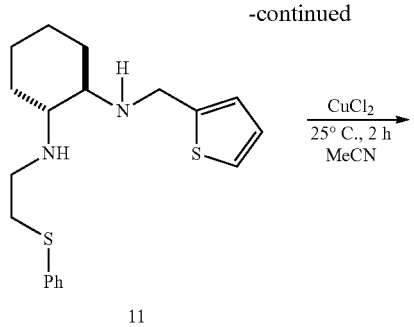

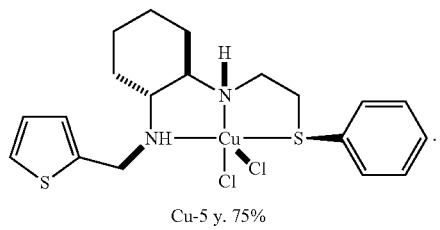

Cu-5 y. 75%

Example 8.1. Synthesis of [Mn(κ²[N,N']-1a)Cl₂] (Mn-1)

A solution of 1a (0.745 mmol, 198 mg) in MeCN (3 mL) was added to a pink suspension of MnCl₂ (0.745 mmol, 94 mg) in MeCN (1 mL) under stirring. White precipitate started to form within 1-2 min. After 24 h, the precipitate was filtered, washed with MeCN (3×2 mL) and diethyl ether (3×4 mL), and vacuum dried overnight. Yield: 220 mg (75%), white powder. The compound is sparingly soluble in dichloromethane, THF, ethanol, and acetonitrile. It dissolves immediately in water on air. The obtained transparent solution slowly produces yellowish precipitate likely due to decomposition. Elem. Anal.: Calcd. for $C_{56}H_{88}Cl_8Mn_4N_8O_4S_4$ (1568.96): C, 42.87; H, 5.65; N, 7.14%. Found (under nitrogen): C, 42.06; H, 5.34; N, 6.92%. $\mu_{eff}$=6.4$\mu_B$ (21° C.).

Example 8.2. Iron Complexes

Example 8.2.1. Synthesis of [Fe(κ²[N,N']-1a)Cl₂] (Fe-1)

A solution of 1a (0.745 mmol, 198 mg) in MeCN (3 mL) was added to a yellowish suspension of FeCl₂ (0.745 mmol, 94 mg) in MeCN (1 mL). The initial suspension slowly transformed into a light-green solution (ca. 1 h). After 2 h, the solution was filtered through a Whatman® syringe filter (PTFE membrane, pore size 0.45 μm), concentrated to ~2 mL, and layered with diethyl ether (~21 mL). Large light-green-blue box-shaped crystals were obtained overnight. Decantation of the mother liquor after 5 days afforded 223 mg of the compound (76%). Elem. Anal.: Calcd. for $C_{14}H_{22}Cl_2FeN_2OS$ (393.15): C, 42.77; H, 5.64; N, 7.13%. Found (under nitrogen): C, 42.12; H, 5.45; N, 6.78%. $\mu_{eff}$=5.5$\mu_B$ (21° C.).

Alternative Work-Up for Fe-1.

After filtering the solution through a Whatman® syringe filter as described above, the solvent was evaporated and the obtained residue was stirred overnight with a diethyl ether (7 mL)-pentane (7 mL) mixture to afford a white precipitate. The precipitate was collected, washed with diethyl ether (3×5 mL), and vacuum dried overnight. Yield: 215 mg (73%), white powder. The paramagnetic material is oxygen-sensitive in both the solid state and immediately in solution. Elem. Anal.: Calcd for $C_{14}H_{22}Cl_2FeN_2OS$ (393.15): C, 42.77; H, 5.64; N, 7.13%. Found (under argon): C, 42.59; H, 5.69; N, 7.01%.

Example 8.2.2. Synthesis of Complex Fe-2

A solution of ligand 8 (0.221 mmol, 70 mg) in MeCN (3 mL) was added to yellowish FeCl₂ (0.221 mmol, 28 mg) under stirring. The obtained solution was stirred for 2 h and layered with diethyl ether (20 mL). The next day a white precipitate was separated, washed with diethyl ether (3×5 mL), and vacuum dried. Yield: 67 mg (68%), off-white powder. Elem. Anal.: Calcd for $C_{17}H_{22}Cl_2FeNOPS$ (446.15): C, 45.77; H, 4.97; N, 3.14%. Found: C, 45.48; H, 4.95; N, 3.06%.

Example 8.3. Cobalt Complexes

Example 8.3.1. Synthesis of [Co(κ²[N,N']-1a)Cl₂] (Co-1)

A solution of 1a (0.745 mmol, 198 mg) in MeCN (3 mL) was added to a blue suspension of CoCl₂ (0.745 mmol, 97 mg) in MeCN (1 mL). The obtained solution was stirred for 2 h, filtered through a Whatman® syringe filter (PTFE membrane, pore size 0.45 μm), concentrated to ~2 mL, and layered with diethyl ether (~21 mL). Blue crystals were obtained overnight. Decantation of the mother liquor after 5 days afforded 236 mg of a visually air-stable compound (80%). Elem. Anal.: Calcd for $C_{14}H_{22}Cl_2CoN_2OS$ (396.24): C, 42.44; H, 5.60; N, 7.07%. Found: C, 42.27; H, 5.63; N, 7.08%. $\mu_{eff}$=5.1$\mu_B$ (21° C.).

Example 8.3.2. Synthesis of [Co(κ³[N,N',S]-3a)Cl₂] (Co-2)

A solution of 3a (0.745 mmol, 209 mg) in MeCN (3 mL) was added to a blue suspension of CoCl₂ (0.745 mmol, 97 mg) in MeCN (1 mL). Addition MeCN (3 mL) was added to the obtained mixture to homogenize the reaction. The thus obtained blue solution was stirred for 2 h, concentrated to about half of the volume, and layered with diethyl ether (~17 mL). Light-blue crystals were obtained overnight. Decantation of the mother liquor afforded 186 mg of visually air-stable compound (61%). Elem. Anal.: Calcd for $C_{15}H_{24}Cl_2CoN_2OS$ (410.26): C, 43.91; H, 5.90; N, 6.83%. Found: C, 44.21; H, 5.92; N, 6.80%. $\mu_{eff}$=4.4$\mu_B$ (25° C.).

Example 8.3.3. Synthesis of Complex Co-3

A solution of ligand 8 (0.209 mmol, 115 mg) in MeCN (4 mL) was added to CoCl₂ (0.209 mmol, 27 mg). The obtained blue solution was stirred for 2 h, filtrated, and layered with diethyl ether (20 mL). The next day a precipitate collected, washed with diethyl ether (3×5 mL), and dried under vacuum overnight. Yield: 66 mg (70%). Elem. Anal.: Calcd for $C_{17}H_{22}Cl_2CoNOPS$ (449.24): C, 45.45; H, 4.94; N, 3.12%. Found: C, 45.33; H, 4.87; N, 3.18%.

Example 8.4. Synthesis of trans-[Ni(κ3[N,N',S]-3a)(EtOH)Cl₂] (Ni-1)

A mixture of NiCl₂ (0.278 mmol, 36 mg) and 3a (0.278 mmol, 79 mg) in anhydrous EtOH (4 mL) was stirred in a KONTES® pressure tube at 90° C. After 44 h, the tube was cooled at −20° C. for 1 h, and a greenish precipitate was collected on a frit filter, washed with EtOH (3×2 mL) and Et$_2$O (3×4 mL), and dried under vacuum overnight. 77 mg of the greenish powder was recovered (61%). Elem. Anal.: Calcd for C$_{17}$H$_{22}$Cl$_2$NiNOPS (456.09): C, 44.77; H, 6.63; N, 6.14%. Found (under nitrogen): C, 45.03; H, 6.50; N, 6.06%. $\mu_{eff}$=3.6$\mu_B$ (25° C.).

Example 8.5. Copper Complexes

Example 8.5.1. Synthesis of [Cu(κ$^3$[N,N',S]-3a)Cl$_2$] (Cu-1)

A solution of ligand 3a (0.745 mmol, 198 mg) in MeCN (3 mL) was added to a brown suspension of CuCl$_2$ (0.745 mmol, 100 mg) in MeCN (1 mL). An immediate color change from brown to green was observed. The obtained solution was stirred for 4 h, filtered, and the solvent was evaporated under vacuum. To the obtained oily residue was added pentane (10 mL), and the mixture was stirred overnight to afford a green precipitate that was collected, washed with pentane, and dried under vacuum overnight. Yield: 272 mg (91%), visually air- and moisture-stable green solid. Elem. Anal.: Calcd. for C$_{14}$H$_{22}$Cl$_2$CuN$_2$OS (400.85): C, 41.95; H, 5.53; N, 6.99%. Found: C, 41.88; H, 5.53; N, 6.84%. $\mu_{eff}$=2.1$\mu_B$ (25° C.).

Example 8.5.2. Synthesis of [Cu(κ$^3$[N,N',S]-3a)Cl$_2$] (Cu-2)

A solution of 3a (0.684 mmol, 192 mg) in MeCN (6 mL) was added to a brown suspension of CuCl$_2$ (0.684 mmol, 92 mg) in MeCN (2 mL). An immediate color change from brown to green was observed. The obtained suspension was stirred for 4 h. The precipitate was filtered, washed with diethyl ether (3×5 mL), and dried under vacuum overnight. Yield: 224 mg (79%), as an air- and moisture-stable sea-green solid. Elem. Anal.: Calcd. for C$_{15}$H$_{24}$Cl$_2$CuN$_2$OS (414.88): C, 43.43; H, 5.83; N, 6.75%. Found: C, 42.83; H, 5.49; N, 6.58%. $\mu_{eff}$=1.9$\mu_B$ (25° C.).

Example 8.5.3. Synthesis of Complex Cu-3

A solution of ligand 8 (0.358 mmol, 115 mg) in MeCN (4 mL) was added to brown CuCl$_2$ (0.358 mmol, 48 mg). A change in color from brown to green was observed (~5 min). The obtained mixture was stirred for 2 h, filtered, and the filtrate was layered with diethyl ether (20 mL). The next day, a precipitate was collected, washed with diethyl ether (3×5 mL), and dried under vacuum overnight. Yield: 122 mg (75%). Elem. Anal.: Calcd. for C$_{17}$H$_{22}$Cl$_2$CuNOPS (453.85): C, 44.99; H, 4.89; N, 3.09%. Found: C, 43.92; H, 4.89; N, 3.03%.

Example 8.5.4. Synthesis of Complex Cu-4

A solution of ligand 10 (153 mg, 0.729 mmol) in MeCN (4 mL) was added to a brown suspension of CuCl$_2$ (98 mg, 0.729 mmol) in MeCN (2 mL) under stirring. An immediate change of the color from brown to blue was observed. In 10 min, the color changed to dark purple and a cyan precipitate started to form. The obtained suspension was stirred for 2 h, and the precipitate was filtered, washed with pentane (3×5 mL), and dried under vacuum overnight. Yield: 186 mg (74%), air- and moisture-stable cyan solid. Elem. Anal.: Calcd for C$_{11}$H$_{18}$Cl$_2$CuN$_2$S (344.79): C, 38.32; H, 5.26; N, 8.12%. Found: C, 38.04; H, 5.11; N, 8.06%. Upon dissolution in different solvents, different colors of solutions are observed: cyan in methanol, yellow in benzene, green in THF.

Example 8.5.5. Synthesis of Complex Cu-5

A solution of ligand 11 (104 mg, 0.298 mmol) in MeCN (2 mL) was added to a brown suspension of CuCl$_2$ (40 mg, 0.298 mmol) in MeCN (2 mL) under stirring. An immediate color change from brown to green was observed. In ~1 min, a precipitate started to form. The obtained suspension was stirred for 2 h, and the precipitate was filtered, washed with diethyl ether (3×5 mL) and pentane (3×5 mL), and dried under vacuum overnight. Yield: 111 mg (77%), light-green air- and moisture-stable solid. Elem. Anal.: Calcd for C$_{19}$H$_{26}$Cl$_2$CuN$_2$S$_2$ (481.00): C, 47.44; H, 5.45; N, 5.82%. Found: C, 46.48; H, 5.33; N, 5.76%.

Example 8.5.6. Synthesis of Water-Soluble Complex

Cu-6 and unique dimeric Cu-7 complex containing two chiral ligands as shown in Scheme 14.

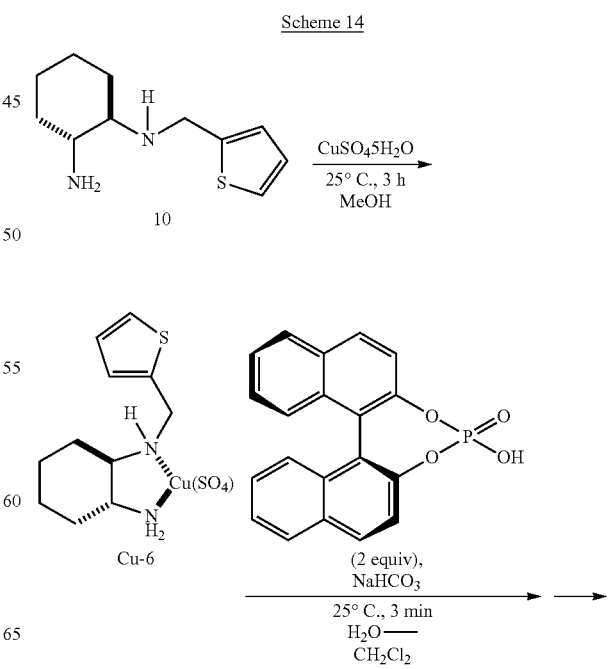

Scheme 14

-continued

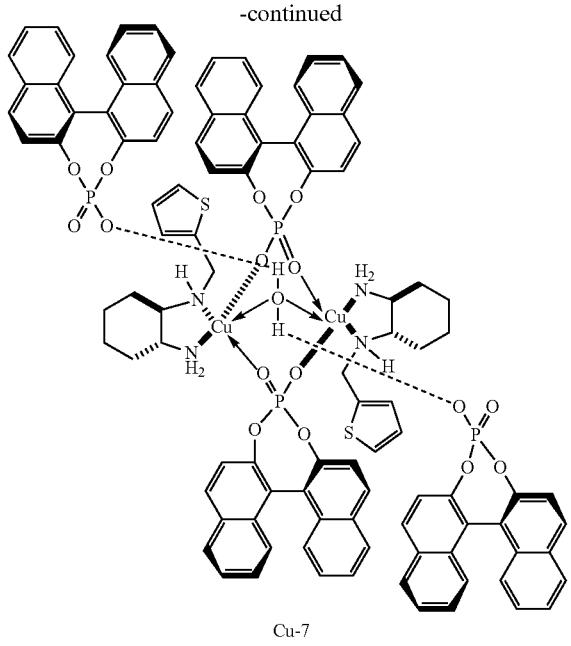

Cu-7

Example 8.5.6.1. Synthesis of Water-Soluble Complex Cu-6

CuSO$_4$.5H$_2$O (500 mg, 2.0 mmol) was dissolved in MeOH (30 mL, ~20 min) under stirring. A solution of ligand 10 (421 mg, 2.0 mmol) in MeOH (10 mL) was added. An immediate change of the color to blue-dark was observed. The mixture was stirred in air for 2 h, and the precipitate was filtered, washed with MeOH (3×10 mL) and diethyl ether (3×25 mL), and vacuum dried to afford 660 mg of the product. Elem. Anal.: Calcd for C$_{11}$H$_{18}$Cl$_2$CuN$_2$O$_4$S$_2$ (369.95): C, 35.71; H, 4.90; N, 7.57%. Found: C, 34.65; H, 4.69; N, 6.96%. The product was air and moisture-stable.

Example 8.5.6.2. Synthesis of Complex Cu-7

A solution of Cu-6 (0.5 equiv, 106 mg, 0.287 mmol) in 10 mL of water was added to a suspension of (S)-(+)-1,1'-Binaphthyl-2,2'-diyl hydrogenphosphate (97% Aldrich, CAS Number 35193-64-7, 200 mg, 0.574 mmol) in 15 mL of dichloromethane. The mixture was stirred in air and NaHCO$_3$ was added via spatula until two clear phases formed. Brine (5 mL) was added. The blue organic phase was separated. The aqueous phase was washed with dichloromethane (2×15 mL). The combined organic phases were dried over MgSO$_4$, filtered, and vacuum dried to afford 146 mg of the product (52% yield). The complex was easily recrystallized from hot acetone in air. Elem. Anal.: Calcd for C$_{102}$H$_{86}$Cu$_2$N$_4$O$_{17}$P$_4$S$_2$ (1954.93): C, 62.67; H, 4.43; N, 2.87%. Found: C, 59.93; H, 4.44; N, 3.02%. This product has also been characterized crystallographically.

Example 9. Catalytic Hydrogenation of Methyl Trifluoroacetate (Scheme 15)

Complexes of the present disclosure were used as pre-catalysts for hydrogenation of methyl trifluoroacetate (MTFA, substrate A), as shown in Scheme 15. It should be appreciated that the hydrogenation of methyl trifluoroacetate by catalysts of the present disclosure is sufficiently novel that the catalytic hydrogenation of this substrate constitutes separate embodiments of the present disclosure. Results are summarized in Table 1 (vide infra).

Scheme 15

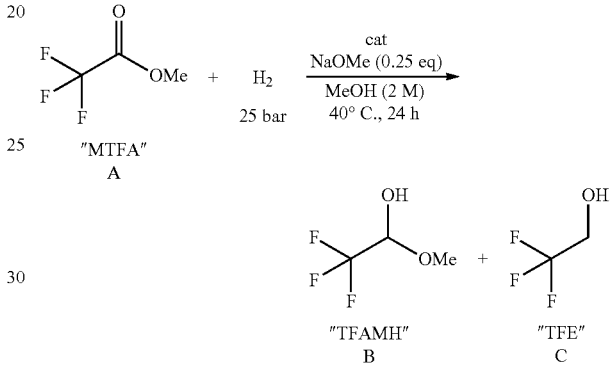

In one set of experiments, the ester methyl trifluoroacetate ("MTFA") was chosen as a substrate because homogeneous hydrogenation of MTFA may afford trifluoroacetaldehyde methyl hemiacetal ("TFAMH") and/or 2,2,2-trifluoroethanol ("TFE") depending on the conditions used. TFAMH is an important synthon in the production of various fluorinated chemicals containing CF$_3$-groups. TFAMH is also used in medicinal chemistry, in agrochemical research, and in materials research. MTFA is typically produced from fluoral and methanol at −78° C., or via a complicated two-step Swartz-type reaction (including a step with HF in the gas-phase), or by stoichiometric hydrogenation of MTFA using borohydride as a reducing agent. The borohydride reduction is neither environmentally nor economically attractive. A method for catalytically converting MTFA (commercially available at $47 for 25 grams) into TFAMH (commercially available at $50 for 250 milligrams) using molecular hydrogen would provide a less expensive, greener alternative to the known methods.

TABLE 1

Hydrogenation of methyl trifluoroacetate A catalyzed by various bifunctional catalysts$^a$.

| run | cat | S/C | temp, °C. | conv., %$^b$ | yield, %$^b$ | B | C | TON$^c$ |
|---|---|---|---|---|---|---|---|---|
| 1 | — | — | 40 | 0 | 0 | 0 | 0 | 0 |
| 2 | Ru-MACHO | 2000 | 40 | 92 | 92 | 1 | 91 | 3660 |
| 3 | Ru-MACHO | 20,000 | 40 | 96 | 96 | 72 | 24 | 24000 |
| 4 | Ru-SNS | 2000 | 40 | 71 | 71 | 59 | 12 | 1660 |
| 5 | Ru-PNN | 2000 | 40 | 43 | 42 | 41 | 1 | 860 |
| 6 | (R,R)-Ts-DENEB | 2000 | 40 | 26 | 26 | 21 | 5 | 620 |
| 7 | (R)-RUCY-XylBINAP | 2000 | 40 | 62 | 62 | 44 | 18 | 1600 |
| 8 | A-1 | 2000 | 40 | 53 | 52 | 35 | 17 | 1380 |

TABLE 1-continued

Hydrogenation of methyl trifluoroacetate A catalyzed by various bifunctional catalysts[a].

| run | cat | S/C | temp, °C. | conv., %[b] | yield, %[b] | B | C | TON[c] |
|---|---|---|---|---|---|---|---|---|
| 9 | A-2 | 2000 | 40 | 69 | 69 | 42 | 27 | 1920 |
| 10 | A-3 | 2000 | 40 | 77 | 77 | 57 | 20 | 1940 |
| 11 | A-6 | 2000 | 40 | 46 | 45 | 31 | 14 | 1180 |
| 12 | J-1 | 2000 | 40 | 20 | 20[d] | 19 | 1 | 420 |
| 13 | J-2 | 2000 | 40 | 27 | 26[d] | 22 | 4 | 600 |
| 14 | L-1 | 2000 | 40 | 39 | 38[d] | 25 | 13 | 1020 |
| 15 | B-1 | 2000 | 40 | 66 | 66 | 39 | 27 | 1860 |
| 16 | C-2 | 2000 | 40 | 60 | 60 | 36 | 23 | 1640 |
| 17 | A-4 | 2000 | 40 | 88 | 87 | 75 | 12 | 1980 |
| 18 | K-1 | 2000 | 40 | 50 | 49 | 46 | 3 | 1040 |
| 19 | A-5 | 2000 | 40 | 36 | 35[e] | 34 | 1 | 720 |
| 20 | D-1 | 2000 | 40 | 72 | 71 | 61 | 10 | 1620 |
| 21 | Ir-PNP | 2000[f] | 40 | 97 | 97 | 13 | 84 | 3620 |
| 22 | Ir-PNP | 20,000 | 40 | 86 | 86 | 51 | 35 | 24200 |
| 23 | M-1 | 2000 | 40 | 90 | 90 | 75 | 15 | 2100 |
| 24 | M-1 | 20 000 | 40 | 29 | 29 | 27 | 1 | 5800 |
| 25 | N-2 | 2000 | 42-46 | 96 | 96 | 68 | 27 | 2440 |
| 26 | N-2 | 20 000 | 40 | 58 | 58 | 56 | 1 | 11600 |
| 27 | N-3 | 2000 | 42-46 | 96 | 96 | 44 | 51 | 2920 |
| 28 | N-3 | 20 000 | 40 | 58 | 58 | 56 | 1 | 11600 |
| 29 | N-4 | 2000 | 40 | 91 | 91 | 62 | 29 | 2400 |
| 30 | N-4 | 20,000 | 40 | 53 | 53 | 51 | 2 | 11000 |
| 31 | N-4 | 20,000[g] | 40 | 0.3 | 0.3 | 0 | 0.3 | 120 |

[a]Experimental conditions: substrate (10 mmol), 5 ml MeOH containing 2.5 mmol MeONa (135 mg), 24 h, 50 ml Parr autoclave.
[b]19F NMR area, see SI for details.
[c]TON = turnover number, calculated as TON (B) + 2 × TON (C).
[d]Reaction mixture was heterogeneous in the end.
[e]Reaction mixture became green upon exposure to air.
[f]30 min.
[g]base = 13.5 mg (0.025 equiv relative to A).

Chart 9

Ru cat:

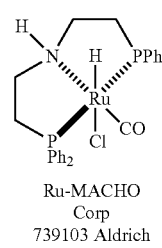

Ru-MACHO Corp
739103 Aldrich

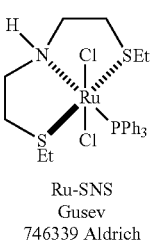

Ru-SNS Gusev
746339 Aldrich

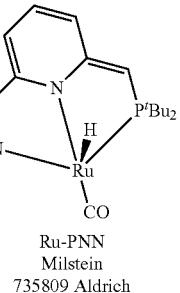

Ru-PNN Milstein
735809 Aldrich

-continued

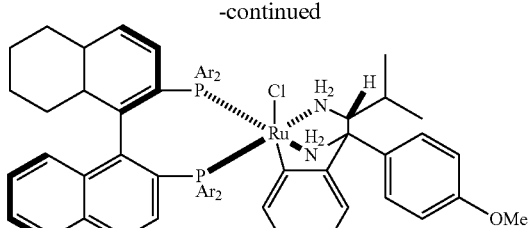

(R)-RUCY-XylBINAP
Takasago Int Corp
R0139 TCI

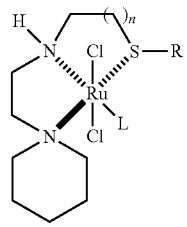

n = 1
A-1: L = PPh$_3$, R = Ph
A-2: L = PPh$_3$, R = Bn
A-3: L = PPh$_3$, R = Me
A-4: L = PCy$_3$, R = Ph
A-4: L = DMSO, R = Ph
n = 2
A-6: L = PPh$_3$, R = Bn

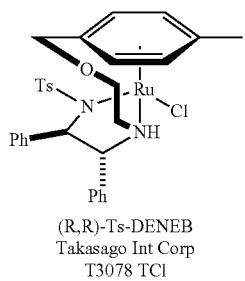

(R,R)-Ts-DENEB
Takasago Int Corp
T3078 TCI

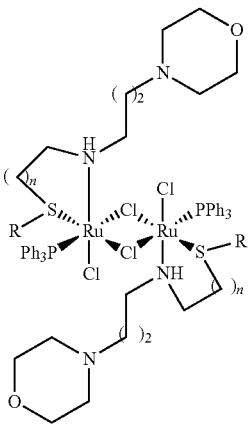

J-1: n = 1, R = Ph
J-2: n = 2, R = Bn

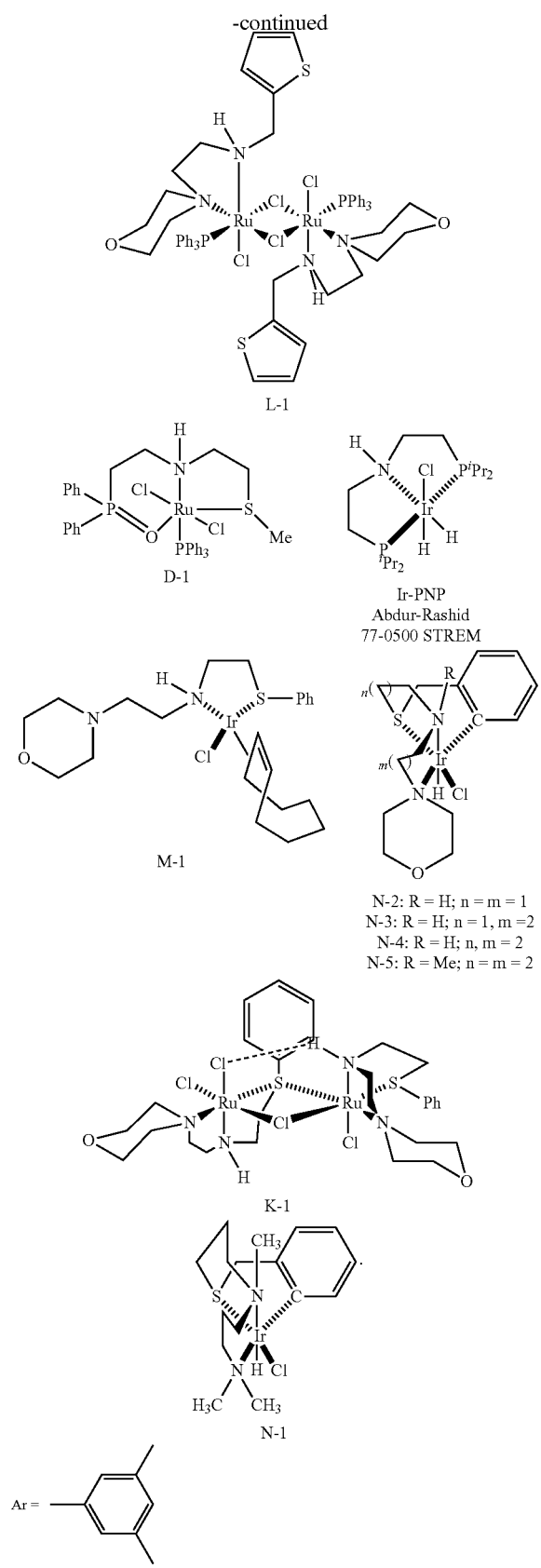

Entries 2-7, 20-21 in Table 1 describe results obtained using various commercially available Ru and Ir complexes as shown in Chart 9. Entries 8-19 and 22-27 represent the results obtained with embodiment complexes under the same conditions. Since the vast majority of esters (and other carboxylic and carbonic acid derivatives) are methyl derived, methanol was chosen as the solvent. The reduction of these compounds will necessarily produce methanol, thus its direct use as the reaction medium greatly simplifies solvent recycling. In this case, no solvent separation steps are required, thus positively impacting environmental aspects of such chemistries (a very important consideration in pharmaceutical and large-scale industrial processes). Unfortunately, many bifunctional catalysts, including some catalysts used for ester hydrogenations, are not active in methanol. For example, Gusev's Ru—SNS complex, which is a versatile catalyst for ester hydrogenation in THF (see e.g., WO2014036650A1, the entire content of which is incorporated herein by reference), hydrogenates substrate A only barely in methanol. Results from Table 1 identify three versatile catalysts for hydrogenation of substrate A in methanol: Ru-MACHO complex, Ir—PNP, and complexes N-2, N-3 and N-4. In addition, catalyst N-5 (see below, Table 2), gives excellent selectivity towards formation of B (96%) and a reasonable TON of 19 000.

Example 9.1. Hydrogenation Under Substrate-to-Catalyst Ratio (S/C)=2000

In a closed vial (loaded in the glovebox), a mixture of complex (0.005 mmol) and MeONa (135 mg, 2.5 mmol) was stirred in methanol (5 mL) for approximately 1 min (except for J-1 and J-2, which were stirred for approximately 15 min to ensure complete dissolution). Methyl trifluoroacetate A (1 mL, 10 mmol) was added via microsyringe and the resulting mixture was stirred for approximately 1 minute more and then transferred into a 50 mL Parr autoclave (Model No. 4792 General Purpose Vessel with a PTFE head gasket) equipped with glass liner and magnetic stirrer. The autoclave was closed, removed from the glovebox, and connected to a hydrogen tank (the line was vented with molecular hydrogen three times). Hydrogen was initially introduced into the autoclave at a pressure of approximately 5 bar, decreased to approximately 1 bar by carefully releasing the stop valve three times, and then finally pressurized to 25 bar. The temperature was carefully increased to 40° C. and monitored via a 4838 Parr Temperature Controller. Observed stability and accuracy was ±1° C. At the end of the reaction time, the reactor was moved into a precooled water bath (0° C.) for 5-10 min and then depressurized. The neat reaction mixture from the liner was then directly analyzed by $^{19}$F NMR spectroscopy (rd (e.g., recycle delay)=10 s; trifluoroacetaldehyde methyl hemiacetal ("TFAMH," B): 6-83.3, d, $^3J_{F-H}$=4 Hz; 2,2,2-trifluoroethanol ("TFE," C): 6-77.0 ppm, t, $^3J_{F-H}$=9 Hz). We noted in some experiments a very minor amount of acetal (<0.5-1%, $^{19}$F NMR: 6-80.5, d, $^3J_{F-H}$=4 Hz). The balance of material present was unreacted starting material. Most of the experiments were performed at least twice.

Example 9.2. Hydrogenation Under Substrate-to-Catalyst Ratio (S/C)=20,000

A stock solution of the complex (0.005 mmol) in methanol (10 mL) was prepared. 1 mL of this stock-solution was added to a mixture of MeONa (135 mg, 2.5 mmol or 13.5 mg, 0.25 mmol) in 4 mL MeOH. The mixture was stirred for approximately 1 min prior to addition of methyl trifluoroacetate (1 mL, 10 mmol). Further manipulations were performed as described above for hydrogenations performed with S/C=2000.

A second set of experiments, focusing on two iridium complexes to verify the effect of methylation of the NH ligand, as well as the amount of base, are described in Table 2.

TABLE 2

| run | Ir cat | S/C | base, equiv[a] | conv., %[b] | yield, %[b] | B | C | TON[c] |
|---|---|---|---|---|---|---|---|---|
| 1 | — | — | — | 0 | 0 | 0 | 0 | 0 |
| 2 | N-4 | 2000 | 500 | 91 | 91 | 62 | 29 | 2400 |
| 3 | N-4 | 5000 | 1250 | 84 | 83 | 74 | 9 | 4600 |
| 4 | N-4 | 20000 | 5000 | 53 | 53 | 51 | 2 | 11000 |
| 5 | N-4 | 2000[e] | 50 | 13 | 13 | 12 | 1 | 280 |
| 6 | N-4 | 5000[e] | 125 | 1.7 | 1.7 | 1.7 | 0 | 85 |
| 7 | N-4 | 20000[e] | 500 | 0.3 | 0.3 | 0.3 | 0 | 60 |
| 8 | N-5 | 2000 | 500 | 92 | 92 | 60 | 32 | 2480 |
| 9 | N-5 | 5000 | 1250 | 92 | 92 | 78 | 14 | 5300 |
| 10 | N-5 | 20000 | 5000 | 91 | 91 | 87 | 4 | 19000 |
| 11 | N-5 | 2000[e] | 50 | ~2.5 | ~2.5 | 2.5 | ~0.04 | ~52 |
| 12 | N-5 | 5000[e] | 125 | 0.9 | 0.9 | 0.9 | 0 | 45 |
| 13 | N-5 | 20000[e] | 500 | 0.2 | 0.2 | 0.2 | 0 | 40 |

[a]Relative to [Ir].
[b]19F NMR area of neat reaction mixture, see SI.
[c]TON = turnover number, calculated as TON (B) + 2 × TON(C).
[e]Ester:base = 1:0.025.

Entries 2-7 and 8-13 in Table 2 summarize results obtained from using complexes N-4 and N-5, respectively.

Entries 4 and 10 provide a comparison of hydrogenation rates of complex N-4 with complex N-5 under otherwise identical reaction conditions. Turnover numbers (TON) for both runs were excellent, exceeding 10,000. Notably, replacement of the NH group of complex XVIII with the $N(CH_3)$ group of complex N-5 resulted in an almost 60% increase in hydrogenation activity. This difference in hydrogenation activity between complex N-4 and complex N-5 was unexpected because it is contrary to what would have been expected based upon the generally accepted behavior and mechanism for bifunctional catalysis in which N-methylated complexes are much less active (if at all) for hydrogenation than their corresponding NH analogs.

Example 10. Catalytic Hydrogenation of Aromatic Ketones (Scheme 16)

The results are summarized in Table 3. Again, the results are focusing on two iridium complexes to verify the effect of methylation of the NH ligand.

Scheme 16

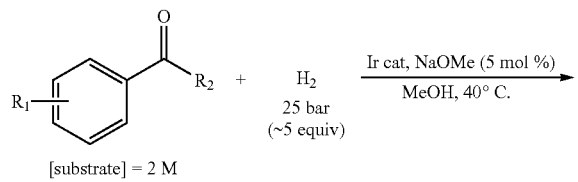

[substrate] = 2 M

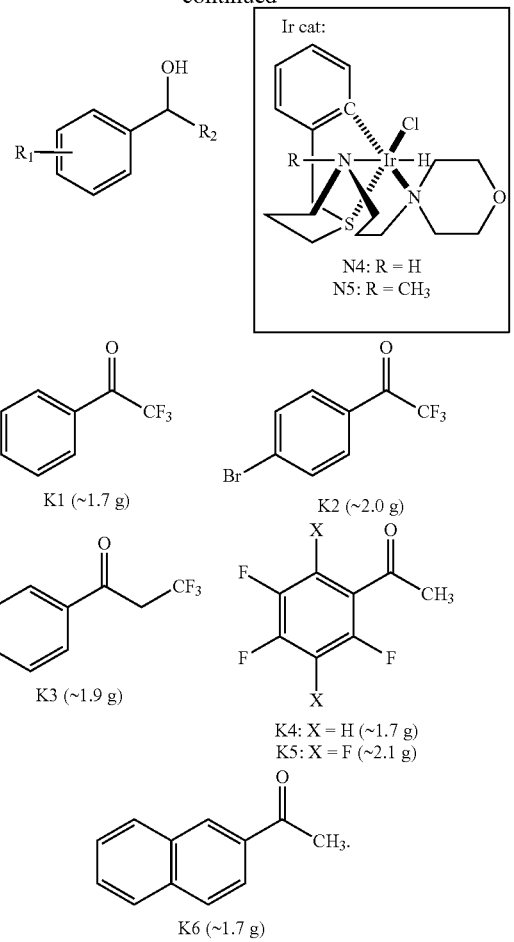

TABLE 3

| Run[a] | cat | subs | S/C | time, h | conv.[b] %[b] | yield.[b] %[b] |
|---|---|---|---|---|---|---|
| 1 | N4 | K1 | 250 000 | 3 | >99 | >99 |
| 2 | N5 | K1 | 250 000 | 3 | >99 | >99 |
| 3 | N4 | K2 | 1 000 | 1 | >99 | >99 |
| 4 | N5 | K2 | 1 000 | 1 | >99 | >99 |
| 5 | N4 | K3 | 1 000 | 3 | 100 | 100 |
| 6 | N5 | K3 | 1 000 | 3 | 100 | 100 |
| 7 | N4 | K4 | 50 000 | 3 | ~0 | ~0 |
| 8 | N5 | K4 | 50 000 | 3 | ~0 | ~0 |
| 9 | N4 | K5 | 1 000 | 3 | ~0 | ~0 |
| 10 | N5 | K5 | 1 000 | 3 | ~0 | ~0 |
| 11 | N4 | K6 | 1 000 | 1 | >98 | >98 |
| 12 | N5 | K6 | 1 000 | 1 | >99 | >99 |

[a]Standard reaction conditions: substrate (10 mmol), solvent (MeOH, 5 mL), 50 mL Parr autoclave, argon atmosphere.
[b] NMR ($^1$H or $^{19}$F, rd = 10 s).

Example 11. Catalytic Hydrogenation of 2, 2, 2-trifluoroacetophenone

The catalyst (0.008 mmol: complex N-4: 4.3 mg, complex N-5: 4.4 mg) was dissolved in methanol (20 mL) with stirring. 5 mL of this stock-solution was added to MeONa (5 mol %: 27 mg). The mixture was stirred for ~1 min prior to addition of 2,2,2-trifluoroacetophenone (1.4 mL, 10 mmol). The obtained mixture was then stirred for an additional ~1 min and then transferred into a 50 mL Parr autoclave (Model No. 4792 General Purpose Vessel with a PTFE head gasket) equipped with glass liner and magnetic stirrer. The autoclave was closed, removed from the glovebox, and connected to a hydrogen tank (the line was vented with molecular hydrogen three times). Hydrogen was initially introduced into the autoclave at a pressure of ~5 bar, decreased to ~1 bar by carefully releasing the stop valve (3 times), and then finally pressurized to 25 bar. The temperature was gently increased to 40° C. and monitored via a 4838 Parr Temperature Controller. Observed stability and accuracy was ±2° C. In 30 min, the reactor was moved into a precooled water bath (0° C.) for 5 min and then depressurized. The neat reaction mixture from the liner was then directly analyzed by $^1$H and $^{19}$F NMR spectroscopy without lock. The balance of material present was unreacted 2,2,2-trifluoroacetophenone ($^{19}$F).

Example 11.1. Transfer Hydrogenation of 2,2,2-trifluoroacetophenone (Scheme 17)

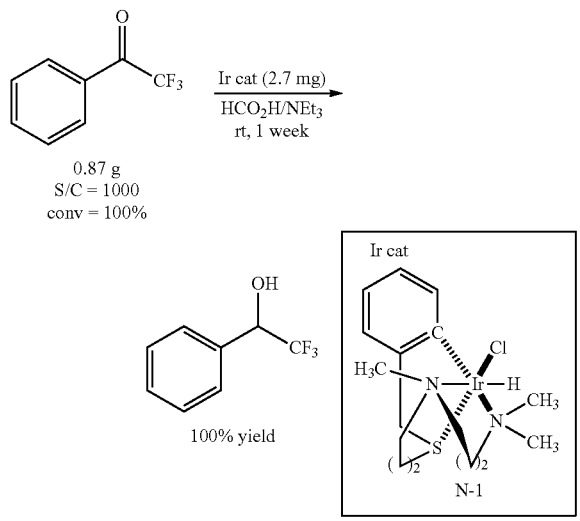

2,2,2-trifluoroacetophenone (5 mmol, 700 mkl) was added under argon via microsyringe to a mixture of complex N-1 (2.7 mg) in 2.5 mL of formic acid-triethyl amine (5:2 azeotropic mixture, Sigma Aldrich, CAS Number 15077-13-1). The solution was stirred for 1 week (the vial was periodically opened under argon to decrease pressure due to $CO_2$ evolution) at room temperature and measured. Full (100%) conversion was observed by NMR spectroscopy.

Example 12: Chemoselective Hydrogenation of α,β-unsaturated Alcohols by Iridium Complexes

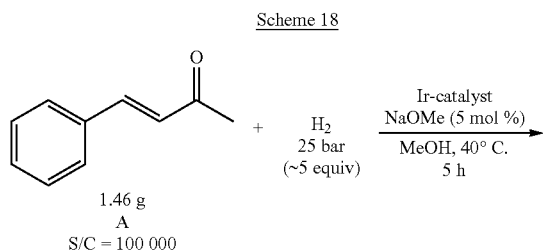

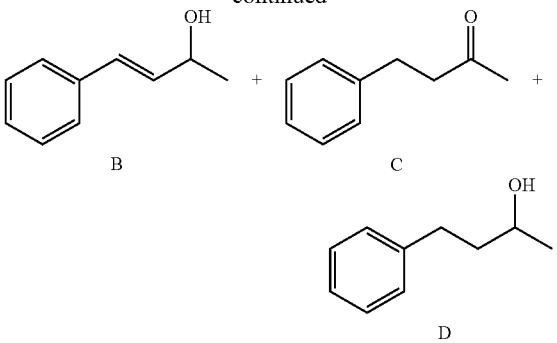

The following was prepared in the glovebox under an argon atmosphere. A stock solution of complex N-4 (5.4 mg) or complex N-5 (5.5 mg) in methanol (10 mL) was prepared. This stock-solution (0.1 mL) was added to a mixture of MeONa (27 mg, 0.5 mmol) in 4.9 mL MeOH under stirring. The mixture was stirred for approximately 1 minute prior to addition of substrate A, 4-Phenyl-3-buten-2-one (10 mmol, 1462 mg, 99% Aldrich). The resulting mixture was stirred for approximately 1 minute more and then transferred into a 50 mL Parr autoclave (Model No. 4792 General Purpose Vessel with a PTFE head gasket) equipped with glass liner and magnetic stirrer. The autoclave was closed, removed from the glovebox, and connected to a hydrogen tank (the line was vented with molecular hydrogen three times). Hydrogen was initially introduced into the autoclave at a pressure of approximately 5 bar, decreased to approximately 1 bar by carefully releasing the stop valve three times, and finally pressurized to 25 bar. The temperature was carefully increased to 40° C. and monitored via a 4838 Parr Temperature Controller. Observed stability and accuracy was ±1° C. At the end of the reaction time, the reactor was moved into a precooled water bath (0° C.) for 5 min and then depressurized. The reaction progress was directly monitored by $^1$H NMR spectroscopy (the balance of material present was unreacted starting material) calibrated against an internal standard (durene). The results are shown in Table 4.

TABLE 4

| Run | Catalyst | conv | Ratio (A:B:C:D) |
|---|---|---|---|
| 1 | N4 | >99% | ~0.4:94:<2:4 |
| 2 | N5 | >81% | 19:75:4:2 |

Although embodiments of the present disclosure have been described with reference to specific details, such details should not be regarded as limiting the scope of embodiments of the present disclosure, except as and to the extent that they are included in the accompanying claims. As those skilled in the art will appreciate, numerous modifications and variations of embodiments of the present disclosure are possible in light of these teachings, and all such are contemplated hereby. For example, in addition to the embodiments described herein, the present disclosure contemplates and claims those inventions resulting from the combination of features of the embodiments cited herein and those of the cited prior art references which complement the features of the present disclosure. Similarly, it will be appreciated that any described material, feature, or article may be used in combination with any other material, feature, or article, and such combinations are considered within the scope of embodiments of the present disclosure.

The entire content of the disclosures of each patent, patent application, and publication cited or described in this document is hereby incorporated by reference herein for all purposes.

What is claimed is:

1. A ligand having a structure represented by Formula (I):

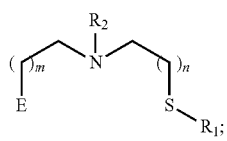

(I)

wherein:

E is:

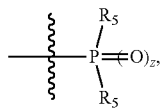

$R_1$ is a substituted or unsubstituted $C_{1-6}$ alkyl group, a substituted or unsubstituted $C_{3-6}$ cycloalkyl group, an unsubstituted phenyl group, a substituted or unsubstituted tolyl group, a substituted or unsubstituted naphthyl group, a substituted or unsubstituted biphenyl group, a substituted or unsubstituted diphenylether group, a substituted or unsubstituted diphenylamine group, a substituted or unsubstituted benzophenone group, a substituted or unsubstituted heteroaryl group, or a substituted or unsubstituted arylalkyl group;

$R_2$ is H, a substituted or unsubstituted $C_{1-6}$ alkyl group, a substituted or unsubstituted $C_{3-5}$ cycloalkyl group, a substituted or unsubstituted aryl group, a substituted or unsubstituted heteroaryl group, or a substituted or unsubstituted arylalkyl group;

$R_5$ is independently at each occurrence a substituted or unsubstituted $C_{1-6}$ alkyl group, a substituted or unsubstituted $C_{3-6}$ cycloalkyl group, a substituted or unsubstituted aryl group, a substituted or unsubstituted heteroaryl group, a substituted or unsubstituted arylalkyl group, or a substituted or unsubstituted aryloxy group;

m is 1, 2, 3, 4, or 5;
n is 1, 2, 3, 4, or 5; and
z is 1.

2. The ligand of claim 1, wherein $R_1$ is methyl, ethyl, propyl, isopropyl, 1-butyl, 2-butyl, isobutyl, tert-butyl, benzyl (-Bn), or phenyl (-Ph).

3. The ligand of claim 2, wherein $R_1$ is benzyl (-Bn).

4. The ligand of claim 1, wherein $R_2$ is H, methyl, ethyl, propyl, isopropyl, 1-butyl, 2-butyl, isobutyl, tert-butyl, benzyl (-Bn), or phenyl (-Ph).

5. The ligand of claim 1, wherein E is diarylphosphine oxide, dialkylphosphine oxide, or alkylarylphosphine oxide.

6. The ligand of claim 1, wherein m and n are each independently 1 or 2.

7. The ligand of claim 1, the ligand having a structure of:

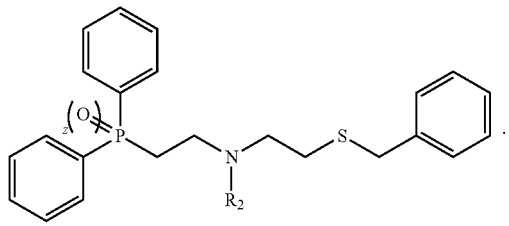

8. The ligand of claim 1, wherein $R_1$ is a substituted or unsubstituted $C_{1-6}$ alkyl group.

9. The ligand of claim 1, wherein $R_1$ is a substituted or unsubstituted arylalkyl group.

10. The ligand of claim 1, wherein $R_1$ is methyl.

11. The ligand of claim 1, wherein $R_2$ is H.

12. The ligand of claim 1, wherein $R_2$ is methyl.

13. The ligand of claim 1, wherein each $R_5$ is phenyl.

14. The ligand of claim 1, wherein at least one $R_5$ is phenyl.

15. The ligand of claim 1, wherein at least one $R_5$ is a substituted or unsubstituted aryl group.

16. The ligand of claim 1, wherein at least one $R_5$ is a substituted or unsubstituted $C_{1-6}$ alkyl group.

17. The ligand of claim 1, wherein at least one $R_5$ is a substituted or unsubstituted $C_{3-6}$ cycloalkyl group.

18. The ligand of claim 8, wherein $R_2$ is H or methyl, and at least one $R_5$ is a substituted or unsubstituted aryl group.

19. The ligand of claim 18, wherein each $R_5$ is phenyl.

20. The ligand of claim 1, wherein the ligand is:

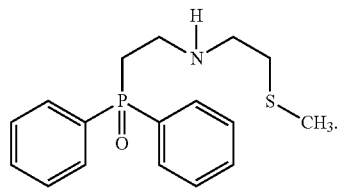 [SMILES: CSCCNCCP(=O)(c1ccccc1)c1ccccc1]

* * * * *